(12) United States Patent
Wagner et al.

(10) Patent No.: US 10,472,346 B2
(45) Date of Patent: Nov. 12, 2019

(54) POTENT GAMMA-SECRETASE MODULATORS

(71) Applicants: The General Hospital Coporation, Boston, MA (US); The Regents of the University of California, Oakland, CA (US); Steven L. Wagner, San Diego, CA (US); William C. Mobley, La Jolla, CA (US); Rudolph E. Tanzi, Hull, MA (US); Graham Johnson, Sanbornton, NH (US); Ronald Buckle, Delmar, NY (US); Nicholas Mayhew, Niskayuna, NY (US); Robert Jason Herr, Voorheesville, NY (US)

(72) Inventors: Steven L. Wagner, San Diego, CA (US); William C. Mobley, La Jolla, CA (US); Rudolph E. Tanzi, Hull, MA (US); Graham Johnson, Sanbornton, NH (US); Ronald Buckle, Delmar, NY (US); Nicholas Mayhew, Niskayuna, NY (US); Robert Jason Herr, Voorheesville, NY (US); Kevin D. Rynearson, La Mesa, CA (US)

(73) Assignees: The General Hospital Corporation, Boston, MA (US); The Regents of the University of California, Oakland, CA (US)

( * ) Notice: Subject to any disclaimer, the term of this patent is extended or adjusted under 35 U.S.C. 154(b) by 41 days.

(21) Appl. No.: 15/522,969

(22) PCT Filed: Oct. 30, 2015

(86) PCT No.: PCT/US2015/058429
§ 371 (c)(1),
(2) Date: Apr. 27, 2018

(87) PCT Pub. No.: WO2016/070107
PCT Pub. Date: May 6, 2016

(65) Prior Publication Data
US 2018/0093967 A1    Apr. 5, 2018

Related U.S. Application Data

(60) Provisional application No. 62/073,553, filed on Oct. 31, 2014.

(51) Int. Cl.
| | | |
|---|---|---|
| *C07D 401/14* | (2006.01) | |
| *C07D 413/14* | (2006.01) | |
| *C07D 487/04* | (2006.01) | |
| *A61P 25/28* | (2006.01) | |

(52) U.S. Cl.
CPC ............ *C07D 401/14* (2013.01); *A61P 25/28* (2018.01); *C07D 413/14* (2013.01); *C07D 487/04* (2013.01)

(58) Field of Classification Search
CPC ... C07D 401/14; C07D 413/14; C07D 487/04
See application file for complete search history.

(56) References Cited

U.S. PATENT DOCUMENTS

| | | |
|---|---|---|
| RE28,819 E | 5/1976 | Thompson |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |

(Continued)

FOREIGN PATENT DOCUMENTS

| | | |
|---|---|---|
| EP | 2585455 | 5/2013 |
| EP | 2968296 | 1/2016 |

(Continued)

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.*

(Continued)

*Primary Examiner* — Shawquia Jackson
(74) *Attorney, Agent, or Firm* — Fish & Richardson P.C.

(57) ABSTRACT

Provided herein are compounds and methods for treating a disorder associated with aberrant Aβ peptide levels, including Alzheimer's disease. Provided herein are compositions and methods for treating a disorder associated with aberrant Aβ peptide levels, including AD. Provided herein are compounds of Formula (A) or a pharmaceutically acceptable salt thereof, wherein, L' is selected from the group consisting of C(O), C(R1)(R2), substituted or unsubstituted —C2-6 alkylene-, and substituted or unsubstituted —C3-6 cycloalkylene.

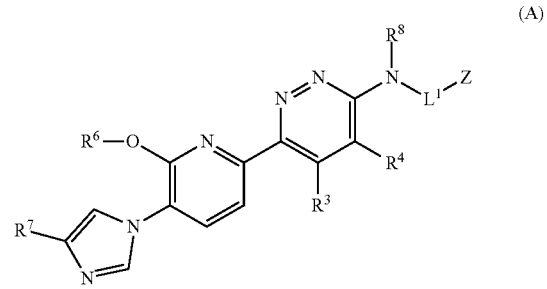

(A)

18 Claims, 11 Drawing Sheets

(56) References Cited

U.S. PATENT DOCUMENTS

| | | | |
|---|---|---|---|
| 4,414,209 | A | 11/1983 | Cook et al. |
| 4,522,811 | A | 6/1985 | Eppstein et al. |
| 5,033,252 | A | 7/1991 | Carter |
| 5,052,558 | A | 10/1991 | Carter |
| 5,323,907 | A | 6/1994 | Kalvelage |
| 5,709,874 | A | 1/1998 | Hanson et al. |
| 5,860,957 | A | 1/1999 | Jacobsen et al. |
| 6,267,983 | B1 | 7/2001 | Fujii et al. |
| 6,316,652 | B1 | 11/2001 | Steliou |
| 7,244,739 | B2 | 7/2007 | Cheng et al. |
| 7,781,442 | B2 | 8/2010 | Cheng et al. |
| 7,799,808 | B2 | 9/2010 | Cheng et al. |
| 8,017,629 | B2 | 9/2011 | Cheng et al. |
| 8,119,680 | B2 | 2/2012 | Cheng et al. |
| 9,403,815 | B2 | 8/2016 | Wagner et al. |
| 2005/0070538 | A1 | 3/2005 | Cheng et al. |
| 2006/0128712 | A1 | 6/2006 | Jolidon et al. |
| 2009/0028787 | A1 | 1/2009 | Gravenfors et al. |
| 2010/0063056 | A1 | 3/2010 | Coleman et al. |
| 2011/0118236 | A1 | 5/2011 | Mochizuki et al. |
| 2013/0023534 | A1 | 1/2013 | Casillas et al. |
| 2013/0143862 | A1 | 6/2013 | Ashcraft et al. |
| 2013/0165416 | A1 | 6/2013 | Wagner et al. |
| 2014/0213570 | A1 | 7/2014 | Cheung et al. |
| 2016/0024073 | A1 | 1/2016 | Tanzi et al. |

FOREIGN PATENT DOCUMENTS

| | | |
|---|---|---|
| JP | 2012180281 | 9/2012 |
| JP | 2012532912 | 12/2012 |
| JP | 2013530987 | 8/2013 |
| WO | WO 2004/018997 | 3/2004 |
| WO | WO 2004/110350 | 12/2004 |
| WO | WO 2007/111904 | 10/2007 |
| WO | WO 2008/088881 | 7/2008 |
| WO | WO 2009/050227 | 4/2009 |
| WO | WO 2010/098487 | 9/2010 |
| WO | WO 2010/098488 | 9/2010 |
| WO | WO 2011/059048 | 5/2011 |
| WO | WO 2011/133882 | 10/2011 |
| WO | WO 2011/163636 | 12/2011 |
| WO | WO 2014/028459 | 2/2014 |
| WO | WO 2014/165263 | 10/2014 |

OTHER PUBLICATIONS

International Search Report and Written Opinion dated Jan. 19, 2016 in international application No. PCT/US2015/058429, 15 pgs.
Extended European Search Report in Application No. 15853792.8, dated Jun. 27, 2018, 6 pages.
Abramoswki et al., "Dynamics of Aβ Turnover and Deposition in Different β-Amyloid Precursor Protein Transgenic Mouse Models Following γ-Secretase Inhibition," J. Pharmacol. Exp. Ther., 2008, 327:411-424.
Anderson et al., "Reductions in beta-amyloid concentrations in vivo by the gamma-secretase inhibitors BMS-289948 and BMS-299897," Biochem. Pharmacol., 2005, 69:689-698.
Bonnelli et. al., Expert Opinion in Pharmacotherapy, 2007, Informa UK Ltd, vol. 8, No. 2, pp. 141-153.
Burbach et al., "Vessel ultrastructure in APP23 transgenic mice after passive anti-Abeta immunotherapy and subsequent intracerebral hemorrhage," Neurobiol Aging, 2007, 28: 202-212.
Coric et al., "Safety and Tolerability of the γ-Secretase Inhibitor Avagacestat in a Phase 2 Study of Mild to Moderate Alzheimer Disease," Arch. Neurol., Nov. 2012, 69:1430-1440.
European Office Action in Application No. 11799023.4, dated Apr. 7, 2017, 7 pages.
European Office Action in European Application No. 11799023.4, dated Oct. 14, 2016, 4 pages.
Extended European Search Report in Application No. 14779909.2, dated Sep. 7, 2016, 7 pages.

Fleisher et al., "Phase II safety trial targeting amyloid beta production with a gamma-secretase inhibitor in Alzheimer's disease," Arch. Neurol., Aug. 2008, 65:1031-1038.
Gilman et al., "Clinical effects of A beta immunization (AN1792) in patients with AD in an interrupted trial," Neurology, 2005, 64:1553-1562.
Graziano et. al., Current Neurology and Neuroscience Reports, 2009, Current Medicine Group LLC, vol. 9, pp. 423-429.
Green et al., "Effect of Tarenflurbil on Cognitive Decline and Activities of Daily Living in Patients With Mild Alzheimer Disease," J. Amer. Med. Asso., 2009, 302:2557-2564.
Hardy and Higgins, "Alzheimer's Disease: The Amyloid Cascade Hypothesis," Science, Apr. 1992, 256: 184-185.
Hardy and Selkoe, "The Amyloid Hypothesis of Alzheimer's Disease: Progress and Problems on the Road to Therapeutics," Science, Jul. 2002, 297:353-356.
Imbimbo, Bruno P., "Therapeutic Potential of g-Secretase Inhibitors and Modulators," Current Topics in Medicinal Chemistry, 2008, 8:54-61.
Imbimbo, Journal of Alzheimer's Disease, 2009, IOS Press, vol. 17, pp. 757-760.
International Preliminary Report on Patentability in International Application No. PCT/US2011/041905, dated Dec. 28, 2012, 5 pages.
International Preliminary Report on Patentability in International Application No. PCT/US2014/025016, dated Sep. 15, 2015, 6 pages.
International Preliminary Report on Patentability in International Application No. PCT/US2015/058429, dated May 2, 2017, 6 pages.
International Search Report and Written Opinion in International Application No. PCT/US2011/041905, dated Feb. 17, 2012, 8 pages.
International Search Report and Written Opinion in International Application No. PCT/US2014/025016, dated Aug. 27, 2014, 10 pages.
Iwatsubo et al., "Visualization of A beta 42(43) and A beta 40 in senile plaques with end-specific A beta monoclonals: evidence that an initially deposited species is A beta 42(43)," Neuron., Jul. 1994 13:45-53.
Japanese Office Action in Japanese Application No. 2013/516839, dated May 20, 2015, 10 pages.
Japanese Office Action in Japanese Application No. 2013-516839, dated Apr. 13, 2016, 3 pages.
Kopan and Ilagan, "γ-Secretase: proteasome of the membrane?" Nat. Rev. Mol. Cell. Biol., 2004, 5:486-488.
Kounnas et al., "Modulation of γ-Secretase Reduces β-Amyloid Deposition in a Transgenic Mouse Model of Alzheimer's Disease," Neuron, Sep. 2010, 67:769-780.
Kukar et al., "Substrate-targeting γ-secretase modulators," Nature, Jun. 2008, 453:925-929.
Kumar-Singh et al., "Mean age-of-onset of familial Alzheimer disease caused by presenilin mutations correlates with both increased Aβ42 and decreased Aβ40," Hum. Mutat., Jul. 2006, 27:686-695.
Lanz et al., "Concentration-Dependent Modulation of Amyloid-β in Vivo and in Vitro Using the γ-Secretase Inhibitor, LY-450139," J. Pharmacol. Exp. Ther., 2006, 319:924-933.
Miles et al., "Bapineuzumab captures the N-terminus of the Alzheimer's disease amyloid-beta peptide in a helical conformation," Sci. Rep., Feb. 2013, 3:1302.
Netzer et al., "Gleevec inhibits β-amyloid production but not Notch cleavage," PNAS, Oct. 2003, 100(21):12444-12449.
Page et al., "Generation of Aβ38 and Aβ42 Is Independently and Differentially Affected by Familial Alzheimer Disease-associated Presenilin Mutations and γ-Secretase Modulation," J. Bio. Chem., Jan. 2008, 283(2):677-683.
Potter et al., "Increased in vivo amyloid-β42 production, exchange and loss in presenilin mutation carriers," Sci Transl Med., Jun. 2013, 5: 189ra77.
Qiu et al., "Epidemiology of Alzheimer's disease: occurrence, determinants, and strategies toward intervention," Dialogues Clin Neurosci., 2009, 11:111-28.

(56) References Cited

OTHER PUBLICATIONS

Sabbagh and Cummings, "Progressive cholinergic decline in Alzheimer's Disease: consideration for treatment with donepezil 23 mg in patients with moderate to severe symptomology," BMC Neurology, 2011, 11:21.
Salloway et al., "Two phase 3 trials of bapineuzimab in mild-to-moderate Alzheimer's disease," N. Engl. J. Med., Jan. 2014, 370:322-333.
Search Report dated Nov. 5, 2014, 26 pages.
Selkoe "Alzheimer's Disease: Genes, Proteins, and Therapy," Physiological Reviews, 2001, 81:741-66.
Smith et al., "The effect of plasma protein binding on in vivo efficacy: misconceptions in drug discovery," Nat. Rev. Drug Discov., 2010, 9:929-939.
Supplementary European Search Report in European Application No. EP 11799023, dated Oct. 24, 2013, 4 pages.
Tanzi and Bertram, "Twenty years of the Alzheimer's disease amyloid hypothesis: A genetic perspective," Cell, Feb. 2005, 120:545-555.
Taylor and Barton, "Synthesis of 2-Aminonicotinamides by Raney Nickel Cleavage of Pyrazolo [3,4-b]-pyridines," J. Am. Chem. Soc., May 1959, 81:2448-52.
Uetrecht and Naisbitt, "Idiosyncratic adverse drug reactions: current concepts," Pharmacol. Rev., 2013, 65:779-808.
U.S. Final Office Action in U.S. Appl. No. 14/775,483, dated Oct. 5, 2016, 15 pages.
U.S. Non-Final Office Action in U.S. Appl. No. 13/806,692, dated Aug. 7, 2015, 26 pages.
U.S. Non-Final Office Action in U.S. Appl. No. 14/775,483, dated May 20, 2016, 20 pages.
U.S. Notice of Allowance in U.S. Appl. No. 13/806,692, dated Dec. 11, 2015, 10 pages.
U.S. Notice of Allowance in U.S. Appl. No. 13/806,692, dated Mar. 22, 2016, 10 pages.
U.S. Restriction Requirement in U.S. Appl. No. 13/806,692, dated Jan. 29, 2015, 14 pages.
U.S. Restriction Requirement in U.S. Appl. No. 14/775,483, dated Feb. 18, 2016, 7 pages.
Wagner et al., "Potential of gamma-secretase modulators in the treatment of Alzheimer's disease," Arch. Neurol., Oct. 2013, 69:1255-1258.
Wagner et al., "Soluble γ-Secretase Modulators Selectively Inhibit Production of the 42-Amino Acid Amyloid β Peptide Variant and Augment the Production of Multiple Carboxy-Truncated Amyloid β Species," Biochemistry, 2014, doi.org/10.1021/bi401537v (PMID 24401146).
Wakabayashi and De Strooper, "Presenilins. Members of the γ-Secretase Quartets, But Part-Time Soloists Too," Physiology, Aug. 2008, 23:194-204.
Office Action in Chinese Application No. 201580071837.8, dated Feb. 28, 2019, 11 pages (with English translation).
AU Office Action in Australian Appln. No. 2015338946, dated Jun. 3, 2019, 3 pages.
JP Office Action in Japanese Appln. No. 2017523912, dated Jul. 16, 2019, 6 pages (with English translation).

* cited by examiner

A

B

A

B

A

B

A

B

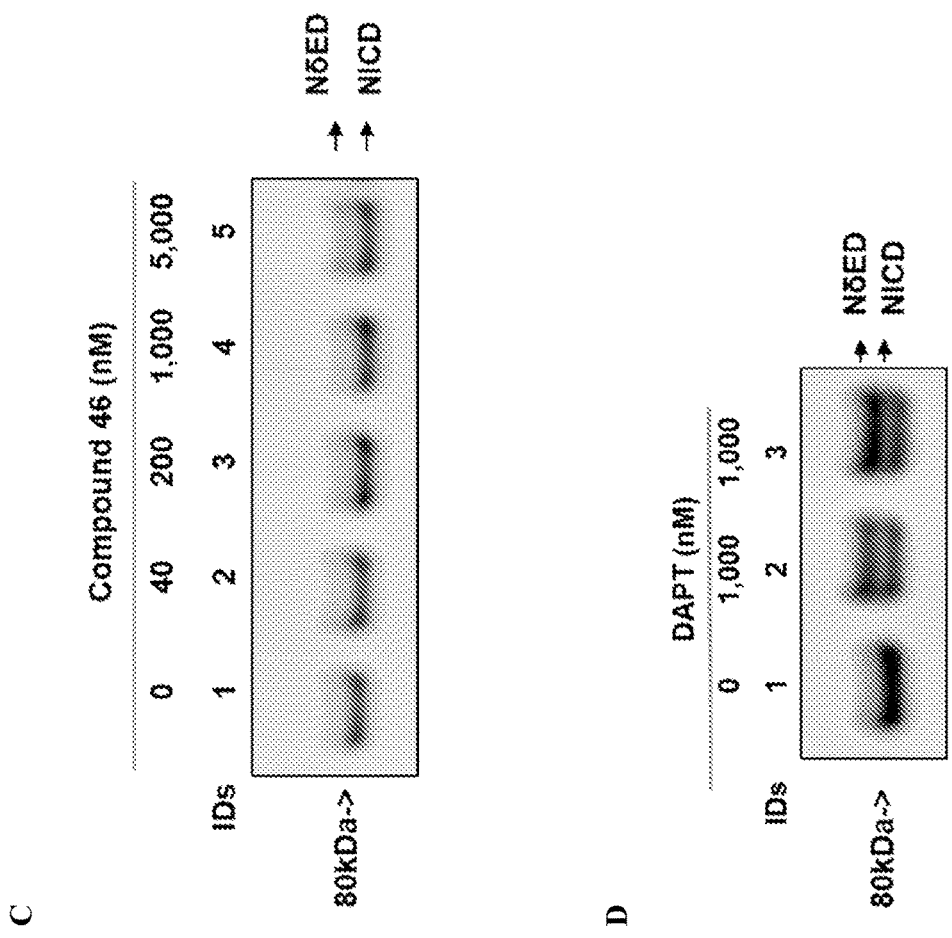
FIG. 10 (con't)

POTENT GAMMA-SECRETASE MODULATORS

CLAIM OF PRIORITY

This application is a § 371 National Stage Application of PCT/US2015/058429, filed Oct. 30, 2015, which claims the benefit of U.S. Provisional Application No. 62/073,553, filed Oct. 31, 2014. The entire contents of the foregoing are hereby incorporated by reference.

STATEMENT AS TO RIGHTS TO INVENTIONS MADE UNDER FEDERALLY SPONSORED RESEARCH AND DEVELOPMENT

This invention was made with government support under Grant No. 1U01NS074501-01 awarded by NIH/NINDS. The government has certain rights in the invention.

BACKGROUND OF THE INVENTION

Alzheimer's disease (AD) is characterized neuropathologically by an abundance of neuritic plaques and neurofibrillary tangles in areas of the brain important for cognition. AD is currently a major health problem that imposes a severe economic burden; short of an effective treatment(s) it is projected to become a dominant source of health care expenditures over the next 3 decades. Unfortunately, existing treatments are palliative and provide only temporary symptomatic benefit. Potential disease-modifying therapeutic approaches for AD have and are being tested, however, none impact disease progression.

In AD, neuritic plaques are composed predominantly of Aβ42 (8) and the most common biochemical phenotype of the more than 200 different familial AD or FAD-linked mutations is an increased ratio of Aβ42/Aβ40 (9). An important therapeutic goal for treating AD should be not just to treat AD but to prevent it. Accordingly, there is a need in the art for therapies for neuropathologies associated with Aβ peptides. Provided herein are solutions to these and other problems in the art

BRIEF SUMMARY OF THE INVENTION

Provided herein are compositions and methods for treating a disorder associated with aberrant Aβ peptide levels, including AD.

Provided herein are compounds of Formula (A):

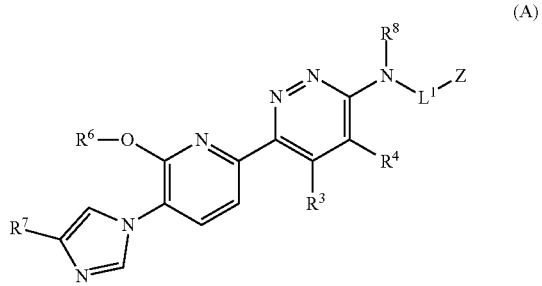

(A)

or a pharmaceutically acceptable salt thereof, wherein, $L^1$ is selected from the group consisting of C(O), C($R^1$)($R^2$), substituted or unsubstituted —$C_{2-6}$ alkylene-, and substituted or unsubstituted —$C_{3-6}$ cycloalkylene-;

Z is selected from the group consisting of halo, CN, OH, $C_{1-6}$ alkyl, $C_{1-6}$ alkoxy, $C_{1-3}$ haloalkyl, $C_{1-3}$ haloalkoxy, amino, $C_{1-3}$ alkylamino, di($C_{1-3}$ alkyl)amino, substituted or unsubstituted $C_{3-6}$ cycloalkyl, substituted or unsubstituted $C_{4-6}$ heterocycloalkyl, substituted or unsubstituted heteroaryl, and a group of Formula (Z-1):

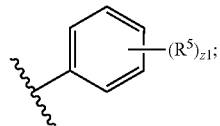

(Z-1)

or $L^1$ is absent and Z is selected from the group consisting of substituted or unsubstituted cycloalkyl, substituted or unsubstituted heterocycloalkyl, and substituted or unsubstituted heteroaryl;

$R^1$ and $R^2$ are independently hydrogen, substituted or unsubstituted alkyl, substituted or unsubstituted heteroalkyl, COO$R^{1A}$, —CON$R^{1A}R^{1B}$, or are optionally joined together to form a substituted or unsubstituted cycloalkyl;

$R^3$ is hydrogen, halogen, —$CF_3$, —CN, —$OR^{3A}$, —$NR^{3A}R^{3B}$, —COO$R^{3A}$, —CON$R^{3A}R^{3B}$, -, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CF_3$, —CN, —$OR^{4A}$, $NR^{4A}R^{4B}$, —COO$R^{4A}$, —CON$R^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

or $R^3$ and $R^4$ are optionally joined together to form a substituted or unsubstituted cycloalkyl;

$R^5$ is independently hydrogen, halogen, —$CF_3$, —CN, —$OR^{5A}$, —$NR^{5A}R^{5B}$, —COO$R^{5A}$, —CON$R^{5A}R^{5B}$, —$SR^{5A}$, —$OCF_3$, —$OCHF_2$, substituted or unsubstituted alkyl, or substituted or unsubstituted heteroalkyl;

$R^6$ and $R^7$ are independently substituted or unsubstituted $C_1$-$C_5$ alkyl;

$R^{1A}$, $R^{1B}$, $R^{3A}$, $R^{3B}$, $R^{4A}$, $R^{4B}$, $R^{5A}$, and $R^{5B}$ are independently hydrogen, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or $R^{1A}$ and $R^{1B}$, $R^{3A}$ and $R^{3B}$, $R^{4A}$ and $R^{4B}$, or $R^{5A}$ and $R^{5B}$ are independently optionally joined together to independently form a substituted or unsubstituted heterocycloalkyl, or substituted or unsubstituted heteroaryl;

$R^8$ is selected from the group consisting of hydrogen, substituted or unsubstituted alkyl, and substituted or unsubstituted heteroalkyl; and z1 is an integer of 0, 1, 2, 3, 4, or 5.

Also provided herein are compounds of Formula (I):

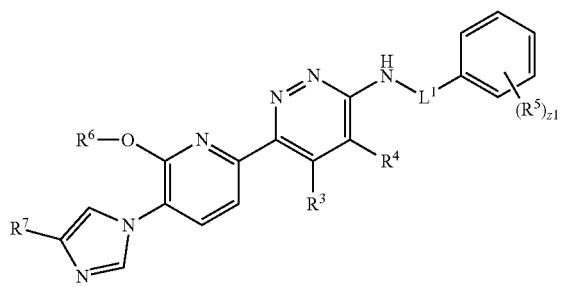

or a pharmaceutically acceptable salt thereof,
wherein,
$L^1$ is C(O) or $C(R^1)(R^2)$;
$R^1$ and $R^2$ are independently hydrogen, substituted or unsubstituted alkyl, substituted or unsubstituted heteroalkyl, or are optionally joined together to form a substituted or unsubstituted cycloalkyl;
$R^3$ is hydrogen, halogen, —$CF_3$, —CN, —$OR^{3A}$, —$NR^{3A}R^{3B}$, —$COOR^{3A}$, —$CONR^{3A}R^{3B}$, -, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^4$ is hydrogen, halogen, —$CF_3$, —CN, —$OR^{4A}$, $NR^{4A}NR^{4B}$, —$COOR^{4A}$, —$CONR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is independently hydrogen, halogen, —$CF_3$, —CN, —$OR^{5A}$, —$NR^{5A}R^{5B}$, —$COOR^{5A}$, —$CONR^{5A}R^{5B}$, —$SR^{5A}$, —$OCF_3$, —$OCHF_2$, substituted or unsubstituted alkyl, or substituted or unsubstituted heteroalkyl;
$R^6$ and $R^7$ are independently substituted or unsubstituted $C_1$-$C_5$ alkyl;
$R^{3A}$, $R^{3B}$, $R^{4A}$, $R^{4B}$, $R^{5A}$, and $R^{5B}$ are independently hydrogen, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or $R^{3A}$ and $R^{3B}$, $R^{4A}$ and $R^{4B}$, or $R^{5A}$ and $R^{5B}$ are independently optionally joined together to independently form a substituted or unsubstituted heterocycloalkyl, or substituted or unsubstituted heteroaryl; and
z1 is an integer of 0, 1, 2, 3, 4, or 5.
In some embodiments, $L^1$ is selected from the group consisting of C(O), $C(R^1)(R^2)$, —$C_{2-6}$ alkylene-, and —$C_{3-6}$ cycloalkylene-, wherein the $C_{1-6}$ alkylene group is optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino. In some embodiments, wherein $L^1$ is selected from the group consisting of C(O), $C(R^1)(R^2)$, —$C_{2-6}$ alkylene-, and —$C_{3-6}$ cycloalkylene-, wherein the $C_{1-6}$ alkylene group is optionally substituted with 1 or 2 substituents independently selected from halo, CN, OH, $C_{1-3}$ alkyl and $C_{1-3}$ alkoxy. In some embodiments, wherein $L^1$ is selected from the group consisting of C(O), $C(R^1)(R^2)$, -ethylene-, -2-methylethylene-, -propylene-, and -cyclopropylene-.

In some embodiments, Z is selected from the group consisting of halo, CN, OH, $C_{1-6}$ alkyl, substituted or unsubstituted $C_{3-6}$ cycloalkyl, substituted or unsubstituted $C_{4-6}$ heterocycloalkyl, substituted or unsubstituted heteroaryl, and a group of Formula (Z-1):

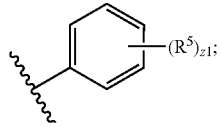

(Z-1)

or $L^1$ is absent and Z is selected from the group consisting of substituted or unsubstituted cycloalkyl, and substituted or unsubstituted heteroaryl.

In some embodiments, Z is selected from the group consisting of halo, OH, $C_{1-6}$ alkyl, and a cyclic group of the following Formulae (Z-1) to (Z-18):

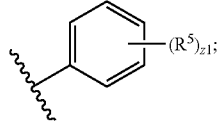

(Z-1)

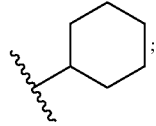

(Z-2)

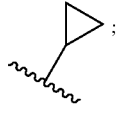

(Z-3)

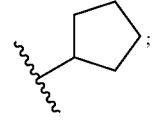

(Z-4)

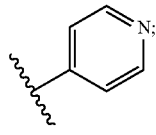

(Z-5)

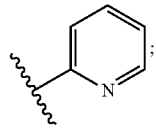

(Z-6)

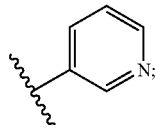

(Z-7)

or L¹ is absent and Z is selected from the group consisting of a cyclic group of Formulae (Z-2), (Z-3), (Z-4), and the following Formulae (Z-19) and (Z-20):

wherein any one of the Formulae (Z-2) to (Z-20) is unsubstituted or substituted.

In some embodiments, Z is selected from the group consisting of halo, OH, $C_{1-6}$ alkyl, and a cyclic group of the following Formulae (Z-1), (Z-2), (Z-5) and (Z-6):

or L¹ is absent and Z is selected from the group consisting of a cyclic group of Formulae (Z-2), and the following Formulae (Z-3), (Z-4) and (Z-19):

-continued (Z-4)

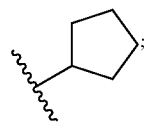

(Z-19)

wherein any one of the Formulae (Z-2), (Z-3), (Z-4), (Z-5), (Z-6), and (Z-19) is unsubstituted or substituted.

In some embodiments, Z is selected from the group consisting of fluoro, OH, methoxy, methyl, ethyl, isopropyl, tert-butyl, phenyl, fluorophenyl, chlorophenyl, methoxyphenyl, (trifluoromethyl)phenyl, difluorophenyl, methylphenyl, bis(trifluoromethyl)phenyl, 4-fluoro-3-methoxyphenyl, 4-fluoro-2-methoxyphenyl, 4-fluoro-3-methylphenyl, 4-fluoro-2-methylphenyl, trifluorophenyl, 4-fluoro-3-(trifluoromethyl)phenyl, 4-fluoro-2-(trifluoromethyl)phenyl, 2-chloro-4-fluorophenyl, cyclohexyl, pyridinyl, fluoropyridinyl, benzo[d]oxazolyl, naphthyl, fluoronaphthyl, cyclopropyl, cyclopentyl, hydroxyphenyl, aminophenyl, 4-trifluoromethyl-3-(methoxy)phenyl, 4-trifluoromethyl-3-(fluoro)phenyl, oxazol-2-yl, pyrazole-5-yl, oxazol-5-yl, oxazol-4-yl, isoxazol-5-yl, isoxazol-3-yl, 1,3,4-oxadiazol-2-yl, 1,2,4-oxadiazol-5-yl, isoxazol-3-one-5-yl, 2-fluoro-3-chlorophenyl, 2-fluoro-3-(trifluoromethyl)phenyl, 3-fluoro-2-methylphenyl, difluoropyridinyl, difluorophenyl, 2-fluoro-5-methylphenyl, and 3-chloro-5-fluorophenyl.

or L$^1$ is absent and Z is selected from the group consisting of cyclopropyl, cyclopentyl, cyclohexyl, 4,4,-difluorocyclohexyl, 4-trifluoromethylcyclohexyl, 2-ethyl-4,5,6,7-tetrahydro-2H-isoindolyl, 3,3-difluorocyclopentyl, 3,3-difluorocyclohexyl, 3-trifluoromethylcyclohexyl, 6-fluoro-1H-indol-3-yl, and 6-fluoro-1-methyl-1H-indol-3-yl.

In some embodiments, Z is selected from the group consisting of fluoro, OH, methoxy, methyl, ethyl, isopropyl, tert-butyl, phenyl, fluorophenyl, chlorophenyl, methoxyphenyl, (trifluoromethyl)phenyl, difluorophenyl, methylphenyl, bis(trifluoromethyl)phenyl, 4-fluoro-3-methoxyphenyl, 4-fluoro-2-methoxyphenyl, 4-fluoro-3-methylphenyl, 4-fluoro-2-methylphenyl, trifluorophenyl, 4-fluoro-3-(trifluoromethyl)phenyl, 4-fluoro-2-(trifluoromethyl)phenyl, 2-chloro-4-fluorophenyl, cyclohexyl, pyridinyl, fluoropyridinyl, and benzo[d]oxazolyl;

or L$^1$ is absent and Z is selected from the group consisting of cyclopropyl, cyclopentyl, cyclohexyl, 4,4,-difluorocyclohexyl, 4-trifluoromethylcyclohexyl, and 2-ethyl-4,5,6,7-tetrahydro-2H-isoindolyl.

In some embodiments, L$^1$ is C(R$^1$)(R$^2$).

In some embodiments, R$^1$ is selected from the group consisting of hydrogen and substituted or unsubstituted alkyl; and R$^2$ is selected from the group consisting of hydrogen, substituted or unsubstituted alkyl, substituted or unsubstituted heteroalkyl, and CONR$^{1A}$R$^{1B}$;

or R$^1$ and R$^2$ are optionally joined together to form a substituted or unsubstituted cycloalkyl.

In some embodiments, R$^1$ is selected from the group consisting of hydrogen and methyl; and R$^2$ is selected from the group consisting of hydrogen, methyl, ethyl, propyl, isopropyl, hydroxymethyl, methoxymethyl, fluoromethyl, 3,3,3-trifluoroethyl, trifluoromethyl, 2-methyl-2-hydroxyethyl, N,N-dimethylaminocarbonyl, and N-pyrrolidinocarbonyl;

or R$^1$ and R$^2$ are joined together to form a cyclopropyl ring.

In some embodiments, R$^1$ and R$^2$ are independently hydrogen or substituted or unsubstituted alkyl. In some embodiments, R$^1$ is selected from the group consisting of hydrogen and substituted or unsubstituted alkyl. In some embodiments, R$^1$ is hydrogen or methyl. In some embodiments, R$^2$ is substituted or unsubstituted alkyl. In some embodiments, R$^2$ is substituted or unsubstituted alkyl. In some embodiments, R$^2$ is unsubstituted C$_1$-C$_5$ alkyl. In some embodiments, R$^2$ is substituted C$_1$-C$_5$ alkyl. In some embodiments, R$^2$ is methyl. In some embodiments, R$^2$ is —CH$_2$OR$^{2A}$ or —C(CH$_3$)$_2$OR$^{2A}$; and R$^{2A}$ is hydrogen or substituted or unsubstituted alkyl. In some embodiments, R$^1$ is hydrogen and R$^2$ is attached to a carbon having (S) stereochemistry. In some embodiments, R$^1$ and R$^2$ are joined together to form a substituted or unsubstituted C$_3$ cycloalkyl.

In some embodiments, R$^3$ is selected from the group consisting of hydrogen, substituted or unsubstituted alkyl, and substituted or unsubstituted heteroalkyl; and R$^4$ is selected from the group consisting of hydrogen, halogen, —CF$_3$, —CN, —OR$^{4A}$, substituted or unsubstituted alkyl, substituted or unsubstituted heteroalkyl;

or R$^3$ and R$^4$ are optionally joined together to form a substituted or unsubstituted cycloalkyl.

In some embodiments, R$^3$ is selected from the group consisting of hydrogen, methyl, ethyl, and methoxy; and R$^4$ is selected from the group consisting of hydrogen, methyl, ethyl, isopropyl, methoxy, —CN, Cl, F, and —CF$_3$;

or R$^3$ and R$^4$ are optionally joined together to form a cyclic ring selected from the group consisting of cyclopentyl and cyclohexyl.

In some embodiments, R$^3$ is selected from the group consisting of hydrogen and methyl; and R$^4$ is selected from the group consisting of hydrogen, methyl, ethyl, isopropyl, and methoxy;

or R$^3$ and R$^4$ are optionally joined together to form a cyclopentyl ring.

In some embodiments, R$^3$ is hydrogen, halogen, —CN, —CF$_3$, —OR$^{3A}$, —NR$^{3A}$R$^{3B}$, substituted or unsubstituted alkyl, or substituted or unsubstituted heteroalkyl, wherein R$^{3A}$ and R$^{3B}$ are independently hydrogen, substituted or unsubstituted alkyl, or substituted or unsubstituted aryl. In some embodiments, R$^3$ is selected from the group consisting of hydrogen, substituted or unsubstituted alkyl, and substituted or unsubstituted heteroalkyl. In some embodiments, R$^3$ is hydrogen, or substituted or unsubstituted alkyl. In some embodiments, R$^3$ is hydrogen. In some embodiments, R$^3$ is substituted or unsubstituted alkyl. In some embodiments, R$^3$ is selected from the group consisting of hydrogen, methyl, ethyl, and methoxy. In some embodiments, R$^3$ is selected from the group consisting of hydrogen and methyl. In some embodiments, R$^3$ is methyl.

In some embodiments, R$^4$ is hydrogen, halogen, —CF$_3$, —CN, —OR$^{4A}$, substituted or unsubstituted alkyl, substituted or unsubstituted heteroalkyl. In some embodiments, R$^4$ is selected form the group consisting of hydrogen, methyl, ethyl, isopropyl, methoxy, —CN, Cl, F, and —CF$_3$. In some embodiments, R$^4$ is hydrogen, methyl, ethyl, isopropyl, and methoxy. In some embodiments, R$^4$ is hydrogen or substituted or unsubstituted alkyl. In some embodiments, R$^4$ is hydrogen. In some embodiments, R$^4$ is substituted or unsubstituted alkyl. In some embodiments, R$^4$ is methyl.

In some embodiments, $R^5$ is selected from the group consisting of halogen, —$CF_3$, —CN, —$OR^{5A}$, —$NR^{5A}R^{5B}$, and substituted or unsubstituted alkyl; and $R^{5A}$ and $R^{5B}$ are each independently hydrogen, substituted or unsubstituted $C_1$-$C_5$ alkyl, or substituted or unsubstituted aryl. In some embodiments, $R^5$ is halogen, —$CF_3$, —$OR^{5A}$, substituted or unsubstituted alkyl, or substituted or unsubstituted heteroalkyl; and $R^{5A}$ is hydrogen, substituted or unsubstituted $C_1$-$C_5$ alkyl, or substituted or unsubstituted aryl. In some embodiments, $R^5$ is selected from the group consisting of fluoro, chloro, CN, methoxy, methyl, trifluoromethyl, OH, and $NH_2$. In some embodiments, $R^5$ is selected from the group consisting of fluoro, chloro, CN, methoxy, methyl, thrifluoromethyl.

In some embodiments, z1 is 0, 1, 2, or 3. In some embodiments, z1 is 0, 1, or 2. In some embodiments, $R^5$ is halogen, —$CF_3$, —$OCH_3$, or methyl; and z1 is 1, 2, or 3.

In some embodiments, $R^5$ is halogen; and z1 is 1, 2, or 3. In some embodiments, $R^5$ is halogen, —$CF_3$, or —$OR^{5A}$ and is substituted at the Para position, wherein $R^{5A}$ is hydrogen, substituted or unsubstituted $C_1$-$C_5$ alkyl, or substituted or unsubstituted aryl.

In some embodiments, $R^6$ is methyl.
In some embodiments, $R^7$ is methyl.
In some embodiments, $R^8$ is selected from the group consisting of methyl, ethyl, fluoroethyl, and methoxyethyl. In some embodiments, $R^8$ is selected from the group consisting of methyl and ethyl.

Also provided herein are compounds of Formula (II):

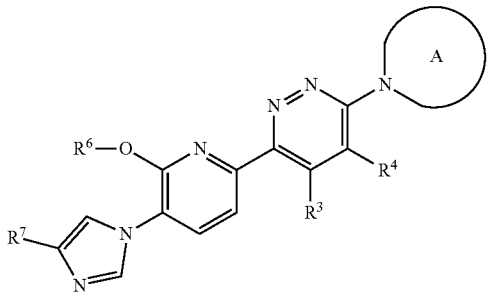

(II)

or a pharmaceutically acceptable salt thereof,
wherein,

A is selected from the group consisting of substituted or unsubstituted fused ring aryl-heterocycloalkyl; and substituted or unsubstituted fused ring heteroaryl-heterocycloalkyl;

$R^3$ is hydrogen, halogen, —$CF_3$, —CN, —$OR^{3A}$, —$NR^{3A}R^{3B}$, —$COOR^{3A}$, —$CONR^{3A}R^{3B}$, —$OR^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CF_3$, —CN, —$OR^{4A}$, $NR^{4A}R^{4B}$, —$COOR^{4A}$, —$CONR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

or $R^3$ and $R^4$ are optionally joined together to form a substituted or unsubstituted cycloalkyl;

$R^6$ and $R^7$ are independently substituted or unsubstituted $C_1$-$C_5$ alkyl; and $R^{3A}$, $R^{3B}$, $R^{4A}$, and $R^{4B}$ are independently hydrogen, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or $R^{1A}$ and $R^{1B}$, $R^{3A}$ and $R^{3B}$, $R^{4A}$ and $R^{4B}$, or $R^{5A}$ and $R^{5B}$ are independently optionally joined together to independently form a substituted or unsubstituted heterocycloalkyl, or substituted or unsubstituted heteroaryl.

In some embodiments, A is selected from the group consisting of substituted or unsubstituted fused ring 6,5-aryl-heterocycloalkyl; and substituted or unsubstituted fused ring 6,5,6-cyclolakyl-heteroaryl-heterocycloalkyl. In some embodiments, A is selected from the group consisting of substituted or unsubstituted isoindolin-2-yl and substituted or unsubstituted 1,2,3,4,7,8,9,10-octahydropyrimido[1,2-b]indazolyl. In some embodiments, A is selected from the group consisting of 1-methyl-isoindolin-2-yl, 5-fluoro-1-methyl-isoindolin-2-yl, 3-methyl-1-imine-isoindolin-2-yl, 3-ethyl-1-imine-isoindolin-2-yl, and 1,2,3,4,7,8,9,10-octahydropyrimido[1,2-b]indazolyl.

In some embodiments, $R^3$ is hydrogen.
In some embodiments, $R^4$ is selected from the group consisting of hydrogen and substituted or unsubstituted alkyl. In some embodiments, $R^4$ is selected from the group consisting of hydrogen and methyl.
In some embodiments, $R^6$ is methyl.
In some embodiments, $R^7$ is methyl.

This disclosure also provides a pharmaceutical composition comprising a compound provided herein, or a pharmaceutically acceptable salt thereof, and a pharmaceutically acceptable excipient.

The compounds provided herein can also be present as prodrugs.

Further provided herein is a method of treating a disorder associated with aberrant Aβ peptide levels in a subject in need thereof, the method comprising administering to the subject a therapeutically effective amount of a compound, or a pharmaceutically acceptable salt thereof, or composition provided herein, thereby treating the disorder.

Also provided herein is a method of preventing a disorder associated with aberrant Aβ peptide levels in a subject in need thereof, the method comprising administering to the subject a therapeutically effective amount of a compound, or a pharmaceutically acceptable salt thereof, or composition provided herein, thereby preventing said disorder.

In some embodiments, the Aβ peptide is an $Aβ_{42}$ Aβ-peptide alloform or $Aβ_{40}$ Aβ-peptide alloform. In some embodiments, the disorder is Alzheimer's disease, Familial Alzheimer's disease, down syndrome, Creutzfeldt-Jakob disease, frontotemporal dementia, amyotrophic lateral sclerosis, Huntington's disease, Parkinson's disease, or hemorrhagic stroke associated with amyloidosis. In some embodiments, the disorder is Alzheimer's disease or Familial Alzheimer's disease.

In addition, a method of decreasing a level of an Aβ-peptide alloform in a cell is provided, the method comprising;
(i) contacting a cell with a compound or composition of any one of claims as described herein; and
(ii) allowing the compound to modulate the activity or processivity of a γ-secretase protein, wherein the modulation decreases the level of the Aβ-peptide alloform.

In some embodiments, the Aβ-peptide alloform is $Aβ_{42}$ or $Aβ_{40}$. In some embodiments, the method further includes increasing the level of $Aβ_{38}$ or $Aβ_{37}$.

DETAILED DESCRIPTION OF THE INVENTION

Figure 1:
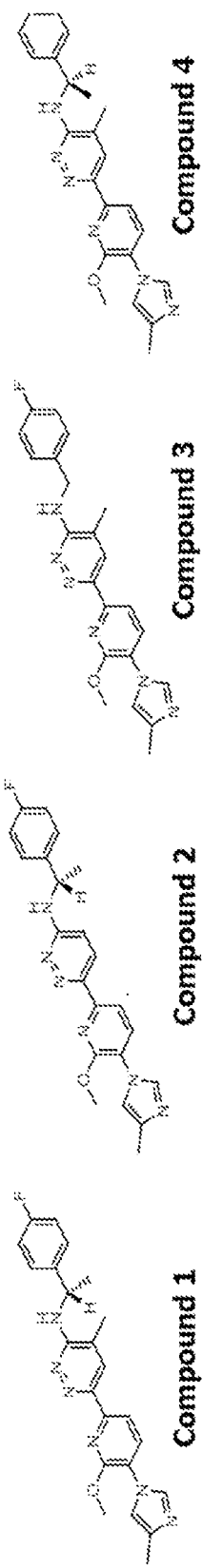
FIG. 1: Tabular results of $A\beta_{42}$ assays conducted on Compound 1 (1), Compound 2 (2), Compound 3 (3) and Compound 4 (4). Assays are $A\beta_{42}$ IC$_{50}$ (nM).

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, and S, and wherein the nitrogen and sulfur atoms may optionally be oxidized, and the nitrogen heteroatom may optionally be quaternized. The heteroatom(s) O, N, P, and S may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring.

The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. The aryl, heteroaryl, heterocycloalkyl of the fused ring aryl-heterocycloalkyl, fused ring heteroaryl-heterocycloalkyl, fused ring heterocycloalkyl-cycloalkyl, or fused ring heterocycloalkyl-heterocycloalkyl can be further fused with aryl, heteroaryl, heterocycloalkyl, or cycloalkyl, thus forming fused ring structures having 2, 3, or more rings. An example of a fused ring aryl-heterocycloalkyl is isoindoline; an example of a fused ring cycloalkyl-heteroaryl-heterocycloalkyl is 1,2,3,4,7,8,9,10-octahydropyrimido[1,2-b]indazole.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R")=NR"', —S(O)R', —S(O)$_2$R', —S(O)$_2$NR'R", —NRSO$_2$R', —NRNR"R"', —ONR'R", —NR'C(O)NR"NR"'R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R")=NR"', —S(O)R', —S(O)$_2$R', —S(O)$_2$NR'R", —NRSO$_2$R', —N(R') N(R"R"'), —ONR'R", —NR'C(O)N(R")N(R"'R""), —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one or more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. The ring-forming substituents may be attached to adjacent members of the base structure. For example, two ring-forming substituents attached to adjacent members of a cyclic base structure create a fused ring structure. The ring-forming substituents may be attached to a single member of the base structure. For example, two ring-forming substituents attached to a single member of a cyclic base structure create a spirocyclic structure. The ring-forming substituents may be attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, SO$_4$H, —SO$_2$NH$_2$, —NHNH$_2$, —ONH$_2$, —NHC(O)NHNH$_2$, —NHC(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

Each substituted group described in the compounds herein may be substituted with at least one substituent group. More specifically, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein may be substituted with at least one substituent group. At least one or all of these groups may be substituted with at least one size-limited substituent group. At least one or all of these groups may be substituted with at least one lower substituent group.

Each substituted or unsubstituted alkyl may be a substituted or unsubstituted $C_1$-$C_{20}$ alkyl, each substituted or unsubstituted heteroalkyl may be a substituted or unsubstituted 2 to 20 membered heteroalkyl, each substituted or unsubstituted cycloalkyl may be a substituted or unsubstituted $C_3$-$C_8$ cycloalkyl, and/or each substituted or unsubstituted heterocycloalkyl may be a substituted or unsubstituted 3 to 8 membered heterocycloalkyl. Each substituted or unsubstituted alkylene may be a substituted or unsubstituted $C_1$-$C_{20}$ alkylene, each substituted or unsubstituted heteroalkylene may be a substituted or unsubstituted 2 to 20 membered heteroalkylene, each substituted or unsubstituted cycloalkylene may be a substituted or unsubstituted $C_3$-$C_8$ cycloalkylene, and/or each substituted or unsubstituted heterocycloalkylene may be a substituted or unsubstituted 3 to 8 membered heterocycloalkylene.

Each substituted or unsubstituted alkyl may be a substituted or unsubstituted $C_1$-$C_8$ alkyl, each substituted or unsubstituted heteroalkyl may be a substituted or unsubstituted 2 to 8 membered heteroalkyl, each substituted or unsubstituted cycloalkyl may be a substituted or unsubstituted $C_3$-$C_7$ cycloalkyl, and/or each substituted or unsubstituted heterocycloalkyl may be a substituted or unsubstituted 3 to 7 membered heterocycloalkyl. Each substituted or unsubstituted alkylene may be a substituted or unsubstituted $C_1$-$C_8$ alkylene, each substituted or unsubstituted heteroalkylene may be a substituted or unsubstituted 2 to 8 membered heteroalkylene, each substituted or unsubstituted cycloalkylene may be a substituted or unsubstituted $C_3$-$C_7$ cycloalkylene, and/or each substituted or unsubstituted heterocycloalkylene may be a substituted or unsubstituted 3 to 7 membered heterocycloalkylene.

Certain compounds herein possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the compounds described herein. The compounds described herein do not include those which are known in art to be too unstable to synthesize and/or isolate. The compounds described herein also are meant to include compounds in racemic and optically pure forms. Optically active (R)- and (S)-, or (D)- and (L)-isomers may be prepared using chiral synthons or chiral reagents (enantioselective synthesis), or resolved using conventional techniques such as fractional crystallization (for compounds that readily form stable acid or base addition salts with a chiral resolving agent), chiral high pressure liquid chromatography (HPLC) or the creation of adducts with a chiral reagent (such as esters or amides). Such products may be more readily separated by normal or reverse phase chromatography and then hydrolyzed back to the resolved product and chiral reagent. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds described herein may exist in tautomeric forms, and that all such tautomeric forms of the compounds may be considered within the scope of the compounds described herein.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds, generally recognized as stable by those skilled in the art, are within the scope of the compounds described herein.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the compounds described herein.

The compounds described herein may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds described herein, whether radioactive or not, are encompassed within the scope of the compounds described herein.

The symbol "⸺" denotes the point of attachment of a chemical moiety to the remainder of a molecule or chemical formula.

Where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman decimal symbol may be used to distinguish each appearance of that particular R group. For example, where multiple $R^{13}$ substituents are present, each $R^{13}$ substituent may be distinguished as $R^{13.1}$, $R^{13.2}$, $R^{13.3}$, $R^{13.4}$, etc., wherein each of $R^{13.1}$, $R^{13.2}$, $R^{13.3C}$, $R^{13.4}$, etc. is defined within the scope of the definition of $R^{13}$ and optionally differently.

Description of compounds described herein is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds described herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds described herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds described herein contain both basic and acidic functionalities that allow the compounds to be converted into either base or acid addition salts.

Thus, the compounds described herein may exist as salts, such as with pharmaceutically acceptable acids. The compounds described herein include such salts. Examples of such salts include hydrochlorides, hydrobromides, sulfates, methanesulfonates, benzenesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the compounds described herein may be provided in a prodrug form. Prodrugs of the compounds described herein include those compounds that readily undergo chemical or enzymatic changes under physiological conditions to provide the compounds described herein. Additionally, prodrugs can be converted to the compounds described herein by chemical or biochemical methods in an ex vivo environment. For example, prodrugs can be slowly converted to the compounds described herein when placed in a transdermal patch reservoir with a suitable enzyme or chemical reagent.

Certain compounds or their acid or base addition salts described herein can exist in unsolvated forms as well as solvated forms, including hydrated forms. In general, the solvated forms are equivalent to unsolvated forms and are encompassed within the scope of the compounds described herein. Certain compounds and their acid or base addition salts described herein may exist in multiple crystalline or amorphous forms. These forms may also be solvated, or hydrated.

As used herein, the term "salt" refers to acid or base salts of the compounds described herein. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

"Analog," or "analogue" are used in accordance with plain ordinary meaning within Chemistry and Biology and refer to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analogue is a compound that is similar or comparable in function and appearance but not in structure or origin to a reference compound.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, or reduce one or more symptoms of a disease or condition). An example of an "effective amount" is an amount sufficient to contribute to the treatment, prevention, or reduction of a symptom or symptoms of a disease, which herein is referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods such as allometric scaling is well within the capabilities of the ordinarily skilled artisan.

Dosages may be varied depending upon the requirements of the patient and the compound being employed. The dose administered to a patient, in the context of the compounds described herein should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. A control may be the measurement of the activity of a protein in the absence of a compound as described herein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. Contacting may include allowing a compound described herein to interact with a protein or enzyme that is involved in a signaling pathway.

As defined herein, the term "inhibition", "inhibit", "inhibiting" and the like refer to negatively affecting (e.g. decreasing) the activity, concentration, amount (i.e. level of), or function of the peptide or protein relative to the activity, concentration, amount or function of the same peptide or protein in the absence of the inhibitor. Inhibition may also refer to reduction of a disease or symptoms of disease. Inhibition may refer to a reduction in the concentration of particular Aβ-peptide alloforms described herein. Thus, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like refer to positively affecting (e.g. increasing) the activity, concentration, amount (i.e. level of), or function of the peptide or protein relative to the activity, concentration or function of the protein in the absence of the activator. Activation may refer to increasing the activity, concentration or function of a γ-secretase protein. Activation may include increasing the activity, concentration or function of a γ-secretase protein thereby modulating levels of another peptide or protein (e.g. particular Aβ-peptide alloforms described herein).

The term "processivity" as used herein refers to consecutive catalysis by a protein without release of the substrate between catalytic steps.

The term "modulator" refers to a composition that increases or decreases the level of a target molecule or the function of a target molecule. A modulator may increase the level of a target protein. A modulator may decrease the level of an Aβ-peptide alloform described herein.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

The term "modulate" or "modulating" with respect to Aβ level refers to a detectable increase or decrease in the amount (or level) of at least one species of the Aβ peptide (such as, for example $A\beta_{43}$, $A\beta_{42}$, $A\beta_{40}$, $A\beta_{39}$, $A\beta_{38}$, $A\beta_{37}$, $A\beta_{34}$.). Modulate also refers to a detectable increase or decrease in the relative amount (or level) of different species of Aβ peptides (such as the ratio of $A\beta_{42}$ to $A\beta_{40}$). Modulate also refers to a detectable increase or decrease in the amount, or relative amount, of Aβ in a particular form (such as monomeric, oligomeric, or fibrillar form; in solution or aggregated in a plaque; in a particular conformation; etc.). Modulate further refers to a detectable increase or decrease in the amount, or relative amount, of a particular Aβ species in a particular location (such as an intracellular, membrane-associated or extracellular location, or in a particular tissue or body fluid). Modulation may refer to detectable decrease in the level of $A\beta_{42}$ or $A\beta_{40}$. Modulation may refer to detectable increase in the level of $A\beta_{37}$ or $A\beta_{38}$. Modulation of Aβ levels can be evidenced by, for example, an increase or decrease of at least 5%, such as at least 10%, 20%, 30%, 40%, 50%, 75%, 90% or more, of the amount, or relative amount, of an Aβ species, or of a particular form of Aβ, relative to a reference level. Modulation can be an increase or decrease that is a statistically significant difference relative co the reference level.

The terms "fibrillogenic," "fibrillogenic Aβ peptide" and the like refer, in the usual and customary sense, to a change in conformation of normally circulating soluble Aβ peptides into amyloid fibrils in the form of senile plaques, as known in the art. Thus, there are provided compounds and methods for modulating (e.g., reducing) levels of fibrillogenic Aβ peptides, e.g., $A\beta_{40}$ and $A\beta_{42}$, and concomitantly modulating (e.g., increasing) the levels of shorter less fibrillogenic Aβ peptides (e.g. $A\beta_{38}$ and $A\beta_{37}$).

"Selective" or "selectivity" or the like of a compound refers to the compound's ability to discriminate between molecular targets. "Specific", "specifically", "specificity", or the like of a compound refers to the compound's ability to cause a particular action, such as activation of a particular protein target with minimal or no action to other proteins in the cell.

The phrase "disorder associated with aberrant Aβ peptide levels" as used herein refers to a disease or condition that is caused by or characterized by increased levels of an Aβ peptide. Such disorders can be further characterized by the presence of particular Aβ-peptide alloforms (e.g. "longer Aβ-peptide alloforms" such as $A\beta_{42}$ or $A\beta_{40}$). Such disorders may alternatively be characterized by the absence of particular Aβ-peptide alloforms (e.g. "shorter Aβ-peptide alloforms" such as $A\beta_{37}$ or $A\beta_{38}$). Exemplary disorders associated with aberrant Aβ peptide levels include, but are not limited to Alzheimer's disease, Familial Alzheimer's disease, Down's syndrome, Creutzfeldt-Jakob disease, frontotemporal dementia, amyotrophic lateral sclerosis, Huntington's disease, Parkinson's disease, or hemorrhagic stroke associated with amyloidosis, Inclusion Body Myositis, Pick's disease, Posterior Cortical Atrophy, Primary Progressive Aphasia, Progressive Supranuclear Palsy, or Congophyllic Cerebral Amyloid Angiopathy.

The terms "Aβ-peptide," "amyloid-beta peptide," "amyloid-beta," and "Abeta" are used interchangeably herein and according to their plain and ordinary meaning. An Aβ-peptide refers to a peptide from a human or other species that (a) results from processing or cleavage of an APP-CTF that is amyloidogenic, (b) is one of the peptide constituents of β-amyloid plaques, (c) is the 42-amino acid sequence of Aβ (GenBank Accession No. P05067), (d) is a fragment of a peptide as set forth in (a), (b) or (c), and/or (e) contains one or more additions, deletions or substitutions relative to (a), (b), (c) or (d). AB is also referred to in the art as βAP, AβP, A4 or βA4. Aβ peptides derived from proteolysis of an APP-CTF, generally are about 4.2 kD proteins and are typically 39 to 43 amino acids in length, depending on the carboxy-terminal end-point, which exhibits heterogeneity. However, Aβ peptides containing less than 39 amino acids, e.g., $A\beta_{38}$, $A\beta_{37}$, and $A\beta_{34}$, also may occur.

Aβ peptides can be produced in an amyloidogenic APP processing pathway in which APP is cleaved by β-secretase (BACE) and one or more gamma-secretase activities. Aβ peptides include those but are not limited to those that begin at position 672 of APP770 and those that begin at position 682 of APP770 (see, for example, GenBank Accession No. P05067). Generally, as used herein, "Aβ" includes any and all Aβ peptides, unless the amino acid residues are specified, such as, for example, 1-43 ($A\beta_{43}$), 1-42 ($A\beta_{42}$), 1-40 ($A\beta_{40}$), 1-39 ($A\beta_{39}$), 1-38 ($A\beta_{38}$), 1-37 ($A\beta_{37}$), 1-34 ($A\beta_{34}$). Additionally amino-terminally-truncated Aβ peptides exists such as 11-43, 11-42, 11-40, 11-39, 11-38, 11-37, 11-34, and other. The various Aβ peptides of differing lengths are referred to herein as "species" of Aβ.

The term "amyloid precursor protein" or "APP" refers to a protein that can be proteolytically processed or cleaved by one or more processing or cleavage reactions to produce Aβ. APP includes all isoforms that are generated by alternative splicing, which can be typically distinguished by the number of amino acids in the particular isoform. For example, APP embraces APP695, APP751, and APP770. Other isoforms of APP include, for example, APP714, L-APP752, L-APP733, L-APP696, L-APP677, APP563, and APP365.

APP also includes all isoforms containing mutations found in families with AD and other amyloidosis conditions. For example, these mutations include the Swedish double mutation; the London mutation, the Indiana mutation, the Austrian mutation, the Iranian mutation, the French mutation, the German mutation, the Florida mutation, the Australian mutation, the Flemish mutation, the Dutch mutation, the Arctic mutation, the Italian mutation, and the Iowa mutation, and the amyloidsis-Dutch type mutation, all as known in the art.

An "Aβ-peptide alloform" as used herein refers to particular Aβ-peptides of discreet size, including, for example, $A\beta_{36}$, $A\beta_{37}$, $A\beta_{38}$, $A\beta_{40}$, or $A\beta_{42}$. Each Aβ-peptide alloform may also have specific secondary or tertiary structure.

"Pharmaceutically acceptable excipient" and "pharmaceutically acceptable carrier" refer to a substance that aids the administration of an active agent to and absorption by a subject and can be included in the compositions of the compounds described herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds described herein. One of skill in the art will recognize that other pharmaceutical excipients are useful in combination with the compounds described herein.

The term "preparation" is intended to include the formulation of an active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" refers oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, or transdermal patches.

The compositions disclosed herein can be delivered transdermally by a topical route, formulated as patches, microneedles, applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The pharmaceutical compositions described herein may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212, 162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995);

or, as microspheres for oral administration (see, e.g., Eyles, *J. Pharm. Pharmacol.* 49:669-674, 1997). The formulations of the compositions of the compounds described herein can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the compounds described herein into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds described herein. Adjustment and manipulation of established dosages (e.g., frequency and duration) are well within the ability of those skilled in the art.

The compounds and complexes described herein can be used in combination with one another, with other active drugs known to be useful in treating a disease (e.g. agents for treating a disorder associated with aberrant Aβ peptide levels) or with adjunctive agents that may not be effective alone, but may contribute to the efficacy of the active agent.

By "co-administer" it is meant that a composition described herein is administered at the same time, just prior to, or just after the administration of one or more additional therapies. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g. agents for treating a disorder associated with aberrant Aβ peptide levels).

Co-administration includes administering one active agent (e.g. a compound described herein) within 0.5, 1, 2, 4, 6, 8, 10, 12, 16, 20, or 24 hours of a second active agent (e.g. agents for treating a disorder associated with aberrant Aβ peptide levels). Co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. The active agents can be formulated separately. The active and/or adjunctive agents may be linked or conjugated to one another. The compounds described herein may be combined with treatments for Alzheimer's disease or familial Alzheimer's disease. The compounds described herein may be combined with treatments for Creutzfeldt-Jakob disease. The compounds described herein may be combined with treatments for frontotemporal dementia. The compounds described herein may be combined with treatments for amyotrophic lateral sclerosis (ALS). The compounds described herein may be combined with treatments for Huntington's disease. The compounds described herein may be combined with treatments for Parkinson's disease. The compounds described herein may be combined with treatments for hemorrhagic stroke associated with amyloidosis.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. A patient may be a human.

"Disease" or "condition" refer to a state of being or health status of a patient or subject capable of being treated with the compounds or methods provided herein. Disease as used herein may refer to a disorder associated with aberrant Aβ peptide levels as described herein.

I. Compounds

Provided herein are compounds of Formula (A):

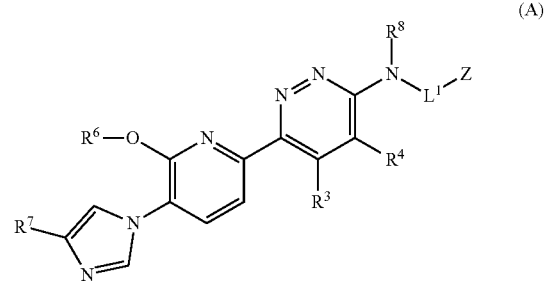

(A)

wherein, $L^1$ is selected from the group consisting of C(O), C($R^1$) ($R^2$), substituted or unsubstituted —$C_{2-6}$ alkylene-, and substituted or unsubstituted —$C_{3-6}$ cycloalkylene;

Z is selected from the group consisting of halo, CN, OH, $C_{1-6}$ alkyl, $C_{1-6}$ alkoxy, $C_{1-3}$ haloalkyl, $C_{1-3}$ haloalkoxy, amino, $C_{1-3}$ alkylamino, di($C_{1-3}$alkyl)amino, substituted or unsubstituted $C_{3-6}$ cycloalkyl, substituted or unsubstituted $C_{4-6}$ heterocycloalkyl, substituted or unsubstituted heteroaryl, and a group of Formula (Z-1):

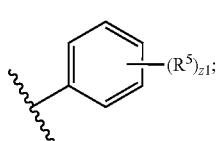

or L¹ is absent and Z is selected from the group consisting of substituted or unsubstituted cycloalkyl, substituted or unsubstituted heterocycloalkyl, and substituted or unsubstituted heteroaryl;

R¹ and R² are independently hydrogen, substituted or unsubstituted alkyl, substituted or unsubstituted heteroalkyl, COOR$^{1A}$, —CONR$^{1A}$R$^{1B}$, or are optionally joined together to form a substituted or unsubstituted cycloalkyl;

R³ is hydrogen, halogen, —CF₃, —CN, —OR$^{3A}$, —NR$^{3A}$R$^{3B}$, —COOR$^{3A}$, —CONR$^{3A}$R$^{3B}$, -, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁴ is hydrogen, halogen, —CF₃, —CN, —OR$^{4A}$, —NR$^{4A}$R$^{4B}$, —COOR$^{4A}$, —CONR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

or R³ and R⁴ are optionally joined together to form a substituted or unsubstituted cycloalkyl;

R⁵ is independently hydrogen, halogen, —CF₃, —CN, —OR$^{5A}$, —NR$^{5A}$R$^{5B}$, —COOR$^{5A}$, —CONR$^{5A}$R$^{5B}$, —SR$^{5A}$, —OCF₃, —OCHF₂, substituted or unsubstituted alkyl, or substituted or unsubstituted heteroalkyl;

R⁶ and R⁷ are independently substituted or unsubstituted C₁-C₅ alkyl;

R$^{1A}$, R$^{1B}$, R$^{3A}$, R$^{3B}$, R$^{4A}$, R$^{4B}$, R$^{5A}$, and R$^{5B}$ are independently hydrogen, —OH, —NH₂, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or R$^{1A}$ and R$^{1B}$, R$^{3A}$ and R$^{3B}$, R$^{4A}$ and R$^{4B}$, or R$^{5A}$ and R$^{5B}$ are independently optionally joined together to independently form a substituted or unsubstituted heterocycloalkyl, or substituted or unsubstituted heteroaryl;

R⁸ is selected from the group consisting of hydrogen, substituted or unsubstituted alkyl, and substituted or unsubstituted heteroalkyl; and z1 is an integer of 0, 1, 2, 3, 4, or 5.

In some embodiments, the C₂₋₆ alkylene group or the C₃₋₆ cycloalkylene group of L¹ are independently optionally substituted with 1, 2, or 3 substituents independently selected from halo, CN, OH, C₁₋₃ alkyl, C₁₋₃ alkoxy, C₁₋₃ haloalkyl, C₁₋₃ haloalkoxy, amino, C₁₋₃ alkylamino, and di(C₁₋₃ alkyl)amino.

In some embodiments, compounds of Formula (A) are compound of Formula (I):

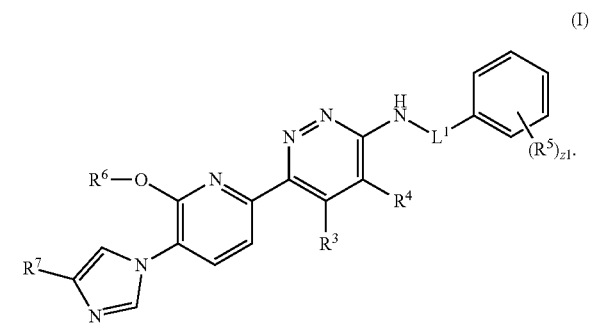

In some embodiments, L¹ is C(O) or C(R¹)(R²); R¹ and R² are independently hydrogen, substituted or unsubstituted alkyl, substituted or unsubstituted heteroalkyl, or are optionally joined together to form a substituted or unsubstituted cycloalkyl; R³ is hydrogen, halogen, —CF₃, —CN, —OR$^{3A}$, —NR$^{3A}$R$^{3B}$, —COOR$^{3A}$, —CONR$^{3A}$R$^{3B}$, -, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R⁴ is hydrogen, halogen, —CF₃, —CN, —OR$^{4A}$, —NR$^{4A}$R$^{4B}$, —COOR$^{4A}$, —CONR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R⁵ is independently hydrogen, halogen, —CF₃, —CN, —OR$^{5A}$, —NR$^{5A}$R$^{5B}$, —COOR$^{5A}$, —CONR$^{5A}$R$^{5B}$, —SR$^{5A}$, —OCF₃, —OCHF₂, substituted or unsubstituted alkyl, or substituted or unsubstituted heteroalkyl; R⁶ and R⁷ are independently substituted or unsubstituted C₁-C₅ alkyl; R$^{3A}$, R$^{3B}$, R$^{4A}$, R$^{4B}$, R$^{5A}$, and R$^{5B}$ are independently hydrogen, —OH, —NH₂, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or R$^{3A}$ and R$^{3B}$, R$^{4A}$ and R$^{4B}$, or R$^{5A}$ and R$^{5B}$ are independently optionally joined together to independently form a substituted or unsubstituted heterocycloalkyl, or substituted or unsubstituted heteroaryl; and z1 is an integer of 0, 1, 2, 3, 4, or 5.

In some embodiments, L¹ is selected from the group consisting of C(O), C(R¹)(R²), —C₂₋₆ alkylene-, and —C₃₋₆ cycloalkylene-, wherein the C₂₋₆ alkylene group is optionally substituted with 1, 2, or 3 substituents independently selected from halo, CN, OH, C₁₋₃ alkyl, C₁₋₃ alkoxy, C₁₋₃ haloalkyl, C₁₋₃ haloalkoxy, amino, C₁₋₃ alkylamino, and di(C₁₋₃ alkyl)amino.

In some embodiments, L¹ is selected from the group consisting of C(O), C(R¹)(R²), —C₂₋₆ alkylene-, and —C₃₋₆ cycloalkylene-, wherein the C₂₋₆ alkylene group is optionally substituted with 1 or 2 substituents independently selected from halo, CN, OH, C₁₋₃ alkyl and C₁₋₃ alkoxy.

In some embodiments, L¹ is selected from the group consisting of C(O), C(R¹)(R²), -ethylene-, -2-methylethylene-, -propylene-, and -cyclopropylene-.

In some embodiments, Z is selected from the group consisting of halo, CN, OH, C₁₋₆ alkyl, substituted or unsubstituted C₃₋₆ cycloalkyl, substituted or unsubstituted C₄₋₆ heterocycloalkyl, substituted or unsubstituted heteroaryl, and a group of Formula (Z-1):

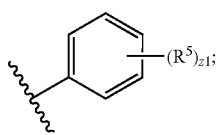 (Z-1)

or L¹ is absent and Z is selected from the group consisting of substituted or unsubstituted cycloalkyl, and substituted or unsubstituted heteroaryl.

In some embodiments, Z is selected from the group consisting of halo, OH, $C_{1-6}$ alkyl, and a cyclic group of the following Formulae (Z-1) to (Z-18):

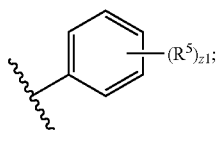 (Z-1)

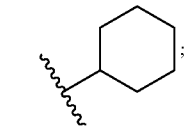 (Z-2)

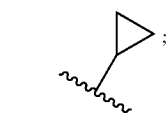 (Z-3)

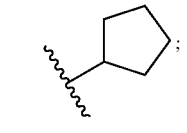 (Z-4)

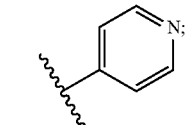 (Z-5)

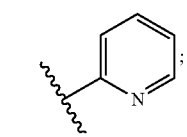 (Z-6)

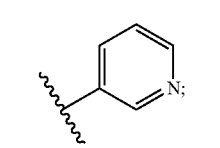 (Z-7)

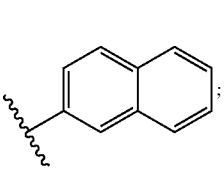 (Z-8)

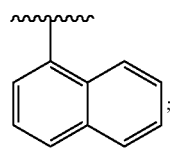 (Z-9)

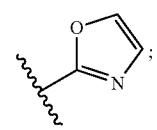 (Z-10)

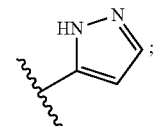 (Z-11)

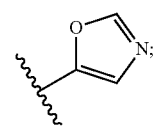 (Z-12)

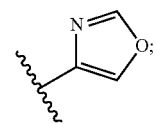 (Z-13)

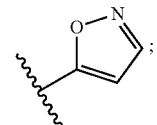 (Z-14)

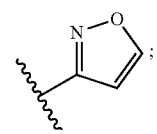 (Z-15)

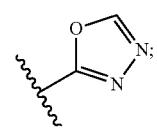 (Z-16)

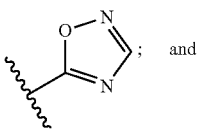 (Z-17) and

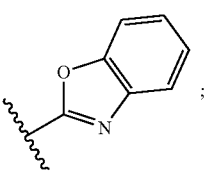 (Z-18)

or L¹ is absent and Z is selected from the group consisting of a cyclic group of Formulae (Z-2), (Z-3), (Z-4), and the following Formulae (Z-19) and (Z-20):

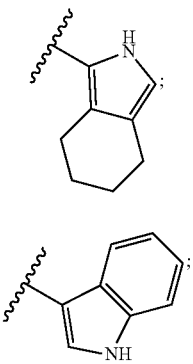
(Z-19)

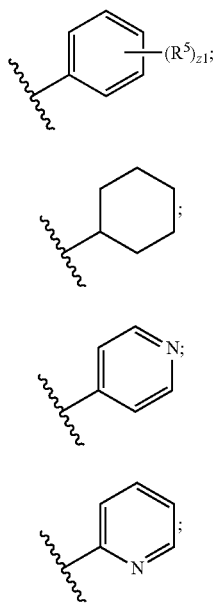
(Z-20)

wherein any one of the Formulae (Z-2) to (Z-20) is unsubstituted or substituted.

In some embodiments, Z is selected from the group consisting of halo, OH, $C_{1-6}$ alkyl, and a cyclic group of the following Formulae (Z-1), (Z-2), (Z-5) and (Z-6):

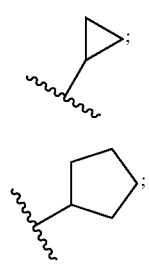

(Z-1)

(Z-2)

(Z-5)

(Z-6)

or $L^1$ is absent and Z is selected from the group consisting of a cyclic group of Formulae (Z-2), and the following Formulae (Z-3), (Z-4) and (Z-19):

(Z-3)

(Z-4)

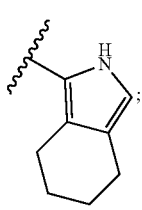
(Z-19)

wherein any one of the Formulae (Z-2), (Z-3), (Z-4), (Z-5), (Z-6), and (Z-19) is unsubstituted or substituted.

In some embodiments, Z is selected from the group consisting of fluoro, OH, methoxy, methyl, ethyl, isopropyl, tert-butyl, phenyl, fluorophenyl, chlorophenyl, methoxyphenyl, (trifluoromethyl)phenyl, difluorophenyl, methylphenyl, bis(trifluoromethyl)phenyl, 4-fluoro-3-methoxyphenyl, 4-fluoro-2-methoxyphenyl, 4-fluoro-3-methylphenyl, 4-fluoro-2-methylphenyl, trifluorophenyl, 4-fluoro-3-(trifluoromethyl)phenyl, 4-fluoro-2-(trifluoromethyl)phenyl, 2-chloro-4-fluorophenyl, cyclohexyl, pyridinyl, fluoropyridinyl, benzo[d]oxazolyl, naphthyl, fluoronaphthyl, cyclopropyl, cyclopentyl, hydroxyphenyl, aminophenyl, 4-trifluoromethyl-3-(methoxy)phenyl, 4-trifluoromethyl-3-(fluoro)phenyl, oxazol-2-yl, pyrazole-5-yl, oxazol-5-yl, oxazol-4-yl, isoxazol-5-yl, isoxazol-3-yl, 1,3,4-oxadiazol-2-yl, 1,2,4-oxadiazol-5-yl, isoxazol-3-one-5-yl, 2-fluoro-3-chlorophenyl, 2-fluoro-3-(trifluoromethyl)phenyl, 3-fluoro-2-methylphenyl, difluoropyridinyl, difluorophenyl, 2-fluoro-5-methylphenyl, and 3-chloro-5-fluorophenyl.

or $L^1$ is absent and Z is selected from the group consisting of cyclopropyl, cyclopentyl, cyclohexyl, 4,4,-difluorocyclohexyl, 4-trifluoromethylcyclohexyl, 2-ethyl-4,5,6,7-tetrahydro-2H-isoindolyl, 3,3-difluorocyclopentyl, 3,3-difluorocyclohexyl, 3-trifluoromethylcyclohexyl, 6-fluoro-1H-indol-3-yl, and 6-fluoro-1-methyl-1H-indol-3-yl.

In some embodiments, Z is selected from the group consisting of fluoro, OH, methoxy, methyl, ethyl, isopropyl, tert-butyl, phenyl, fluorophenyl, chlorophenyl, methoxyphenyl, (trifluoromethyl)phenyl, difluorophenyl, methylphenyl, bis(trifluoromethyl)phenyl, 4-fluoro-3-methoxyphenyl, 4-fluoro-2-methoxyphenyl, 4-fluoro-3-methylphenyl, 4-fluoro-2-methylphenyl, trifluorophenyl, 4-fluoro-3-(trifluoromethyl)phenyl, 4-fluoro-2-(trifluoromethyl)phenyl, 2-chloro-4-fluorophenyl, cyclohexyl, pyridinyl, fluoropyridinyl, and benzo[d]oxazolyl;

or $L^1$ is absent and Z is selected from the group consisting of cyclopropyl, cyclopentyl, cyclohexyl, 4,4,-difluorocyclohexyl, 4-trifluoromethylcyclohexyl, and 2-ethyl-4,5,6,7-tetrahydro-2H-isoindolyl.

In some embodiments, $L^1$ is $C(R^1)(R^2)$.

In some embodiments, $R^1$ is selected from the group consisting of hydrogen and substituted or unsubstituted alkyl; and $R^2$ is selected from the group consisting of hydrogen, substituted or unsubstituted alkyl, substituted or unsubstituted heteroalkyl, and $CONR^{1A}R^{1B}$;

or $R^1$ and $R^2$ are optionally joined together to form a substituted or unsubstituted cycloalkyl.

In some embodiments, $R^1$ is selected from the group consisting of hydrogen and methyl; and $R^2$ is selected from the group consisting of hydrogen, methyl, ethyl, propyl, isopropyl, hydroxymethyl, methoxymethyl, fluoromethyl, 3,3,3-trifluoroethyl, trifluoromethyl, 2-methyl-2-hydroxyethyl, N,N-dimethylaminocarbonyl, and N-pyrrolidinocarbonyl;

or $R^1$ and $R^2$ are joined together to form a cyclopropyl ring.

In some embodiments, $R^1$ and $R^2$ are independently hydrogen or substituted or unsubstituted alkyl.

In some embodiments, $R^1$ is selected from the group consisting of hydrogen and substituted or unsubstituted alkyl.

In some embodiments, $R^1$ is hydrogen or methyl.

In some embodiments, $R^2$ is substituted or unsubstituted alkyl.

In some embodiments, $R^2$ is substituted or unsubstituted alkyl.

In some embodiments, $R^2$ is unsubstituted $C_1$-$C_5$ alkyl.

In some embodiments, $R^2$ is substituted $C_1$-$C_5$ alkyl.

In some embodiments, $R^2$ is methyl.

In some embodiments, $R^2$ is —$CH_2OR^{2A}$ or —$C(CH_3)_2OR^{2A}$; and $R^{2A}$ is hydrogen or substituted or unsubstituted alkyl.

In some embodiments, $R^1$ is hydrogen and $R^2$ is attached to a carbon having (S) stereochemistry.

In some embodiments, $R^1$ and $R^2$ are joined together to form a substituted or unsubstituted $C_3$ cycloalkyl.

In some embodiments, $R^3$ is selected from the group consisting of hydrogen, substituted or unsubstituted alkyl, and substituted or unsubstituted heteroalkyl; and $R^4$ is selected from the group consisting of hydrogen, halogen, —$CF_3$, —CN, —$OR^{4A}$, substituted or unsubstituted alkyl, substituted or unsubstituted heteroalkyl;

or $R^3$ and $R^4$ are optionally joined together to form a substituted or unsubstituted cycloalkyl.

In some embodiments, $R^3$ is selected from the group consisting of hydrogen, methyl, ethyl, and methoxy; and $R^4$ is selected from the group consisting of hydrogen, methyl, ethyl, isopropyl, methoxy, —CN, Cl, F, and —$CF_3$;

or $R^3$ and $R^4$ are optionally joined together to form a cyclic ring selected from the group consisting of cyclopentyl and cyclohexyl.

In some embodiments, $R^3$ is selected from the group consisting of hydrogen and methyl; and $R^4$ is selected from the group consisting of hydrogen, methyl, ethyl, isopropyl, and methoxy;

or $R^3$ and $R^4$ are optionally joined together to form a cyclopentyl ring.

In some embodiments, $R^3$ is hydrogen, halogen, —CN, —$CF_3$, —$OR^{3A}$, —$NR^{3A}R^{3B}$, substituted or unsubstituted alkyl, or substituted or unsubstituted heteroalkyl, wherein $R^{3A}$ and $R^{3B}$ are independently hydrogen, substituted or unsubstituted alkyl, or substituted or unsubstituted aryl.

In some embodiments, $R^3$ is selected from the group consisting of hydrogen, substituted or unsubstituted alkyl, and substituted or unsubstituted heteroalkyl.

In some embodiments, $R^3$ is hydrogen, or substituted or unsubstituted alkyl.

In some embodiments, $R^3$ is hydrogen.

In some embodiments, $R^3$ is substituted or unsubstituted alkyl.

In some embodiments, $R^3$ is selected from the group consisting of hydrogen, methyl, ethyl, and methoxy.

In some embodiments, $R^3$ is selected from the group consisting of hydrogen and methyl.

In some embodiments, $R^3$ is methyl.

In some embodiments, $R^4$ is hydrogen, halogen, —$CF_3$, —CN, —$OR^{4A}$, substituted or unsubstituted alkyl, substituted or unsubstituted heteroalkyl.

In some embodiments, $R^4$ is selected form the group consisting of hydrogen, methyl, ethyl, isopropyl, methoxy, —CN, Cl, F, and —$CF_3$.

In some embodiments, $R^4$ is hydrogen, methyl, ethyl, isopropyl, and methoxy.

In some embodiments, $R^4$ is hydrogen or substituted or unsubstituted alkyl.

In some embodiments, $R^4$ is hydrogen.

In some embodiments, $R^4$ is substituted or unsubstituted alkyl.

In some embodiments, $R^4$ is methyl.

In some embodiments, $R^5$ is selected from the group consisting of halogen, —$CF_3$, —CN, —$OR^{5A}$, —$NR^{5A}R^{5B}$, and substituted or unsubstituted alkyl; and $R^{5A}$ and $R^{5B}$ are each independently hydrogen, substituted or unsubstituted $C_1$-$C_5$ alkyl, or substituted or unsubstituted aryl.

In some embodiments, $R^5$ is halogen, —$CF_3$, —$OR^{5A}$, substituted or unsubstituted alkyl, or substituted or unsubstituted heteroalkyl; and $R^{5A}$ is hydrogen, substituted or unsubstituted $C_1$-$C_5$ alkyl, or substituted or unsubstituted aryl.

In some embodiments, $R^5$ is selected from the group consisting of fluoro, chloro, CN, methoxy, methyl, thrifluoromethyl, OH, and $NH_2$.

In some embodiments, $R^5$ is selected from the group consisting of fluoro, chloro, CN, methoxy, methyl, thrifluoromethyl.

In some embodiments, z1 is 0, 1, 2, or 3.

In some embodiments, z1 is 0, 1, or 2.

In some embodiments, $R^5$ is halogen, —$CF_3$, —$OCH_3$, or methyl; and z1 is 1, 2, or 3.

In some embodiments, $R^5$ is halogen; and z1 is 1, 2, or 3.

In some embodiments, $R^5$ is halogen, —$CF_3$, or —$OR^{5A}$ and is substituted at the Para position, wherein $R^{5A}$ is hydrogen, substituted or unsubstituted $C_1$-$C_5$ alkyl, or substituted or unsubstituted aryl.

In some embodiments, $R^6$ is methyl.

In some embodiments, $R^7$ is methyl.

In some embodiments, $R^8$ is selected from the group consisting of methyl, ethyl, fluoroethyl, and methoxyethyl.

In some embodiments, $R^8$ is selected from the group consisting of methyl and ethyl.

In some embodiments, $L^1$ is C(O), C($R^1$)($R^2$), $CH_2C(R^1)(R^2)$, or $C(R^1)(R^2)CH_2$. In some such embodiments, $R^1$ and $R^2$ are independently hydrogen, substituted or unsubstituted alkyl, substituted or unsubstituted heteroalkyl, or are optionally joined together to form a substituted or unsubstituted cycloalkyl. In some such embodiments, $R^3$ is hydrogen, halogen, —$N_3$, —$CF_3$, —$CCl_3$, —$CBr_3$, —$CI_3$, —CN, —$OR^{3A}$, —$NR^{3A}R^{3B}$, —$COOR^{3A}$, —$CONR^{3A}R^{3B}$, —$NO_2$, —$SR^{3A}$, —$S(O)_{n3}$, —$S(O)_{n3}R^{3A}$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some such embodiments, $R^4$ is hydrogen, halogen, —$N_3$, —$CF_3$, —$CCl_3$, —$CBr_3$, —$CI_3$, —CN, —$OR^{4A}$, —$NR^{4A}R^{4B}$, —$COOR^{4A}$, —$CONR^{4A}R^{4B}$, —$NO_2$, —$SR^{4A}$, —$S(O)_{n4}$, —$S(O)_{n4}R^{4A}$, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some such embodiments, $R^5$ is independently hydrogen, halogen, —$N_3$, —$CF_3$, —$CCl_3$, —$CBr_3$, —$CI_3$, —CN, —$OR^{5A}$, —$NR^{5A}R^{5B}$, —$COOR^{5A}$, —$CONR^{5A}R^{5B}$, —$NO_2$, —$SR^{5A}$, —$S(O)_{n5}R^{5A}$, —$OCF_3$, —$OCHF_2$, substituted or unsubstituted alkyl, or substituted or unsubstituted heteroalkyl. In some such embodiments, $R^6$ and $R^7$ are independently substituted or unsubstituted $C_1$-$C_5$ alkyl. In some such embodiments, $R^{3A}$, $R^{3B}$, $R^{4A}$, $R^{4B}$, $R^{5A}$, and $R^{5B}$ are independently hydrogen, —$CF_3$, —CN, —OH, —$NH_2$, —COOH, —$CONH_2$, —$NO_2$, —SH, —$SO_2$, —$S(O)_2Cl$, —$S(O)_3H$, —$S(O)_4H$, —$S(O)_2NH_2$, —$NHNH_2$, —$ONH_2$, —NHC(O) $NHNH_2$, —$NHC(O)NH_2$, —$NHS(O)_2H$, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or $R^{3A}$ and $R^{3B}$, $R^{4A}$ and $R^{4B}$, or $R^{5A}$ and $R^{5B}$ are independently optionally joined together to independently form a substituted or unsubstituted heterocycloalkyl, or substituted or unsubstituted heteroaryl. In some such embodiments, the symbols n3, n4, and n5 are independently an integer of 1, 2, 3, or 4. In some such embodiments, the symbol z1 is an integer of 0, 1, 2, 3, 4, or 5.

In some embodiments, $L^1$ is C(O), $C(R^1)(R^2)$, $CH_2C(R^1)(R^2)$, or $C(R^1)(R^2)CH_2$. In some such embodiments, $R^1$ and $R^2$ are independently hydrogen, substituted or unsubstituted alkyl, substituted or unsubstituted heteroalkyl, or are optionally joined together to form a substituted or unsubstituted cycloalkyl. In some such embodiments, $R^3$ is hydrogen, halogen, —$CF_3$, —CN, —$OR^{3A}$, —$NR^{3A}R^{3B}$, —$COOR^{3A}$, —$CONR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some such embodiments, $R^4$ is hydrogen, halogen, —$CF_3$, —CN, —$OR^{4A}$, —$NR^{4A}R^{4B}$, —$COOR^{4A}$, —$CONR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some such embodiments, $R^5$ is independently hydrogen, halogen, —$CF_3$, —CN, —$OR^{5A}$, —$NR^{5A}R^{5B}$, —$COOR^{5A}$, —$CONR^{5A}R^{5B}$, —$SR^{5A}$, $OCF_3$, —$OCHF_2$, substituted or unsubstituted alkyl, or substituted or unsubstituted heteroalkyl. In some such embodiments, $R^6$ and $R^7$ are independently substituted or unsubstituted $C_1$-$C_5$ alkyl. $R^{3A}$, $R^{3B}$, $R^{4A}$, $R^{4B}$, $R^{5A}$, and $R^{5B}$ are independently hydrogen, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or $R^{3A}$ and $R^{3B}$, $R^{4A}$ and $R^{4B}$, or $R^{5A}$ and $R^{5B}$ are independently optionally joined together to independently form a substituted or unsubstituted heterocycloalkyl, or substituted or unsubstituted heteroaryl. In some such embodiments, the symbol z1 is an integer of 0, 1, 2, 3, 4, or 5.

In some embodiments, $L^1$ is C(O) or $C(R^1)(R^2)$. In some embodiments, $L^1$ is C(O). In some embodiments, $L^1$ may be $C(R^1)(R^2)$. When $L^1$ is $C(R^1)(R^2)$, $R^1$ and $R^2$ can independently be hydrogen, substituted or unsubstituted alkyl, or optionally join together to form a substituted or unsubstituted cycloalkyl. When joined, $R^1$ and $R^2$ can form a substituted or unsubstituted $C_3$-$C_6$ cycloalkyl. $R^1$ and $R^2$ can join together to form a substituted $C_3$-$C_6$ cycloalkyl. $R^1$ and $R^2$ can join together to form an unsubstituted $C_3$-$C_6$ cycloalkyl. $R^1$ and $R^2$ can join to form a substituted or unsubstituted $C_3$ cycloalkyl. $R^1$ and $R^2$ can join to form a substituted $C_3$ cycloalkyl. $R^1$ and $R^2$ can join to form an unsubstituted $C_3$ cycloalkyl.

In some embodiments, $R^1$ may be hydrogen, substituted or unsubstituted alkyl or substituted or unsubstituted heteroalkyl. In some embodiments, $R^1$ is hydrogen or substituted or unsubstituted alkyl. In some embodiments, $R^1$ is hydrogen. In some embodiments, $R^1$ is a substituted or unsubstituted alkyl. In some embodiments, $R^1$ is a substituted alkyl. In some embodiments, $R^1$ is an unsubstituted alkyl. In some embodiments, $R^1$ is a substituted or unsubstituted $C_1$-$C_5$ alkyl. In some embodiments, $R^1$ is a substituted $C_1$-$C_8$ alkyl. In some embodiments, $R^1$ is an unsubstituted $C_1$-$C_5$ alkyl. In some embodiments, $R^1$ is methyl. In some embodiments, $R^1$ is ethyl.

In some embodiments, $R^1$ is hydrogen or substituted or unsubstituted heteroalkyl. In some embodiments, $R^1$ is a substituted heteroalkyl. In some embodiments, $R^1$ is an unsubstituted heteroalkyl. In some embodiments, $R^1$ is a substituted or unsubstituted 2 to 6 membered heteroalkyl. In some embodiments, $R^1$ is a substituted 2 to 6 membered heteroalkyl. In some embodiments, $R^1$ is an unsubstituted 2 to 6 membered heteroalkyl. In some embodiments, $R^1$ is a —$CH_2OR^{1A}$ or —$C(CH_3)_2OR^{1A}$. In some such embodiments, $R^{1A}$ is hydrogen, substituted or unsubstituted alkyl, or substituted or unsubstituted aryl. In some embodiments, $R^1$ is —$CH_2OCH_3$. In some embodiments, $R^1$ is —$C(CH_3)_2OH$.

In some embodiments, $R^2$ is hydrogen, substituted or unsubstituted alkyl or substituted or unsubstituted heteroalkyl. In some embodiments, $R^2$ is hydrogen or substituted or unsubstituted alkyl. In some embodiments, $R^2$ is hydrogen. In some embodiments, $R^2$ is substituted or unsubstituted alkyl. In some embodiments, $R^2$ is substituted alkyl. $R^2$ is unsubstituted alkyl. In some embodiments, $R^2$ is substituted or unsubstituted $C_1$-$C_5$ alkyl. In some embodiments, $R^2$ is substituted $C_1$-$C_5$ alkyl. In some embodiments, $R^2$ is unsubstituted $C_1$-$C_5$ alkyl. In some embodiments, $R^2$ is methyl. In some embodiments, $R^2$ is ethyl.

In some embodiments, $R^2$ is hydrogen or substituted or unsubstituted heteroalkyl. $R^2$ is substituted heteroalkyl. In some embodiments, $R^2$ is unsubstituted heteroalkyl. In some embodiments, $R^2$ is substituted or unsubstituted 2 to 6 membered heteroalkyl. In some embodiments, $R^2$ is substituted 2 to 6 membered heteroalkyl. In some embodiments, $R^2$ is unsubstituted 2 to 6 membered heteroalkyl. In some embodiments, $R^2$ is —$CH_2OR^{2A}$ or —$C(CH_3)_2OR^{2A}$ where $R^{2A}$ is hydrogen, substituted or unsubstituted alkyl, or substituted or unsubstituted aryl. In some embodiments, $R^2$ is —$CH_2OCH_3$. In some embodiments, $R^2$ is —$C(CH_3)_2OH$.

In some embodiments, $R^1$ is hydrogen and $R^2$ may substituted or unsubstituted alkyl or substituted or unsubstituted heteroalkyl. In some embodiments, $R^1$ is hydrogen and $R^2$ is unsubstituted heteroalkyl. In some embodiments, $R^1$ is hydrogen and $R^2$ is —$CH_2OR^{2A}$ or —$C(CH_3)_2OR^{2A}$ where $R^{2A}$ is hydrogen or substituted or unsubstituted alkyl. In some embodiments, $R^1$ is hydrogen and $R^2$ is —$CH_3OH$. In some embodiments, $R^1$ is hydrogen and $R^2$ is —$CH_3OCH_3$. In some embodiments, $R^1$ is hydrogen and $R^2$ is —$C(CH_3)_2OH$. In some embodiments, when $R^1$ is hydrogen, $R^2$ is attached to a carbon having (S) stereochemistry. In some embodiments, when $R^1$ is hydrogen, $R^2$ is attached to a carbon having (R) stereochemistry. In some embodiments, $R^1$ and $R^2$ is hydrogen (i.e. $L^1$ is $CH_2$). In some such embodiments, $L^1$ is $CH_2(CR^1R^2)$ or $(CR^1R^2)CH_2$, where $R^1$ and $R^2$ are as described herein. In some such embodiments, $L^1$ is $CH_2(CR^1R^2)$ or $(CR^1R^2)CH_2$, where $R^1$ and $R^2$ are hydrogen (i.e. $L^1$ is $CH_2CH_2$).

In some embodiments, $R^1$ is hydrogen and $R^2$ is substituted or unsubstituted alkyl. In some embodiments, $R^1$ is hydrogen and $R^2$ is substituted alkyl. $R^1$ is hydrogen and $R^2$ is unsubstituted alkyl. In some embodiments, $R^1$ is hydrogen and $R^2$ is substituted or unsubstituted $C_1$-$C_5$ alkyl. In some embodiments, $R^1$ is hydrogen and $R^2$ is substituted $C_1$-$C_5$ alkyl. In some embodiments, $R^1$ is hydrogen and $R^2$ is unsubstituted $C_1$-$C_5$ alkyl. In some embodiments, $R^1$ is hydrogen and $R^2$ is methyl. In some embodiments, $R^1$ is hydrogen and $R^2$ is ethyl. In some embodiments, when $R^1$ is hydrogen, $R^2$ is attached to a carbon having (S) stereochemistry. In some embodiments, when $R^1$ is hydrogen, $R^2$ is attached to a carbon having (R) stereochemistry.

In some embodiments, $R^1$ is methyl and $R^2$ is unsubstituted heteroalkyl. In some embodiments, $R^1$ is methyl and $R^2$ is —$CH_2OR^{2A}$ or —$C(CH_3)_2OR^{2A}$ where $R^{2A}$ is hydrogen or substituted or unsubstituted alkyl. In some embodiments, $R^1$ is methyl and $R^2$ is —$CH_3OH$. In some embodiments, $R^1$ is methyl and $R^2$ is —$CH_3OCH_3$. In some embodiments, $R^1$ is methyl and $R^2$ is —$C(CH_3)_2OH$.

In some embodiments, $R^1$ is methyl and $R^2$ is substituted or unsubstituted alkyl. In some embodiments, $R^1$ is methyl and $R^2$ is substituted alkyl. In some embodiments, $R^1$ is methyl and $R^2$ is unsubstituted alkyl. In some embodiments, $R^1$ is methyl and $R^2$ is substituted or unsubstituted $C_1$-$C_5$ alkyl. In some embodiments, $R^1$ is methyl and $R^2$ is substituted $C_1$-$C_5$ alkyl. In some embodiments, $R^1$ is methyl and $R^2$ is unsubstituted $C_1$-$C_5$ alkyl. In some embodiments, $R^1$ is hydrogen and $R^2$ is methyl.

In some embodiments, $R^1$ and $R^2$ are independently hydrogen, unsubstituted heteroalkyl, or substituted or unsubstituted alkyl. In some embodiments, $R^1$ and $R^2$ are independently hydrogen, unsubstituted heteroalkyl, or unsubstituted alkyl.

In some embodiments, $R^2$ is attached to a carbon having (S) stereochemistry. In some embodiments, $R^2$ is attached to a carbon having (R) stereochemistry.

In some embodiments, $R^1$ and $R^2$ are independently hydrogen, halogen, —$N_3$, —$CF_3$, —$CCl_3$, —$CBr_3$, —$CI_3$, —CN, —CHO, —OH, —$NH_2$, —COON, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, substituted or unsubstituted alkyl (e.g. $C_1$ to $C_8$ alkyl), substituted or unsubstituted heteroalkyl (e.g. 2 to 8 membered heteroalkyl), substituted or unsubstituted cycloalkyl (e.g. $C_3$-$C_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl).

In some embodiments, $R^1$ and $R^2$ are independently hydrogen, —$CF_3$, substituted or unsubstituted alkyl (e.g. $C_1$ to $C_8$ alkyl), substituted or unsubstituted heteroalkyl (e.g. 2 to 8 membered heteroalkyl), substituted or unsubstituted cycloalkyl (e.g. $C_3$-$C_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl).

In some embodiments, $R^3$ is independently hydrogen, halogen, —$N_3$, —$CF_3$, —$CCl_3$, —$CBr_3$, —$CI_3$, —CN, —CHO, —$OR^{3A}$, —$NR^{3A}R^{3B}$, —$COOR^{3A}$, —$CONR^{3A}R^{3B}$, —$NO_2$, —$SR^{3A}$, —$SO_2$, —$SO_3H$, —$SO_4H$, —$SO_2NR^{3A}R^{3B}$, —$NHNR^{3A}R^{3B}$, —$ONR^{3A}R^{3B}$, —$NHC(O)NHNR^{3A}R^{3B}$, substituted or unsubstituted alkyl (e.g. $C_1$ to $C_8$ alkyl), substituted or unsubstituted heteroalkyl (e.g. 2 to 8 membered heteroalkyl), substituted or unsubstituted cycloalkyl (e.g. $C_3$-$C_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl). In some such embodiments, $R^{3A}$ and $R^{3B}$ are independently hydrogen, —OH, —$NH_2$, substituted or unsubstituted alkyl (e.g. $C_1$-$C_5$ alkyl), substituted or unsubstituted heteroalkyl (e.g. 2 to 6 membered heteroaryl), or substituted or unsubstituted aryl (e.g. phenyl). $R^{3A}$ and $R^{3B}$ may independently be hydrogen, substituted or unsubstituted alkyl (e.g. $C_1$-$C_5$ alkyl), or substituted or unsubstituted aryl (e.g. phenyl).

In some embodiments, $R^3$ is hydrogen, halogen, —$CF_3$, —CN, —$OR^{3A}$, —$NR^{3A}R^{3B}$, —$COOR^{3A}$, —$CONR^{3A}R^{3B}$, substituted or unsubstituted alkyl, or substituted or unsubstituted heteroalkyl. In some embodiments, $R^3$ is hydrogen, halogen, —$CF_3$, —$OR^{3A}$, —$NR^{3A}R^{3B}$, substituted or unsubstituted alkyl, or substituted or unsubstituted heteroalkyl. In some embodiments, $R^3$ is hydrogen or substituted or unsubstituted alkyl. In some embodiments, $R^3$ is hydrogen. In some embodiments, $R^3$ is substituted or unsubstituted alkyl. In some embodiments, $R^3$ is substituted alkyl. In some embodiments, $R^3$ is unsubstituted alkyl. In some embodiments, $R^3$ is substituted or unsubstituted $C_1$-$C_5$ alkyl. In some embodiments, $R^3$ is substituted $C_1$-$C_5$ alkyl. In some embodiments, $R^3$ is unsubstituted $C_1$-$C_5$ alkyl. In some embodiments, $R^3$ is methyl. In some embodiments, $R^3$ is ethyl.

In some embodiments, $R^3$ is substituted or unsubstituted heteroalkyl. In some embodiments, $R^3$ is substituted heteroalkyl. $R^3$ is unsubstituted heteroalkyl. In some embodiments, $R^3$ is substituted or unsubstituted 2 to 6 membered heteroalkyl. In some embodiments, $R^3$ is substituted 2 to 6 membered heteroalkyl. In some embodiments, $R^3$ is unsubstituted 2 to 6 membered heteroalkyl. In some embodiments, $R^3$ is —$OCH_3$ or —$OCH_2CH_3$.

In some embodiments, $R^3$ is a substituted or unsubstituted cycloalkyl (e.g. $C_3$-$C_6$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl).

In some embodiments, $R^4$ is independently hydrogen, halogen, —$N_3$, —$CF_3$, —$CCl_3$, —$CBr_3$, —$CI_3$, —CN, —CHO, —$OR^{4A}$, —$NR^{4A}R^{4B}$, —$COOR^{4A}$, —$CONR^{4A}R^{4B}$, —$NO_2$, —$SR^{4A}$, —$SO_2$, —$SO_3H$, —$SO_4H$, —$SO_2NR^{4A}R^{4B}$, $NHNR^{4A}R^{4B}$, —$ONR^{4A}R^{4B}$, —$NHC(O)NHNR^{4A}R^{4B}$, substituted or unsubstituted alkyl (e.g. $C_1$ to $C_8$ alkyl), substituted or unsubstituted heteroalkyl (e.g. 2 to 8 membered heteroalkyl), substituted or unsubstituted cycloalkyl (e.g. $C_3$-$C_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl). In some such embodiments, $R^{4A}$ and $R^{4B}$ are independently hydrogen, —OH, —$NH_2$, substituted or unsubstituted alkyl (e.g. $C_1$-$C_5$ alkyl), substituted or unsubstituted heteroalkyl (e.g. 2 to 6 membered heteroaryl), or substituted or unsubstituted aryl (e.g. phenyl). In some such embodiments, $R^{4A}$ and $R^{4B}$ may independently be hydrogen, substituted or unsubstituted alkyl (e.g. $C_1$-$C_5$ alkyl), or substituted or unsubstituted aryl (e.g. phenyl).

In some embodiments, $R^4$ is hydrogen, halogen, —$CF_3$, —CN, —$OR^{4A}$, —$NR^{4A}R^{4B}$, —$COOR^{4A}$, —$CONR^{4A}R^{4B}$, substituted or unsubstituted alkyl, or substituted or unsubstituted heteroalkyl. In some embodiments, $R^4$ is hydrogen, halogen, —$CF_3$, —$OR^{4A}$, $NR^{4A}R^{4B}$, or unsubstituted alkyl, or substituted or unsubstituted heteroalkyl. In some embodiments, $R^4$ is hydrogen or substituted or unsubstituted alkyl. In some embodiments, $R^4$ is hydrogen. $R^4$ is substituted or unsubstituted alkyl. In some embodiments, $R^4$ is substituted alkyl. In some embodiments, $R^4$ is unsubstituted alkyl. $R^4$ is substituted or unsubstituted $C_1$-$C_5$ alkyl. In some embodiments, $R^4$ is substituted $C_1$-$C_5$ alkyl. In some embodiments, $R^4$ is unsubstituted $C_1$-$C_5$ alkyl. In some embodiments, $R^4$ is methyl. In some embodiments, $R^4$ is ethyl.

In some embodiments, $R^4$ is hydrogen, halogen, —$CF_3$, —CN, —$OR^{4A}$, —$NR^{4A}R^{4B}$, —$COOR^{4A}$, —$CONR^{4A}R^{4B}$, substituted or unsubstituted alkyl, or substituted or unsubstituted heteroalkyl. In some embodiments, $R^4$ is hydrogen or substituted or unsubstituted alkyl. In some embodiments, $R^4$ is hydrogen. In some embodiments, $R^4$ is substituted or unsubstituted alkyl. In some embodiments, $R^4$ is substituted alkyl. In some embodiments, $R^4$ is unsubstituted alkyl. In some embodiments, $R^4$ is substituted or unsubstituted $C_1$-$C_5$ alkyl. In some embodiments, $R^4$ is substituted $C_1$-$C_5$ alkyl. In some embodiments, $R^4$ is unsubstituted $C_1$-$C_5$ alkyl. In some embodiments, $R^4$ is methyl. $R^4$ is ethyl.

In some embodiments, $R^4$ is substituted or unsubstituted heteroalkyl. In some embodiments, $R^4$ is substituted heteroalkyl. In some embodiments, $R^4$ is unsubstituted heteroalkyl. In some embodiments, $R^4$ is substituted or unsubstituted 2 to 6 membered heteroalkyl. In some embodiments, $R^4$ is substituted 2 to 6 membered heteroalkyl. In some embodiments, $R^4$ is unsubstituted 2 to 6 membered heteroalkyl. In some embodiments, $R^4$ is —$OCH_3$ or —$OCH_2CH_3$.

In some embodiments, $R^4$ is a substituted or unsubstituted cycloalkyl (e.g. $C_3$-$C_6$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl).

In some embodiments, $R^4$ is hydrogen, halogen, —CN, —$OR^{4A}$, or —$CF_3$. $R^4$ may be hydrogen, halogen, —CN, —$OR^{4A}$, or —$CF_3$ where $R^{4A}$ is hydrogen or substituted or unsubstituted $C_1$-$C_5$ alkyl.

In some embodiments, $R^3$ and $R^4$ are independently hydrogen, halogen, —$N_3$, —$CF_3$, —$CCl_3$, —$CBr_3$, —$CI_3$, —CN, —CHO, —OH, —$NH_2$, —COON, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)$NHNH_2$, substituted or unsubstituted alkyl (e.g. $C_1$ to $C_8$ alkyl), substituted or unsubstituted heteroalkyl (e.g. 2 to 8 membered heteroalkyl), substituted or unsubstituted cycloalkyl (e.g. $C_3$-$C_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl), or optionally joined together to form a substituted or unsubstituted cycloalkyl (e.g. $C_3$-$C_8$ cycloalkyl), heterocycloalkyl (e.g. 3 to 6 membered heterocycloalkyl), aryl (e.g. phenyl), or heteroaryl (e.g. 5 or 6 membered heteroaryl).

In some embodiments, $R^3$ and $R^4$ are independently hydrogen, halogen, —$CF_3$, —CN, —OH, —$NH_2$, —COOH, —$CONH_2$, substituted or unsubstituted alkyl (e.g. $C_1$ to $C_8$ alkyl), substituted or unsubstituted heteroalkyl (e.g. 2 to 8 membered heteroalkyl), substituted or unsubstituted cycloalkyl (e.g. $C_3$-$C_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl), or optionally joined together to form a substituted or unsubstituted cycloalkyl (e.g. $C_3$-$C_8$ cycloalkyl), heterocycloalkyl (e.g. 3 to 6 membered heterocycloalkyl), aryl (e.g. phenyl), or heteroaryl (e.g. 5 or 6 membered heteroaryl).

In embodiments, $R^3$ and $R^4$ are independently hydrogen, halogen, —$CF_3$, —CN, —OH, —$NH_2$, substituted or unsubstituted alkyl (e.g. $C_1$ to $C_8$ alkyl), or substituted or unsubstituted heteroalkyl (e.g. 2 to 8 membered heteroalkyl). In some embodiments, when $R^3$ is hydrogen, $R^4$ is methyl. In some embodiments, when $R^3$ is hydrogen, $R^4$ is ethyl. In some embodiments, $R^3$ and $R^4$ is hydrogen. In some embodiments, $R^3$ and $R^4$ is methyl. In some embodiments, $R^3$ and $R^4$ is ethyl.

In some embodiments, each $R^5$ is independently a substituted or unsubstituted alkyl. In some embodiments, each $R^5$ is independently be substituted alkyl. In some embodiments, each $R^5$ is independently an unsubstituted alkyl. In some embodiments, each $R^5$ is independently a substituted or unsubstituted $C_1$-$C_5$ alkyl. In some embodiments, each $R^5$ is independently a substituted $C_1$-$C_5$ alkyl. In some embodiments, each $R^5$ is independently an unsubstituted $C_1$-$C_5$ alkyl. In some embodiments, each $R^5$ is independently methyl. In some embodiments, each $R^5$ is independently ethyl. In some embodiments, each $R^5$ is independently propyl.

In some embodiments, each $R^5$ is independently a substituted or unsubstituted heteroalkyl. In some embodiments, each $R^5$ is independently a substituted heteroalkyl. In some embodiments, each $R^5$ is independently an unsubstituted heteroalkyl. In some embodiments, each $R^5$ is independently a substituted or unsubstituted 2 to 6 membered heteroalkyl. In some embodiments, each $R^5$ is independently a substituted 2 to 6 membered heteroalkyl. In some embodiments, each $R^5$ is independently an unsubstituted 2 to 6 membered heteroalkyl.

In some embodiments, each $R^5$ is independently halogen, —$CF_3$, —CN, —$OR^{5A}$, —$COOR^{5A}$, —$NR^{5A}R^{5B}$, $CONR^{5A}R^{5B}$, substituted or unsubstituted alkyl, or substituted or unsubstituted heteroalkyl. In some embodiments, each $R^5$ is independently halogen, —$CF_3$, —$OR^{5A}$, substituted or unsubstituted alkyl, or substituted or unsubstituted heteroalkyl. In some such embodiments, $R^{5A}$ and $R^{5B}$ are independently hydrogen, substituted or unsubstituted $C_1$-$C_5$ alkyl, or substituted or unsubstituted aryl (e.g. phenyl).

In some embodiments, each $R^5$ is independently halogen, —$CF_3$, —OH, —$NH_2$, —$OCH_3$, or methyl. In some embodiments, each $R^5$ is independently halogen, —$CF_3$, —$OCH_3$, or methyl where z1 is 1, 2, or 3. In some embodiments, z1 is 1. In some embodiments, z1 is 2. In some embodiments, z1 is 3. In some embodiments, each $R^5$ is independently halogen. In some embodiments, each $R^5$ is —$C_1$. In some embodiments, each $R^5$ is —F. In some embodiments, each $R^5$ is —Br. In some embodiments, each $R^5$ is —I. In some embodiments, each $R^5$ is independently halogen when z1 is 1, 2, or 3. In some embodiments, each $R^5$ is halogen, —$CF_3$, or —$OR^{5A}$ where $R^5$ is substituted at the Para position. In some embodiments, each $R^5$ is halogen, —$CF_3$, or —$OR^{5A}$ where $R^5$ is only substituted at the Para position.

In some embodiments, each $R^5$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)$NHNH_2$, substituted or unsubstituted alkyl (e.g. $C_1$ to $C_8$ alkyl), substituted or unsubstituted heteroalkyl (e.g. 2 to 8 membered heteroalkyl), substituted or unsubstituted cycloalkyl (e.g. $C_3$-$C_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl).

In some embodiments, each $R^5$ is independently hydrogen, halogen, —$CF_3$, —CN, —OH, —$NH_2$, —COOH, —CONH$_2$, —NO$_2$, —SH, —SO$_2$NH$_2$, substituted or unsubstituted alkyl (e.g. C$_1$ to C$_8$ alkyl), substituted or unsubstituted heteroalkyl (e.g. 2 to 8 membered heteroalkyl), substituted or unsubstituted cycloalkyl (e.g. C$_3$-C$_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl).

In some embodiments, each R$^5$ is independently hydrogen, halogen, —CF$_3$, —CN, —OR$^{5A}$, —NR$^{5A}$R$^{5B}$, —CONH$_2$, —SH, —SO$_2$NH$_2$, substituted or unsubstituted alkyl (e.g. C$_1$ to C$_8$ alkyl), substituted or unsubstituted heteroalkyl (e.g. 2 to 8 membered heteroalkyl), substituted or unsubstituted cycloalkyl (e.g. C$_3$-C$_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl). In some such embodiments, R$^{5A}$ and R$^{5A}$ are independently hydrogen, substituted or unsubstituted alkyl, or substituted or unsubstituted aryl.

In some embodiments, each R$^6$ and R$^7$ are independently a substituted or unsubstituted C$_1$-C$_5$ alkyl. In some embodiments, R$^6$ and R$^7$ are independently substituted C$_1$-C$_5$ alkyl. In some embodiments, R$^6$ and R$^7$ are independently unsubstituted C$_1$-C$_5$ alkyl. In some embodiments, R$^6$ and R$^7$ are independently methyl, ethyl, or propyl. In some embodiments, R$^6$ and R$^7$ are methyl. In some embodiments, R$^6$ and R$^7$ are ethyl. In some embodiments, R$^6$ and R$^7$ are propyl.

In some embodiments, R$^{1A}$, R$^{2A}$, R$^{3A}$, R$^{3B}$, R$^{4A}$, R$^{4B}$, R$^{5A}$, and R$^{5B}$ are independently hydrogen, halogen, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl (e.g. C$_1$ to C$_8$ alkyl), substituted or unsubstituted heteroalkyl (e.g. 2 to 8 membered heteroalkyl), substituted or unsubstituted cycloalkyl (e.g. C$_3$-C$_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl).

In some embodiments, R$^{1A}$, R$^{2A}$, R$^{3A}$, R$^{3B}$, R$^{4A}$, R$^{4B}$, R$^{5A}$, and R$^{5B}$ are independently hydrogen, —OH, —NH$_2$, substituted or unsubstituted alkyl (e.g. C$_1$ to C$_8$ alkyl), substituted or unsubstituted heteroalkyl (e.g. 2 to 8 membered heteroalkyl), substituted or unsubstituted cycloalkyl (e.g. C$_3$-C$_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl). In some embodiments, R$^{1A}$, R$^{2A}$, R$^{3A}$, R$^{3B}$, R$^{4A}$, R$^{4B}$, R$^{5A}$, and R$^{5B}$ are independently hydrogen, substituted or unsubstituted alkyl (e.g. C$_1$ to C$_8$ alkyl), substituted or unsubstituted heteroalkyl (e.g. 2 to 8 membered heteroalkyl), substituted or unsubstituted cycloalkyl (e.g. C$_3$-C$_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl).

In some embodiments, the compound of Formula (A) or Formula (I) is a compound selected from:

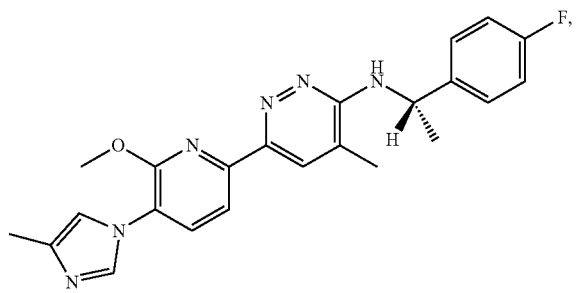

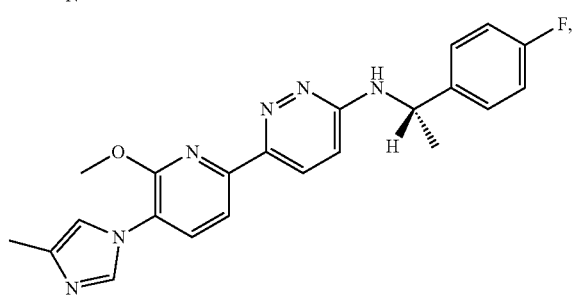

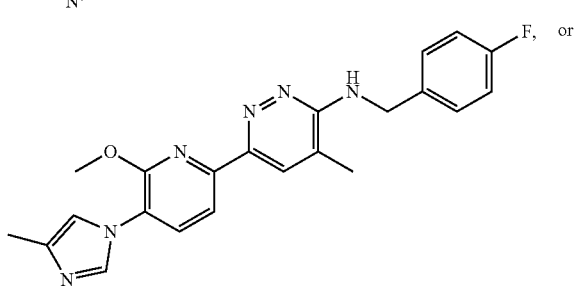

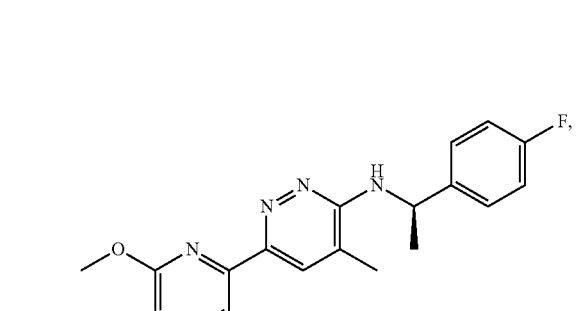

or a pharmaceutically acceptable salt thereof.

In some embodiments, the compound of Formula (A) or Formula (I) may have the formula:

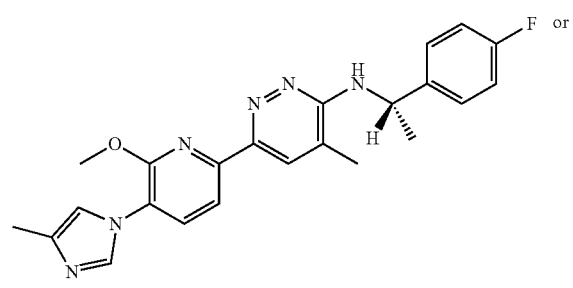

-continued

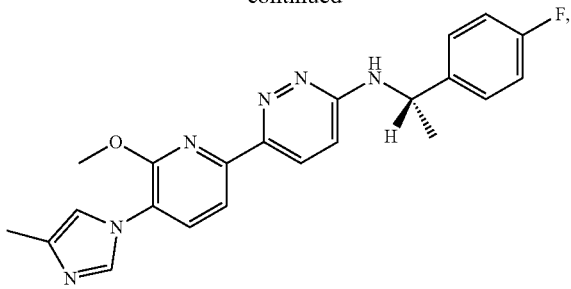

or a pharmaceutically acceptable salt thereof.

In some embodiments, the compound of Formula (A) or Formula (I) may have the formula:

(Compound 1)

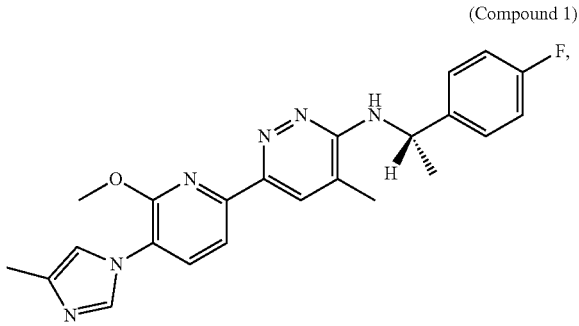 [SMILES: COc1nc(-c2cc(C)c(N[C@@H](C)c3ccc(F)cc3)nn2)ccc1-n1cnc(C)c1]

or a pharmaceutically acceptable salt thereof.

In some embodiments, the compound of Formula (A) or Formula (I) may have the formula:

(Compound 2)

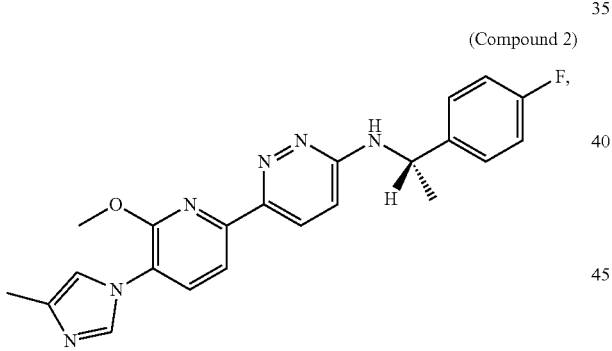

or a pharmaceutically acceptable salt thereof.

In some embodiments, the compound of Formula (A) or Formula (I) may have the formula:

(Compound 3)

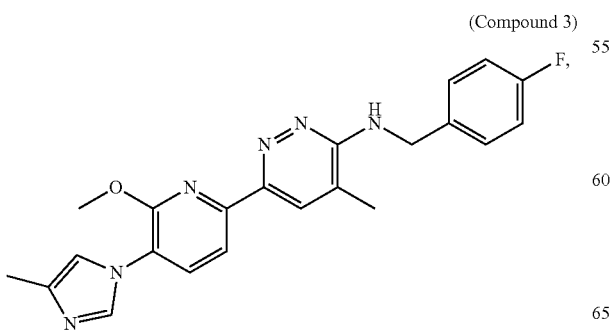

or a pharmaceutically acceptable salt thereof.

In some embodiments, the compound of Formula (A) or Formula (I) may have the formula:

(Compound 4)

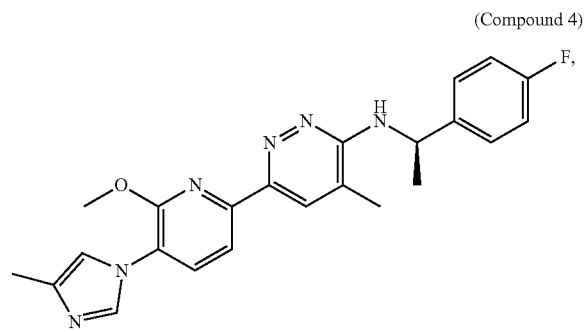 [SMILES: COc1nc(-c2cc(C)c(N[C@H](C)c3ccc(F)cc3)nn2)ccc1-n1cnc(C)c1]

or a pharmaceutically acceptable salt thereof.

In some embodiments, the compound of Formula (A) or Formula (I) may have the formula:

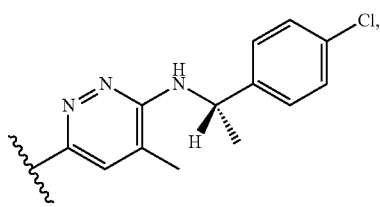

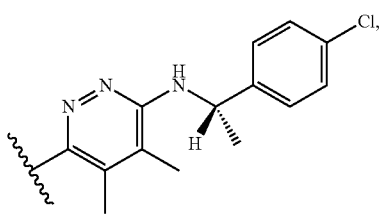

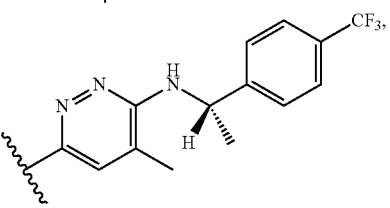

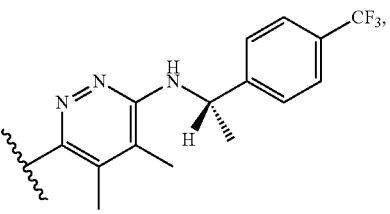

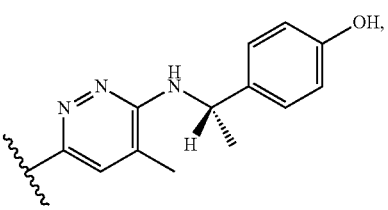

-continued
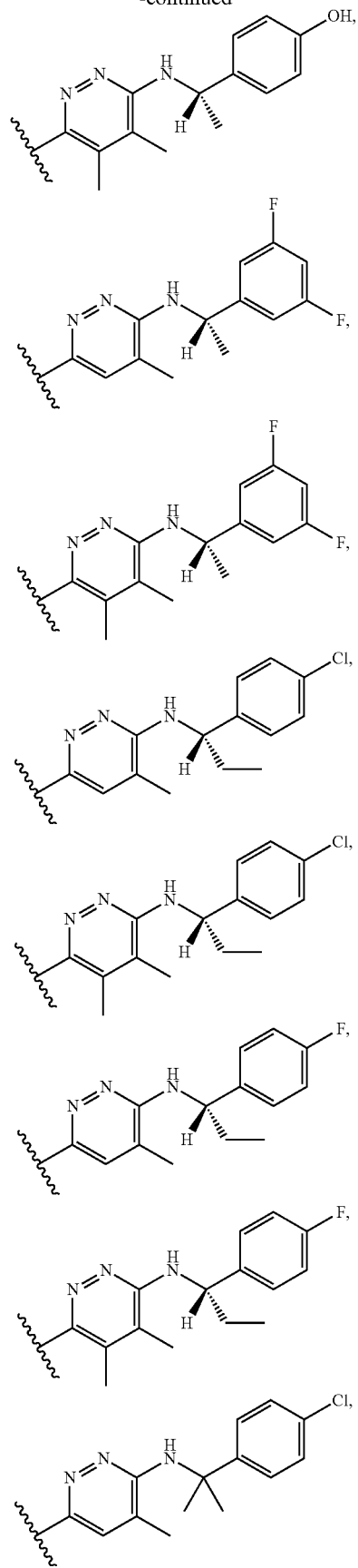
-continued
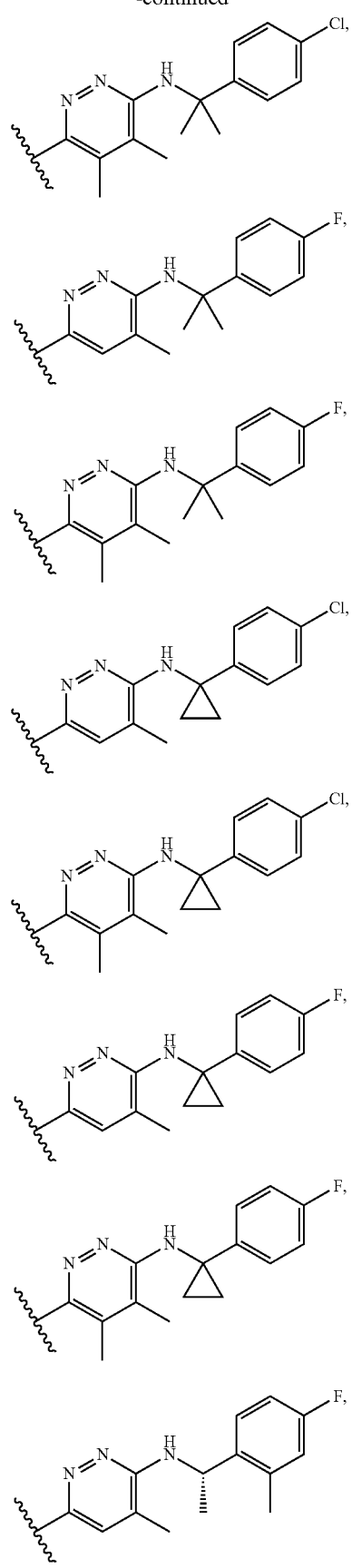

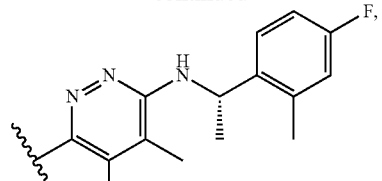
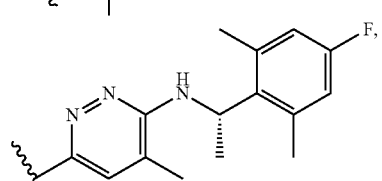
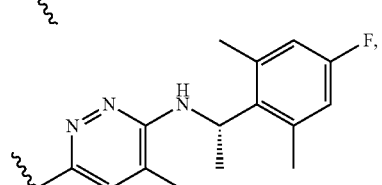
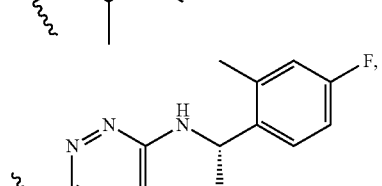
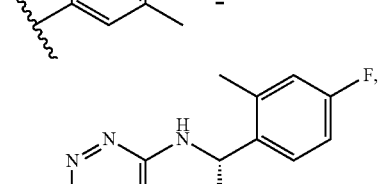
or a pharmaceutically acceptable salt thereof, wherein
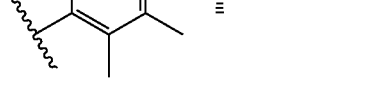 is 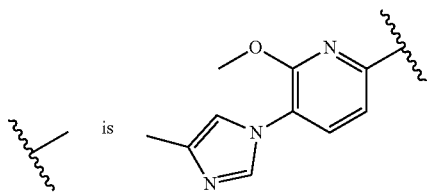
in the structures above.
In some embodiments, the compound of Formula (A) or Formula (I) may have the formula:
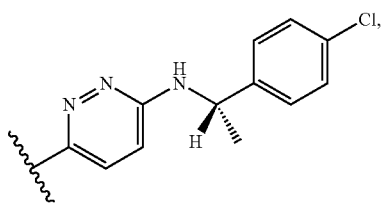
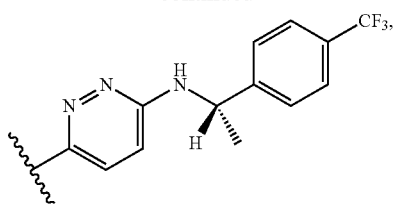
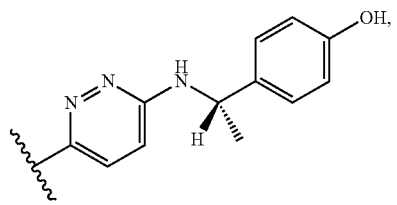
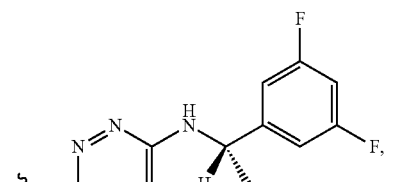
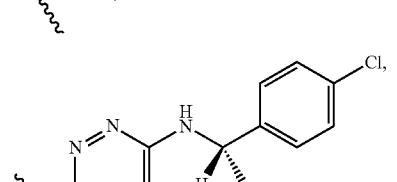
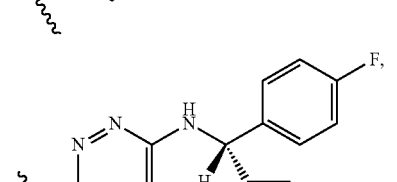
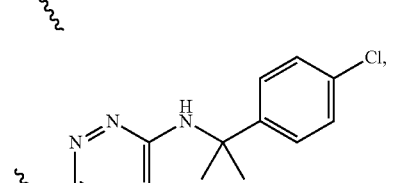
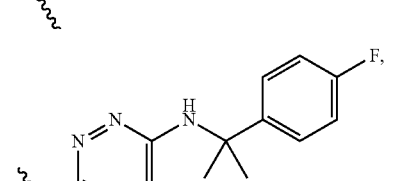
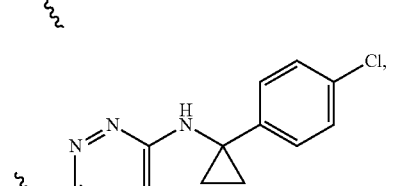

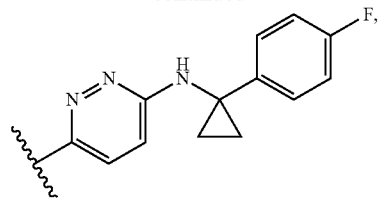
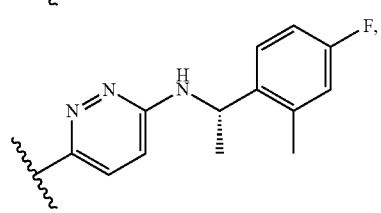
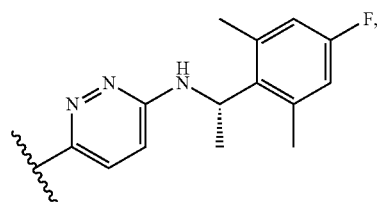
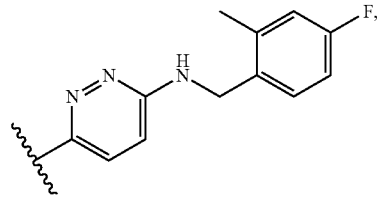
or a pharmaceutically acceptable salt thereof, wherein
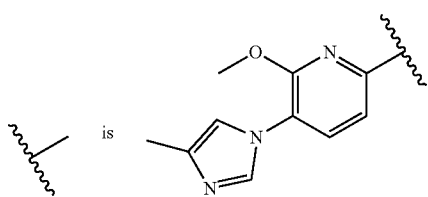
in the structures above.
In some embodiments, the compound of Formula (A) or Formula (I) may have the formula:
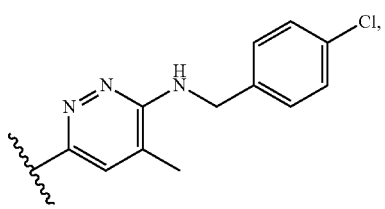
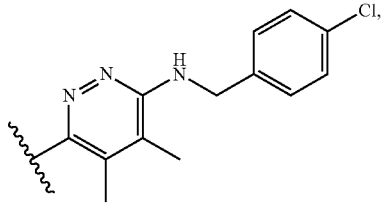
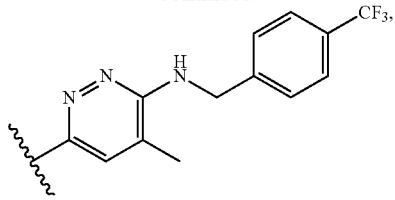
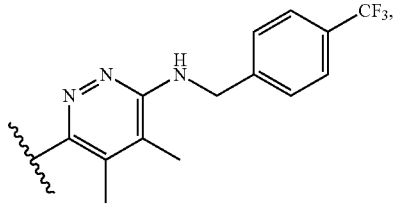
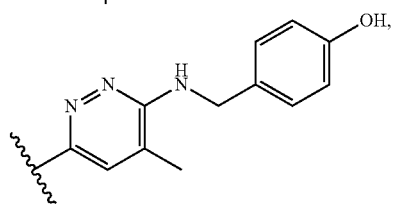
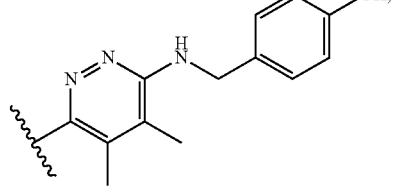
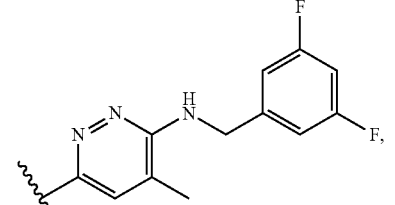
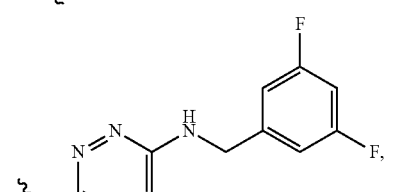
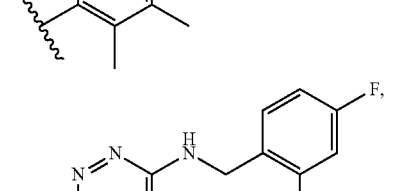
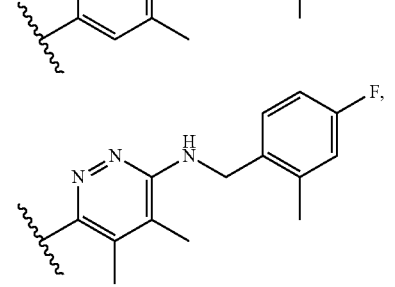

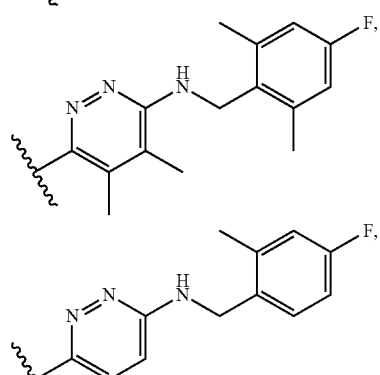
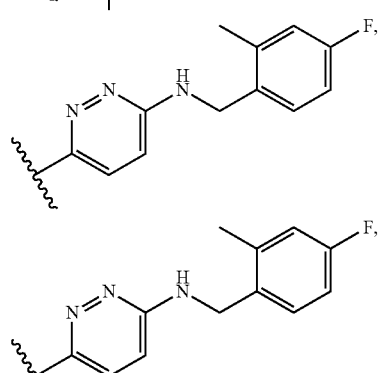
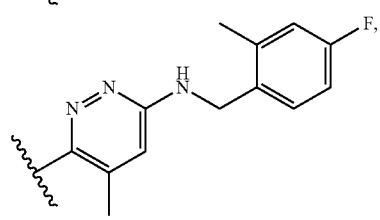
or a pharmaceutically acceptable salt thereof, wherein
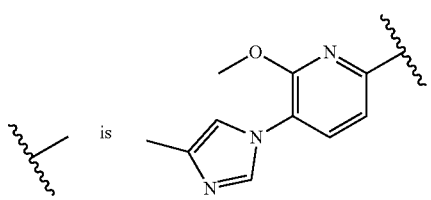
in the structures above.
In some embodiments, the compound of Formula (A) or Formula (I) may have the formula:
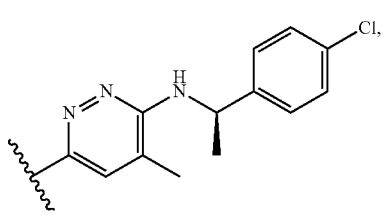
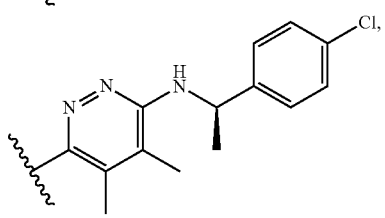
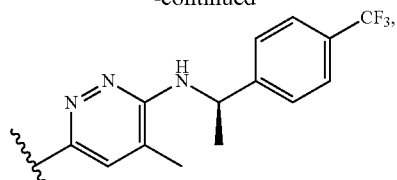
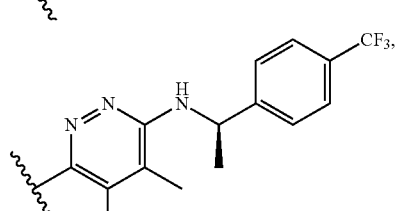
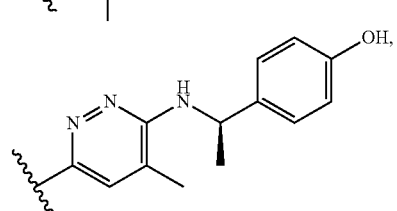
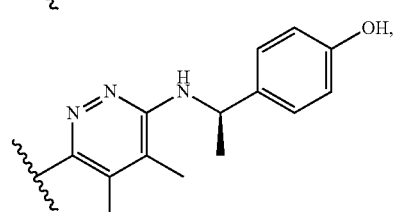
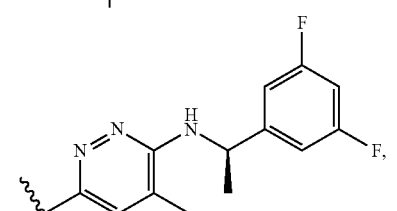
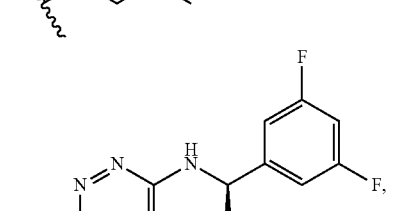
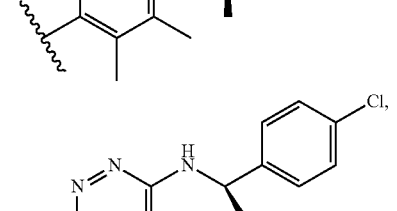
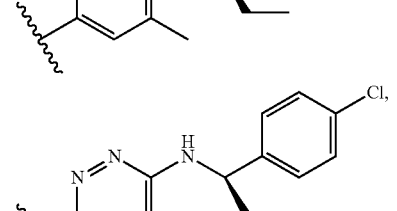

-continued
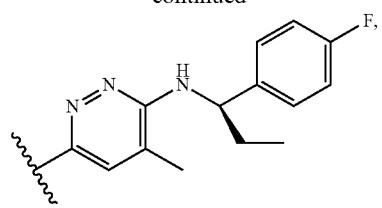
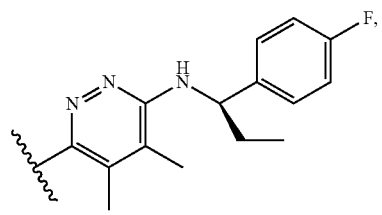
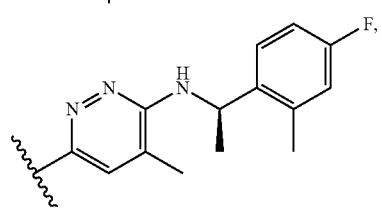
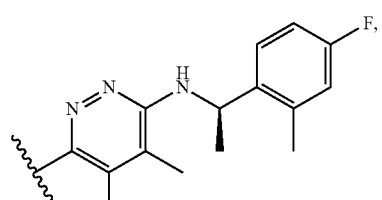
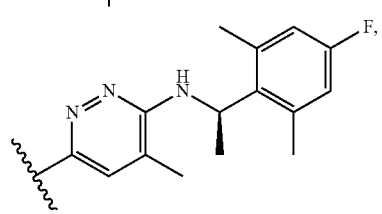
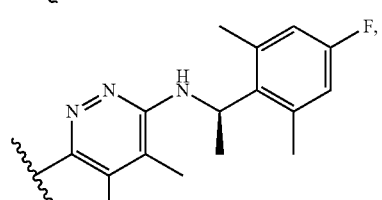
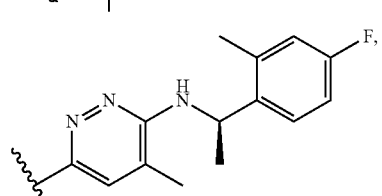
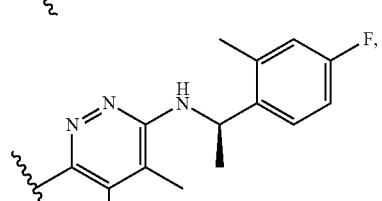
or a pharmaceutically acceptable salt thereof, wherein
 is 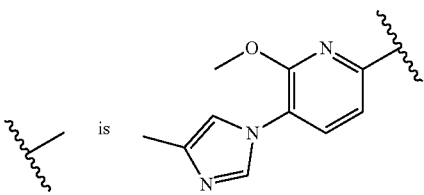
in the structures above.
In some embodiments, the compound of formula (A) are selected from the group consisting of:
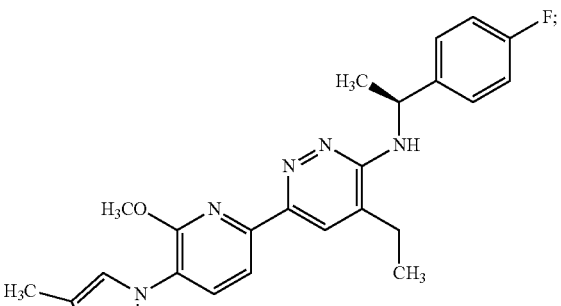
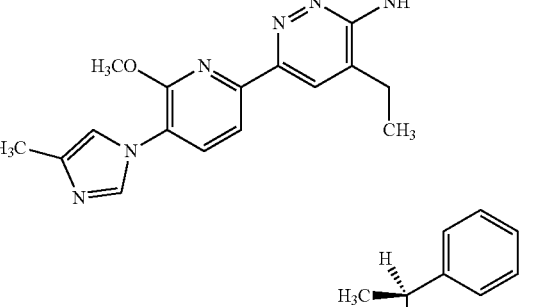
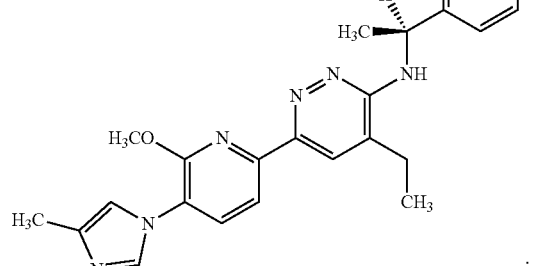
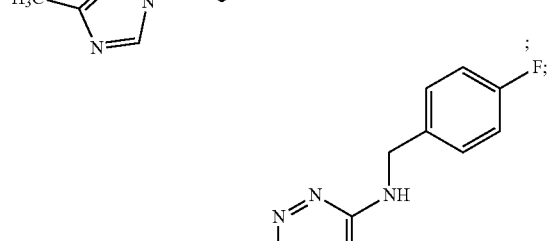
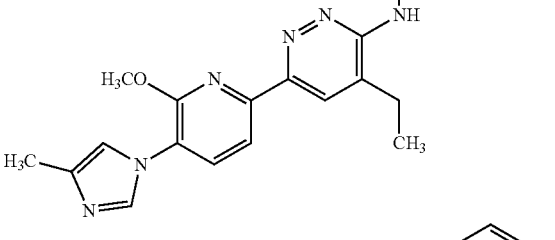
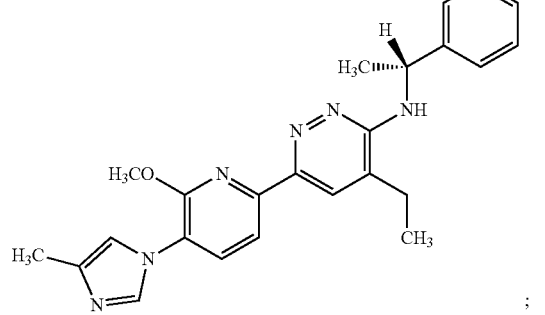
;

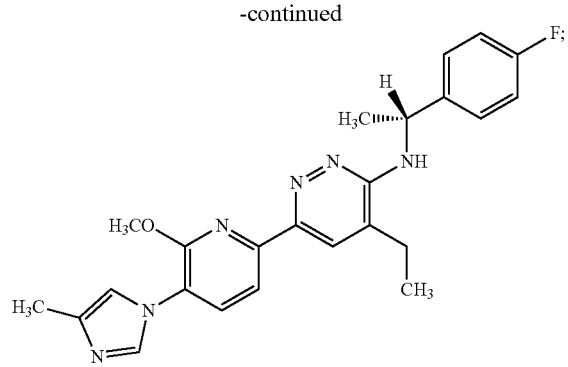
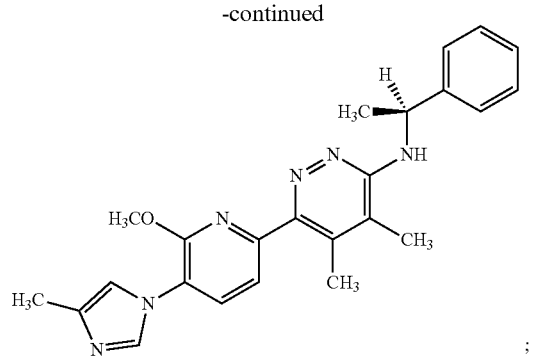

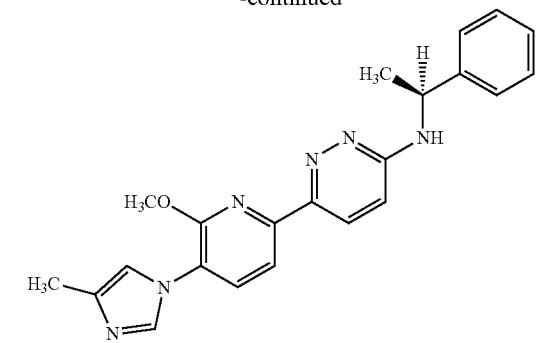
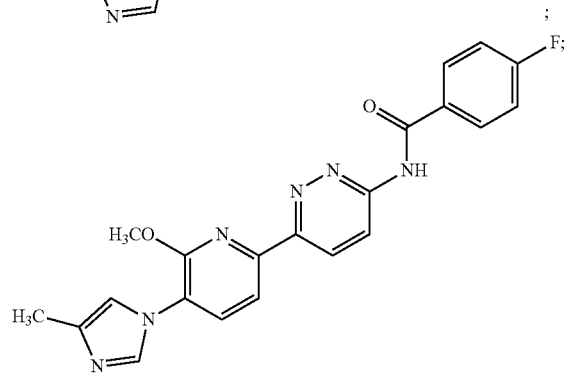
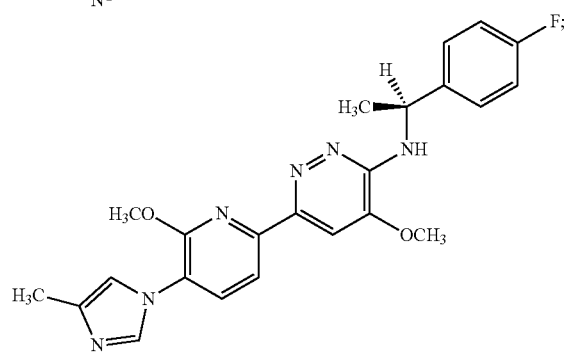
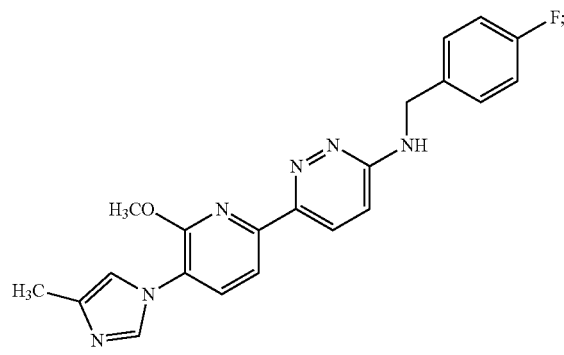
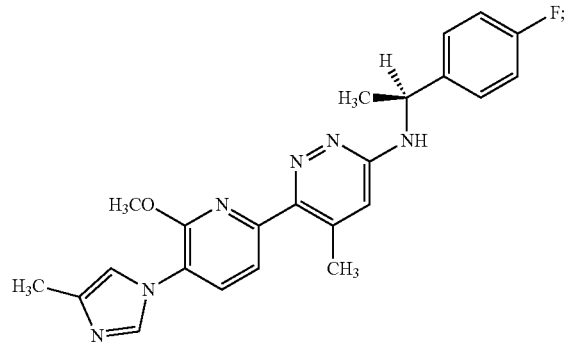
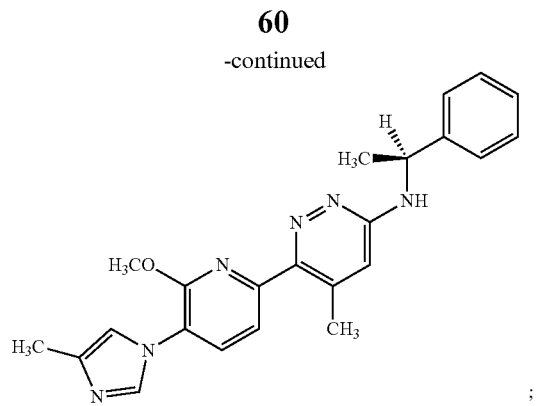
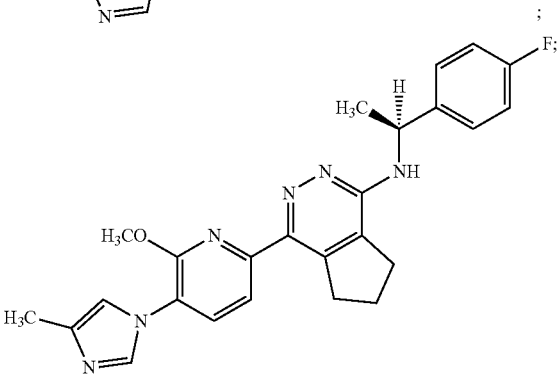
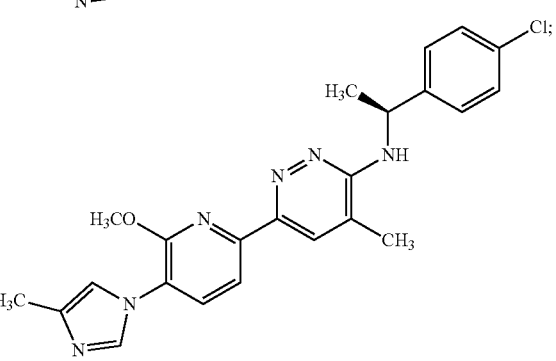
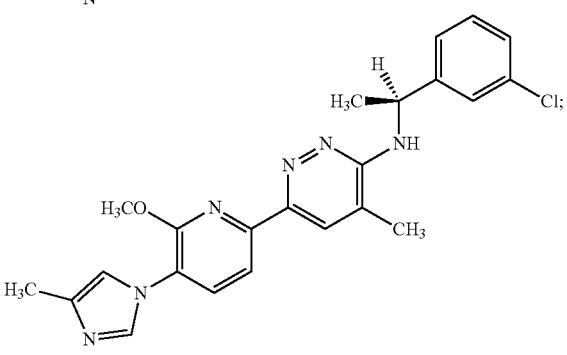
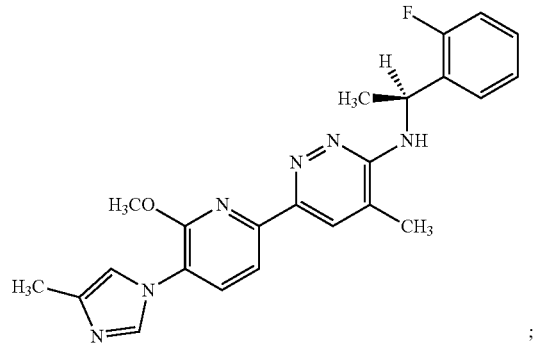

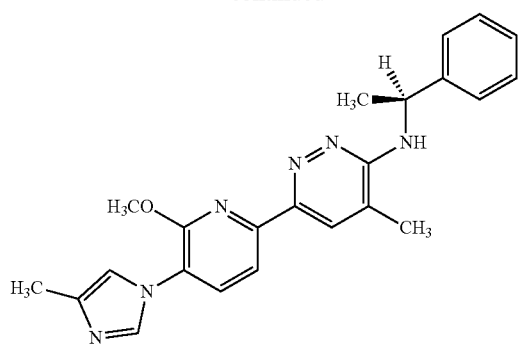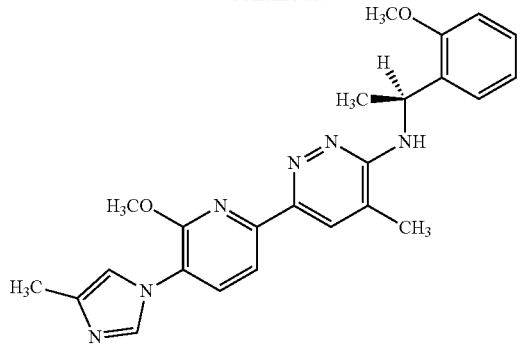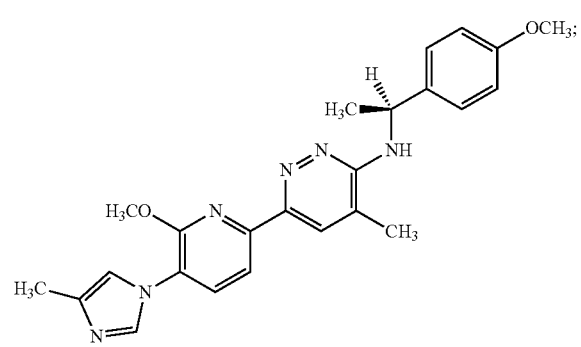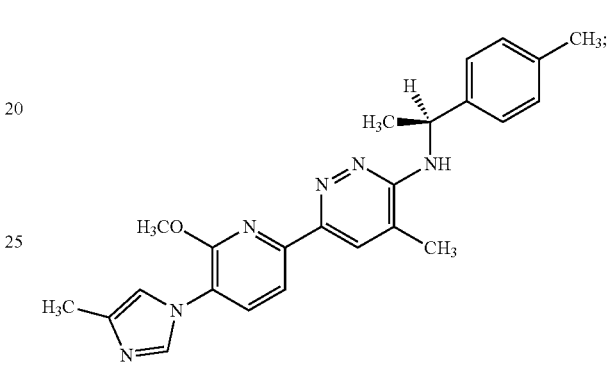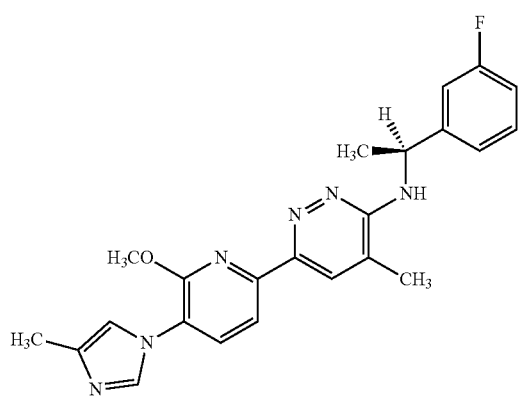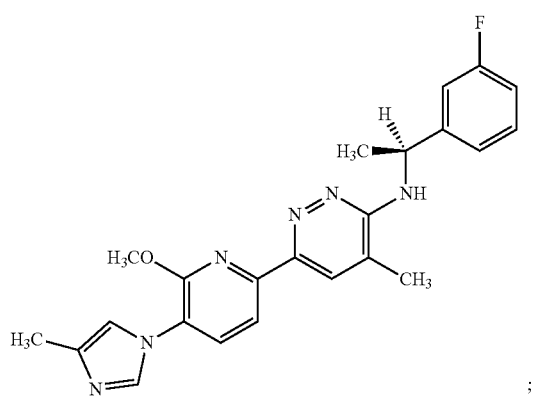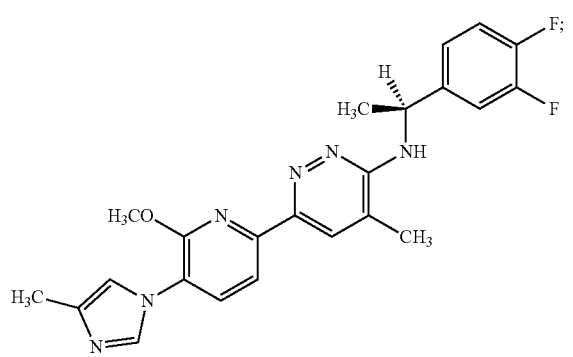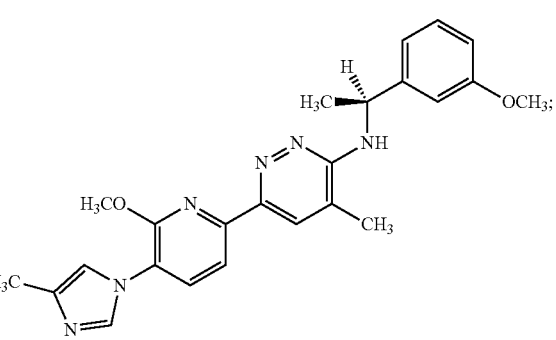

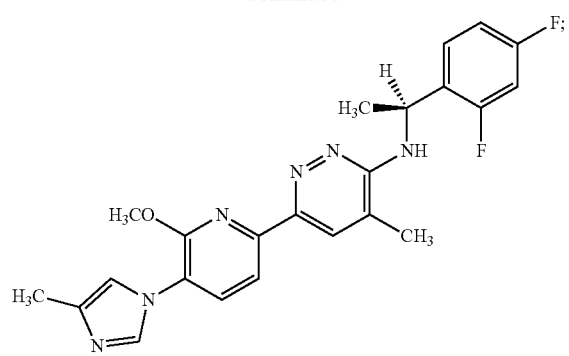
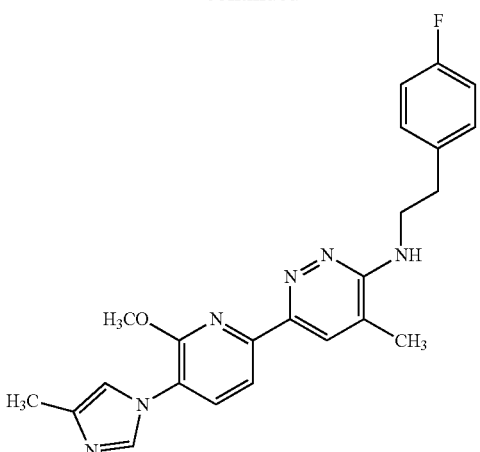
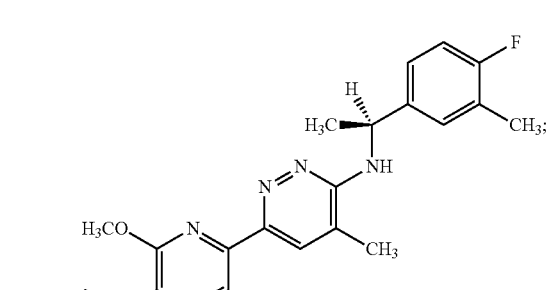
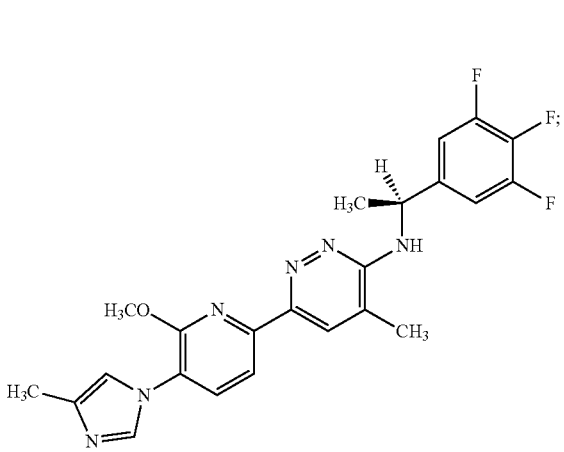
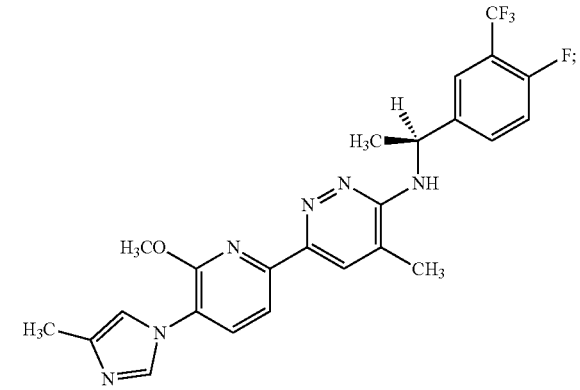

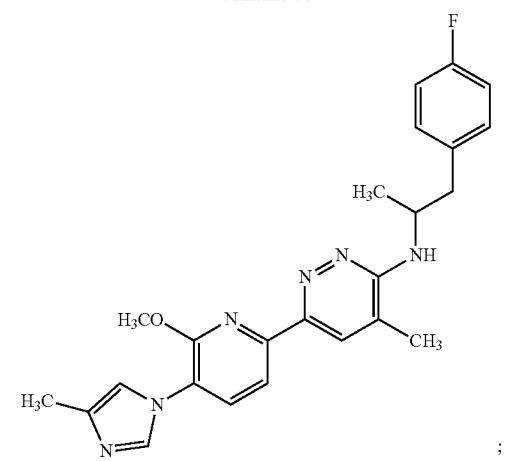
;
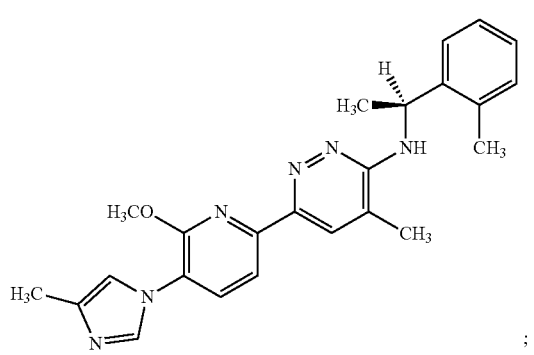
;
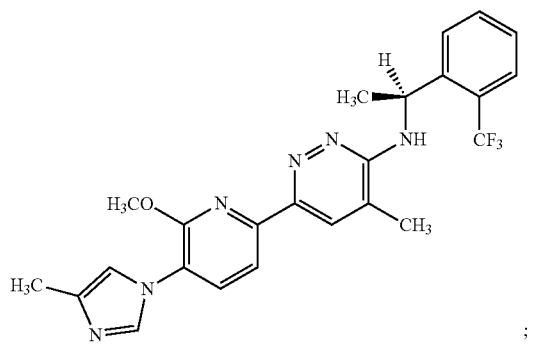
;
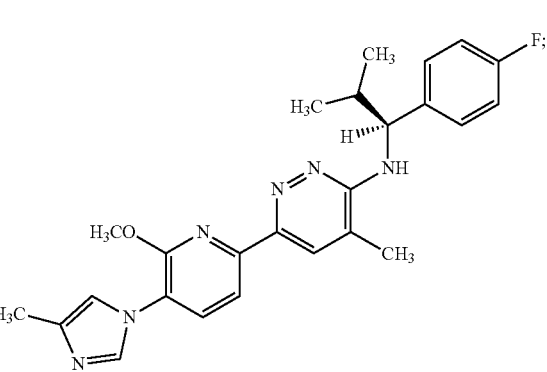
;
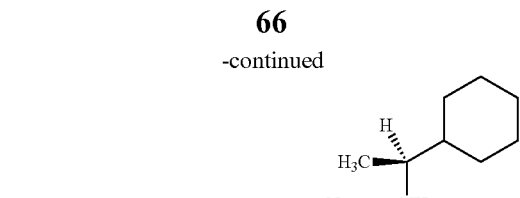
;
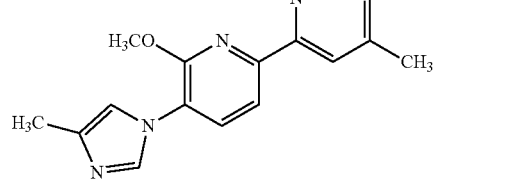
;
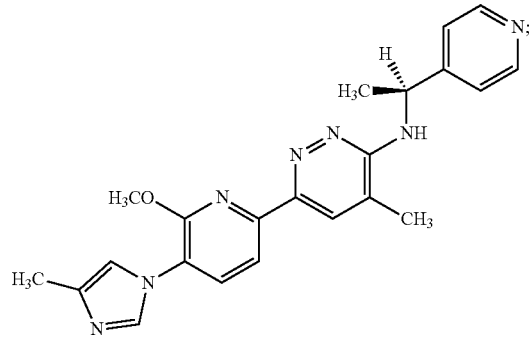
;
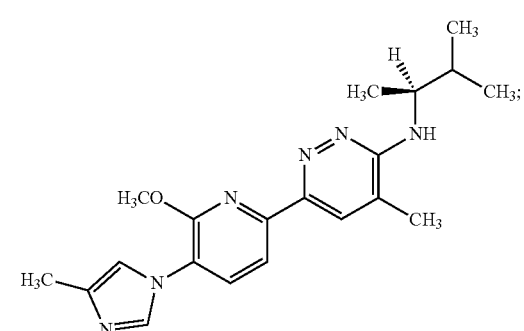
;
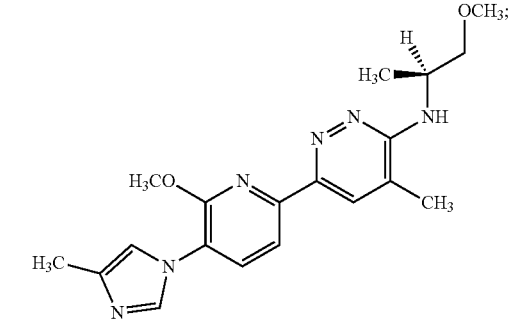
;
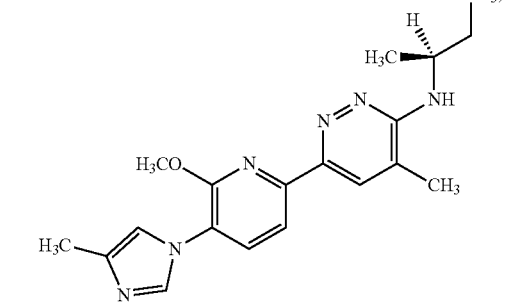
;

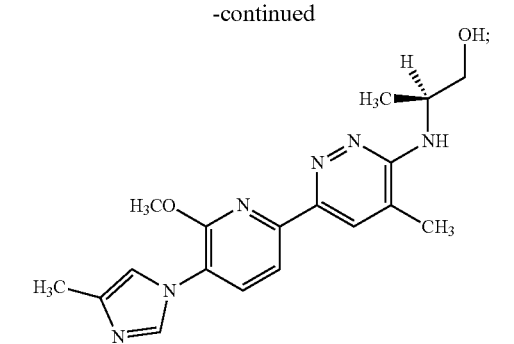
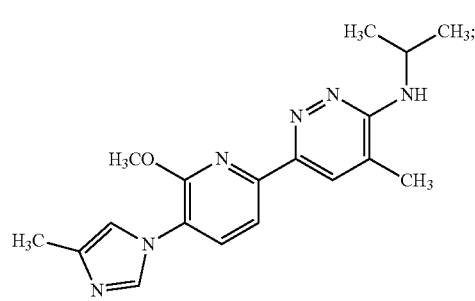
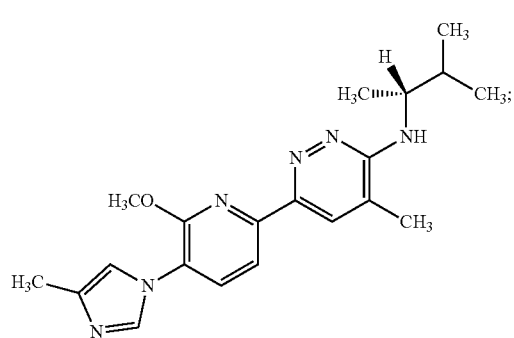
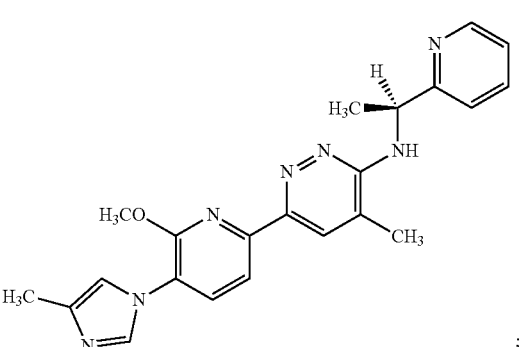
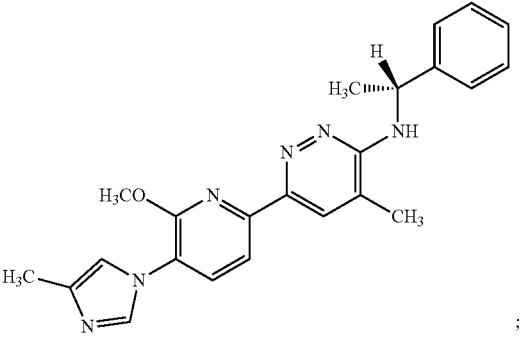
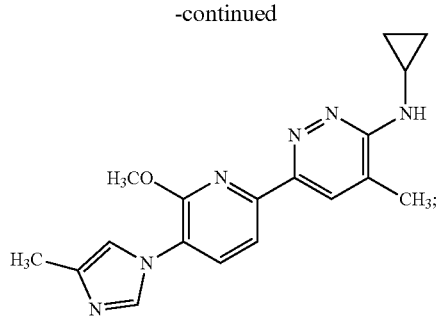
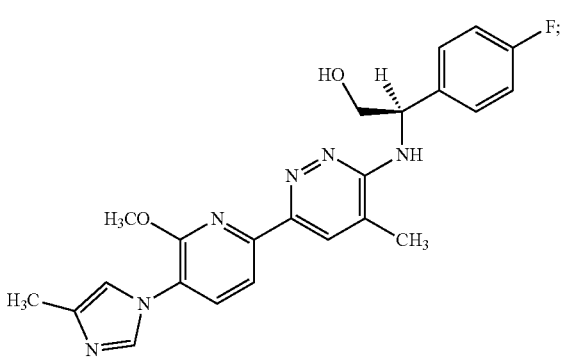
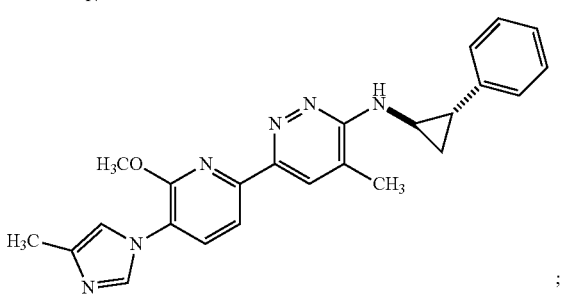
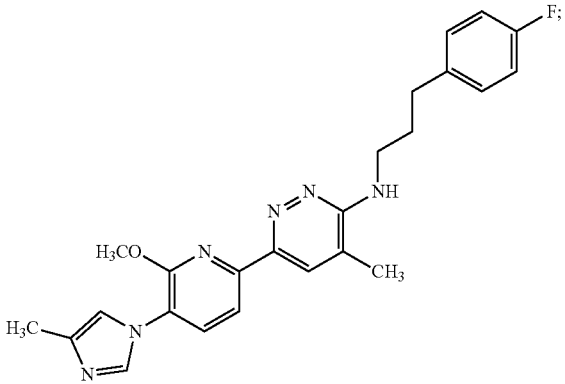
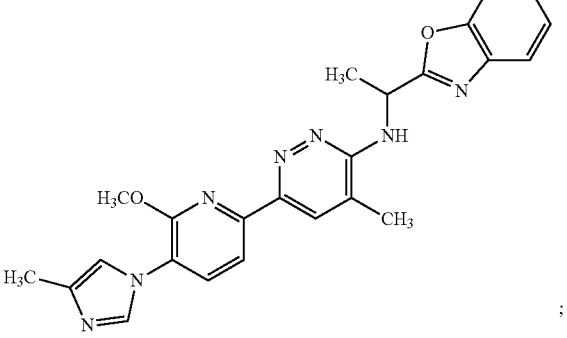

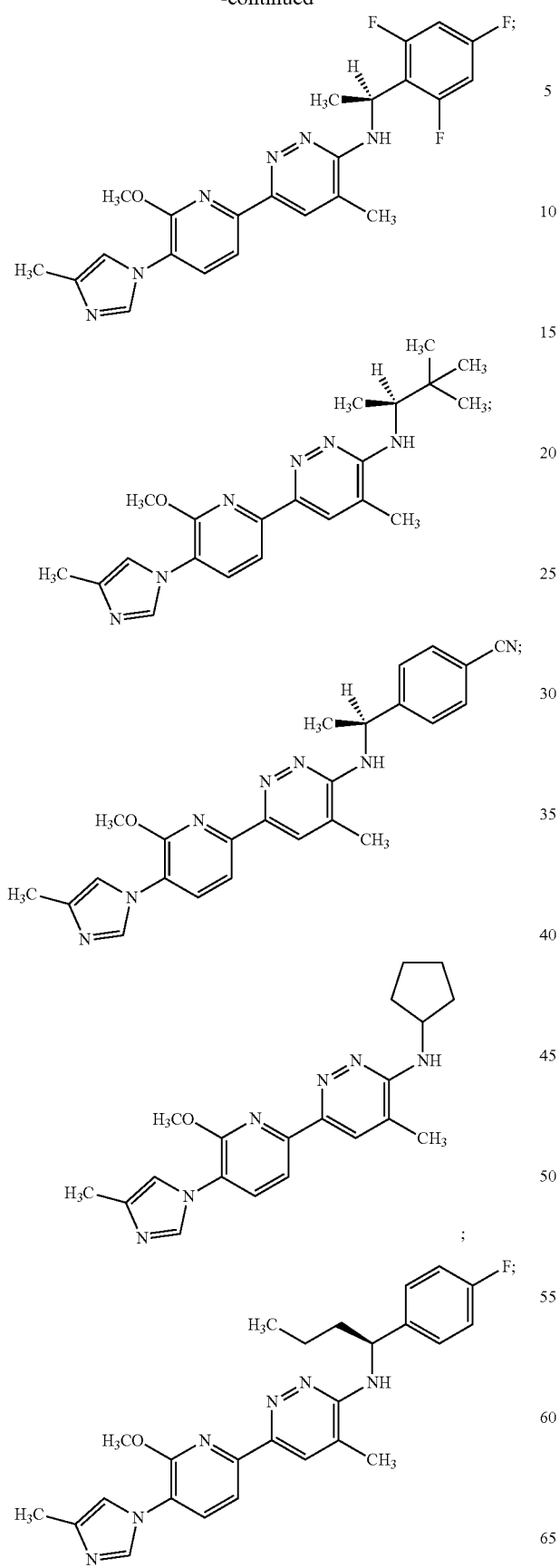
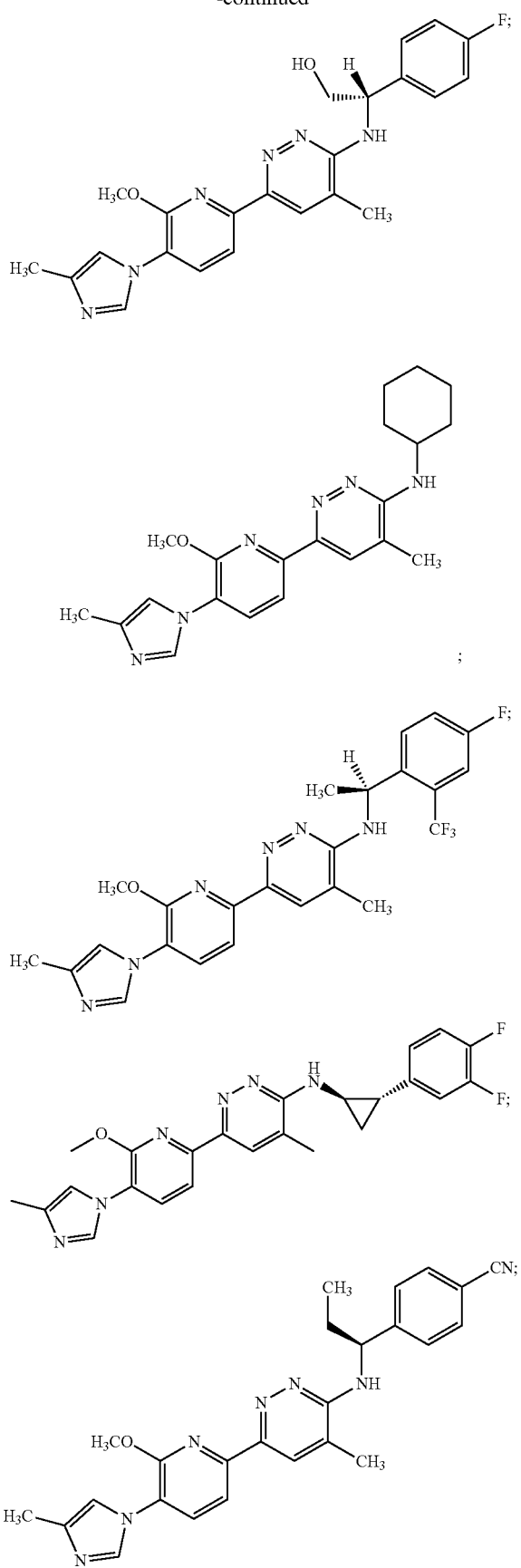

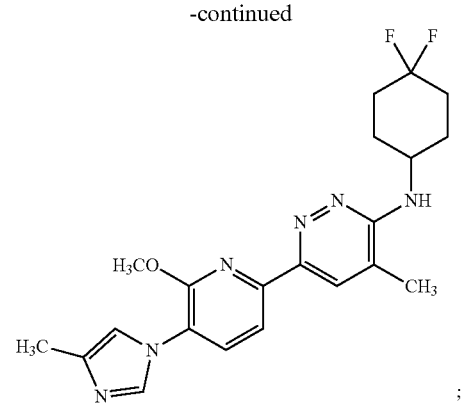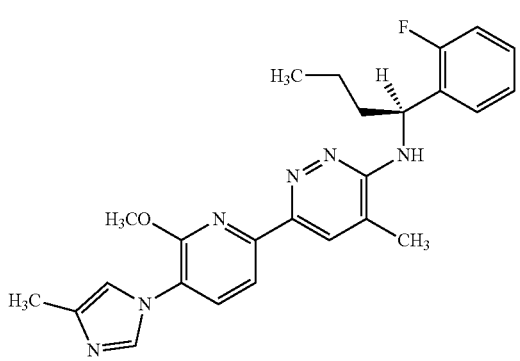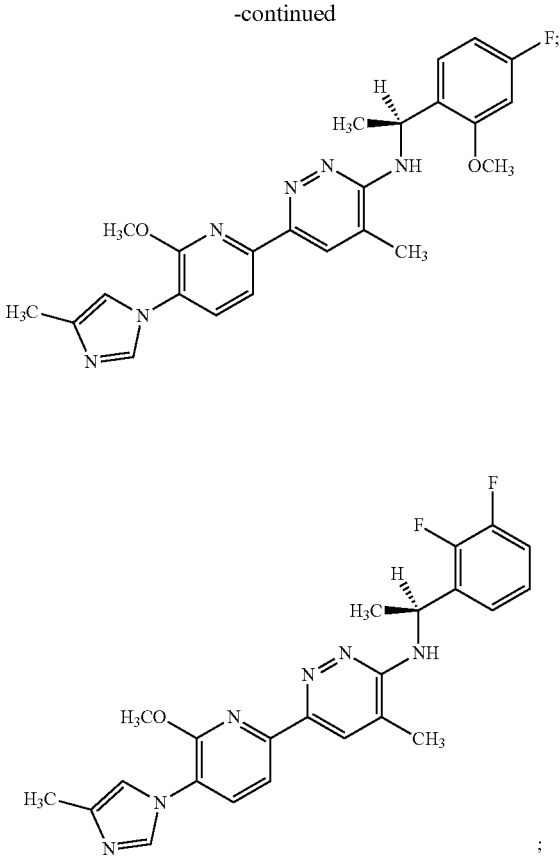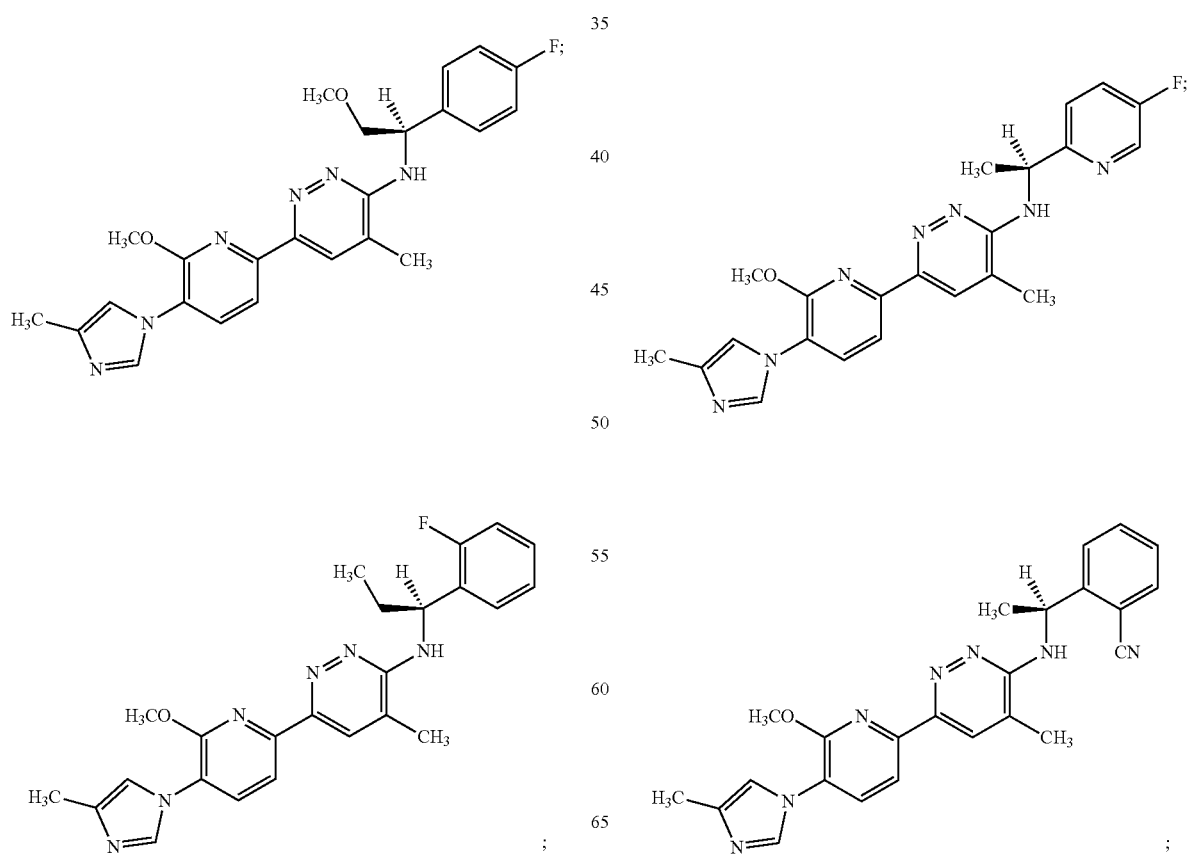

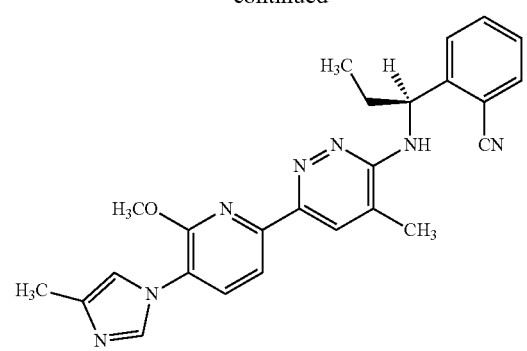
;
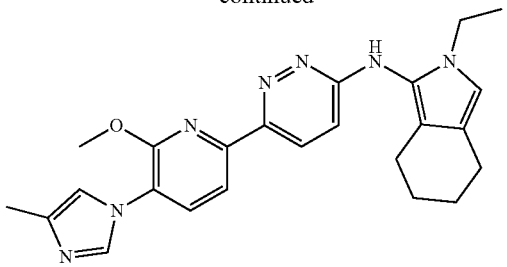
;
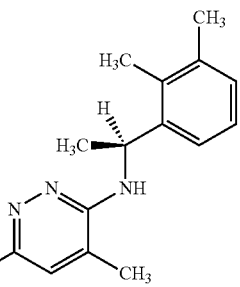
;
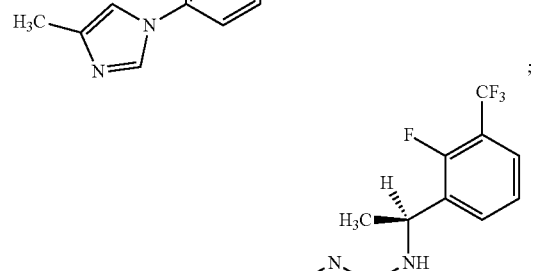
;
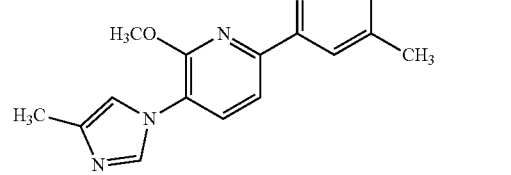
;
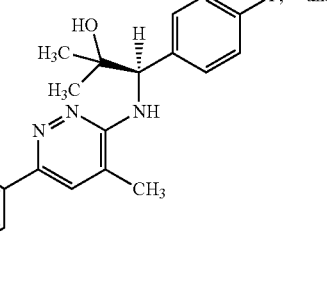
; and
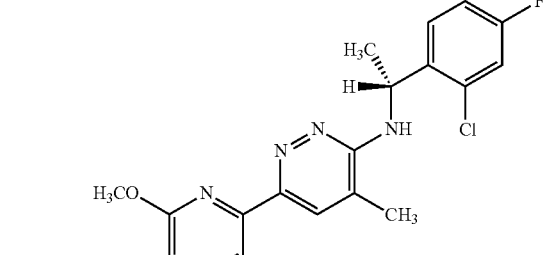
or a pharmaceutically acceptable salt thereof.

In some embodiments, the compound of formula (A) are having the following formula:
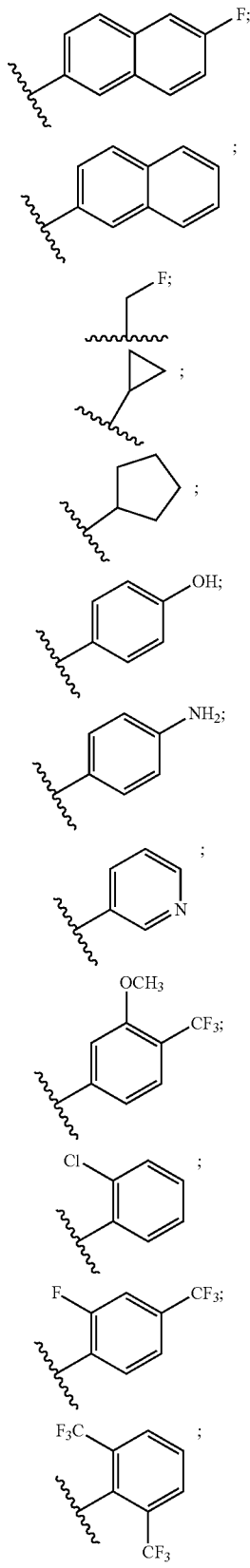
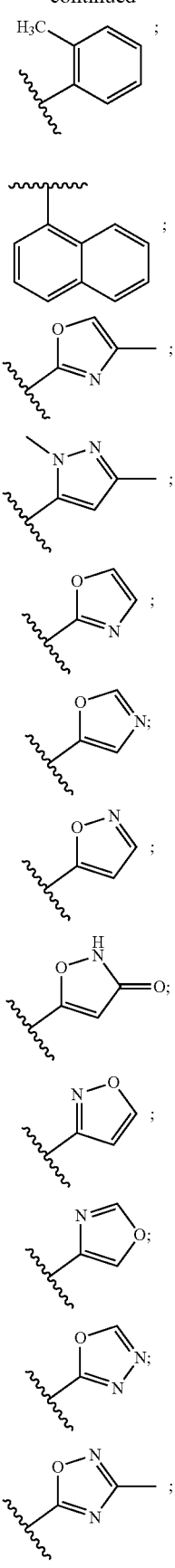

-continued
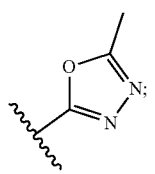
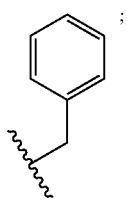
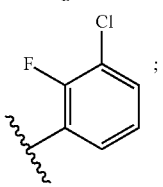
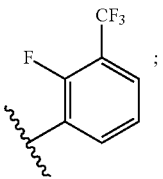
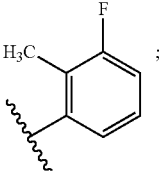
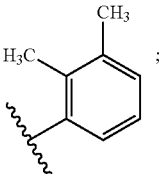
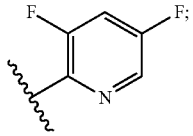
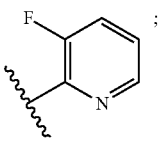
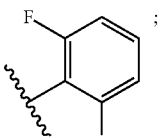
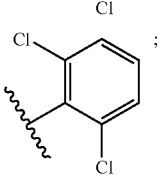
-continued
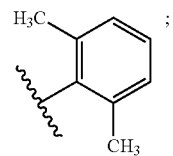
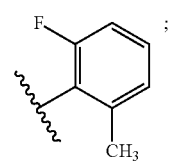
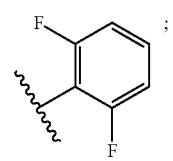
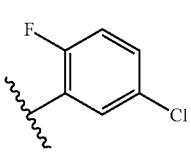
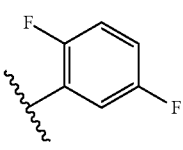
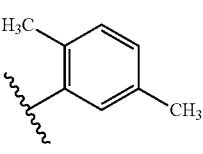
or a pharmaceutically acceptable salt thereof; wherein
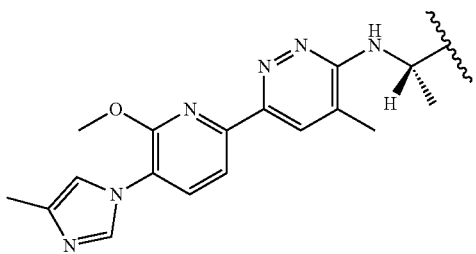
in the structures above.

In some embodiments, the compound of formula (A) are selected from the group consisting of:
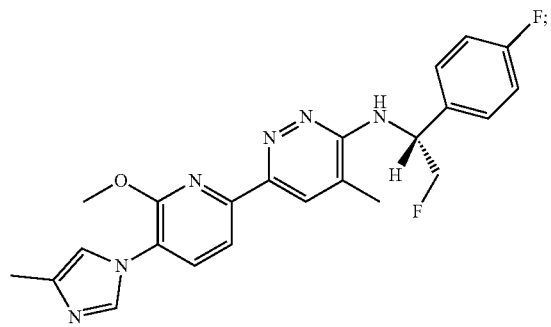
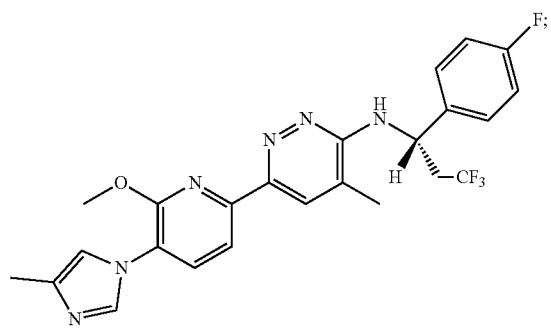
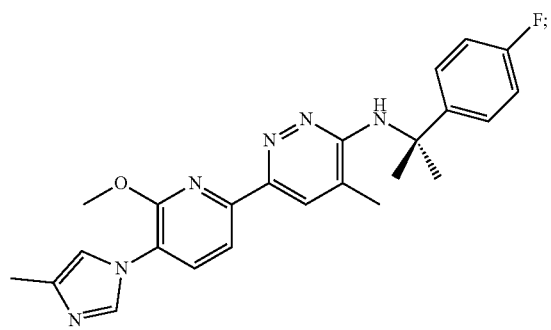
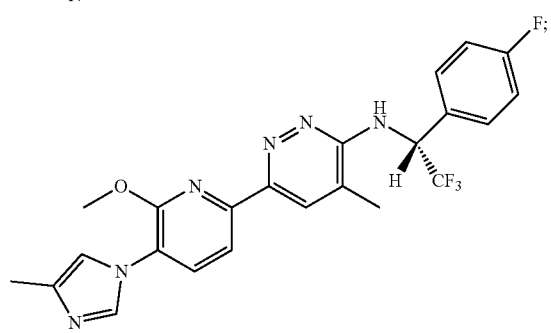
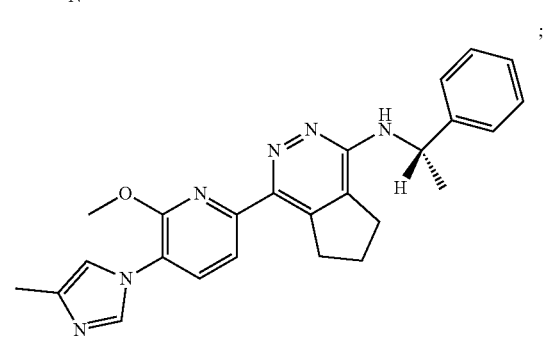
-continued
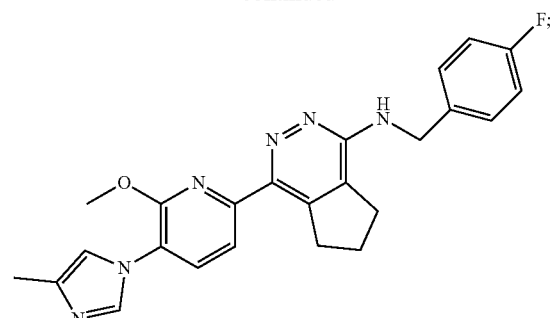
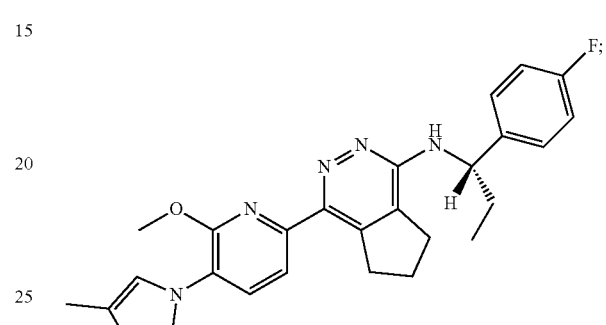
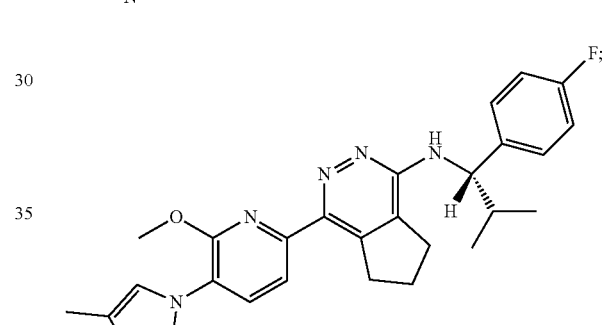
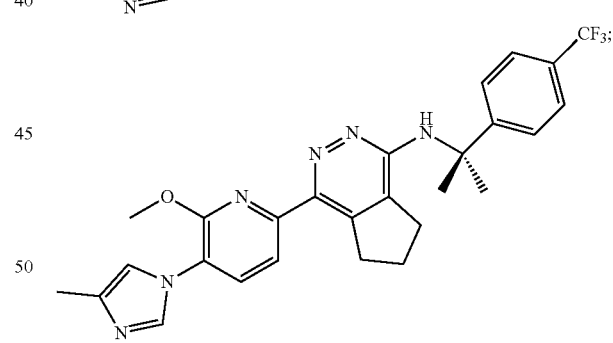
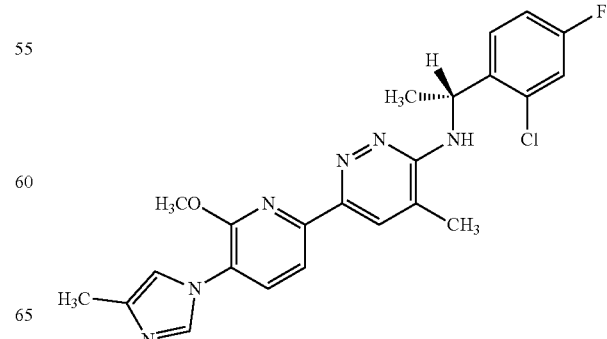

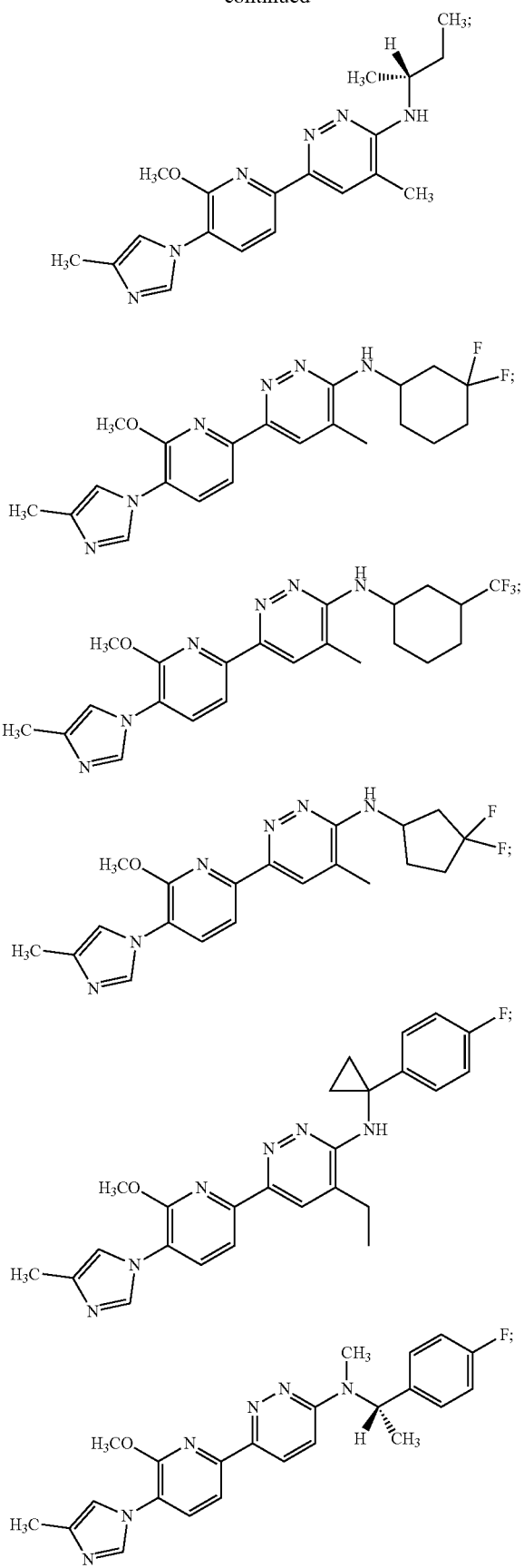
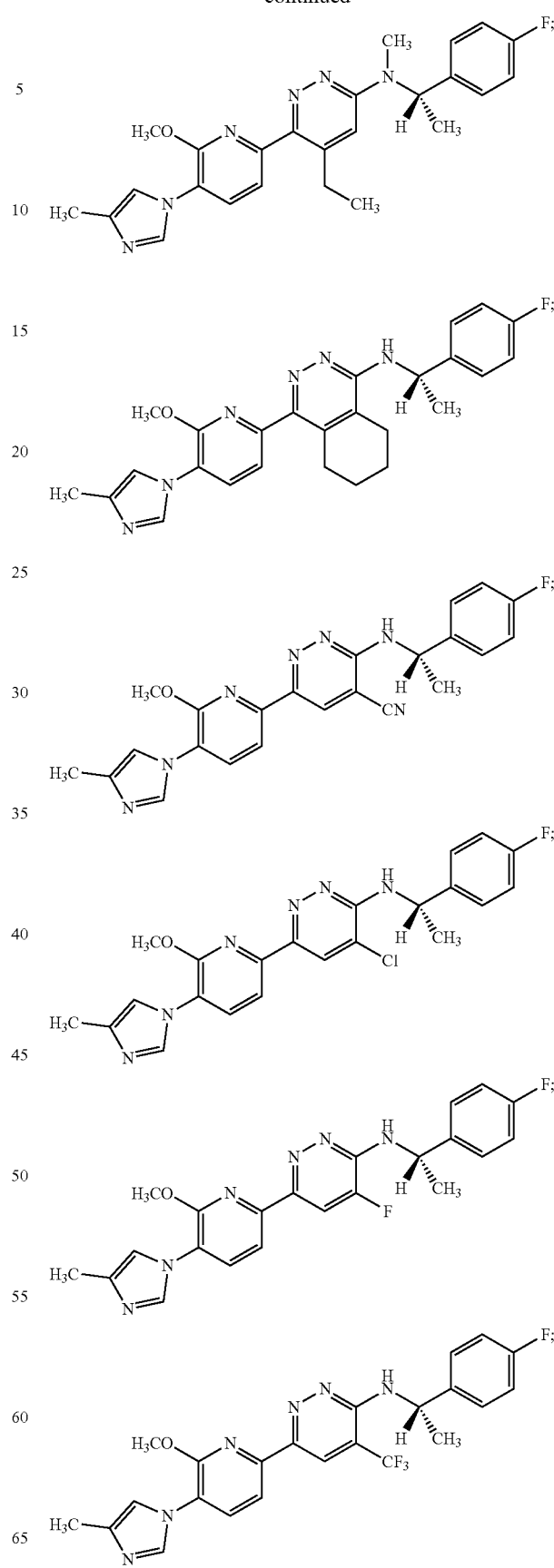

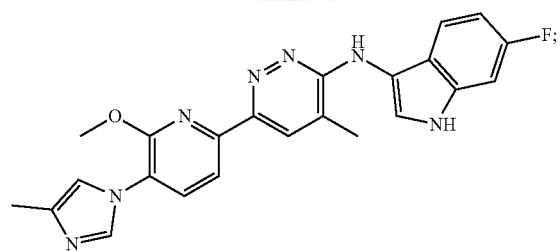
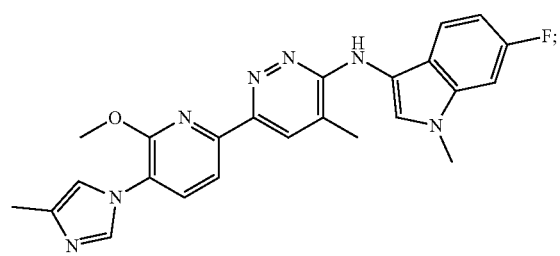
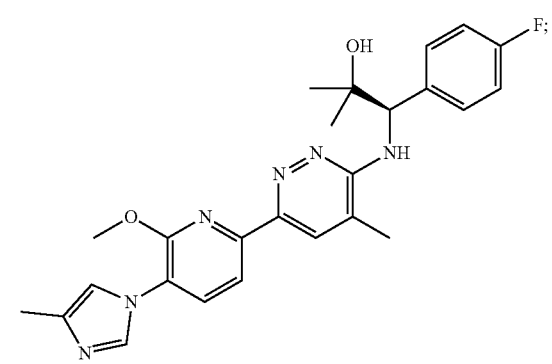
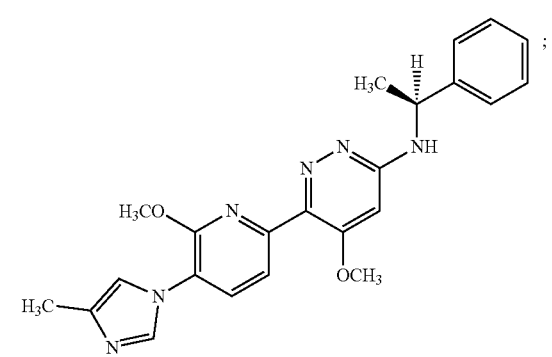
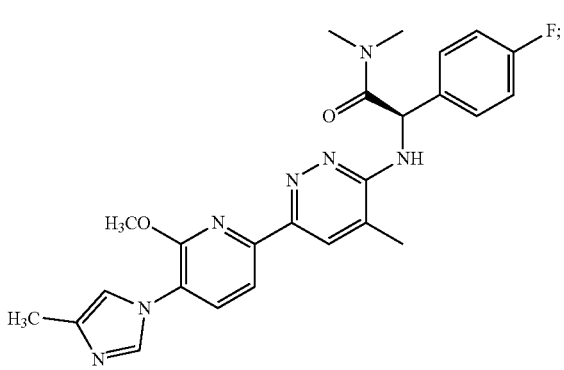
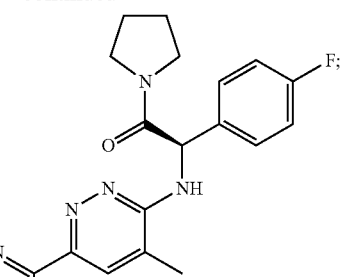
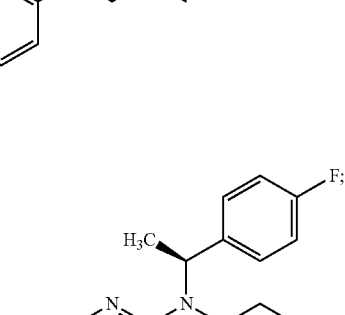
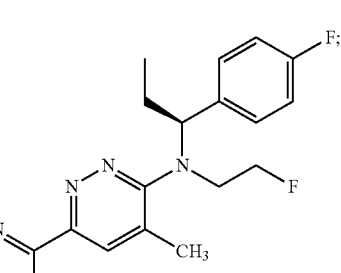
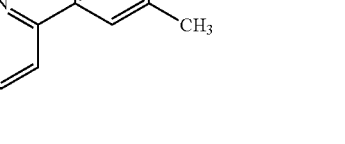
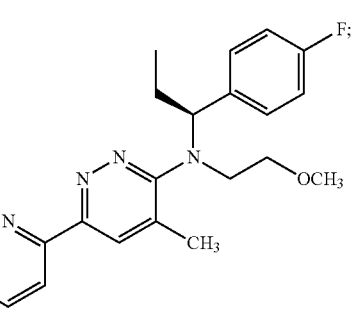

-continued

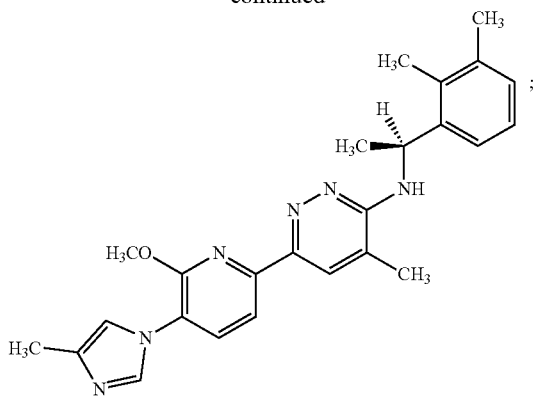

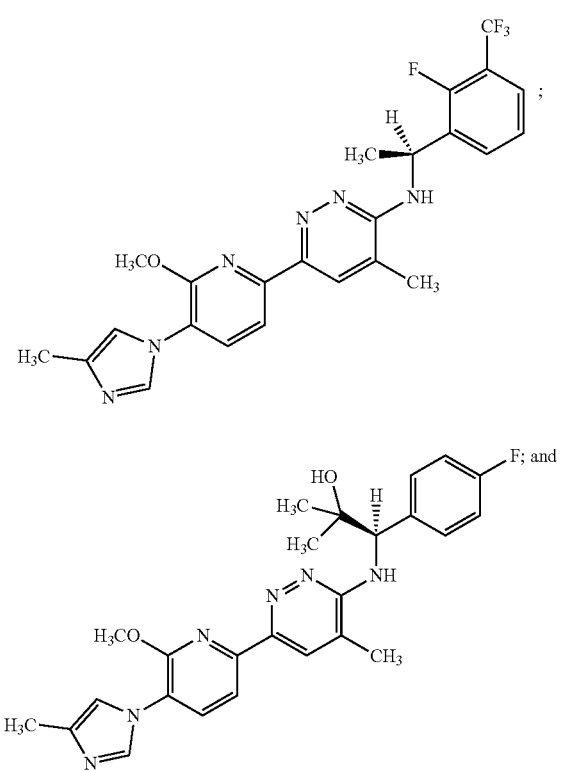

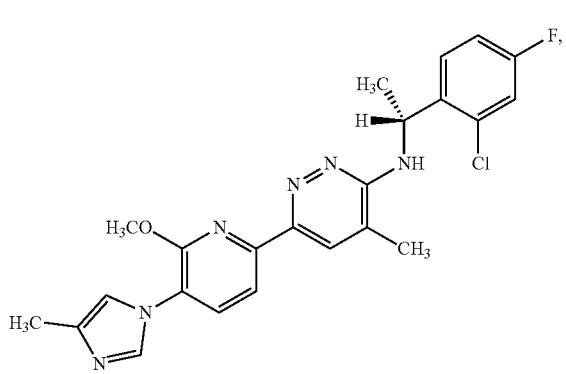

or a pharmaceutically acceptable salt thereof.

Provided herein are compounds of Formula (II):

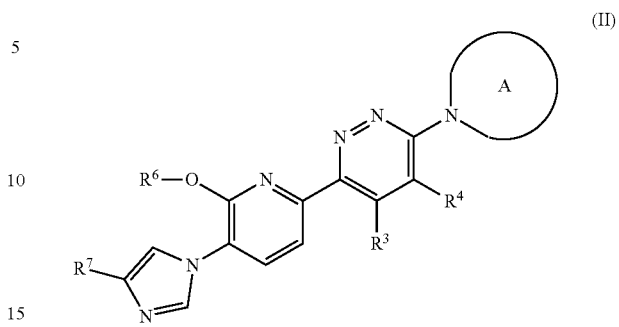

(II)

wherein,

A is selected from the group consisting of substituted or unsubstituted fused ring aryl-heterocycloalkyl; and substituted or unsubstituted fused ring heteroaryl-heterocycloalkyl;

$R^3$ is hydrogen, halogen, —$CF_3$, —CN, —$OR^{3A}$, —$NR^{3A}R^{3B}$, —$COOR^{3A}$, —$CONR^{3A}R^{3B}$, —$OR^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CF_3$, —CN, —$OR^{4A}$, —$NR^{4A}R^{4B}$, —$COOR^{4A}$, —$CONR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

or $R^3$ and $R^4$ are optionally joined together to form a substituted or unsubstituted cycloalkyl;

$R^6$ and $R^7$ are independently substituted or unsubstituted $C_1$-$C_5$ alkyl; and $R^{3A}$, $R^{3B}$, $R^{4A}$, and $R^{4B}$ are independently hydrogen, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or $R^{1A}$ and $R^{1B}$, $R^{3A}$ and $R^{3B}$, $R^{4A}$ and $R^{4B}$, or $R^{5A}$ and $R^{5B}$ are independently optionally joined together to independently form a substituted or unsubstituted heterocycloalkyl, or substituted or unsubstituted heteroaryl.

In some embodiments, A is selected from the group consisting of substituted or unsubstituted fused ring 6,5-aryl-heterocycloalkyl; and substituted or unsubstituted fused ring 6,5,6-cyclolakyl-heteroaryl-heterocycloalkyl.

In some embodiments, A is selected from the group consisting of substituted or unsubstituted isoindolin-2-yl and substituted or unsubstituted 1,2,3,4,7,8,9,10-octahydropyrimido[1,2-b]indazolyl.

In some embodiments, A is selected from the group consisting of 1-methyl-isoindolin-2-yl, 5-fluoro-1-methyl-isoindolin-2-yl, 3-methyl-1-imine-isoindolin-2-yl, 3-ethyl-1-imine-isoindolin-2-yl, and 1,2,3,4,7,8,9,10-octahydropyrimido[1,2-b]indazolyl.

In some embodiments, $R^3$ is hydrogen.

In some embodiments, $R^4$ is selected from the group consisting of hydrogen and substituted or unsubstituted alkyl.

In some embodiments, $R^4$ is selected from the group consisting of hydrogen and methyl.

In some embodiments, $R^6$ is methyl.

In some embodiments, $R^7$ is methyl.

In some embodiments, the compound of Formula (II) is selected from the group consisting of:

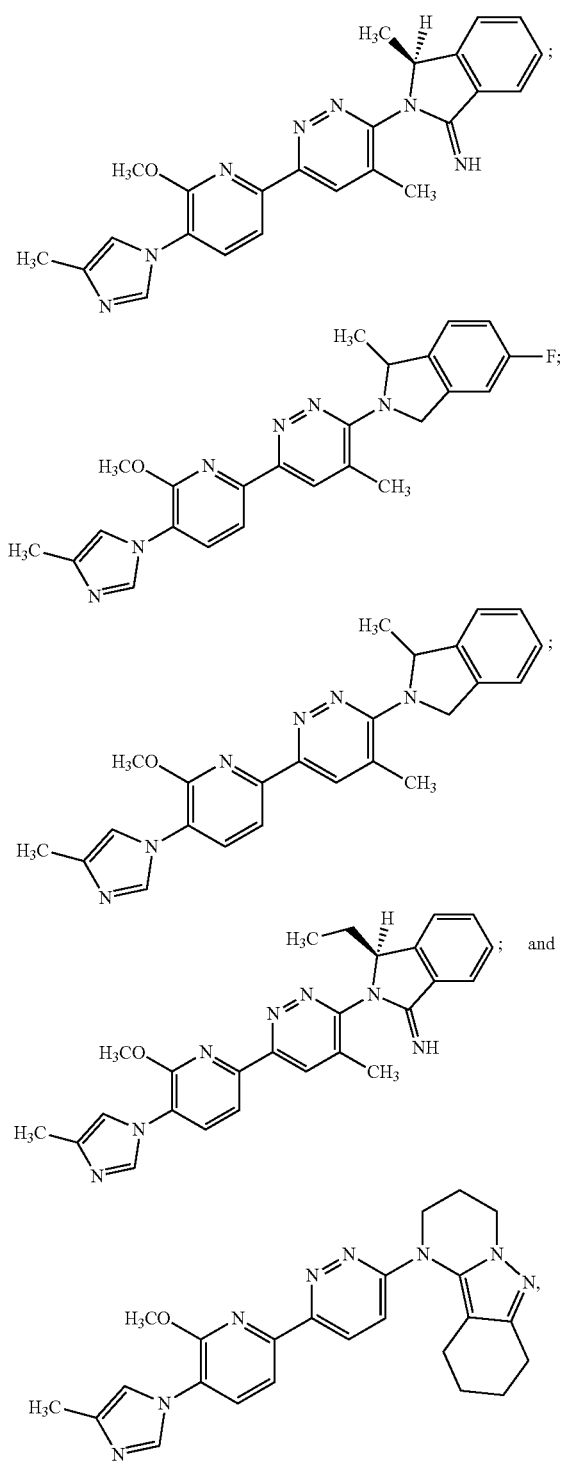

or a pharmaceutically acceptable salt thereof.

The compounds described herein may form prodrugs as described herein.

The compounds provided herein can be prepared using methods understood by those having ordinary skill in the art. For example, compounds provided herein can be prepared using the methods described in Examples 1-103. Other methods for preparing compounds of the disclosure will be readily apparent to the person of ordinary skill in the art in light of the provided reaction schemes and examples. The skilled artisan is thoroughly equipped to prepare these compounds by those methods given the literature and this disclosure. For example, in some embodiments, compounds provided herein can also be prepared as shown in Schemes 1-4.

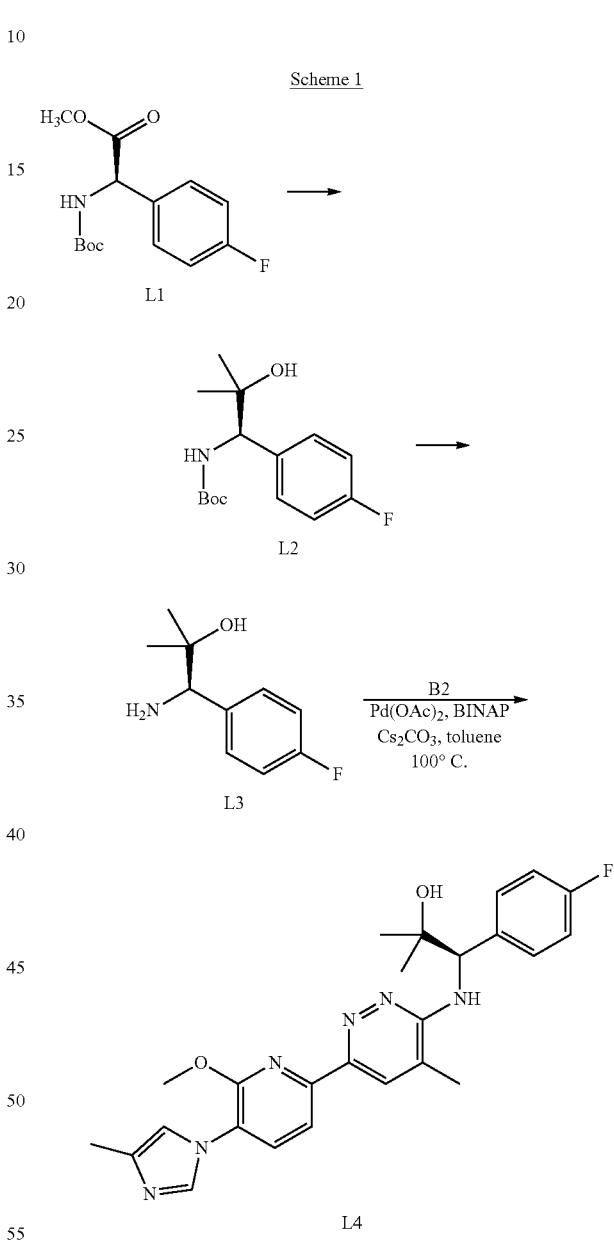

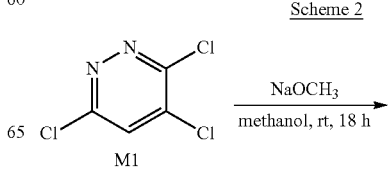

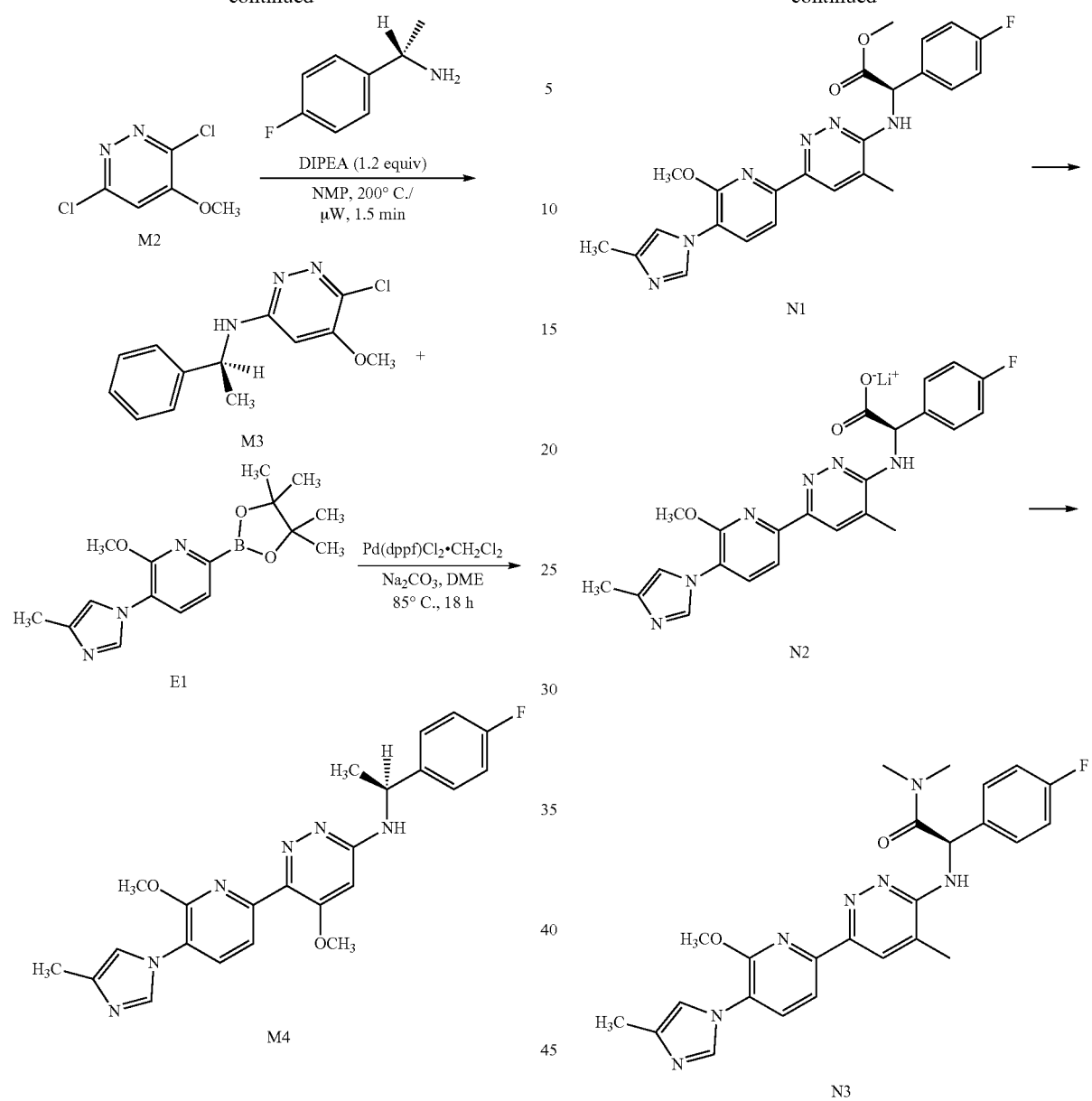
Scheme 3
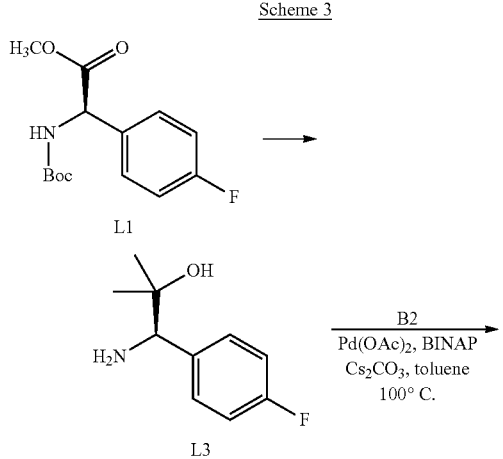
Scheme 4.
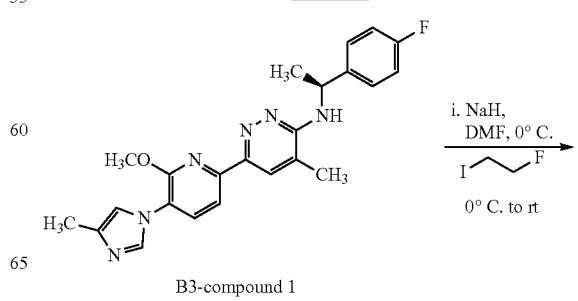

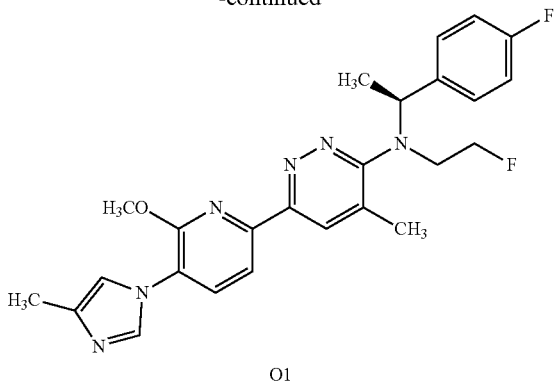

O1

II. Pharmaceutical Compositions

Also provided herein are pharmaceutical compositions that include a compound described herein and a pharmaceutically acceptable excipient.

1. Formulations

The pharmaceutical composition may be prepared and administered in a wide variety of dosage formulations. Compounds described herein may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

For compounds described herein or combinations thereof, the therapeutically effective amounts can be initially determined from cell culture assays. Therapeutically effective amounts for use in humans may be determined from animal models. For example, a dose for humans can be formulated to achieve a concentration that has been found to be effective in animals. The dosage in humans can be adjusted upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

III. Methods of Treatment and Prevention

Further provided herein are methods of treating one or more symptoms of a disorder associated with aberrant Aβ peptide levels in a subject in need thereof. In one aspect is a method of treating one or more symptoms of a disorder associated with aberrant Aβ peptide levels in a subject in need thereof by administering to the subject a therapeutically effective amount of a compound described herein, or a pharmaceutically acceptable salt thereof.

Further provided herein are methods of treating a disorder associated with aberrant AP peptide levels in a subject in need thereof. In one aspect is a method of treating a disorder associated with aberrant Aβ peptide levels in a subject in need thereof by administering to the subject a therapeutically effective amount of a compound described herein. The subject may be human.

The Aβ peptide may be an $A\beta_{42}$ Aβ-peptide alloform or $A\beta_{40}$ Aβ-peptide alloform. The Aβ peptide may be an $A\beta_{42}$ Aβ-peptide alloform. The Aβ peptide may be an $A\beta_{40}$ Aβ-peptide alloform.

Also provided herein are methods of preventing a disorder associated with aberrant AP peptide levels in a subject in need thereof. In one aspect is a method of preventing a disorder associated with aberrant Aβ peptide levels in a subject in need thereof by administering to the subject a prophylactically effective amount of a compound described herein. The subject may be human. The Aβ peptide may be an $A\beta_{42}$ Aβ-peptide alloform or $A\beta_{40}$ Aβ-peptide alloform. The AP peptide may be an $A\beta_{42}$ Aβ-peptide alloform. The Aβ peptide may be an $A\beta_{40}$ Aβ-peptide alloform. The subject may be monitored during therapy to determine whether the disorder associated with aberrant Aβ peptide levels is prevented or otherwise kept in remission.

The disorder associated with aberrant Aβ peptide levels may be Alzheimer's disease. The disorder associated with aberrant Aβ peptide levels may be Familial Alzheimer's disease. The disorder associated with aberrant Aβ peptide levels may be down syndrome. The disorder associated with aberrant Aβ peptide levels may be Creutzfeldt-Jakob disease. The disorder associated with aberrant Aβ peptide levels may be frontotemporal dementia. The disorder associated with aberrant Aβ peptide levels may be amyotrophic lateral sclerosis. The disorder associated with aberrant Aβ peptide levels may be Huntington's disease. The disorder associated with aberrant Aβ peptide levels may be Parkinson's disease. The disorder associated with aberrant Aβ peptide levels may be hemorrhagic stroke associated with amyloidosis. The disorder associated with aberrant Aβ peptide levels may be Alzheimer's disease or Familial Alzheimer's disease.

In some embodiments, the present application provides a method of treating symptoms of a neurological disorder in a subject in need thereof, the method comprising administering to the subject a therapeutically effective amount of a compound described herein, or a pharmaceutically acceptable salt thereof.

In some embodiments, the present application provides a method of treating a neurological disorder in a subject in need thereof, the method comprising administering to the subject a therapeutically effective amount of a compound described herein, or a pharmaceutically acceptable salt thereof.

In some embodiments, the neurological disorder is a neurodegenerative disease. In some embodiments, the neurodegenerative disease is selected from the group consisting of Parkinson's disease (PD), Huntington's Disease (HD), motor neurone disease (MND), and Prion disease.

In some embodiments, the neurological disorder is selected from the group consisting of cerebral amyloid angiopathy, vascular cognitive impairment (VCI), dementia, dementia with Lewy bodies, frontotemporal dementia (FTD), amyotrophic lateral sclerosis (ALS), multiple sclerosis, hippocampal sclerosis, Binswanger's disease, and Creutzfeldt-Jakob disease.

In some embodiments, the neurological disorder is selected from the group consisting of AIDS dementia and HIV-1 induced neurotoxicity; amylotrophic lateral sclerosis, cerebral ischaemia, cerebrovascular ischemia, brain ischemia, cerebral palsy; cerebral tumour; chemotherapy-induced brain damage; cisplatin-induced neurotoxicity, Creutzfeldt-Jacob disease and its new variant associated with "mad cow" disease; diabetic neuropathy; Down's syndrome; drowning; epilepsy and post-traumatic epilepsy; Friedreich's ataxia; frontotemporal dementia; Hallervorden-Spatz disease; Huntington's disease; Lewy body disease; stroke, ischaemic stroke; mascular degeneration; methanol-induced neurotoxicity; meningitis (aseptic and tuberculous); motor neuron disease; multiple sclerosis; multiple system atrophy; neoplasia; Parkinson's disease; perinatal asphyxia; Pick's disease; progressive supra-nuclear palsy; radiotherapy-induced brain damage; senile dementia; schizophrenia; depression, major depressive disorder, subharrachnoid haemorrage/cerebral vasospasm; surgical trauma, including neurosurgery; neurosurgical trauma, transient ischaemic attack (TIA); traumatic brain injury (TBI); traumatic spinal injury; vascular dementia; viral meningitis; encephalitis, and viral encephalitis.

The compounds described herein may be administered orally, safely, and for decades before the onset of AD in both genetically defined AD as well as those at risk in the general population.

IV. Method of Decreasing Aβ-peptide Alloform Levels in a Cell

Also provided herein are methods of decreasing a level of an Aβ-peptide alloform in a cell. In one aspect is a method of decreasing a level of an Aβ-peptide alloform in a cell by contacting a cell with a compound as described herein and allowing the compound to modulate the activity or processivity of a γ-secretase protein. The modulation decreases the level of the Aβ-peptide alloform. The Aβ-peptide alloform may be $A\beta_{42}$ or $A\beta_{40}$. The Aβ-peptide alloform may be $A\beta_{42}$. The Aβ-peptide alloform may be $A\beta_{40}$. The method may also include increasing the level of $A\beta_{38}$ or $A\beta_{37}$. In some embodiments, the method is an in vitro method. In some embodiments, the method is an in vivo method.

EXAMPLES

Chemical Synthesis.
Experimental Details:
Unless otherwise noted, reagents and solvents were used as received from commercial suppliers. Nuclear magnetic resonance spectra were obtained on a Bruker AV 300 spectrometer or on a Bruker AV 500 spectrometer. Spectra are given in ppm (δ) and coupling constants, J, are reported in Hertz. Tetramethylsilane was used as an internal standard for proton spectra. Flash chromatography often utilized the Isco Combiflash Companion MPLC system or the Isco Combiflash $R_f$ MPLC system. Mass spectral data was acquired using a Waters Aquity system, a Agilent 1200 system, or a Varian 1200 L system.

Intermediate 1 (Compound A7)

General Procedure A: Preparation of 1-(6-methoxy-5-(4-methyl-1H-imidazol-1-yl)pyridin-2-yl)ethanone (A7). Preparation of A7 can follow the chemical synthesis scheme set forth in Scheme 5 following.

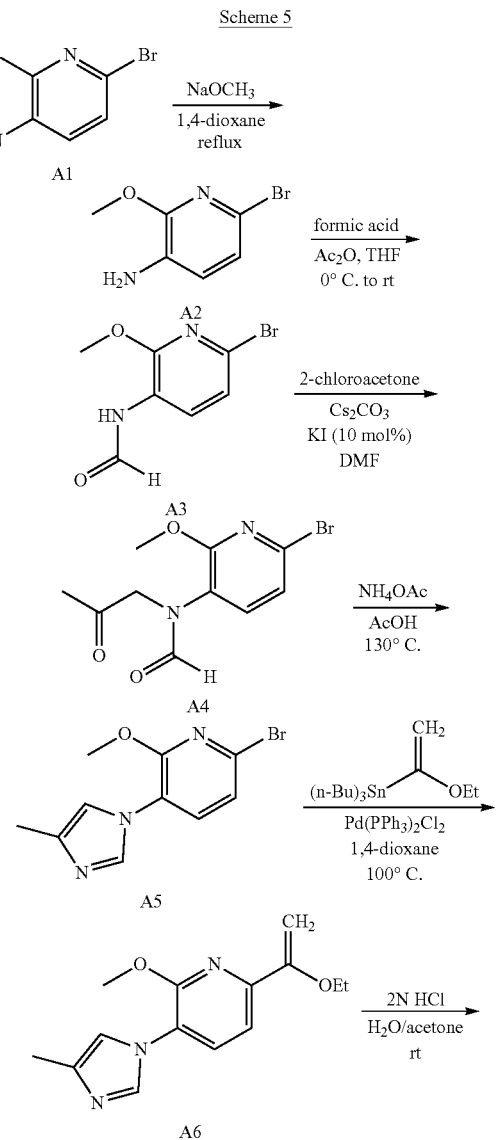

-continued

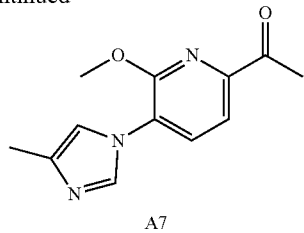

A7

Step 1. 6-Bromo-2-methoxypyridin-3-amine (A2). Sodium methoxide (53.5 g, 0.991 mol) was added to a solution of commercially available 2,6-dibromopyridin-3-amine (A1, 24.97 g, 99.1 mmol) in 1,4-dioxane (250 mL) at room temperature under nitrogen. The resulting mixture was heated to 100° C. for 18 h. The reaction mixture was cooled initially to room temperature, then further cooled to 0° C. and quenched by the careful addition of saturated aqueous ammonium chloride (700 mL). The mixture was stirred for 15 minutes and extracted with ethyl acetate (700 mL; 300 mL). The combined organic layer was washed with brine (400 mL), dried over magnesium sulfate, filtered and the solvents were removed under reduced pressure to afford 6-bromo-2-methoxypyridin-3-amine (A2) as a purple solid (19.62 g, 97%) that was suitable for use without further purification: Multimode MS (M+H) 203; $^1$H NMR (500 MHz, CDCl$_3$) δ 6.86 (d, J=7.5 Hz, 1H), 6.76 (d, J=7.5 Hz, 1H), 3.98 (s, 3H), 3.74 (br s, 2H).

Step 2. N-(6-Bromo-2-methoxypyridin-3-yl)formamide (A3). Acetic anhydride (30.4 g, 28.1 mL, 298 mmol) was added drop-wise via an addition funnel over 10 minutes to formic acid (34.3 g, 28.1 mL, 746 mmol) at 0° C. under nitrogen. The ice bath was removed and the reaction was left to warm to room temperature. After stirring for 4 h, the mixture was recooled to 0° C. and stirred for 15 minutes. A solution of 6-bromo-2-methoxypyridin-3-amine (A2, 20.18 g, 99.4 mmol) in THF (125 mL) was added drop-wise over 1 h and the resulting mixture stirred at 0° C. for 30 minutes, after which the ice bath was removed and the reaction stirred at room temperature for 18 h. The reaction mixture was poured into 1:1 ice/water (500 mL), stirred for 30 minutes and filtered. The solids were further dried under high vacuum for 18 h to afford N-(6-bromo-2-methoxypyridin-3-yl)formamide (A3) as a red-brown solid (21.2 g, 92%) that was suitable for use without further purification: Multimode MS (M+H) 232; $^1$H NMR (500 MHz, CDCl$_3$) δ 8.49 (d, J=8.0 Hz, 1H), 8.48 (s, 1H), 7.60 (br s, 1H), 7.07 (d, J=8.0 Hz, 1H), 4.03 (s, 3H).

Step 3. N-(6-Bromo-2-methoxypyridin-3-yl)-N-(2-oxopropyl)formamide (A4). Cesium carbonate (199.94 g, 614 mmol) and potassium iodide (2.91 g, 17.5 mmol) were added to a solution of N-(6-bromo-2-methoxypyridin-3-yl)formamide (A3, 40.51 g, 175 mmol) in N,N-dimethylformamide (270 mL) at 0° C. under nitrogen. To the resulting mixture was added 2-chloroacetone (40.55 g, 34.9 mL, 438 mmol) drop-wise via a syringe pump (~1 mL/min) over 35 minutes, after which the ice bath was removed and the mixture warmed to room temperature and stirred for 3.5 h. The resulting purple suspension was carefully poured into 1:1 ice/water (1000 mL) and stirred vigorously for 25 minutes, then filtered. The solids were air-dried under vacuum for 15 minutes and further dried overnight under high vacuum at 50° C. to afford N-(6-bromo-2-methoxypyridin-3-yl)-N-(2-oxopropyl)formamide (A4) as a light purple solid (45.82 g, 91%) that was suitable for use without further purification: $^1$H NMR (500 MHz, CDCl$_3$) δ 8.22 (s, 1H), 7.48 (d, J=8.0 Hz, 1H), 7.13 (d, J=8.0 Hz, 1H), 4.47 (s, 2H), 3.99 (s, 3H), 2.17 (s, 3H).

Step 4. 6-Bromo-2-methoxy-3-(4-methyl-1H-imidazol-1-yl)pyridine (A5). Ammonium acetate (33.56 g, 435 mmol) was added to a stirred solution of N-(6-bromo-2-methoxypyridin-3-yl)-N-(2-oxopropyl)formamide (A4, 25.00 g, 87.1 mmol) in acetic acid (200 mL) at room temperature. After addition, the mixture was heated to 130° C. for 6 h. After cooling to room temperature, the mixture was concentrated under vacuum at 60° C. to remove most of the acetic acid. The resulting residue was diluted with ethyl acetate (600 mL), then slowly neutralized with saturated aqueous sodium bicarbonate to pH>7. The layers were separated, and the aqueous phase was extracted with ethyl acetate (2×400 mL). The combined organic phase was dried over anhydrous sodium sulfate, filtered, and concentrated. The resulting residue was purified by flash column chromatography on silica gel, eluted with heptane/methanol/ethyl acetate (gradient of 100% heptane to 4% methanol/ethyl acetate over 20 minutes), to afford 6-bromo-2-methoxy-3-(4-methyl-1H-imidazol-1-yl)pyridine (A5, 16.94 g, 73%) as a light brown solid: Multimode MS (M+H) 268; $^1$H NMR (500 MHz, CDCl$_3$) δ 7.72 (d, J=1.5 Hz, 1H), 7.39 (d, J=8.0 Hz, 1H), 7.16 (d, J=8.0 Hz, 1H), 6.92 (m, 1H), 4.03 (s, 3H), 2.29 (s, 3H).

Step 5. 6-(1-Ethoxyvinyl)-2-methoxy-3-(4-methyl-1H-imidazol-1-yl)pyridine (A6). A solution of 6-bromo-2-methoxy-3-(4-methyl-1H-imidazol-1-yl)pyridine (A5, 16.94 g, 63.2 mmol) and tributyl(1-ethoxyvinyl)stannane (25.10 g, 69.5 mmol) in 1,4-dioxane (530 mL) at room temperature was purged with nitrogen for 5 minutes, after which dichlorobis(triphenylphosphine)palladium(II) (2.22 g, 3.16 mmol) was added, and the mixture was purged with nitrogen for an additional 2 minutes. The brown suspension was heated to 100° C. for 18 h, and then cooled to room temperature. To the mixture was added ~50 g silica gel, and the resulting suspension was then concentrated under reduced pressure. The resulting solid was purified by flash column chromatography on silica gel, eluting with heptane/methanol/ethyl acetate (gradient of 100% heptane to 4% methanol/ethyl acetate over 20 minutes), to afford 6-(1-ethoxyvinyl)-2-methoxy-3-(4-methyl-1H-imidazol-1-yl)pyridine (A6) as an orange solid (16.12 g, 98%) that was suitable for use without further purification: Multimode MS (M+H) 260; $^1$H NMR (500 MHz, CDCl$_3$) δ 7.78 (s, 1H), 7.52 (d, J=8.0 Hz, 1H), 7.37 (d, J=8.0 Hz, 1H), 6.96 (m, 1H), 5.47 (d, J=2.0 Hz, 1H), 4.38 (d, J=2.0 Hz, 1H), 4.04 (s, 3H), 3.98 (q, J=7.0 Hz, 2H), 2.30 (s, 3H), 1.44 (t, J=7.0 Hz, 3H).

Step 6. 1-(6-Methoxy-5-(4-methyl-1H-imidazol-1-yl)pyridin-2-yl)ethanone (A7). Aqueous hydrochloric acid (2 N, 115 mL, 230 mmol) was added to a solution of 6-(1-ethoxyvinyl)-2-methoxy-3-(4-methyl-1H-imidazol-1-yl)pyridine (A6, 16.12 g, 62.2 mmol) in acetone (450 mL) at room temperature, after which the mixture was stirred for 18 h. The organic solvent was removed under reduced pressure and the mixture diluted with water (300 mL) and extracted with 1:1 hexanes/ethyl acetate (200 mL). The aqueous layer was carefully neutralized with saturated aqueous sodium bicarbonate to pH>9. The resulting mixture was extracted with ethyl acetate (1×500 mL; 2×300 mL). The combined organic layer was dried over anhydrous sodium sulfate, filtered and concentrated to afford 1-(6-methoxy-5-(4-methyl-1H-imidazol-1-yl)pyridin-2-yl)ethanone (A7) as a light yellow solid (14.18 g, 98%) that was suitable for use without further purification: Multimode MS (M+H) 232; $^1$H NMR (300 MHz, CDCl$_3$) δ 7.91 (d, J=1.5 Hz, 1H), 7.76 (d, J=8.0 Hz, 1H), 7.67 (d, J=8.0 Hz, 1H), 7.04 (m, 1H), 4.18 (s, 3H), 2.71 (s, 3H), 2.31 (d, J=0.9 Hz, 3H).

Example 1 (B3—Compound 1)

General Procedure B: Preparation of 3-Aminopyridazine Analogs. Preparation of 3-aminopyridazine compounds disclosed herein can be afforded as set forth in Scheme 6 following.

Scheme 6

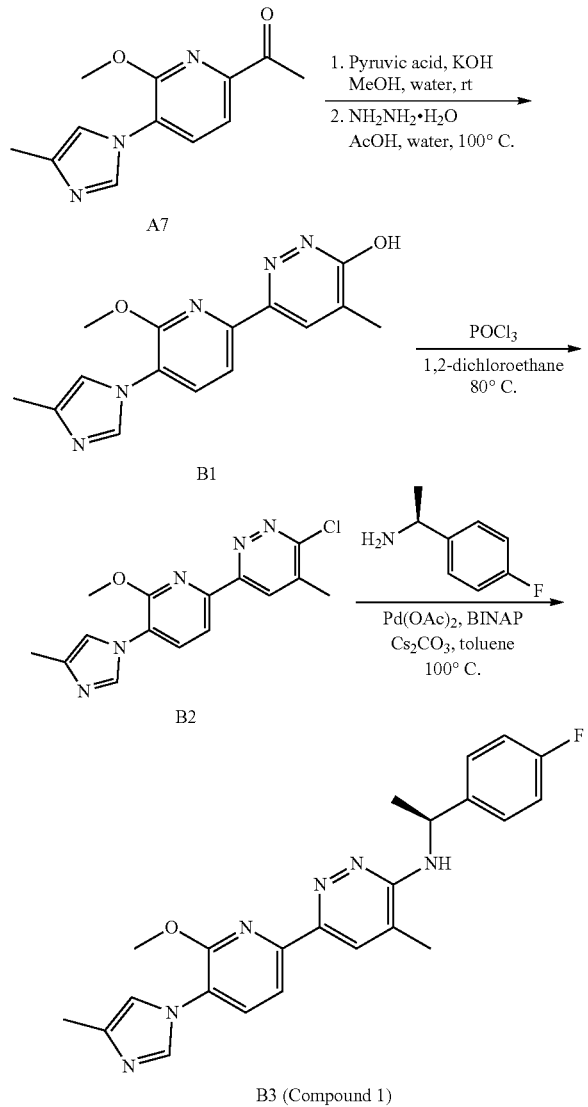

Preparation of (S)—N-(1-(4-fluorophenyl)ethyl)-6-(6-methoxy-5-(4-methyl-1H-imidazol-1-yl)pyridin-2-yl)-4-methylpyridazin-3-amine (B3-) can be afforded as described below. compound 1

Step 1. 6-(6-Methoxy-5-(4-methyl-1H-imidazol-1-yl) pyridin-2-yl)-4-methylpyridazin-3-ol (B1). Potassium hydroxide (20% (w/v) solution in water) was added drop wise to a solution of pyruvic acid (1.25 g, 14.27 mmol) in water (20 mL) at 0° C. (ice/water bath) to pH=7. A solution of 1-(6-methoxy-5-(4-methyl-1H-imidazol-1-yl)pyridin-2-yl)ethanone (A7, 3.00 g, 12.97 mmol) in methanol (40 mL) was then added, followed by powdered potassium hydroxide (909 mg, 16.21 mmol), and the reaction allowed to warm to room temperature overnight with stirring (Note: do not remove ice/water bath). In the morning the methanol was removed under reduced pressure (Note: do not heat water bath) and water added (100 mL). Acetic acid was then added portion wise to pH=5, followed by hydrazine monohydrate (0.94 mL, 19.46 mmol), and the reaction placed in an oil bath and heated to 100° C. overnight with stirring. In the morning the reaction was allowed to cool to room temperature and then saturated sodium bicarbonate added to pH=8. The organics were extracted with chloroform (3×150 mL), and the combined organic phases dried over anhydrous magnesium sulfate, filtered, and concentrated. The resulting residue was purified by flash column chromatography on silica gel, eluted with CMA (80% chloroform; 18% methanol; 2% ammonium hydroxide)/methylene chloride (gradient of 10% to 15% CMA/methylene chloride over 40 minutes), to afford 6-(6-methoxy-5-(4-methyl-1H-imidazol-1-yl)pyridin-2-yl)-4-methylpyridazin-3-ol (B1, 0.98 g, 25%) as a light yellow: APCI MS (M+H) 298; $^1$H NMR (300 MHz, DMSO-d$_6$) δ 13.23 (s, 1H), 8.20 (d, J=1.2 Hz, 1H), 7.96 (d, J=1.2 Hz, 1H), 7.95 (d, J=8.1 Hz, 1H), 7.73 (d, J=8.1 Hz, 1H) 7.29 (s, 1H), 4.07 (s, 3H), 2.17 (m, 6H).

Step 2. 3-Chloro-6-(6-methoxy-5-(4-methyl-1H-imidazol-1-yl)pyridin-2-yl)-4-methylpyridazine (B2). Phosphorous (V) oxychloride (5.60 mL, 61.21 mmol) was added to a solution of 6-(6-methoxy-5-(4-methyl-1H-imidazol-1-yl) pyridin-2-yl)-4-methylpyridazin-3-ol (B1, 0.91 g, 3.06 mmol) in 1,2-dichloromethane (60 mL). The reaction was placed in an oil bath and heated to 80° C. with stirring for three hours. The reaction mixture was then poured into 1:1 ice/water (200 mL), and 2 N sodium hydroxide added to pH=7. The layers were separated, and the aqueous phase was extracted with chloroform (3×150 mL). The combined organic phase was washed with saturated sodium bicarbonate (100 mL), dried over magnesium sulfate, filtered and concentrated to afford 3-chloro-6-(6-methoxy-5-(4-methyl-1H-imidazol-1-yl)pyridin-2-yl)-4-methylpyridazine (B2) as a white solid (830 mg, 86%) that was suitable for use without further purification: APCI MS (M+H) 316; $^1$H NMR (300 MHz, DMSO-d$_6$) δ 8.54 (s, 1H), 8.22 (d, J=8.1 Hz, 1H), 8.07 (d, J=8.1 Hz, 1H) 8.04 (s, 1H), 7.36 (s, 1H), 4.12 (s, 3H), 2.55-2.45 (m, 3H), 2.18 (m, 3H).

Step 3. (S)—N-(1-(4-Fluorophenyl)ethyl)-6-(6-methoxy-5-(4-methyl-1H-imidazol-1-yl)pyridin-2-yl)-4-methyl-pyridazin-3-amine (B3—compound 1). Palladium acetate (131 mg, 0.58 mmol), BINAP (726 mg, 1.16 mmol) and cesium carbonate (2.47 g, 7.57 mmol), were added to a solution of 3-chloro-6-(6-methoxy-5-(4-methyl-1H-imidazol-1-yl)pyridin-2-yl)-4-methylpyridazine (B2, 1.84 g, 5.82 mmol) in anhydrous toluene (160 mL) under nitrogen. (S)-1-(4-Fluorophenyl)ethanamine (2.02 g, 14.56 mmol) was then added and the reaction transferred to an oil bath and heated to 100° C. overnight. The reaction mixture was then allowed to cool and the reaction mixture concentrated under reduced pressure. The resulting slurry was dissolved in chloroform (200 mL) and the solids filtered and washed with chloroform (50 mL). The filtrate was concentrated under reduced pressure and purified by flash column chromatography on silica gel, eluted with methanol/chloroform (gradient of 1% to 1.5% methanol/chloroform over 40 minutes), to afford (S)—N-(1-(4-fluorophenyl)ethyl)-6-(6-methoxy-5-(4-methyl-1H-imidazol-1-yl)pyridin-2-yl)-4-methylpyridazin-3-amine (B3—compound 1) as an off-white solid (1.70 g, 70%).

APCI MS (M+H) 419; ¹H NMR (300 MHz, DMSO-d₆) δ 8.01 (s, 1H), 7.99 (d, J=8.1 Hz, 1H), 7.93 (d, J=1.2 Hz, 1H), 7.91 (d, J=8.1 Hz, 1H), 7.48 (dd, J=5.7, 3.0 Hz, 2H), 7.27 (s, 1H), 7.12 (t, J=8.7 Hz, 2H), 6.84 (d, J=7.5 Hz, 1H), 5.49 (q, J=7.2 Hz, 1H), 4.05 (s, 3H), 2.30 (s, 3H), 2.16 (s, 3H), 1.56 (d, J=6.9 Hz, 3H); mp: 96-104° C. [α]²⁰$_D$ −93.0° (c 0.50, MeOH).

Pyridazine Analogs. Compounds disclosed herein incorporating a Pyridazine at ring C, and analogs thereof, were synthesized according to general procedure B and characterized as follows.

Example 2 (Compound 2)

(S)—N-(1-(4-Fluorophenyl)ethyl)-6-(6-methoxy-5-(4-methyl-1H-imidazol-1-yl)pyridin-2-yl)pyridazin-3-amine (compound 2)

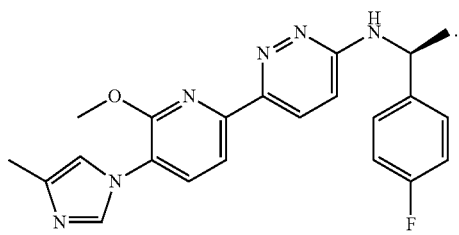 [SMILES: COc1nc(-c2ccc(N[C@@H](C)c3ccc(F)cc3)nn2)ccc1-n1cnc(C)c1]

APCI MS (M+H) 405; ¹H NMR (300 MHz, DMSO-d₆) δ 8.14 (d, J=9.3 Hz, 1H), 7.98 (d, J=8.1 Hz, 1H), 7.93 (s, 1H), 7.93 (d, J=8.1 Hz, 1H), 7.73 (d, J=7.8 Hz, 1H), 7.44 (dd, J=8.5, 5.5 Hz, 2H), 7.27 (s, 1H), 7.14 (t, J=8.8 Hz, 2H), 6.99 (d, J=9.6 Hz, 1H), 5.23 (m, 1H), 4.03 (s, 3H), 2.15 (s, 3H), 1.49 (d, J=6.6 Hz, 3H); mp: 96-102° C.

Example 3 (Compound 4)

(R)—N-(1-(4-Fluorophenyl)ethyl)-6-(6-methoxy-5-(4-methyl-1H-imidazol-1-yl)pyridin-2-yl)-4-methyl-pyridazin-3-amine (compound 4)

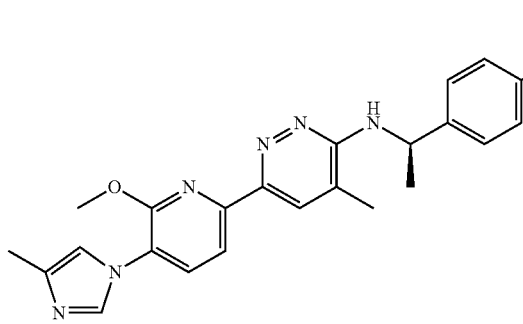

APCI MS (M+H) 419; ¹H NMR (300 MHz, DMSO-d₆) δ 8.01 (d, J=0.9 Hz, 1H), 7.99 (d, J=8.1 Hz, 1H), 7.93 (s, 1H), 7.91 (d, J=8.1 Hz, 1H), 7.48 (dd, J=8.7, 5.7 Hz, 2H), 7.26 (s, 1H), 7.12 (t, J=8.8 Hz, 2H), 6.83 (d, J=7.5 Hz, 1H), 5.48 (m, 1H), 4.05 (s, 3H), 2.30 (s, 3H), 2.16 (s, 3H), 1.56 (d, J=6.9 Hz, 3H); mp: 85-90° C.

Example 4 (Compound 3)

N-(4-Fluorobenzyl)-6-(6-methoxy-5-(4-methyl-1H-imidazol-1-yl)pyridin-2-yl)-4-methylpyridazin-3-amine (compound 3)

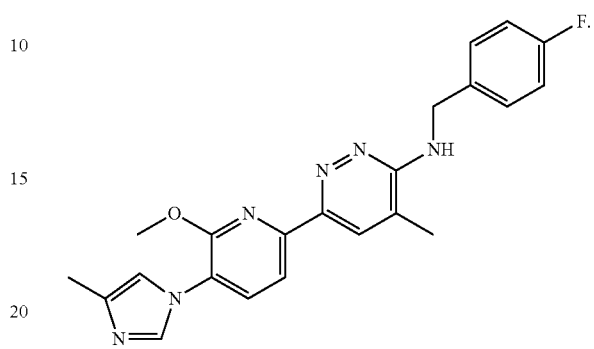

APCI MS (M+H) 405; ¹H NMR (300 MHz, DMSO-d₆) δ 8.04 (s, 1H), 8.01 (d, J=7.8 Hz, 1H), 7.96 (s, 1H), 7.92 (d, J=8.1 Hz, 1H), 7.42 (dd, J=8.5, 6.0 Hz, 2H), 7.30 (m, 2H), 7.13 (t, J=8.7 Hz, 2H), 4.73 (d, J=6.0 Hz, 2H), 4.06 (s, 3H), 2.26 (s, 3H), 2.16 (s, 3H).

Example 5 (C3—Compound 5)

General Procedure C. Preparation of 4-Ethyl-3-Aminopyridazine Analogs. Preparation of 4-ethyl-3-aminopyridazine compounds disclosed herein can be afforded as set forth in Scheme 7.

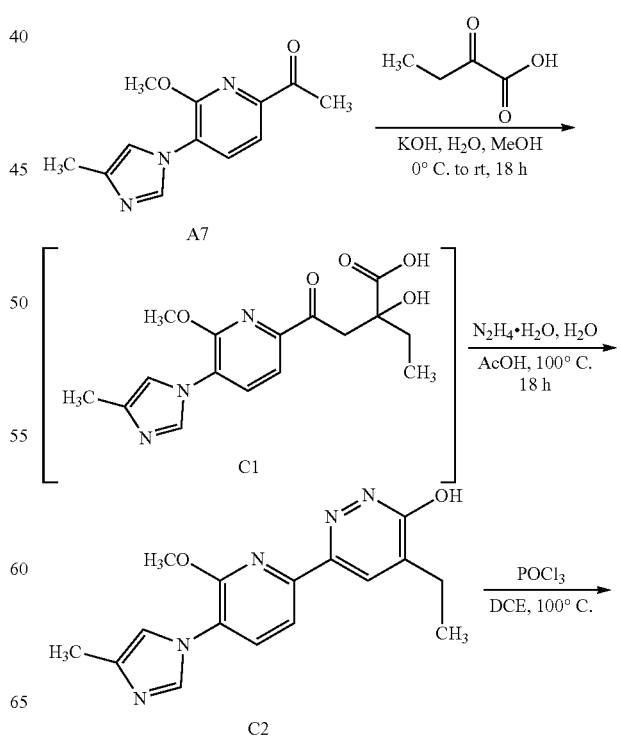

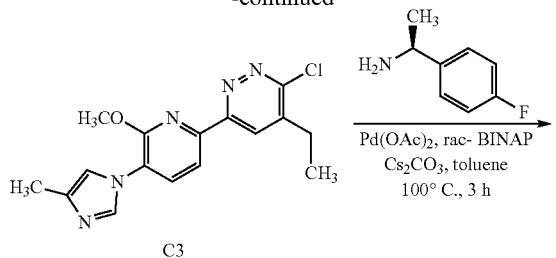

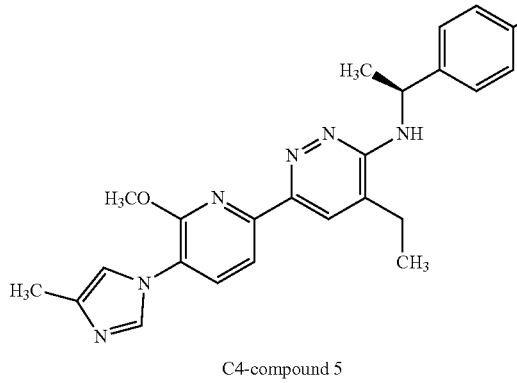

C4-compound 5

Preparation of (S)-4-Ethyl-N-(1-(4-fluorophenyl)ethyl)-6-(6-methoxy-5-(4-methyl-1H-imidazol-1-yl)pyridin-2-yl)pyridazin-3-amine (C4—compound 5) can be afforded as described below Steps 1 and 2. 4-Ethyl-6-(6-methoxy-5-(4-methyl-1H-imidazol-1-yl)pyridin-2-yl)pyridazin-3-ol (C2).

A 50 mL round bottom flask, equipped with magnetic stirring, was charged with α-ketobutyric acid (486 mg, 4.77 mmol) and methanol (2.0 mL). To the reaction mixture at 0° C. was added potassium hydroxide [20% (w/w) in water] to pH=8 (3.0 mL). A solution of 1-(6-methoxy-5-(4-methyl-1H-imidazol-1-yl)pyridin-2-yl)ethanone (A7, 1.00 g, 4.32 mmol) in methanol (10 mL) was then added, followed by solid potassium hydroxide (48 mg, 0.86 mmol), and the reaction was allowed to warm to room temperature overnight. The reaction mixture was concentrated in vacuo to near dryness using a 23° C. water bath and re-dissolved in water (20 mL). The aqueous phase was extracted with ethyl acetate (2×20 mL) and the combined organics were concentrated in vacuo to obtain 760 mg (76% recovery) of A7 as a crude yellow solid. The aqueous phase containing C1 (confirmed by LCMS) was stored within the freezer. The recovered starting material (A7, 760 mg) was re-subjected using the same procedure described above (α-ketobutyric acid, 369 mg, 3.61 mmol). Recovered 591 mg (77% recovery) of A7 as a crude yellow solid and aqueous phase was stored within the freezer. The recovered starting material (A7, 591 mg) was re-subjected for a final time (α-ketobutyric acid, 287 mg, 2.81 mmol). Recovered starting material A7 (383 mg, 64% recovery) as a crude yellow solid. Combined all three aqueous phases and adjusted to pH=5 with acetic acid (6.0 mL). Added hydrazine monohydrate (0.74 mL, 15 mmol; based on total amount of α-ketobutyric acid used) in one portion and the reaction mixture was heated to 100° C. overnight. A white precipitate formed and the reaction was cooled to room temperature. The precipitate was collected by vacuum filtration, washed with water (50 mL), and dried in a vacuum oven at 58° C. for 4 h to afford 4-ethyl-6-(6-methoxy-5-(4-methyl-1H-imidazol-1-yl)pyridin-2-yl)pyridazin-3-ol (C2, 524 mg, 39%) as a tan solid: ESI MS (M+H) 312; $^1$H NMR (500 MHz, DMSO-$d_6$) δ 13.2 (s, 1H), 8.12 (s, 1H), 7.96-7.95 (m, 2H), 7.73 (d, J=8.0 Hz, 1H), 7.28 (s, 1H), 4.06 (s, 3H), 2.59-2.54 (m, 2H), 2.16 (d, J=1.0 Hz, 3H), 1.19 (t, J=7.5 Hz, 3H).

Step 3. 3-Chloro-4-ethyl-6-(6-methoxy-5-(4-methyl-1H-imidazol-1-yl)pyridin-2-yl)pyridazine (C3). A 50 mL round bottom flask, equipped with a magnetic stir bar and condenser, was charged with 4-ethyl-6-(6-methoxy-5-(4-methyl-1H-imidazol-1-yl)pyridin-2-yl)pyridazin-3-ol (C2, 524 mg, 1.68 mmol) and 1,2-dichloroethane (5.0 mL). To the flask was added phosphorous (V) oxychloride (0.24 mL, 2.5 mmol) in one portion. The reaction mixture was then heated to reflux for 5 h (monitored by LCMS). The reaction mixture was cooled to room temperature and poured into a 1:1 mixture of ice/water (50 mL) and methylene chloride (50 mL). Adjusted to pH=8 with saturated aqueous sodium bicarbonate and stirred for 1 h. The aqueous phase was separated and extracted with methylene chloride (2×50 mL). The combined organic phases were dried over $MgSO_4$, filtered and concentrated in vacuo to afford 3-chloro-4-ethyl-6-(6-methoxy-5-(4-methyl-1H-imidazol-1-yl)pyridin-2-yl)pyridazine (C3, 497 mg, 90%) as a white solid: ESI MS (M+H) 330; $^1$H NMR (500 MHz, DMSO-$d_6$) δ 8.48 (s, 1H), 8.21 (d, J=8.0 Hz, 1H), 8.08 (d, J=8.0 Hz, 1H), 8.03 (d, J=0.5 Hz, 1H), 7.35 (s, 1H), 4.12 (s, 3H), 2.85 (q, J=7.5 Hz, 2H), 2.18 (d, J=0.5 Hz, 3H), 1.30 (t, J=7.5 Hz, 3H).

Step 4. (S)-4-Ethyl-N-(1-(4-fluorophenyl)ethyl)-6-(6-methoxy-5-(4-methyl-1H-imidazol-1-yl)pyridin-2-yl)pyridazin-3-amine (C4—compound 5). An oven dried 20 mL microwave vial, equipped with a magnetic stir bar and under a nitrogen atmosphere, was charged with 3-chloro-4-ethyl-6-(6-methoxy-5-(4-methyl-1H-imidazol-1-yl)pyridin-2-yl)pyridazine (C3, 125 mg, 0.379 mmol), (S)-1-(4-fluorophenyl)ethanamine (0.13 mL, 0.95 mmol), $Cs_2CO_3$ (161 mg, 0.493 mmol), Pd(OAc)$_2$ (9 mg, 0.04 mmol), and rac-BINAP (51 mg, 0.075 mmol). The reaction vessel was purged with nitrogen using evac/refill cycle (1×). Toluene (8 mL) was added and the reaction mixture was degassed further by sparging with argon for 5-10 min. The reaction mixture was then heated to 100° C. for 3 h. Upon reaction completion (monitored by LCMS), the reaction mixture was cooled to room temperature and concentrated in vacuo to give a crude residue. The residue was purified by flash column chromatography (silica, 50-100% ethyl acetate/hexanes), which was followed by a second column (0-10% methanol/methylene chloride) to afford (S)-4-ethyl-N-(1-(4-fluorophenyl)ethyl)-6-(6-methoxy-5-(4-methyl-1H-imidazol-1-yl)pyridin-2-yl)pyridazin-3-amine (C4—compound 5, 95 mg, 56%) as an amorphous white solid. ESI MS (M+H) 433; $^1$H NMR (500 MHz, DMSO-$d_6$) δ 8.00-7.98 (m, 2H), 7.92-7.90 (m, 2H), 7.48-7.45 (m, 2H), 7.26 (t, J=1.0 Hz, 1H), 7.11 (t, J=9.0 Hz, 2H), 6.85 (d, J=7.5 Hz, 1H), 5.46 (m, 1H), 4.05 (s, 3H), 2.85 (q, J=7.5 Hz, 2H), 2.18 (d, J=0.5 Hz, 3H), 1.56 (d, J=7.0 Hz, 3H), 1.30 (t, J=7.5 Hz, 3H); mp range: 90-98° C.; $[\alpha]^{20}_D$ −98.2° (c 0.14, MeOH).

4-Ethyl-3-aminopyridazine Analogs. Compounds disclosed herein incorporating a 4-ethyl-3-aminopyridazine at ring C, and analogs thereof, were synthesized according to general procedure C and characterized as follows:

Example 7

(S)-4-ethyl-6-(6-methoxy-5-(4-methyl-1H-imidazol-1-yl)pyridin-2-yl)-N-(1-phenylethyl)pyridazin-3-amine

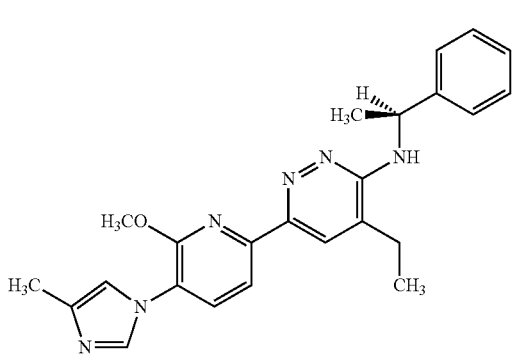 [SMILES: CCc1cc(-c2ccc(-n3cnc(C)c3)c(OC)n2)nnc1N[C@@H](C)c1ccccc1]

ESI MS (M+H) 415; $^1$H NMR (500 MHz, DMSO-d$_6$) δ 7.99-7.98 (m, 2H), 7.92-7.90 (m, 2H), 7.43 (d, J=7.5 Hz, 2H), 7.30 (t, J=7.5 Hz, 2H), 7.26 (s, 1H), 7.18 (t, J=7.5 Hz, 1H), 6.84 (d, J=7.5 Hz, 1H), 5.52 (sym m, 1H), 4.05 (s, 3H), 2.68 (q, J=7.5 Hz, 2H), 2.16 (s, 3H), 1.56 (d, J=7.0 Hz, 3H), 1.27 (t, J=7.5 Hz, 3H); mp range: 86-94° C.; [α]$^{20}$$_D$ −58.9° (c 0.13, MeOH).

Example 8

4-ethyl-N-(4-fluorobenzyl)-6-(6-methoxy-5-(4-methyl-1H-imidazol-1-yl)pyridin-2-yl)pyridazin-3-amine

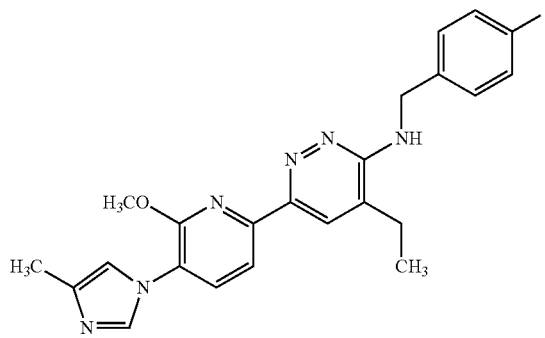

ESI MS (M+H) 419; $^1$H NMR (500 MHz, DMSO-d$_6$) δ 8.02-8.00 (m, 2H), 7.93-7.92 (m, 2H), 7.41 (q, J=3.0, 5.5 Hz, 2H), 7.32 (t, J=6.0 Hz, 1H), 7.27 (t, J=1.0 Hz, 1H) 7.13 (t, J=9.0 Hz, 2H), 4.74 (d, J=6.0 Hz, 2H), 4.06 (s, 3H), 2.60 (q, J=7.5 Hz, 2H), 2.16 (d, J=1.0 Hz, 3H), 1.26 (t, J=7.5 Hz, 3H); mp range: 86-99° C.

Example 9

(R)-4-ethyl-6-(6-methoxy-5-(4-methyl-1H-imidazol-1-yl)pyridin-2-yl)-N-(1-phenylethyl)pyridazin-3-amine

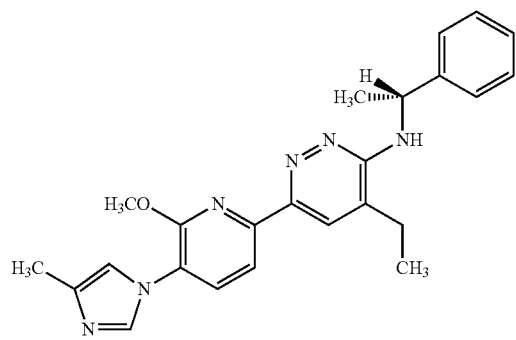 [SMILES: CCc1cc(-c2ccc(-n3cnc(C)c3)c(OC)n2)nnc1N[C@H](C)c1ccccc1]

ESI MS (M+H) 415; $^1$H NMR (500 MHz, DMSO-d$_6$) δ 7.99-7.98 (m, 2H), 7.92-7.90 (m, 2H), 7.44 (d, J=7.5 Hz, 2H), 7.30-7.26 (m, 3H), 7.18 (t, J=6.5 Hz, 1H), 6.84 (d, J=7.5 Hz, 1H), 5.52 (sym m, 1H), 4.05 (s, 3H), 2.68 (q, J=7.8 Hz, 2H), 2.16 (d, J=1.0 Hz, 3H), 1.57 (d, J=7.0 Hz, 3H), 1.27 (t, J=7.5 Hz, 3H); mp range: 88-87° C.; [α]$^{20}$$_D$ +91.0° (c 0.16, MeOH).

Example 10

(R)-4-ethyl-N-(1-(4-fluorophenyl)ethyl)-6-(6-methoxy-5-(4-methyl-1H-imidazol-1-yl)pyridin-2-yl)pyridazin-3-amine

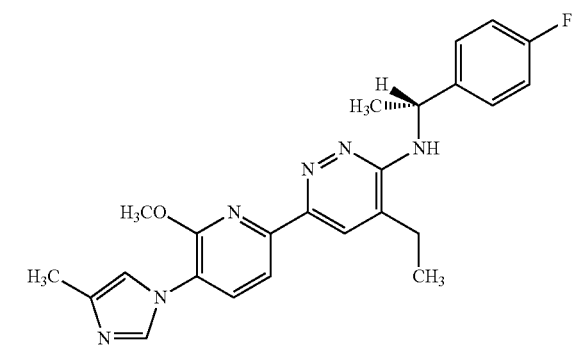 [SMILES: CCc1cc(-c2ccc(-n3cnc(C)c3)c(OC)n2)nnc1N[C@H](C)c1ccc(F)cc1]

ESI MS (M+H) 433; $^1$H NMR (300 MHz, DMSO-d$_6$) δ 8.01-7.98 (m, 2H), 7.93-7.90 (m, 2H), 7.49-7.44 (m, 2H), 7.27 (t, J=1.2 Hz, 1H), 7.12 (t, J=9.0 Hz, 2H), 6.89 (d, J=7.5 Hz, 1H), 5.50 (sym m, 1H), 4.05 (s, 3H), 2.67 (q, J=7.8 Hz, 2H), 2.16 (d, J=1.0 Hz, 3H), 1.56 (d, J=7.0 Hz, 3H), 1.27 (t, J=7.5 Hz, 3H); mp range: 93-104° C.; [α]$^{20}$$_D$ +109.0° (c 0.10, MeOH).

Example 11 (D4—Compound 11)

General Procedure D: Preparation of 4-Isopropyl-3-Aminopyridazine Analogs. Preparation of 4-Isopropyl-3-aminopyridazine compounds disclosed herein can be afforded as set forth in Scheme 8.

Scheme 8

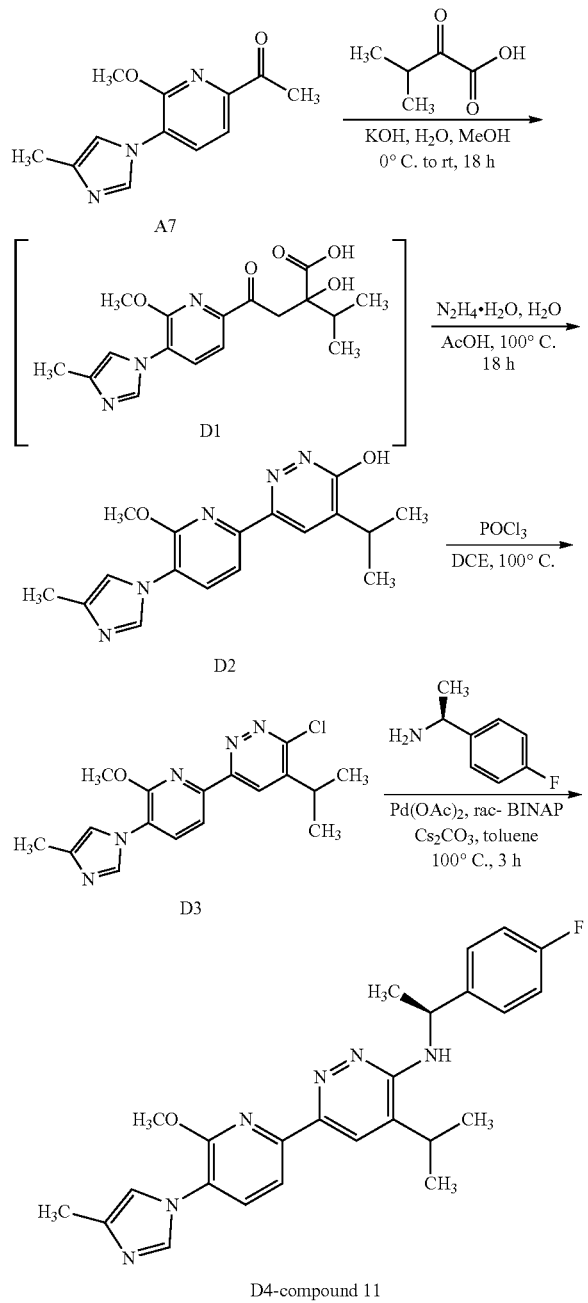

Preparation of (S)—N-(1-(4-fluorophenyl)ethyl)-4-isopropyl-6-(6-methoxy-5-(4-methyl-1H-imidazol-1-yl)pyridin-2-yl)pyridazin-3-amine (D4—compound 11) can be afforded as described below:

Steps 1 and 2. 4-Isopropyl-6-(6-methoxy-5-(4-methyl-1H-imidazol-1-yl)pyridin-2-yl)pyridazin-3-ol (D2). A 50 mL round bottom flask, equipped with magnetic stirring, was charged with 3-methyl-2-oxobutanoic acid (554 mg, 4.77 mmol) and methanol (2.0 mL). To the reaction mixture at 0° C. was added potassium hydroxide [20% (w/w) in water] to pH=8 (3.0 mL). A solution of 1-(6-methoxy-5-(4-methyl-1H-imidazol-1-yl)pyridin-2-yl)ethanone (A7, 1.00 g, 4.32 mmol) in methanol (10 mL) was then added, followed by solid potassium hydroxide (48 mg, 0.86 mmol), and the reaction was allowed to warm to room temperature overnight. The reaction mixture was concentrated in vacuo to near dryness using a 23° C. water bath and re-dissolved in water (20 mL). The aqueous phase was extracted with ethyl acetate (2×20 mL) and the combined organics were concentrated in vacuo to obtain 568 mg (57% recovery) of A7 as a crude yellow solid. The aqueous phase containing D1 (confirmed by LCMS) was used in the next step. The aqueous phase was adjusted to pH=5 with acetic acid (2.0 mL). Hydrazine monohydrate (0.32 mL, 6.5 mmol; based on total amount of 3-methyl-2-oxobutanoic acid used) was added in one portion and the reaction mixture was heated to 100° C. overnight. A white precipitate formed and the reaction mixture was cooled to room temperature. The precipitate was collected by vacuum filtration and washed with water (50 mL) to afford 4-isopropyl-6-(6-methoxy-5-(4-methyl-1H-imidazol-1-yl)pyridin-2-yl)pyridazin-3-ol (D2) as an off-white solid. The aqueous filtrate was adjusted to pH=7 with saturated aqueous NaHCO$_3$ to give a second crop (D2) as a yellow solid, which was collected by vacuum filtration. Both solids were dried in the oven at 58° C. for 4 h and combined to give (D2, 451 mg, 32%) as a light yellow solid: ESI MS (M+H) 326; $^1$H NMR (500 MHz, DMSO-d$_6$) δ 13.2 (s, 1H), 8.08 (d, J=1.0 Hz, 1H), 7.97-7.95 (m, 2H), 7.74 (d, J=8.0 Hz, 1H), 7.29 (t, J=1.5 Hz, 1H), 4.06 (s, 3H), 3.11-3.06 (m, 1H), 2.16 (d, J=1.0 Hz, 3H), 1.22 (d, J=6.5 Hz, 6H).

Step 3. 3-Chloro-4-isopropyl-6-(6-methoxy-5-(4-methyl-1H-imidazol-1-yl)pyridin-2-yl)pyridazine (D3). A 50 mL round bottom flask, equipped with a magnetic stir bar and condenser, was charged with 4-ethyl-6-(6-methoxy-5-(4-methyl-1H-imidazol-1-yl)pyridin-2-yl)pyridazin-3-ol (D2, 451 mg, 1.39 mmol) and 1,2-dichloroethane (4.0 mL). To the flask was added phosphorous (V) oxychloride (0.4 mL, 2 mmol) in one portion. The reaction mixture was then heated to reflux for 5 h (monitored by LCMS). The reaction mixture was cooled to room temperature and poured into a 1:1 mixture of ice/water (50 mL) and methylene chloride (50 mL). The pH was adjusted to pH=8 with solid NaHCO$_3$ and stirred for 1 h. The aqueous phase was separated and extracted with methylene chloride (2×50 mL). The combined organic phases were dried over MgSO$_4$, filtered and concentrated in vacuo to afford 3-chloro-4-isopropyl-6-(6-methoxy-5-(4-methyl-1H-imidazol-1H-yl)pyridin-2-yl)pyridazine (D3, 401 mg, 84%) as a white solid: ESI MS (M+H) 344; $^1$H NMR (500 MHz, DMSO-d$_6$) δ 8.44 (s, 1H), 8.21 (d, J=8.0 Hz, 1H), 8.10-8.07 (m, 2H), 7.36 (s, 1H), 4.12 (s, 3H), 3.31-3.24 (m, 1H), 2.18 (s, 3H), 1.34 (d, J=7.0 Hz, 6H).

Step 4. (S)—N-(1-(4-Fluorophenyl)ethyl)-4-isopropyl-6-(6-methoxy-5-(4-methyl-1H-imidazol-1-yl)pyridin-2-yl)pyridazin-3-amine (D4—compound 11). An oven dried 20 mL microwave vial, equipped with a magnetic stir bar and under a nitrogen atmosphere, was charged with 3-chloro-4-ethyl-6-(6-methoxy-5-(4-methyl-1H-imidazol-1-yl)pyridin-2-yl)pyridazine (D3, 125 mg, 0.364 mmol), (S)-1-(4-fluorophenyl)ethanamine (0.12 mL, 0.91 mmol), Cs$_2$CO$_3$ (154 mg, 0.473 mmol), Pd(OAc)$_2$ (9 mg, 0.04 mmol), and rac-BINAP (51 mg, 0.075 mmol). The reaction vessel was purged with nitrogen using evac/refill cycle (1×). Toluene (8 mL) was added and the reaction mixture was degassed further by sparging with argon for 5-10 min. The reaction mixture was then heated to 100° C. overnight. Upon reaction completion (monitored by LCMS), the reaction mixture was cooled to room temperature and concentrated in vacuo to give a crude residue. The residue was purified by flash column chromatography (silica, 50-100% ethyl acetate/hexanes) to give an off-white solid. The solid was dissolved in methylene chloride (20 mL) and extracted with 0.5 M HCl. The aqueous phase was washed with methylene chloride (20 mL) and then adjusted to pH=8 with solid NaHCO$_3$. The aqueous phase was extracted with methylene chloride (2×20 mL). The combined organics phases were dried over MgSO$_4$, filtered, and concentrated in vacuo to give (S)—N-(1-(4-fluorophenyl)ethyl)-4-isopropyl-6-(6-methoxy-5-(4-methyl-1H-imidazol-1-yl)pyridin-2-yl)pyridazin-3-amine (D4—compound 11, 78 mg, 48%) as an amorphous white solid. ESI MS (M+H) 447; $^1$H NMR (500 MHz, DMSO-d$_6$) δ 8.01 (s, 1H), 7.98 (d, J=8.0 Hz, 1H), 7.92 (d, J=8.0 Hz, 2H), 7.47 (q, J=3.0, 6.0 Hz, 2H), 7.26 (s, 1H), 7.12 (t, J=9.0 Hz, 2H), 6.91 (d, J=7.5 Hz, 1H), 5.52 (sym m, 1H), 4.05 (s, 3H), 3.26-3.21 (m, 1H), 2.16 (d, J=0.5 Hz, 3H), 1.56 (d, J=7.0 Hz, 3H), 1.27 (dd, J=6.5, 9.0 Hz, 6H); mp range: 99-111° C.; [α]$^{20}$$_D$ -84.8° (c 0.16, MeOH).

4-Isopropyl-3-aminopyridazine Analogs. Compounds disclosed herein incorporating a 4-Isopropyl-3-aminopyridazine at ring C, and analogs thereof, were synthesized according to general procedure D and characterized as follows:

Example 13

N-(4-fluorobenzyl)-4-isopropyl-6-(6-methoxy-5-(4-methyl-1H-imidazol-1-yl)pyridin-2-yl)pyridazin-3-amine

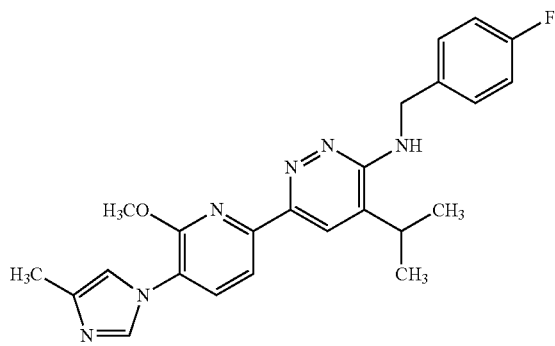 [SMILES: COc1nc(-c2cc(C(C)C)c(NCc3ccc(F)cc3)nn2)ccc1-n1cnc(C)c1]

ESI MS (M+H) 433; $^1$H NMR (500 MHz, DMSO-d$_6$) δ 8.03 (s, 1H), 8.00 (d, J=8.0 Hz, 1H), 7.94-7.92 (m, 2H), 7.42-7.39 (m, 3H), 7.27 (t, J=1.0 Hz, 1H) 7.13 (t, J=9.0 Hz, 2H), 4.74 (d, J=6.0 Hz, 2H), 4.06 (s, 3H), 3.10-3.04 (m, 1H), 2.16 (d, J=1.0 Hz, 3H), 1.26 (d, J=6.5 Hz, 6H); mp: 245-246° C.

Example 14

(S)-4-isopropyl-6-(6-methoxy-5-(4-methyl-1H-imidazol-1-yl)pyridin-2-yl)-N-(1-phenylethyl)pyridazin-3-amine

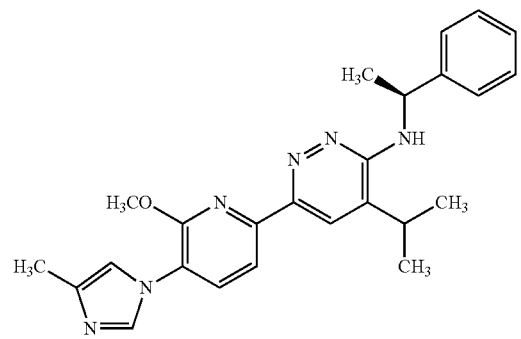 [SMILES: COc1nc(-c2cc(C(C)C)c(N[C@@H](C)c3ccccc3)nn2)ccc1-n1cnc(C)c1]

ESI MS (M+H) 429; $^1$H NMR (500 MHz, DMSO-d$_6$) δ 8.01 (s, 1H), 7.98 (d, J=8.0 Hz, 1H), 7.92-7.91 (m, 2H), 7.44 (d, J=7.5 Hz, 2H), 7.30 (t, J=7.5 Hz, 2H), 7.26 (s, 1H), 7.18 (t, J=7.5 Hz, 1H), 6.90 (d, J=7.5 Hz, 1H), 5.54 (sym m, 1H), 4.05 (s, 3H), 3.28-3.22 (m, 1H), 2.16 (s, 3H), 1.57 (d, J=7.0 Hz, 3H), 1.27 (dd, J=6.5, 9.0 Hz, 6H); mp range: 83-94° C.; [α]$^{20}$$_D$ -87.2° (c 0.18, MeOH).

Example 15 (E3—Compound 15)

General Procedure E: Preparation of 4,5-Dimethyl-3-Aminopyridazine Analogs. Preparation of 4,5-dimethyl-3-aminopyridazine compounds disclosed herein can be afforded as set forth in Scheme 9.

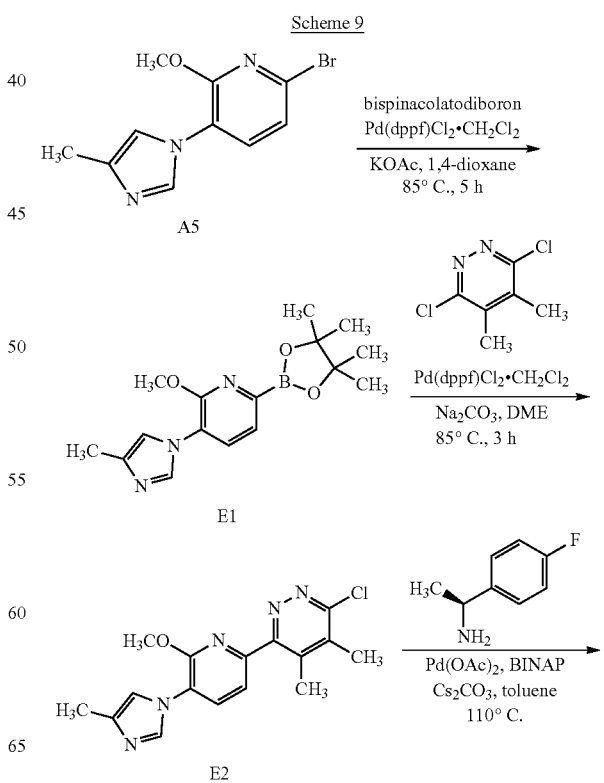

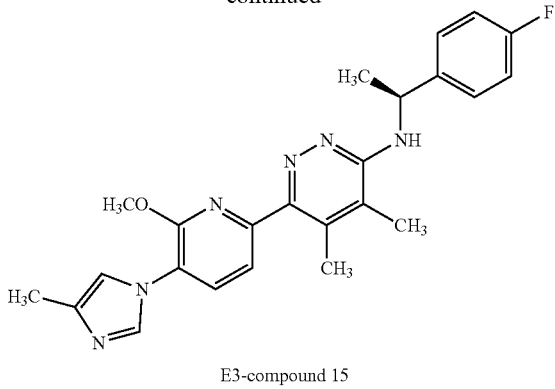

E3-compound 15

Preparation of (S)—N-(1-(4-Fluorophenyl)ethyl)-6-(6-methoxy-5-(4-methyl-1H-imidazol-1-yl)pyridin-2-yl)-4,5-dimethylpyridazin-3-amine (E3—compound 15) can be afforded as described below:

Step 1. 2-Methoxy-3-(4-methyl-1H-imidazol-1-yl)-6-(4,4,5,5-tetramethyl-1,3,2-dioxaborolan-2-yl)pyridine (E1). To a solution of 6-bromo-2-methoxy-3-(4-methyl-1H-imidazol-1-yl)pyridine (A5, 2.0 g, 7.5 mmol) and bispinacolatodiboron (2.3 g, 9.0 mmol) in 1,4-dioxane (25 mL) was added KOAc (1.8 g, 18 mmol) and PdCl$_2$(dppf).CH$_2$Cl$_2$ (310 mg, 0.37 mmol). The mixture was degassed with nitrogen gas for 10 min and stirred at 85° C. for 4.75 h. The reaction mixture was cooled to room temperature and concentrated under reduced pressure to give 2-methoxy-3-(4-methyl-1H-imidazol-1-yl)-6-(4,4,5,5-tetramethyl-1,3,2-dioxaborolan-2-yl)pyridine (E1, 2.5 g, crude) as a dark brown residue which was used directly in the next step: ESI MS (M+H) 234 (mass of boronic acid).

Step 2. 3-Chloro-6-(6-methoxy-5-(4-methyl-1H-imidazol-1-yl)pyridin-2-yl)-4,5-dimethylpyridazine (E2). To a solution of 2-methoxy-3-(4-methyl-1H-imidazol-1-yl)-6-(4,4,5,5-tetramethyl-1,3,2-dioxaborolan-2-yl)pyridine (E1, 2.4 g, 7.5 mmol) and 3,6-dichloro-4,5-dimethylpyridazine (1.6 g, 9.0 mmol) in 1,2-dimethoxyethane (20 mL) was added 1 M aqueous Na$_2$CO$_3$ (13 mL) and PdCl$_2$(dppf).CH$_2$Cl$_2$ (610 mg, 0.75 mmol). The mixture was sparged with nitrogen for 10 min and stirred at 85° C. for 3 h. After cooling to room temperature, the reaction mixture was diluted with methylene chloride (125 mL) and filtered to remove solids. The organic layer was washed with water (25 mL) and then the aqueous layer was extracted with methylene chloride (35 mL). The combined organic layers were dried over Na$_2$SO$_4$, decanted, and concentrated under reduced pressure. The residue was purified by flash column chromatography (silica, 5-100% ethyl acetate/methylene chloride) to afford 3-chloro-6-(6-methoxy-5-(4-methyl-1H-imidazol-1-yl)pyridin-2-yl)-4,5-dimethylpyridazine (E2, 1.3 g, 53%) as an off-white solid: ESI MS (M+H) 330; $^1$H NMR (300 MHz, CD$_3$OD) δ 8.03 (d, J=1.2 Hz, 1H), 7.99 (d, J=7.8 Hz, 1H), 7.61 (d, J=7.8 Hz, 1H), 7.27-7.26 (m, 1H), 4.05 (s, 3H), 2.55 (s, 3H), 2.54 (s, 3H), 2.26 (d, J=1.2 Hz, 3H).

Step 3. (S)—N-(1-(4-Fluorophenyl)ethyl)-6-(6-methoxy-5-(4-methyl-1H-imidazol-1-yl)pyridin-2-yl)-4,5-dimethyl-pyridazin-3-amine (E3). Toluene (8 mL), in an oven dried 20 mL microwave vial, was purged with nitrogen. To this, with a continuous nitrogen sparge and magnetic stirring, was added Pd(OAc)$_2$ (8.5 mg, 0.038 mmol) and rac-BINAP (35 mg, 0.057 mmol). After a few minutes, Cs$_2$CO$_3$ (160 mg, 0.49 mmol), 3-chloro-6-(6-methoxy-5-(4-methyl-1H-imidazol-1-yl)pyridin-2-yl)-4,5-dimethylpyridazine (E2, 125 mg, 0.379 mmol) and (S)-1-(4-fluorophenyl)ethanamine (67 μL, 0.49 mmol) were added. The reaction vessel was capped and the reaction mixture was then heated to 110° C. for 4.75 h. Upon reaction completion (monitored by LCMS), the reaction mixture was cooled to room temperature, diluted with ethyl acetate (15 mL) and filtered through filter paper. The filtrate was diluted with additional ethyl acetate (80 mL), washed with water (80 mL) and then extracted with 0.5 N HCl (80 mL). The acidic aqueous layer was basified with solid sodium bicarbonate to pH=8 and extracted with ethyl acetate (2×50 mL). The combined organic layers were dried over Na$_2$SO$_4$, decanted, and concentrated under reduced pressure. The residue was purified by flash column chromatography (silica, 0-100% ethyl acetate/methanol), which was followed by a second column (5-100% ethyl acetate/methylene chloride). The material was lyophilized (acetonitrile/water) to afford (S)—N-(1-(4-fluorophenyl)ethyl)-6-(6-methoxy-5-(4-methyl-1H-imidazol-1-yl)pyridin-2-yl)-4,5-dimethylpyridazin-3-amine (E3, 37 mg, 23%) as an amorphous white solid. ESI MS (M+H) 433; $^1$H NMR (300 MHz, DMSO-d$_6$) δ 7.94-7.91 (m, 2H), 7.49-7.43 (m, 3H), 7.28 (t, J=1.2 Hz, 1H), 7.14-7.08 (m, 2H), 6.60 (d, J=7.8 Hz, 1H), 5.45 (sym m, 1H), 3.92 (s, 3H), 2.34 (s, 3H), 2.21 (s, 3H), 2.16 (d, J=0.9 Hz, 3H), 1.54 (d, J=7.2 Hz, 3H); mp range: 85-95° C.; $[\alpha]^{20}_D$ −251.6° (c 0.11, MeOH).

4,5-Dimethyl-3-Aminopyridazine Analogs. Compounds disclosed herein incorporating a 4,5-Dimethyl-3-Aminopyridazine at ring C, and analogs thereof, were synthesized according to general procedure E and characterized as follows:

Example 17

(S)-6-(6-methoxy-5-(4-methyl-1H-imidazol-1-yl)pyridin-2-yl)-4,5-dimethyl-N-(1-phenylethyl)pyridazin-3-amine

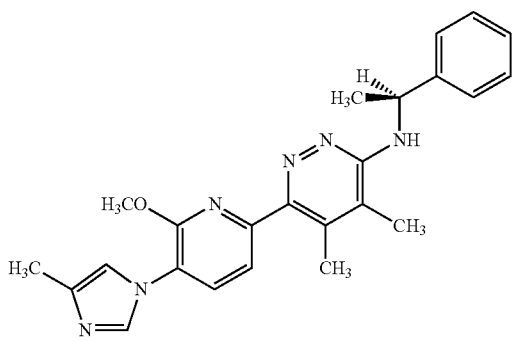 [SMILES: COc1nc(-c2nnc(N[C@@H](C)c3ccccc3)c(C)c2C)ccc1-n1cnc(C)c1]

ESI MS (M+H) 415; $^1$H NMR (500 MHz, DMSO-d$_6$) δ 7.93-7.90 (m, 2H), 7.47-7.42 (m, 3H), 7.31-7.27 (m, 3H), 7.19-7.16 (m, 1H), 6.55 (d, J=7.5 Hz, 1H), 5.47 (sym m, 1H), 3.93 (s, 3H), 2.34 (s, 3H), 2.22 (s, 3H), 2.16 (s, 3H), 1.55 (d, J=7.0 Hz, 3H); mp range: 77-83° C.; $[\alpha]^{20}_D$ −84.0° (c 0.13, MeOH).

Example 18

N-(4-fluorobenzyl)-6-(6-methoxy-5-(4-methyl-1H-imidazol-1-yl)pyridin-2-yl)-4,5-dimethylpyridazin-3-amine

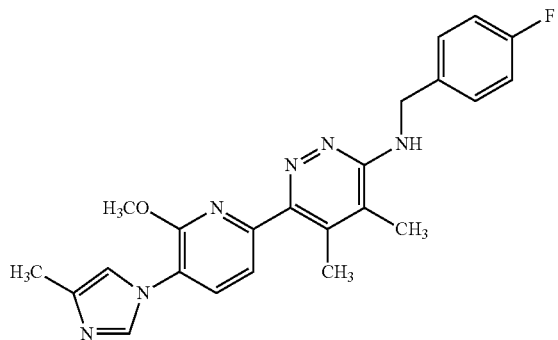 [SMILES: COc1nc(-c2nnc(NCc3ccc(F)cc3)c(C)c2C)ccc1-n1cnc(C)c1]

ESI MS (M+H) 419; $^1$H NMR (500 MHz, DMSO-$d_6$) δ 7.94-7.92 (m, 2H), 7.50 (d, J=8.0 Hz, 1H), 7.41-7.38 (m, 2H), 7.29-7.28 (m, 1H), 7.14-7.10 (m, 2H), 7.06-7.04 (m, 1H), 4.71 (d, J=5.5 Hz, 2H), 3.94 (s, 3H), 2.36 (s, 3H), 2.17 (s, 6H); mp range: 72-78° C.

Example 19

General Procedure F: Preparation of Alkylated 3-Aminopyridazine Analogs. Preparation of alkylated 3-aminopyridazine compounds disclosed herein can be afforded as set forth in Scheme 10.

Scheme 10

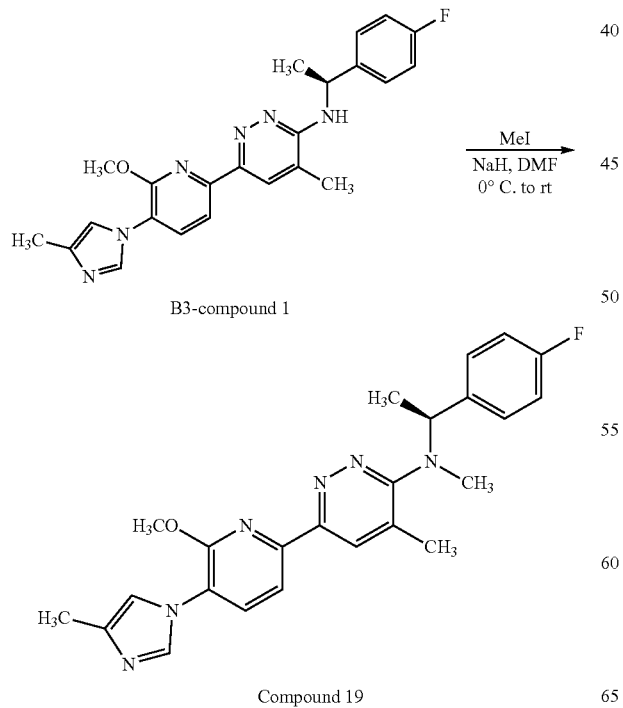

Compound 19

Preparation of (S)—N-(1-(4-fluorophenyl)ethyl)-6-(6-methoxy-5-(4-methyl-1H-imidazol-1-yl)pyridin-2-yl)-N,4-dimethylpyridazin-3-amine can be afforded as described below:

Step 1. (S)—N-(1-(4-Fluorophenyl)ethyl)-6-(6-methoxy-5-(4-methyl-1H-imidazol-1-yl)pyridin-2-yl)-N,4-dimethylpyridazin-3-amine. A solution of (S)—N-(1-(4-fluorophenyl)ethyl)-6-(6-methoxy-5-(4-methyl-1H-imidazol-1-yl)pyridin-2-yl)-4-methylpyridazin-3-amine (B3—compound 1, 220 mg, 0.52 mmol) in N,N-dimethylformamide (4 mL) was placed under a nitrogen atmosphere and cooled in a 0° C. ice-water bath. To this was added sodium hydride (60% dispersion in mineral oil, 25 mg, 0.63 mmol) and the reaction mixture was stirred at 0° C. for 0.5 h. After this time, iodomethane (36 µL, 0.58 mmol) was added and the ice bath was removed. After 1.25 h, the reaction mixture was diluted with ethyl acetate (50 mL) and washed with water (50 mL), 5% aqueous LiCl (50 mL), dried over $Na_2SO_4$, decanted, and concentrated under reduced pressure. The residue was purified by flash column chromatography (silica, 20-100% ethyl acetate/hexanes), and dried under vacuum at 45° C. overnight to afford (S)—N-(1-(4-fluorophenyl)ethyl)-6-(6-methoxy-5-(4-methyl-1H-imidazol-1-yl)pyridin-2-yl)-N,4-dimethylpyridazin-3-amine (compound 19, 60 mg, 26%) as an amorphous pale yellow solid. ESI MS (M+H) 433; $^1$H NMR (300 MHz, DMSO-$d_6$) δ 8.21 (s, 1H), 8.13 (d, J=8.1 Hz, 1H), 8.01-7.98 (m, 2H), 7.41-7.36 (m, 2H), 7.31 (s, 1H), 7.21-7.14 (m, 2H), 5.15 (q, J=6.9 Hz, 1H), 4.09 (s, 3H), 2.73 (s, 3H), 2.47 (s, 3H), 2.18 (s, 3H), 1.59 (d, J=6.9 Hz, 3H); mp range: 65-70° C.; $[α]^{20}_D$ −175.4° (c 0.12, MeOH).

Alkylated 3-Aminopyridazine Analogs. Compounds disclosed herein incorporating an alkylated-3-aminopyridazine at ring C, and analogs thereof, were synthesized according to general procedure F and characterized as follows:

Example 20

(S)—N-ethyl-N-(1-(4-fluorophenyl)ethyl)-6-(6-methoxy-5-(4-methyl-1H-imidazol-1-yl)pyridin-2-yl)-4-methylpyridazin-3-amine ESI MS (M+H) 447; $^1$H NMR (500 MHz, DMSO-$d_6$) δ 8.25 (s, 1H), 8.16 (d, J=8.0 Hz, 1H), 8.02-7.98 (m, 2H), 7.45-7.42 (m, 2H), 7.32 (s, 1H), 7.19-7.15 (m, 2H), 4.92 (q, J=6.5 Hz, 1H), 4.10 (s, 3H), 3.41-3.36 (m, 1H), 3.08-3.03 (m, 1H), 2.36 (s, 3H), 2.18 (s, 3H), 1.51 (d, J=7.0 Hz, 3H), 0.92 (t, J=7.0 Hz, 3H); mp range: 55-60° C.; $[α]^{20}_D$ −142.2° (c 0.14, MeOH).

Example 21

(S)—N-(1-(4-fluorophenyl)propyl)-6-(6-methoxy-5-(4-methyl-1H-imidazol-1-yl)pyridin-2-yl)-N,4-dimethylpyridazin-3-amine

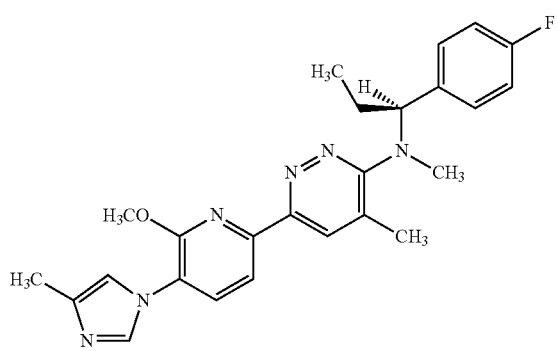 [SMILES: CC[C@@H](c1ccc(F)cc1)N(C)c1nnc(-c2ccc(-n3cnc(C)c3)c(OC)n2)cc1C]

ESI MS (M+H) 447; $^1$H NMR (500 MHz, DMSO-d$_6$) δ 8.17 (d, J=0.50 Hz, 1H), 8.11 (d, J=8.00 Hz, 1H), 7.99-7.97 (m, 2H), 7.39-7.36 (m, 2H), 7.31-7.30 (m, 1H), 7.17-7.13 (m, 2H), 4.99 (t, J=7.5 Hz, 1H), 4.09 (s, 3H), 2.80 (s, 3H), 2.46 (d, J=0.50 Hz, 3H), 2.17 (d, J=1.0 Hz, 3H), 2.16-2.02 (m, 2H), 0.89 (t, J=7.5 Hz, 3H); mp range: 57-64° C.; $[\alpha]^{20}$ −240.6° (c 0.11, MeOH).

Example 22 (G3—Compound 22)

General Procedure G: Preparation of Desmethyl-3-Aminopyridazine Analogs. Preparation of Desmethyl-3-Aminopyridazine compounds disclosed herein can be afforded as set forth in Scheme 11.

Scheme 11

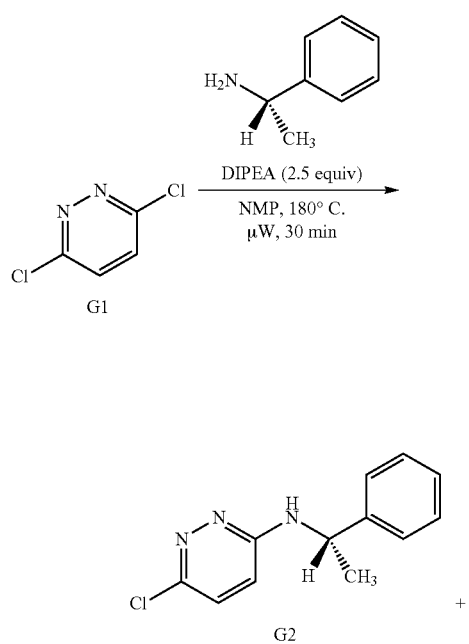

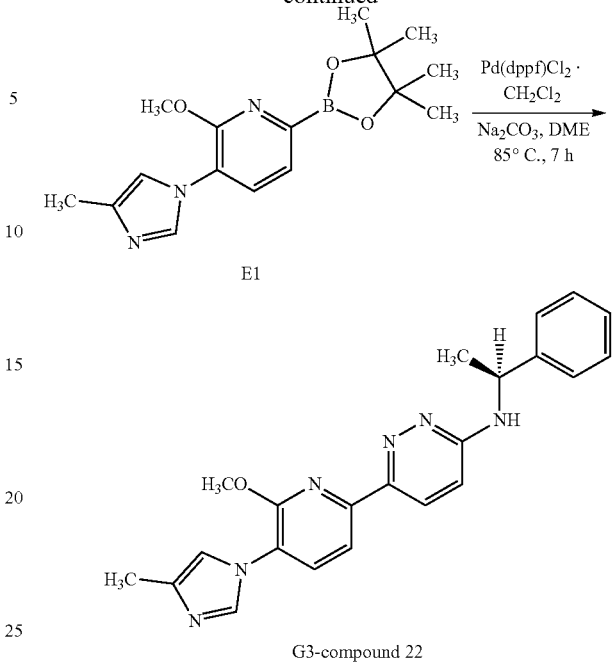

G3-compound 22

Preparation of (S)-6-(6-methoxy-5-(4-methyl-1H-imidazol-1-yl)pyridin-2-yl)-N-(1-phenylethyl)pyridazin-3-amine (G3—compound 22) can be afforded as described below:

Step 1. (S)-6-Chloro-N-(1-phenylethyl)pyridazin-3-amine (E2). To a solution of 3,6-dichloropyridazine (G1, 300 mg, 2.01 mmol) and (S)-1-phenylethanamine (0.25 mL, 2.01 mmol) in NMP (1 mL) was added N,N-diisopropylethylamine (0.64 g, 0.88 mL, 4.95 mmol). The mixture was stirred and sonicated until all the solids dissolved, then heated at 180° C. using microwave irradiation in a sealed microwave vial. The reaction mixture was left to cool to room temperature and transferred to a round-bottomed flask using methylene chloride. The methylene chloride and some of the residual DIPEA and NMP were removed under reduced pressure and the resulting residue was combined with the crude material obtained from another reaction of similar scale. The combined mixture was wet loaded (methylene chloride) onto silica gel. The residue was purified by flash column chromatography (silica, 0-40% ethyl acetate/hexanes) to afford G2 (234 mg, 24%) as a light pink solid: ESI MS (M+H) 234; $^1$H NMR (300 MHz, CDCl$_3$) δ 7.35-7.20 (m, 5H), 7.08 (d, J=9.3 Hz, 1H), 6.45 (d, J=9.3 Hz, 1H), 5.30 (m, 1H), 4.82 (sym m, 1H), 1.60 (d, J=6.7 Hz, 3H).

Step 2. (S)-6-(6-Methoxy-5-(4-methyl-1H-imidazol-1-yl)pyridin-2-yl)-N-(1-phenylethyl)pyridazin-3-amine (G3—compound 22). A suspension of 2-methoxy-3-(4-methyl-1H-imidazol-1-yl)-6-(4,4,5,5-tetramethyl-1,3,2-dioxaborolan-2-yl)pyridine (E1, 394 mg, 1.25 mmol) and G2 (234 mg, 1.00 mmol) in 1,2-dimethoxyethane (7 mL) was purged with nitrogen for 5 min. To the resulting mixture was added 1 M aqueous Na$_2$CO$_3$ (1.75 mL) and PdCl$_2$(dppf).CH$_2$Cl$_2$ (82 mg, 0.10 mmol). The mixture was purged with nitrogen for 5 min and stirred at 85° C. for 7 h. After cooling to room temperature, the reaction mixture was diluted with methylene chloride (125 mL). The organic layer was washed with water (25 mL) and then the aqueous layer was extracted with methylene chloride (35 mL). The combined organic layers were dried over MgSO$_4$, filtered, and concentrated under reduced pressure. The residue was purified by flash column chromatography (silica, 0-100% ethyl acetate/methylene chloride) to afford G3—compound 22 (87 mg, 22%) as an off-white solid: ESI MS (M+H) 387; $^1$H NMR (500 MHz, DMSO-$d_6$) δ 8.13 (d, J=9.5 Hz, 1H), 7.98 (d, J=8.0 Hz, 1H), 7.93-7.91 (m, 2H), 7.70 (d, J=7.5 Hz, 1H), 7.41 (d, J=7.0 Hz, 2H), 7.34-7.31 (m, 2H), 7.27-7.26 (m, 1H), 7.23-7.19 (m, 1H), 6.99 (d, J=9.5 Hz, 1H), 4.24 (sym m, 1H), 4.03 (s, 3H), 2.16 (d, J=1.0 Hz, 3H), 1.51 (d, J=7.0 Hz, 3H); mp range: 107-115° C.; $[\alpha]^{20}{}_D$ −114.5° (c 0.12, MeOH).

Example 23 (H2—Compound 23)

General Procedure H: Preparation of Desmethyl 3-Aminopyridazine Analogs. Preparation of desmethyl 3-aminopyridazine compounds disclosed herein can be afforded as set forth in Scheme 12.

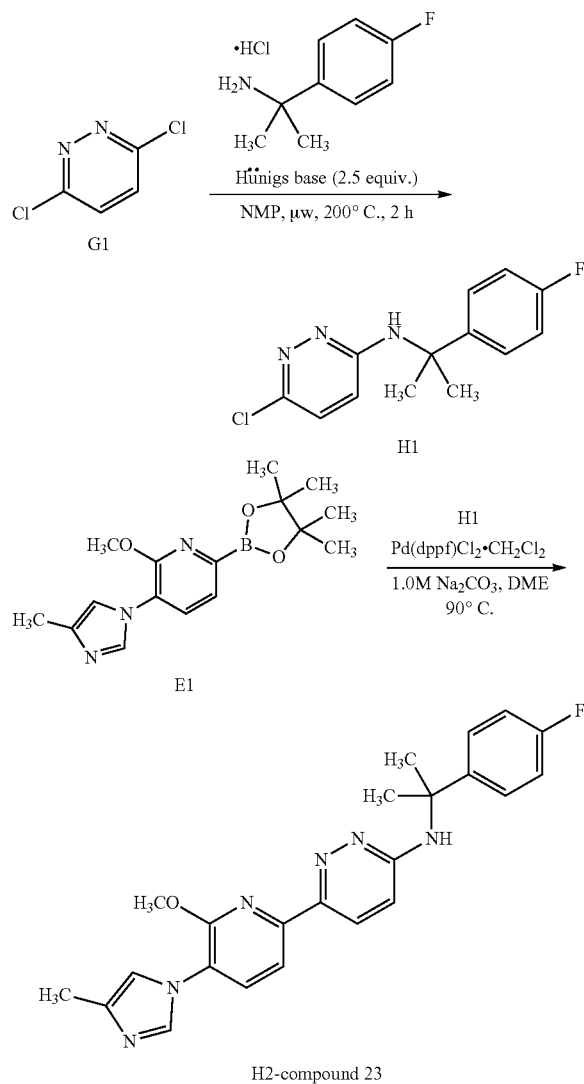

H2-compound 23

Preparation of N-(2-(4-Fluorophenyl)propan-2-yl)-6-(6-methoxy-5-(4-methyl-1H-imidazol-1-yl)pyridin-2-yl)pyridazin-3-amine (H1—compound 23) can be afforded as described below:
Step 1. 6-Chloro-N-(2-(4-fluorophenyl)propan-2-yl)pyridazin-3-amine (H1). To a solution of 3,6-dichloropyridazine (G1, 196 mg, 1.32 mmol) and 2-(4-fluorophenyl)propan-2-amine hydrochloride (250 mg, 1.32 mmol) in NMP (1 mL) was added N,N-diisopropylethylamine (0.58 mL, 3.3 mmol). The mixture was sonicated until all the solids were dissolved and then heated at 200° C. using microwave irradiation in a sealed microwave vial for 2 h. The reaction mixture was left to cool to room temperature and transferred to a round-bottomed flask using methylene chloride. The methylene chloride and some of the residual DIPEA and NMP were removed under reduced pressure and the resulting residue was purified by flash column chromatography (silica, 0-50% ethyl acetate/hexanes) to afford H1 (23 mg, 7%) as a tan solid, which was carried into the next step without additional purification: ESI MS (M+H) 266.
Step 2. N-(2-(4-Fluorophenyl)propan-2-yl)-6-(6-methoxy-5-(4-methyl-1H-imidazol-1-yl)pyridin-2-yl)pyridazin-3-amine (H2—compound 23). A suspension of 2-methoxy-3-(4-methyl-1H-imidazol-1-yl)-6-(4,4,5,5-tetramethyl-1,3,2-dioxaborolan-2-yl)pyridine (E1, 47 mg, 0.15 mmol), H1 (47 mg, 0.18 mmol) and PdCl$_2$(dppf)·CH$_2$Cl$_2$ (16 mg, 0.02 mmol) in 1,2-dimethoxyethane (0.5 mL) was sparged with nitrogen for 10 min. To the resulting mixture was added 1 M aqueous Na$_2$CO$_3$ (0.33 mL). The mixture was sparged with argon for 30 min and stirred at 90° C. for 2.5 h. After cooling to ambient temperature, the reaction mixture was concentrated in vacuo. The crude residue was purified by flash column chromatography (silica, 50-100% ethyl acetate/hexanes), followed by a second column (silica, 0-10% methanol/methylene chloride) to afford H2—compound 23 (3.0 mg, 4%) as a white solid: ESI MS (M+H) 419; $^1$H NMR (500 MHz, DMSO-$d_6$) δ 8.10 (d, J=9.5 Hz, 1H), 7.94-7.89 (m, 3H), 7.57 (s, 1H), 7.44-7.42 (m, 2H), 7.26 (s, 1H), 7.09 (t, J=9.0 Hz, 2H), 6.96 (d, J=9.5 Hz, 1H), 4.02 (s, 3H), 2.15 (d, J=1.0 Hz, 3H), 1.73 (s, 6H); mp range: 89-101° C.

Example 24A (I1—Compound 24A)

6-(6-Methoxy-5-(4-methyl-1H-imidazol-1-yl)pyridin-2-yl)pyridazin-3-amine

Preparation of 6-(6-Methoxy-5-(4-methyl-1H-imidazol-1-yl)pyridin-2-yl)pyridazin-3-amine can be afforded as set forth in Scheme 13A:

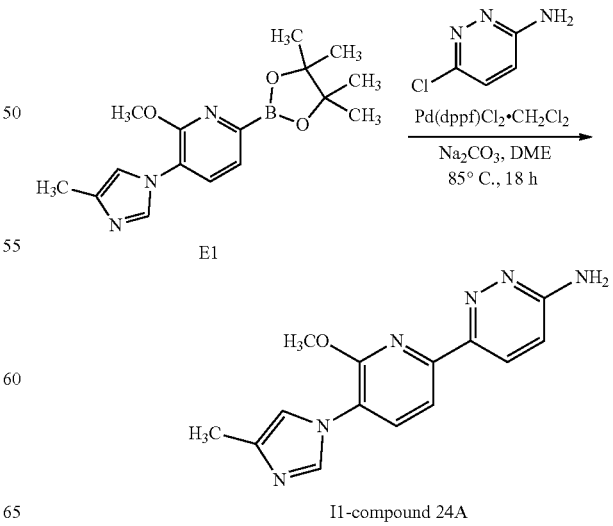

I1-compound 24A

Step 1. 6-(6-Methoxy-5-(4-methyl-1H-imidazol-1-yl)pyridin-2-yl)pyridazin-3-amine. To a solution of 2-methoxy-3-(4-methyl-1H-imidazol-1-yl)-6-(4,4,5,5-tetramethyl-1,3,2-dioxaborolan-2-yl)pyridine (E1, 500 mg, 1.59 mmol) and 6-chloropyridazin-3-amine (206 mg, 1.59 mmol) in 1,2-dimethoxyethane (4.0 mL) was added 1 M aqueous Na$_2$CO$_3$ (2.7 mL) and PdCl$_2$(dppf).CH$_2$Cl$_2$ (130 mg, 0.159 mmol). The mixture was sparged with nitrogen for 10 min and stirred at 85° C. for 18 h. After cooling to room temperature, the reaction mixture was diluted with methylene chloride (40 mL). The organic layer was washed with water (30 mL), dried over Na$_2$SO$_4$, decanted, and concentrated under reduced pressure. The residue was purified by flash column chromatography (silica, 0-10% methanol/methylene chloride) to afford I1 (127 mg, 28%) as gray solid: ESI MS (M+H) 283; $^1$H NMR (500 MHz, DMSO-d$_6$) δ 8.15 (d, J=9.5 Hz, 1H), 8.02 (d, J=8.0 Hz, 1H), 7.94-7.92 (m, 2H), 7.27 (s, 1H), 6.91 (d, J=9.0 Hz, 1H), 6.72 (s, 2H), 4.05 (s, 3H), 2.17 (d, J=0.5 Hz, 3H); mp: >250° C.

Example 24 (12—Compound 24)

General Procedure I: Preparation of Desmethyl 3-Aminopyridazine Analogs. Preparation of desmethyl 3-aminopyridazine compounds disclosed herein can be afforded as set forth in Scheme 13B.

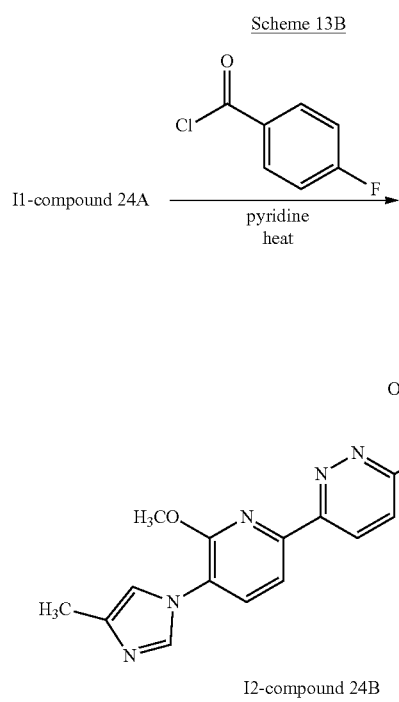

Preparation of 4-Fluoro-N-(6-(6-methoxy-5-(4-methyl-1H-imidazol-1-yl)pyridin-2-yl)pyridazin-3-yl)benzamide (I2—compound 24) can be afforded as described below:

Step 1. 4-Fluoro-N-(6-(6-methoxy-5-(4-methyl-1H-imidazol-1-yl)pyridin-2-yl)pyridazin-3-yl)benzamide (12—compound 24). A suspension of I1 (105 mg, 0.372 mmol) in pyridine (5 mL) was heated with a heat gun until all the material was dissolved. After cooling to room temperature, 4-fluorobenzoyl chloride (48 µl, 0.41 mmol) was added. After 10 min a precipitate formed and the suspension was stirred at room temperature. After 2 h, additional 4-fluorobenzoyl chloride (96 µl, 0.82 mmol) was added and the suspension was heated with a heat gun until a gentle reflux was reached. The suspension was allowed to stir at room temperature overnight. The reaction mixture was diluted with methylene chloride and the solids were collected by vacuum filtration. The resulting solids were triturated in hot pyridine (3 mL), collected by vacuum filtration while still warm and rinsed with methylene chloride. The solids were dried under vacuum at 50° C. to afford 12 (62 mg, 41%) as an off white solid: ESI MS (M+H) 405; $^1$H NMR (500 MHz, DMSO-d$_6$) δ 11.73 (s, 1H), 9.39 (s, 1H), 8.65 (d, J=9.5 Hz, 1H), 8.59 (d, J=9.0 Hz, 1H), 8.32 (d, J=8.0 Hz, 1H), 8.26 (d, J=8.0 Hz, 1H), 8.21-8.17 (m, 2H), 7.85 (s, 1H), 7.43-7.38 (m, 2H), 4.14 (s, 3H), 2.37 (s, 3H); mp: >250° C.

4-Methoxy-3-Aminopyridazine Analog Prepared (synthesized in an analogous manner to that described in Procedure H):

Example 25

(S)—N-(1-(4-fluorophenyl)ethyl)-4-methoxy-6-(6-methoxy-5-(4-methyl-1H-imidazol-1-yl)pyridin-2-yl)pyridazin-3-amine

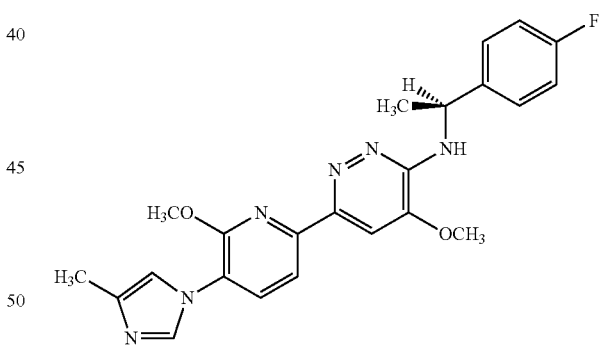

ESI MS (M+H) 435; $^1$H NMR (300 MHz, DMSO-d$_6$) δ 7.93 (d, J=1.2 Hz, 1H), 7.88 (d, J=7.8 Hz, 1H), 7.68 (d, J=7.8 Hz, 1H), 7.53-7.44 (m, 2H), 7.30-7.22 (m, 2H), 7.19-7.10 (m, 2H), 6.84 (s, 1H), 4.66 (sym m, 1H), 3.95 (s, 3H), 3.74 (s, 3H), 2.15 (d, J=0.9 Hz, 3H), 1.55 (d, J=6.9 Hz, 3H); mp range: 192-195° C.; [α]$^{20}$$_D$ −132.9° (c 0.15, MeOH).

Desmethyl 3-Aminopyridazine Analogs. Compounds disclosed herein incorporating a desmethyl 3-aminopyridazine at ring C, and analogs thereof, were synthesized according to any one of general procedures G, H, and I, and characterized as follows:

Example 26

N-(4-fluorobenzyl)-6-(6-methoxy-5-(4-methyl-1H-imidazol-1-yl)pyridin-2-yl)pyridazin-3-amine

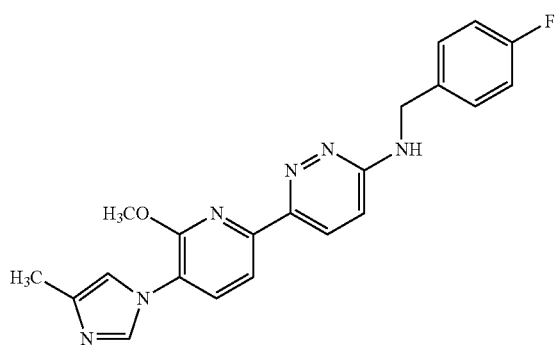 [SMILES: COc1nc(-c2ccc(NCc3ccc(F)cc3)nn2)ccc1-n1cnc(C)c1]

ESI MS (M+H) 391; $^1$H NMR (300 MHz, DMSO-$d_6$) δ 8.17 (d, J=9.3 Hz, 1H), 8.02 (d, J=8.1 Hz, 1H), 7.95 (d, J=8.1 Hz, 1H), 7.94 (d, J=1.2 Hz, 1H), 7.77 (m, 1H), 7.45-7.40 (m, 2H), 7.28 (s, 1H), 7.20-7.14 (m, 2H), 7.01 (d, J=9.3 Hz, 1H), 4.64 (d, J=5.7 Hz, 2H), 4.04 (s, 3H), 2.16 (s, 3H); mp: 170-172° C.

5-Methyl-3-Aminopyridazine Analogs. Compounds disclosed herein incorporating a 5-Methyl-3-Aminopyridazine at ring C, and analogs thereof, were synthesized according to general procedure H and characterized as follows:

Example 27

(S)—N-(1-(4-fluorophenyl)ethyl)-6-(6-methoxy-5-(4-methyl-1H-imidazol-1-yl)pyridin-2-yl)-5-methyl-pyridazin-3-amine

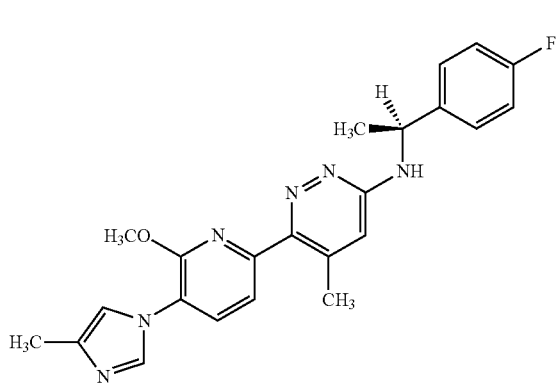 [SMILES: COc1nc(-c2nnc(N[C@@H](C)c3ccc(F)cc3)cc2C)ccc1-n1cnc(C)c1]

ESI MS (M+H) 419; $^1$H NMR (500 MHz, DMSO-$d_6$) δ 7.94-7.94 (m, 2H), 7.66 (d, J=8.0 Hz, 1H), 7.51 (d, J=8.0 Hz, 1H), 7.46-7.42 (m, 2H), 7.28-7.27 (m, 1H), 7.16-7.11 (m, 2H), 6.74 (d, J=1.0 Hz, 1H), 5.22 (sym m, 1H), 3.95 (s, 3H), 2.47 (s, 3H), 2.16 (d, J=0.5 Hz, 3H), 1.48 (d, J=7.0 Hz, 3H); mp range: 93-102° C.; $[α]^{20}_D$ −118.6° (c 0.14, MeOH).

Example 28

(S)-6-(6-methoxy-5-(4-methyl-1H-imidazol-1-yl)pyridin-2-yl)-5-methyl-N-(1-phenylethyl)pyridazin-3-amine

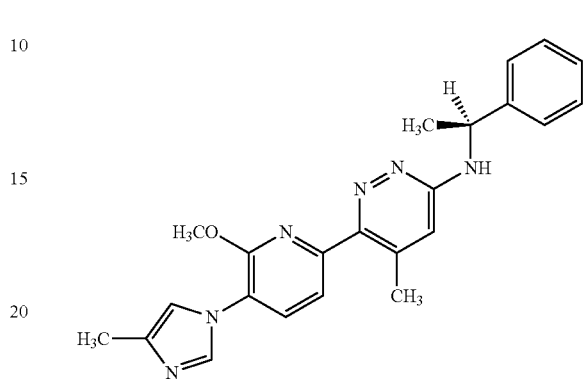

ESI MS (M+H) 401; $^1$H NMR (500 MHz, DMSO-$d_6$) δ 7.93-7.91 (m, 2H), 7.67 (d, J=8.0 Hz, 1H), 7.50 (d, J=8.0 Hz, 1H), 7.42-7.40 (m, 2H), 7.33-7.30 (m, 2H), 7.28-7.27 (m, 1H), 7.22-7.19 (m, 1H), 6.74 (s, 1H), 5.21 (sym m, 1H), 3.95 (s, 3H), 2.47 (s, 3H), 2.16 (d, J=1.0 Hz, 3H), 1.49 (d, J=7.0 Hz, 3H); mp: 140-143° C.; $[α]^{20}_D$ −102.0° (c 0.10, MeOH).

Example 29 (J5—Compound 29)

General Procedure J: Preparation of 4,5-Fused Cyclopentyl-3-Aminopyridazine Analogs. Preparation of 4,5-fused cyclopentyl-3-aminopyridazine compounds disclosed herein can be afforded as set forth in Scheme 14.

Scheme 14

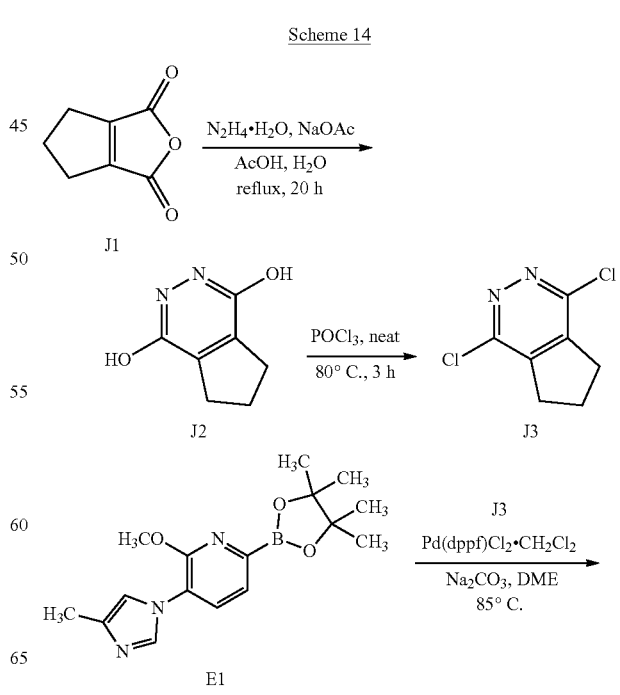

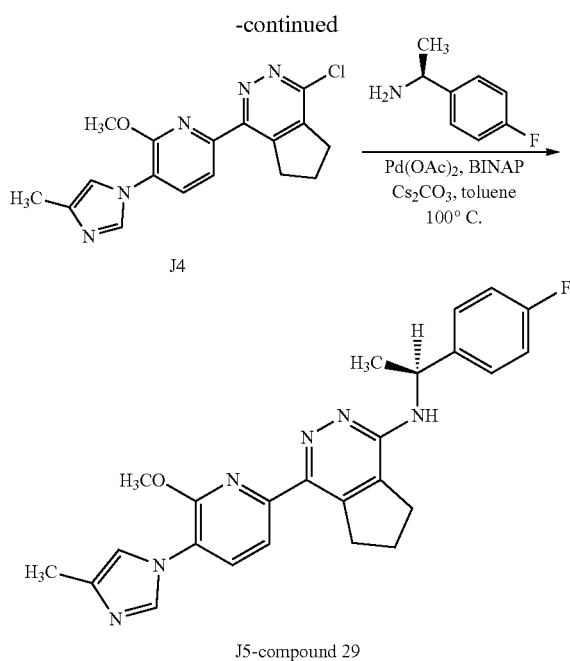

J4

J5-compound 29

Preparation of (S)—N-(1-(4-Fluorophenyl)ethyl)-4-(6-methoxy-5-(4-methyl-1H-imidazol-1-yl) pyridine-2-yl)-6,7-dihydro-5H-cyclopenta[d]pyridazin-1-amine (J5—compound 29) can be afforded as described below:

Step 1. 6,7-Dihydro-5H-cyclopenta[d]pyridazine-1,4-diol (J2). A 50 mL round bottom flask, equipped with a condenser and a magnetic stir bar, was charged with 1-cyclopentene-1,2-dicarboxylic anhydride (J1, 1.00 g, 7.24 mmol), NaOAc (712 mg, 8.68 mmol), $H_2O$ (18 mL), and AcOH (9.50 mL, 167 mmol). To the reaction mixture was added hydrazine monohydrate (0.42 mL, 8.7 mmol) in one portion and the mixture was heated at reflux for 20 h. After this time, the reaction mixture was cooled to ambient temperature, filtered through a medium fritted funnel, and the solid was washed with $H_2O$ (2×20 mL). The solid was dried in a vacuum oven for 5 h at 58° C. to J2 (827 mg, 75%) as a tan solid, which was carried into the next step without additional purification: ESI MS (M+H) 153.

Step 2. 1,4-Dichloro-6,7-dihydro-5H-cyclopenta[d]pyridazine (J3). A 50 mL round bottom flask, equipped with a condenser, magnetic stir bar, and under a nitrogen atmosphere, was charged with J2 (701 mg, 4.61 mmol) and phosphorous oxychloride (4.3 mL, 46 mmol). The reaction mixture was then heated to 80° C. for 3 h. After this time, the reaction mixture was cooled to ambient temperature. The reaction mixture was then poured into a mixture of ice cold saturated aqueous $NaHCO_3$ (50 mL) and ethyl acetate (50 mL). The solution was adjusted to pH=8 and stirred for 1 h. After this time, the phases were partitioned and extracted with ethyl acetate (50 mL). The organic phase was dried over $MgSO_4$, filtered, and concentrated in vacuo to afford J3 (318 mg, 37%) as a light golden solid: ESI MS (M+H) 189.

Step 3. 1-Chloro-4-(6-methoxy-5-(4-methyl-1H-imidazol-1-yl)pyridin-2-yl)-6,7-dihydro-5H-cyclopenta[d]pyridazine (J4). An oven dried 20 mL microwave vial, equipped with a magnetic stir bar and under a nitrogen atmosphere, was charged with 2-methoxy-3-(4-methyl-1H-imidazol-1-yl)-6-(4,4,5,5-tetramethyl-1,3,2-dioxaborolan-2-yl)pyridine (C1, 600 mg, 1.90 mmol), J3 (300 mg, 1.58 mmol), $PdCl_2(dppf) \cdot CH_2Cl_2$ (155 mg, 0.158 mmol), and 1,2-dimethoxyethane (8.0 mL). To the solution was added 1.0 M aqueous $Na_2CO_3$ (5.1 mL). The reaction mixture was purged with argon for 1 h and heated to 90° C. for 5 h. After this time, the reaction mixture was cooled to ambient temperature, diluted with methylene chloride (20 mL), and filtered through a plug of Celite®. The filtrate was collected, concentrated in vacuo, and the residue was purified by flash column chromatography (silica, 0-50% ethyl acetate/hexanes), followed by another column (silica, 0-10% methanol/methylene chloride) to afford J4 (125 mg, 23%) as a tan solid: ESI MS (M+H) 342.

Step 4. (S)—N-(1-(4-Fluorophenyl)ethyl)-4-(6-methoxy-5-(4-methyl-1H-imidazol-1-yl)pyridin-2-yl)-6,7-dihydro-5H-cyclopenta[d]pyridazin-1-amine (J5—compound 29). An oven dried 20 mL microwave vial, equipped with a magnetic stir bar and under a nitrogen atmosphere, was charged J4 (125 mg, 0.379 mmol), (S)-1-(4-fluorophenyl)ethanamine (0.12 mL, 0.91 mmol), $Cs_2CO_3$, (155 mg, 0.476 mmol), $Pd(OAc)_2$ (9 mg, 0.04 mmol), and rac-BINAP (45 mg, 0.073 mmol). The reaction vessel was purged with nitrogen using evac/refill cycle (1×). Toluene (8 mL) was added and the reaction mixture was degassed further by purging with argon for 5-10 min. The reaction mixture was then heated to 100° C. for 18 h. Upon reaction completion (monitored by LCMS), the reaction mixture was cooled to room temperature and concentrated in vacuo to give a crude residue. The residue was purified by flash column chromatography (silica, 50-100% ethyl acetate/hexanes). The resulting residue was re-dissolved in methylene chloride (20 mL), extracted with 0.5 M HCl (20 mL), and the aqueous layer was adjusted to pH≥8 using $NaHCO_3$. The cloudy solution was extracted with methylene chloride (2×20 mL), dried over $MgSO_4$, filtered and concentrated in vacuo. The resulting solid was lyophilized in $MeCN/H_2O$ to afford J5—compound 29 (46 mg, 28%) as an amorphous white solid. ESI MS (M+H) 445; $^1H$ NMR (300 MHz, DMSO-$d_6$) δ 7.98-7.89 (m, 3H), 7.49-7.44 (m, 2H), 7.27 (d, J=1.2 Hz, 1H), 7.12 (t, J=9.0 Hz, 2H), 6.99 (d, J=7.5 Hz, 1H), 5.49 (sym m, 1H), 3.99 (s, 3H), 3.44-3.39 (m, 2H), 2.88-2.84 (m, 2H), 2.16 (d, J=0.9 Hz, 3H), 2.12-2.07 (m, 2H), 1.54 (d, J=7.2 Hz, 3H); mp range: 111-122° C.; $[\alpha]^{20}_D$ −126.0° (c 0.10, MeOH).

4,5-Fused Cyclopentyl-3-Aminopyridazine Analogs. Compounds disclosed herein incorporating a 4,5-Fused Cyclopentyl-3-Aminopyridazine at ring C, and analogs thereof, were synthesized according to general procedure J and characterized as follows:

Example 31 (K2—Compound 31)

General Procedure K: Preparation of 4-Methyl-3-Aminopyridazine Analogs. Preparation of 4-methyl-3-aminopyridazine compounds disclosed herein can be afforded as set forth in Scheme 15.

Scheme 15

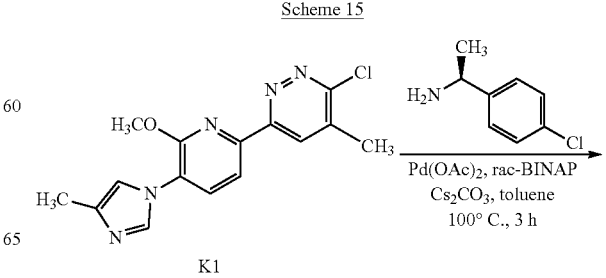

K1

-continued

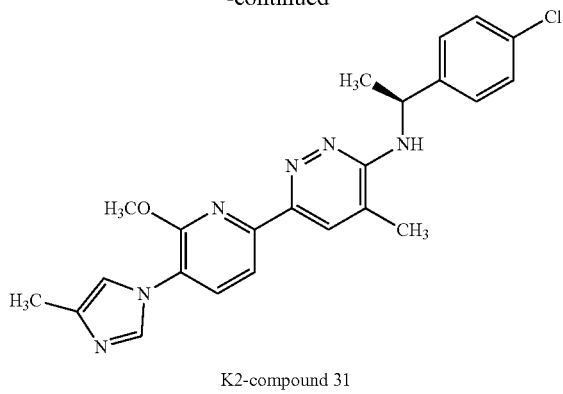

K2-compound 31

Preparation of (S)—N-(1-(4-chlorophenyl)ethyl)-6-(6-methoxy-5-(4-methyl-1H-imidazol-1-yl)pyridin-2-yl)-4-methylpyridazin-3-amine (K1—compound 31) can be afforded as described below Step 1. (S)—N-(1-(4-Chlorophenyl)ethyl)-6-(6-methoxy-5-(4-methyl-1H-imidazol-1-yl)pyridin-2-yl)-4-methyl-pyridazin-3-amine (K2—compound 31). An oven dried 20 mL microwave vial, equipped with a magnetic stir bar and under a nitrogen atmosphere, was charged with 3-chloro-6-(6-methoxy-5-(4-methyl-1H-imidazol-1-yl)pyridin-2-yl)-4-methylpyridazine (K1, 125 mg, 0.396 mmol), (S)-1-(4-chlorophenyl)ethanamine (0.14 mL, 0.99 mmol), $Cs_2CO_3$ (168 mg, 0.515 mmol), $Pd(OAc)_2$ (9 mg, 0.04 mmol), and rac-BINAP (50 mg, 0.075 mmol). The reaction vessel was purged with nitrogen using evac/refill cycle (1×). Toluene (8 mL) was added and the reaction mixture was degassed further by sparging with argon for 5-10 min. The reaction mixture was then heated to 100° C. overnight. Upon reaction completion, the reaction mixture was cooled to room temperature and concentrated in vacuo to give a crude residue. The residue was purified by flash column chromatography (silica, 50-100% ethyl acetate/hexanes) to give a yellow residue. The residue was re-subjected to flash column chromatography (silica, 0-10% methanol/methylene chloride) to afford K2 (63 mg, 36%) as an amorphous white powder. ESI MS (M+H) 435; $^1$H NMR (500 MHz, DMSO-$d_6$) δ 8.01 (s, 1H), 7.98 (d, J=8.0 Hz, 1H), 7.92 (d, J=1.5 Hz, 1H), 7.91 (d, J=7.5 Hz, 1H), 7.46 (d, J=8.5 Hz, 2H), 7.35 (d, J=8.5 Hz, 2H), 7.26 (s, 1H), 6.83 (d, J=7.5 Hz, 1H), 5.46 (sym m, 1H), 4.05 (s, 3H), 2.31 (s, 3H), 2.16 (s, 3H), 1.56 (d, J=7.0 Hz, 3H); mp range: 103-114° C.

4-Methyl-3-Aminopyridazine Analogs. Compounds disclosed herein incorporating a 4-Methyl-3-Aminopyridazine at ring C, and analogs thereof, were synthesized according to general procedure K and characterized as follows:

Example 33

(S)—N-(1-(3-chlorophenyl)ethyl)-6-(6-methoxy-5-(4-methyl-1H-imidazol-1-yl)pyridin-2-yl)-4-methyl-pyridazin-3-amine

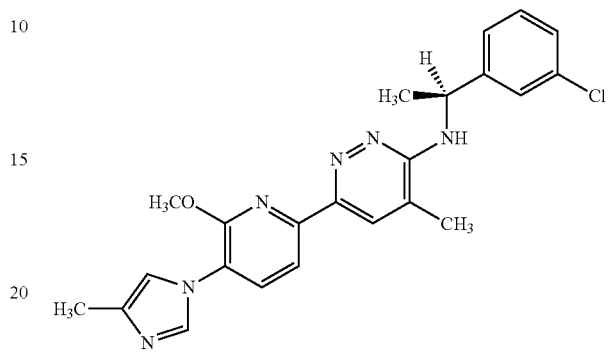

ESI MS (M+H) 435; $^1$H NMR (500 MHz, DMSO-$d_6$) δ 8.02 (s, 1H), 7.99 (d, J=8.0 Hz, 1H), 7.92 (d, J=1.5 Hz, 1H), 7.91 (d, J=7.5 Hz, 1H), 7.50 (t, J=1.5 Hz, 1H), 7.41 (d, J=8.0 Hz, 1H), 7.33 (t, J=7.5 Hz, 1H), 7.26-7.24 (m, 2H), 6.85 (d, J=7.5 Hz, 1H), 5.46 (sym m, 1H), 4.05 (s, 3H), 2.32 (s, 3H), 2.16 (s, 3H), 1.56 (d, J=7.0 Hz, 3H); mp range: 110-117° C.

Example 34

(S)—N-(1-(2-fluorophenyl)ethyl)-6-(6-methoxy-5-(4-methyl-1H-imidazol-1-yl)pyridin-2-yl)-4-methyl-pyridazin-3-amine

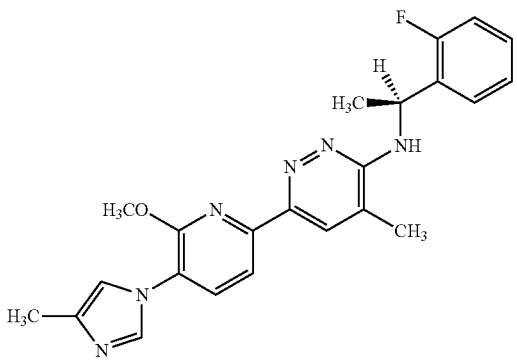 [SMILES: COc1nc(-c2cc(C)c(N[C@@H](C)c3ccccc3F)nn2)ccc1-n1cnc(C)c1]

ESI MS (M+H) 419; $^1$H NMR (500 MHz, DMSO-$d_6$) δ 8.03 (s, 1H), 7.98 (d, J=8.0 Hz, 1H), 7.92 (d, J=1.0 Hz, 1H), 7.91 (d, J=8.0 Hz, 1H), 7.46 (dt, J=8.0, 1.5 Hz, 1H), 7.27-7.22 (m, 2H), 7.17-7.14 (m, 1H), 7.11 (dt, J=7.5, 1.0 Hz, 1H), 6.85 (d, J=7.5 Hz, 1H), 5.72 (sym m, 1H), 4.05 (s, 3H), 2.36 (s, 3H), 2.16 (s, 3H), 1.57 (d, J=7.0 Hz, 3H); mp range: 107-113° C.

Example 35

(S)-6-(6-methoxy-5-(4-methyl-1H-imidazol-1-yl)pyridin-2-yl)-4-methyl-N-(1-phenylethyl)pyridazin-3-amine

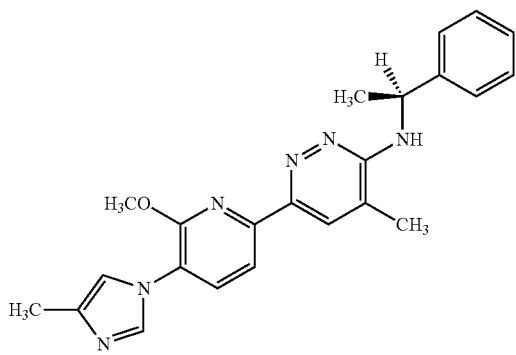 [SMILES: COc1nc(-c2cc(C)c(N[C@@H](C)c3ccccc3)nn2)ccc1-n1cnc(C)c1]

ESI MS (M+H) 401; $^1$H NMR (500 MHz, DMSO-d$_6$) δ 8.00 (d, J=0.5 Hz, 1H), 7.98 (d, J=8.0 Hz, 1H), 7.92 (d, J=1.0 Hz, 1H), 7.90 (d, J=8.0 Hz, 1H), 7.44 (t, J=7.0 Hz, 2H), 7.33-7.28 (m, 2H), 7.28 (s, 1H), 7.22-7.16 (m, 1H), 6.79 (d, J=8.0 Hz, 1H), 5.51 (sym m, 1H), 4.05 (s, 3H), 2.31 (d, J=0.5 Hz, 3H), 2.16 (d, J=1.0 Hz, 3H), 1.57 (d, J=7.0 Hz, 3H); mp range: 76-86° C.

Example 36

(S)-6-(6-methoxy-5-(4-methyl-1H-imidazol-1-yl)pyridin-2-yl)-N-(1-(4-methoxyphenyl)ethyl)-4-methylpyridazin-3-amine

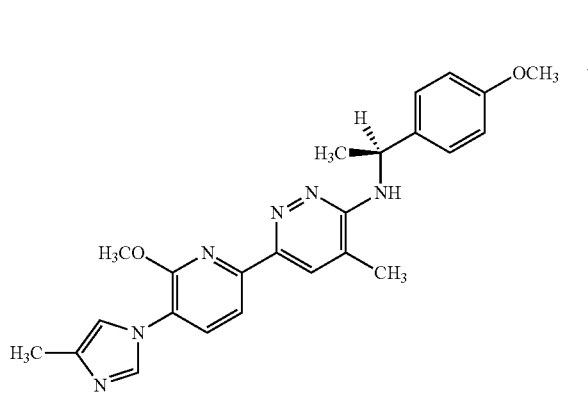

ESI MS (M+H) 431; $^1$H NMR (300 MHz, DMSO-d$_6$) δ 8.00 (d, J=1.2 Hz, 1H), 7.99 (d, J=7.8 Hz, 1H), 7.93 (s, 1H), 7.91 (d, J=7.8 Hz, 1H), 7.36 (d, J=8.7 Hz, 2H), 7.27 (s, 1H), 6.86 (d, J=8.7 Hz, 2H), 6.74 (d, J=7.8 Hz, 1H), 5.46 (sym m, 1H), 4.05 (s, 3H), 3.70 (s, 3H), 2.29 (s, 3H), 2.16 (s, 3H), 1.54 (d, J=6.9 Hz, 3H); mp range: 102-108° C.

Example 37

(S)-6-(6-methoxy-5-(4-methyl-1H-imidazol-1-yl)pyridin-2-yl)-4-methyl-N-(1-(4-(trifluoromethyl)phenyl)ethyl)pyridazin-3-amine

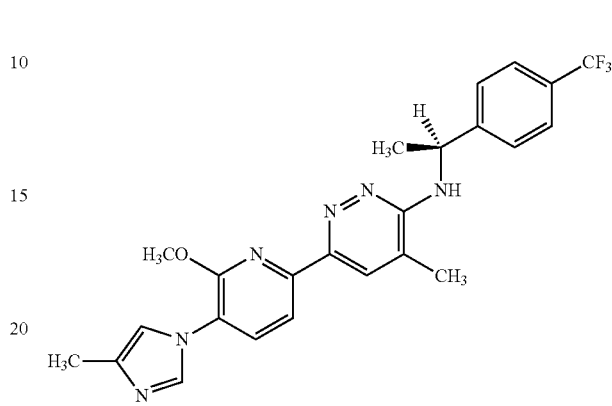

ESI MS (M+H) 469; $^1$H NMR (500 MHz, DMSO-d$_6$) δ 8.02 (s, 1H), 7.98 (d, J=8.0 Hz, 1H), 7.92 (d, J=1.5 Hz, 1H), 7.90 (d, J=8.0 Hz, 1H) 7.66 (s, 4H), 7.26 (s, 1H), 6.93 (d, J=7.5 Hz, 1H), 5.52 (sym m, 1H), 4.05 (s, 3H), 2.33 (s, 3H), 2.15 (s, 3H), 1.59 (d, J=7.0 Hz, 3H); mp range: 119-134° C.

Example 38

(S)—N-(1-(3-fluorophenyl)ethyl)-6-(6-methoxy-5-(4-methyl-1H-imidazol-1-yl)pyridin-2-yl)-4-methylpyridazin-3-amine

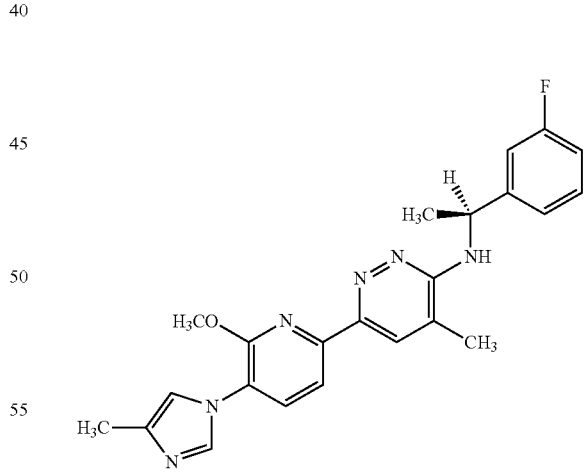

ESI MS (M+H) 419; $^1$H NMR (500 MHz, DMSO-d$_6$) δ 8.02 (d, J=0.5 Hz, 1H), 7.92 (d, J=1.0 Hz, 1H), 7.93-7.90 (m, 2H), 7.36-7.32 (m, 1H), 7.29-7.25 (m, 3H), 7.03-6.99 (m, 1H), 6.83 (d, J=7.5 Hz, 1H), 5.50 (sym m, 1H), 4.06 (s, 3H), 2.32 (s, 3H), 2.16 (s, 3H), 1.57 (d, J=7.0 Hz, 3H); mp range: 112-120° C.

Example 39

(S)—N-(1-(3,4-difluorophenyl)ethyl)-6-(6-methoxy-5-(4-methyl-1H-imidazol-1-yl)pyridin-2-yl)-4-methylpyridazin-3-amine

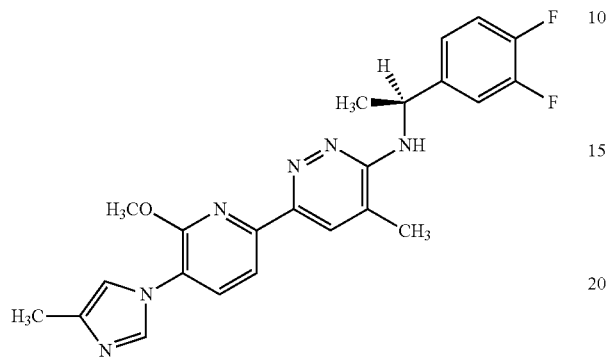

ESI MS (M+H) 437; $^1$H NMR (300 MHz, DMSO-d$_6$) δ 8.03 (d, J=0.9 Hz, 1H), 7.99 (d, J=8.1 Hz, 1H), 7.93-7.90 (m, 2H), 7.54-7.46 (m, 1H), 7.40-7.26 (m, 3H), 6.85 (d, J=7.5 Hz, 1H), 5.46 (sym m, 1H), 4.05 (s, 3H), 2.31 (s, 3H), 2.16 (s, 3H), 1.56 (d, J=6.9 Hz, 3H); mp range: 109-121° C.

Example 40

(S)—N-(1-(4-fluorophenyl)propyl)-6-(6-methoxy-5-(4-methyl-1H-imidazol-1-yl)pyridin-2-yl)-4-methylpyridazin-3-amine

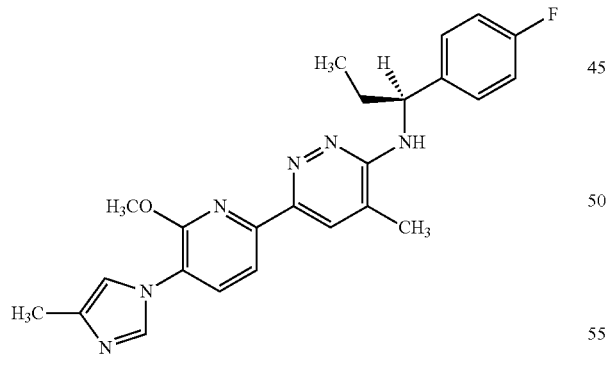

ESI MS (M+H) 433; $^1$H NMR (500 MHz, DMSO-d$_6$) δ 8.00-7.98 (m, 2H), 7.92-7.89 (m, 2H), 7.50-7.47 (m, 2H), 7.26 (s, 1H), 7.12 (t, J=9.0 Hz, 2H), 6.75 (d, J=8.0 Hz, 1H), 5.26 (sym m, 1H), 4.05 (s, 3H), 2.30 (s, 3H), 2.16 (s, 3H), 2.03-1.96 (m, 1H), 1.86-1.80 (m, 1H), 1.49 (t, J=7.0 Hz, 3H); mp range: 102-109° C.; [α]$^{20}_D$ −151.2° (c 0.11, MeOH).

Example 41

(S)-6-(6-methoxy-5-(4-methyl-1H-imidazol-1-yl)pyridin-2-yl)-N-(1-(2-methoxyphenyl)ethyl)-4-methylpyridazin-3-amine

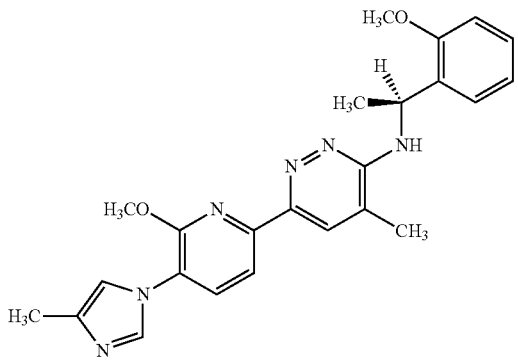 [SMILES: COc1ccccc1[C@H](C)Nc1nnc(-c2ccc(-n3cnc(C)c3)c(OC)n2)cc1C]

ESI MS (M+H) 431; $^1$H NMR (300 MHz, DMSO-d$_6$) δ 8.02-7.89 (m, 4H), 7.23-7.26 (m, 2H), 7.21-7.15 (m, 1H), 7.00-6.98 (m, 1H), 6.88-6.82 (m, 1H), 6.71 (d, J=9.0 Hz, 1H), 5.78 (sym m, 1H), 4.05 (s, 3H), 3.88 (s, 3H), 2.34 (s, 3H), 2.15 (s, 3H), 1.49 (d, J=6.9 Hz, 3H); mp range: 114-120° C.; [α]$^{20}_D$ −19.50 (c 0.11, MeOH).

Example 42

(S)-6-(6-methoxy-5-(4-methyl-1H-imidazol-1-yl)pyridin-2-yl)-4-methyl-N-(1-(p-tolyl)ethyl)pyridazin-3-amine

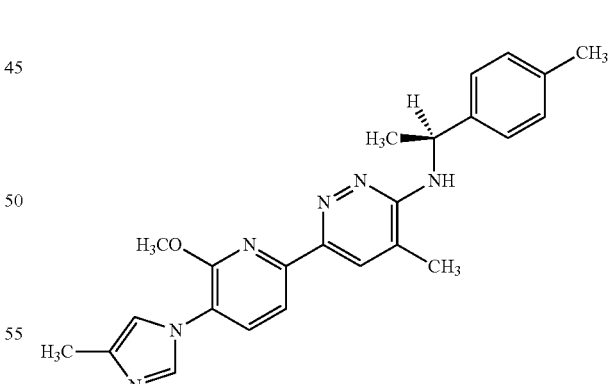

ESI MS (M+H) 415; $^1$H NMR (300 MHz, DMSO-d$_6$) δ 8.00-7.87 (m, 4H), 7.32 (d, J=8.0 Hz, 2H), 7.27 (d, J=0.9 Hz, 1H), 7.10 (d, J=8.0 Hz, 2H), 6.77 (d, J=7.5 Hz, 1H), 5.46 (sym m, 1H), 4.05 (s, 3H), 2.30 (s, 3H), 2.25 (s, 3H), 2.16 (d, J=0.9 Hz, 3H), 1.54 (d, J=6.9 Hz, 3H); mp range: 84-92° C.; [α]$^{20}_D$ −112.5° (c 0.21, Methanol).

Example 43

(S)—N-(1-(3,5-bis(trifluoromethyl)phenyl)ethyl)-6-(6-methoxy-5-(4-methyl-1H-imidazol-1-yl)pyridin-2-yl)-4-methylpyridazin-3-amine

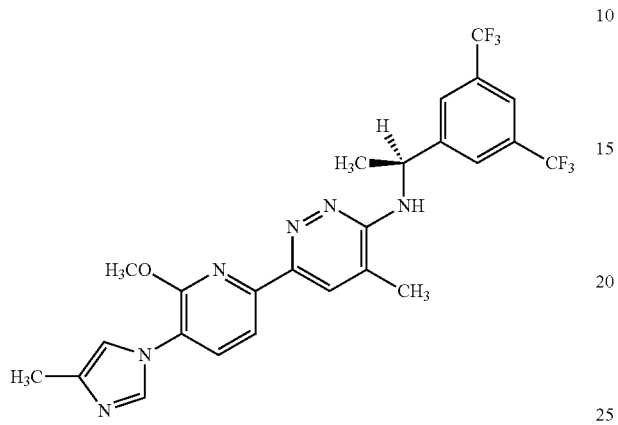

ESI MS (M+H) 537; ¹H NMR (300 MHz, DMSO-d₆) δ 8.18 (s, 2H), 8.05 (d, J=1.2 Hz, 1H), 7.99-7.89 (m, 4H), 7.27 (t, J=1.2 Hz, 1H), 7.05 (d, J=7.5 Hz, 1H), 5.62 (sym m, 1H), 4.05 (s, 3H), 2.35 (s, 3H), 2.16 (s, 3H), 1.62 (d, J=7.2 Hz, 3H); mp range: 122-130° C.; $[\alpha]^{20}_D$ −87.9° (c 0.13, MeOH).

Example 44

(S)-6-(6-methoxy-5-(4-methyl-1H-imidazol-1-yl)pyridin-2-yl)-N-(1-(3-methoxyphenyl)ethyl)-4-methylpyridazin-3-amine

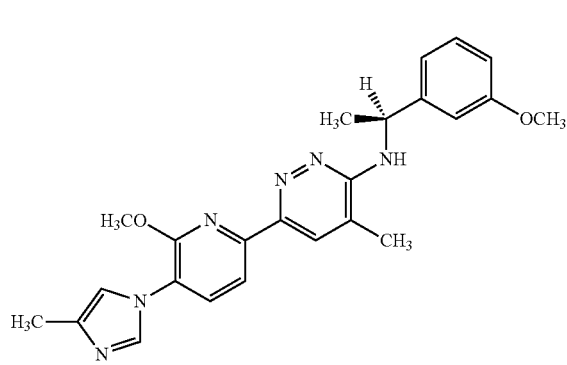 [SMILES: COc1cccc([C@H](C)Nc2nnc(-c3ccc(-n4cnc(C)c4)c(OC)n3)cc2C)c1]

ESI MS (M+H) 431; ¹H NMR (500 MHz, DMSO-d₆) δ 8.00-7.98 (m, 2H), 7.92-7.90 (m, 2H), 7.26 (s, 1H), 7.21 (t, J=8.0 Hz, 1H), 7.02 (s, 1H), 7.00 (s, 1H), 6.77-6.75 (m, 2H), 5.47 (sym m, 1H), 4.05 (s, 3H), 3.73 (s. 3H), 2.31 (s, 3H), 2.16 (s, 3H), 1.56 (d, J=7.0 Hz, 3H); mp range: 90-102° C.; $[\alpha]^{20}_D$ −151.2° (c 0.15, MeOH).

Example 45

(S)—N-(1-(2,4-difluorophenyl)ethyl)-6-(6-methoxy-5-(4-methyl-1H-imidazol-1-yl)pyridin-2-yl)-4-methylpyridazin-3-amine

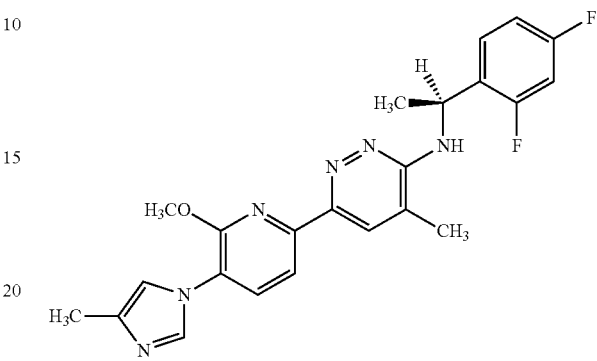

ESI MS (M+H) 437; ¹H NMR (500 MHz, DMSO-d₆) δ 8.02 (d, J=1.0 Hz, 1H), 7.98 (d, J=8.0 Hz, 1H), 7.92 (d, J=1.0 Hz, 1H), 7.91 (d, J=8.0 Hz, 1H), 7.51-7.47 (m, 1H), 7.26 (t, J=1.0 Hz, 1H), 7.22-7.17 (m, 1H), 7.00 (td, J=2.5, 8.5 Hz, 1H), 6.86 (d, J=7.5 Hz, 1H), 5.66 (sym m, 1H), 4.05 (s, 3H), 2.33 (s, 3H), 2.16 (s, 3H), 1.56 (d, J=7.0 Hz, 3H); mp range: 119-136° C.; $[\alpha]^{20}_D$ −62.5° (c 0.12, MeOH).

Example 46

(S)—N-(1-(3,5-difluorophenyl)ethyl)-6-(6-methoxy-5-(4-methyl-1H-imidazol-1-yl)pyridin-2-yl)-4-methylpyridazin-3-amine

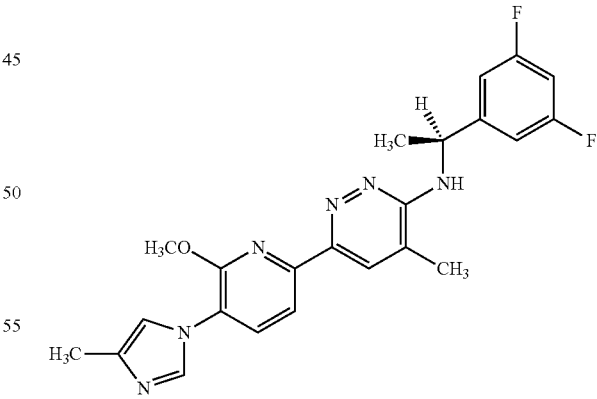

ESI MS (M+H) 437; ¹H NMR (300 MHz, DMSO-d₆) δ 8.04 (d, J=0.9 Hz, 1H), 7.99 (d, J=8.1 Hz, 1H), 7.93 (s, 1H), 7.92 (d, J=8.1 Hz, 1H), 7.27 (s, 1H), 7.23-7.13 (m, 2H), 7.05 (m, 1H), 6.88 (d, J=7.5 Hz, 1H), 5.46 (sym m, 1H), 4.06 (s, 3H), 2.33 (d, J=0.6 Hz, 3H), 2.16 (d, J=0.9 Hz, 3H), 1.56 (d, J=7.2 Hz, 3H); mp range: 80-90° C.; $[\alpha]^{20}_D$ −81.4° (c 0.09, Methanol).

Example 47

(S)—N-(1-(4-fluoro-3-methoxyphenyl)ethyl)-6-(6-methoxy-5-(4-methyl-1H-imidazol-1-yl)pyridin-2-yl)-4-methylpyridazin-3-amine

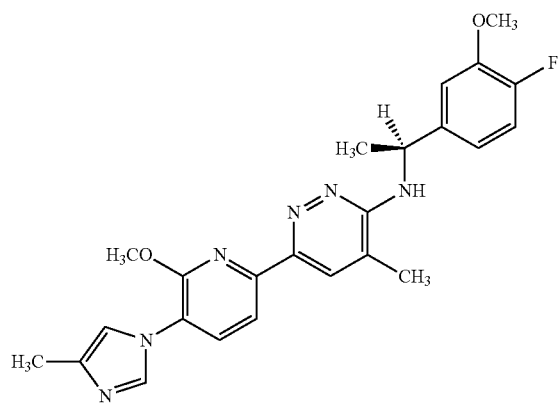 [SMILES: COc1cc([C@H](C)Nc2nnc(-c3ccc(-n4cnc(C)c4)c(OC)n3)cc2C)ccc1F]

ESI MS (M+H) 449; ¹H NMR (500 MHz, DMSO-d$_6$) δ 8.01-7.98 (m, 2H), 7.93-7.90 (m, 2H), 7.29-7.26 (m, 2H), 7.12-7.08 (m, 1H), 7.00-6.97 (m, 1H), 6.77 (d, J=7.5 Hz, 1H), 5.49 (sym m, 1H), 4.05 (s, 3H), 3.84 (s, 3H), 2.31 (s, 3H), 2.16 (s, 3H), 1.57 (d, J=7.0 Hz, 3H); mp range: 105-111° C.; [α]$^{20}$$_D$ −59.1° (c 0.13, MeOH).

Example 48

(S)-6-(6-methoxy-5-(4-methyl-1H-imidazol-1-yl)pyridin-2-yl)-4-methyl-N-(1-(m-tolyl)ethyl)pyridazin-3-amine

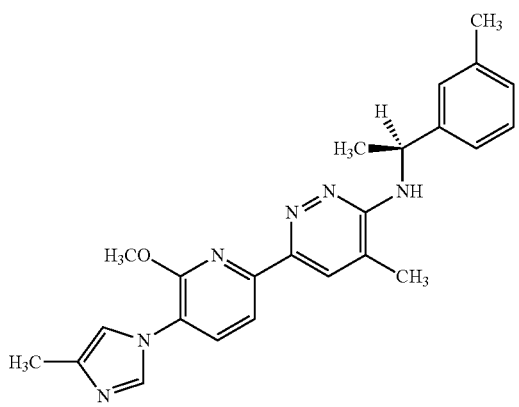

ESI MS (M+H) 415; ¹H NMR (500 MHz, DMSO-d$_6$) δ 8.00-7.97 (m, 2H), 7.92-7.90 (m, 2H), 7.26-7.22 3H), 7.20-7.16 (m, 1H), 7.00 (d, J=7.5 Hz, 1H), 6.75 (d, J=8.0 Hz, 1H), 5.47 (sym m, 1H), 4.05 (s, 3H), 2.31 (d, J=0.5 Hz, 3H), 2.29 (s, 3H), 2.16 (d, J=0.5 Hz, 3H), 1.55 (d, J=7.0 Hz, 3H); mp range: 100-106° C.; [α]$^{20}$$_D$ −84.0° (c 0.12, MeOH).

Example 49

(S)-6-(6-methoxy-5-(4-methyl-1H-imidazol-1-yl)pyridin-2-yl)-4-methyl-N-(1-(3-(trifluoromethyl)phenyl)ethyl)pyridazin-3-amine

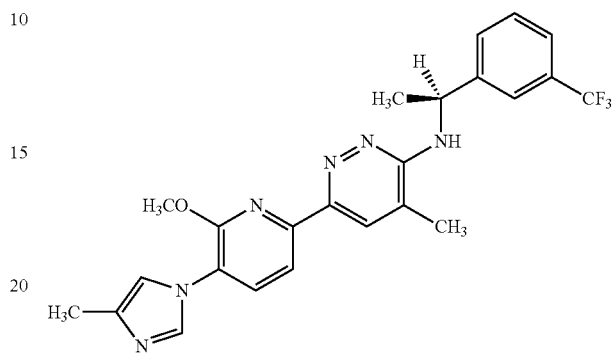

ESI MS (M+H) 469; ¹H NMR (500 MHz, DMSO-d$_6$) δ 8.03 (d, J=1.0 Hz, 1H), 7.98 (d, J=8.5 Hz, 1H), 7.93-7.90 (m, 2H), 7.81 (s, 1H), 7.76 (t, J=1.5 Hz, 1H), 7.56-7.54 (m, 2H), 7.26 (d, J=1.0 Hz, 1H), 6.93 (d, J=7.5 Hz, 1H), 5.55 (sym m, 1H), 4.05 (s, 3H), 2.33 (d, J=0.5 Hz, 3H), 2.16 (d, J=1.0 Hz, 3H), 1.59 (d, J=7.0 Hz, 3H); mp range: 106-116° C.; [α]$^{20}$$_D$ −19.5° (c 0.12, MeOH).

Example 50

N-(4-fluorophenethyl)-6-(6-methoxy-5-(4-methyl-1H-imidazol-1-yl)pyridin-2-yl)-4-methylpyridazin-3-amine

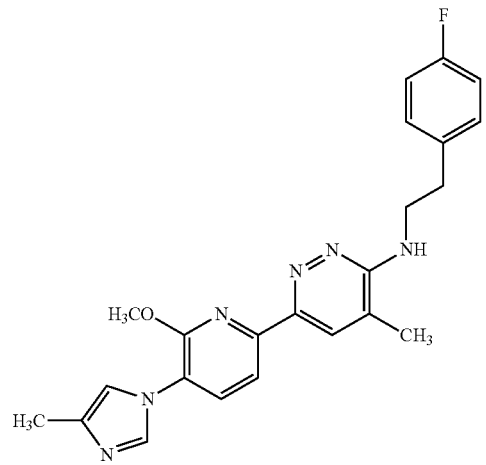 [SMILES: COc1nc(-c2cc(C)c(NCCc3ccc(F)cc3)nn2)ccc1-n1cnc(C)c1]

ESI MS (M+H) 419; ¹H NMR (300 MHz, DMSO-d$_6$) δ 8.06 (d, J=8.1 Hz, 1H), 8.03 (d, J=0.9 Hz, 1H), 7.95 (d, J=8.1 Hz, 1H), 7.94 (d, J=1.5 Hz, 1H), 7.33-7.28 (m, 3H), 7.17-7.10 (m, 2H), 6.74 (m, 1H), 4.07 (s, 3H), 3.78-3.69 (symmetrical m, 2H), 3.00-2.93 (symmetrical m, 2H), 2.17 (d, J=0.9 Hz, 3H), 2.16 (d, J=0.9 Hz, 3H); mp: 204-206° C.

Example 51

(S)—N-(1-(4-fluoro-3-methylphenyl)ethyl)-6-(6-methoxy-5-(4-methyl-1H-imidazol-1-yl)pyridin-2-yl)-4-methylpyridazin-3-amine

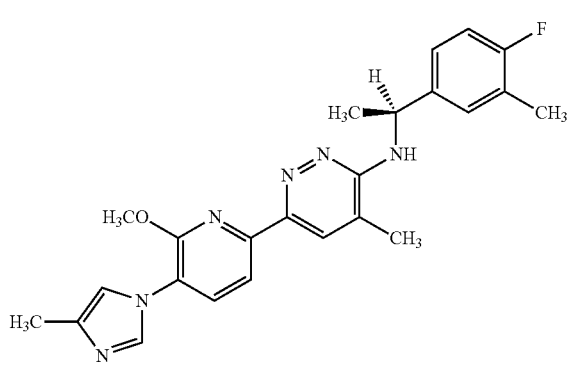 [SMILES: COc1nc(-c2cc(C)c(N[C@@H](C)c3ccc(F)c(C)c3)nn2)ccc1-n1cnc(C)c1]

ESI MS (M+H) 433; ¹H NMR (300 MHz, DMSO-d$_6$) δ 8.01-8.00 (m, 2H), 7.97-7.89 (m, 2H), 7.36-7.25 (m, 3H), 7.05 (t, J=8.4 Hz, 1H), 6.80 (d, J=7.5 Hz, 1H), 5.44 (sym m, 1H), 4.05 (s, 3H), 2.30 (d, J=0.9 Hz, 3H), 2.21 (d, J=1.5 Hz, 3H), 2.16 (d, J=1.0 Hz, 3H), 1.54 (d, J=7.0 Hz, 3H); mp range: 106-119° C.; [α]$^{20}$$_D$ −95.3° (c, 0.14, MeOH).

Example 52

(S)-6-(6-methoxy-5-(4-methyl-1H-imidazol-1-yl)pyridin-2-yl)-4-methyl-N-(1-(3,4,5-trifluorophenyl)ethyl)pyridazin-3-amine

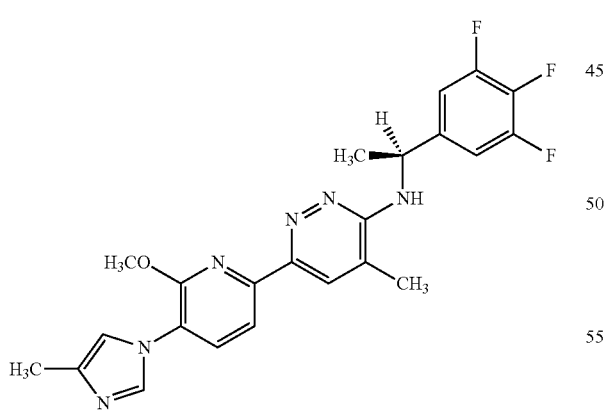

ESI MS (M+H) 455; ¹H NMR (500 MHz, DMSO-d$_6$) δ 8.04 (s, 1H), 7.99 (d, J=8.0 Hz, 1H), 7.93-7.38 (m, 2H), 7.42-7.38 (m, 2H), 7.27 (s, 1H), 6.84-6.82 (m, 1H), 5.43 (sym m, 1H), 4.06 (s, 3H), 2.33 (s, 3H), 2.16 (s, 3H), 1.55 (d, J=7.0 Hz, 3H); mp range: 118-126° C.; [α]$^{20}$$_D$−92.2° (c 0.12, MeOH).

Example 53

(S)—N-(1-(4-fluoro-3-(trifluoromethyl)phenyl)ethyl)-6-(6-methoxy-5-(4-methyl-1H-imidazol-1-yl)pyridin-2-yl)-4-methylpyridazin-3-amine

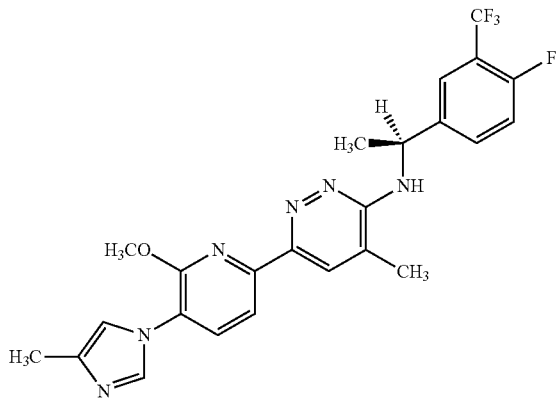 [SMILES: COc1nc(-c2cc(C)c(N[C@@H](C)c3ccc(F)c(C(F)(F)F)c3)nn2)ccc1-n1cnc(C)c1]

ESI MS (M+H) 487; ¹H NMR (500 MHz, DMSO-d$_6$) δ 8.03 (s, 1H), 7.98 (d, J=8.0 Hz, 1H), 7.92-7.90 (m, 2H), 7.87-7.85 (m, 1H), 7.84-7.81 (m, 1H), 7.47-7.42 (m, 1H), 7.26 (s, 1H), 6.92 (d, J=7.5 Hz, 1H), 5.30 (sym m, 1H), 4.06 (s, 3H), 2.32 (s, 3H), 2.16 (s, 3H), 1.58 (d, J=7.0 Hz, 3H); mp range: 55-60° C.; [α]$^{20}$$_D$ −65.9° (c 0.12, MeOH).

Example 54

(+/−)—N-(1-(4-fluorophenyl)propan-2-yl)-6-(6-methoxy-5-(4-methyl-1H-imidazol-1-yl)pyridin-2-yl)-4-methylpyridazin-3-amine

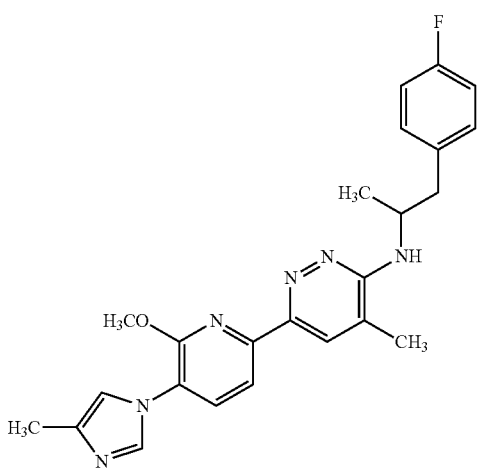 [SMILES: COc1nc(-c2cc(C)c(NC(C)Cc3ccc(F)cc3)nn2)ccc1-n1cnc(C)c1]

ESI MS (M+H) 433; ¹H NMR (500 MHz, DMSO-d$_6$) δ 8.03 (d, J=8.0 Hz, 1H), 7.98 (d, J=1.0 Hz, 1H), 7.94-7.92 (m, 2H), 7.32-7.29 (m, 2H), 7.27-7.26 (m, 1H), 7.11-7.07 (m, 2H), 6.25 (d, J=8.0 Hz, 1H), 4.59 (sym m, 1H), 4.06 (s, 3H), 3.06-3.02 (m, 1H), 2.80-2.76 (m, 1H), 2.18 (d, J=1.0 Hz, 3H), 2.16 (d, J=1.0 Hz, 3H), 1.23 (d, J=7.0 Hz, 3H); mp range: 85-93° C.

Example 55

(S)-6-(6-methoxy-5-(4-methyl-1H-imidazol-1-yl)pyridin-2-yl)-4-methyl-N-(1-(o-tolyl)ethyl)pyridazin-3-amine

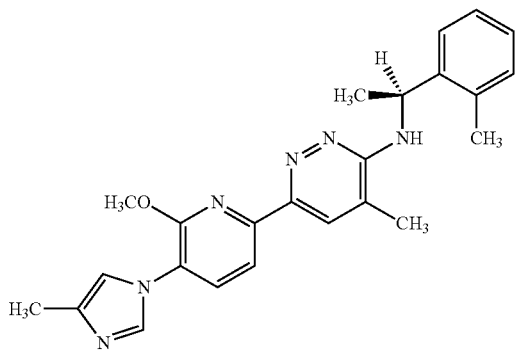

ESI MS (M+H) 415; $^1$H NMR (500 MHz, DMSO-d$_6$) δ 7.99-7.97 (m, 2H), 7.92-7.89 (m, 2H), 7.46 (d, J=8.0 Hz, 1H), 7.26 (s, 1H), 7.14-7.06 (m, 3H), 6.80 (d, J=7.5 Hz, 1H), 5.62 (sym m, 1H), 4.05 (s, 3H), 2.46 (s, 3H), 2.32 (s, 3H), 2.16 (s, 3H), 1.51 (d, J=7.0 Hz, 3H); mp range: 111-120° C.; [α]$^{20}_D$ −37.0° (c 0.10, MeOH).

Example 56

(S)-6-(6-methoxy-5-(4-methyl-1H-imidazol-1-yl)pyridin-2-yl)-4-methyl-N-(1-(2-(trifluoromethyl)phenyl)ethyl)pyridazin-3-amine

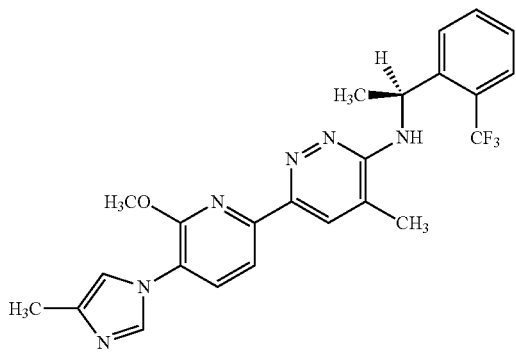 [SMILES: COc1nc(-c2cc(C)c(N[C@@H](C)c3ccccc3C)nn2)ccc1-n1cnc(C)c1]

ESI MS (M+H) 469; $^1$H NMR (500 MHz, DMSO-d$_6$) δ 8.01 (d, J=1.0 Hz, 1H), 7.97 (d, J=8.5 Hz, 1H), 7.93-7.87 (m, 3H), 7.70 (d, J=8.0 Hz, 1H), 7.61 (t, J=7.5 Hz, 1H), 7.42 (t, J=7.5 Hz, 1H), 7.26 (s, 1H), 6.86 (d, J=7.5 Hz, 1H), 5.77 (sym m, 1H), 4.05 (s, 3H), 2.35 (s, 3H), 2.15 (d, J=1.0 Hz, 3H), 1.57 (d, J=7.0 Hz, 3H); mp range: 133-146° C.; [α]$^{20}_D$ −2.2° (c 0.14, MeOH).

Example 57

(S)—N-(1-(4-fluorophenyl)-2-methylpropyl)-6-(6-methoxy-5-(4-methyl-1H-imidazol-1-yl)pyridin-2-yl)-4-methylpyridazin-3-amine

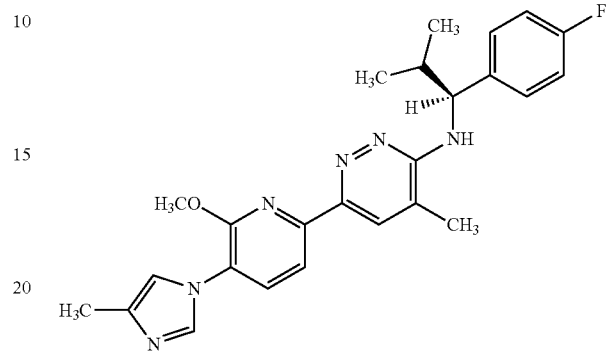

ESI MS (M+H) 447; $^1$H NMR (300 MHz, DMSO-d$_6$) δ 8.00-7.98 (m, 2H), 7.92-7.89 (m, 2H), 7.54-7.49 (m, 2H), 7.27 (t, J=1.2 Hz, 1H), 7.12 (t, J=9.0 Hz, 2H), 6.75 (d, J=7.5 Hz, 1H), 5.02 (t, J=9.6 Hz, 1H), 4.04 (s, 3H), 2.29-2.26 (m, 4H), 2.16 (d, J=1.0 Hz, 3H), 1.09 (d, J=6.6 Hz, 3H), 0.73 (d, J=6.6 Hz, 3H); mp range: 106-119° C.; [α]$^{20}_D$ −203.4° (c 0.13, MeOH).

Example 58

(S)—N-(1-cyclohexylethyl)-6-(6-methoxy-5-(4-methyl-1H-imidazol-1-yl)pyridin-2-yl)-4-methyl-pyridazin-3-amine

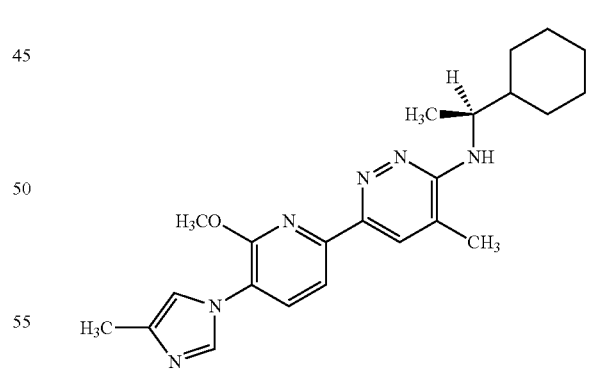

ESI MS (M+H) 407; $^1$H NMR (500 MHz, DMSO-d$_6$) δ 8.03 (d, J=8.0 Hz, 1H), 7.97 (d, J=1.0 Hz, 1H), 7.94-7.92 (m, 2H), 7.27 (s, 1H), 6.05 (d, J=8.5 Hz, 1H), 4.37-4.27 (m, 1H), 4.06 (s, 3H), 2.21 (s, 3H), 2.17 (s, 3H), 1.83-1.80 (m, 2H), 1.75-1.68 (m, 2H), 1.63-1.60 (m, 2H), 1.23-1.09 (m, 6H), 1.05-0.96 (m, 2H); mp range: 88-100° C; [α]$^{20}_D$ −1.5° (c 0.14, MeOH).

Example 59

(S)-6-(6-methoxy-5-(4-methyl-1H-imidazol-1-yl)pyridin-2-yl)-4-methyl-N-(1-(pyridin-4-yl)ethyl)pyridazin-3-amine

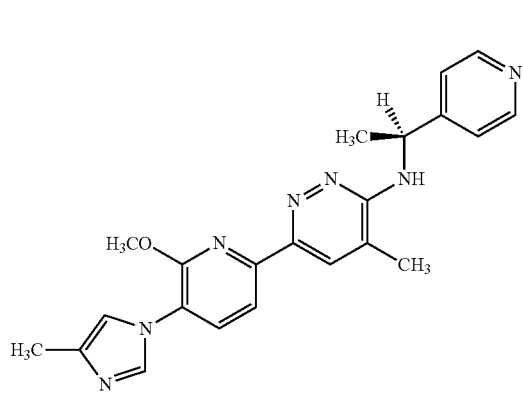 [SMILES: COc1nc(-c2cc(C)c(N[C@@H](C)c3ccncc3)nn2)ccc1-n1cnc(C)c1]

ESI MS (M+H) 402; $^1$H NMR (500 MHz, DMSO-d$_6$) δ 8.48 (dd, J=5.0, 1.5 Hz, 2H), 8.04 (s, 1H), 7.97 (d, J=8.0 Hz, 1H), 7.93-7.89 (m, 2H), 7.42 (d, J=6.0 Hz, 2H), 7.26 (s, 1H), 6.91 (d, J=7.5 Hz, 1H), 5.44 (sym m, 1H), 4.06 (s, 3H), 2.35 (s, 3H), 2.16 (s, 3H), 1.58 (d, J=7.5 Hz, 3H); mp range: 122-135° C.; [α]$^{20}$$_D$ +77.0° (c 0.11, MeOH).

Example 60

N-(1-(4-fluorophenyl)cyclopropyl)-6-(6-methoxy-5-(4-methyl-1H-imidazol-1-yl)pyridin-2-yl)-4-methyl-pyridazin-3-amine

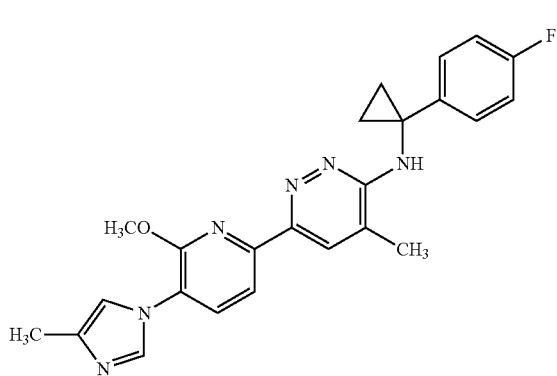 [SMILES: COc1nc(-c2cc(C)c(NC3(c4ccc(F)cc4)CC3)nn2)ccc1-n1cnc(C)c1]

ESI MS (M+H) 431; $^1$H NMR (500 MHz, DMSO-d$_6$) δ 8.03-7.91 (m, 4H), 7.50 (s, 1H), 7.28-7.24 (m, 3H), 7.06 (t, J=9.0 Hz, 2H), 4.05 (s, 3H), 2.27 (s, 3H), 2.16 (d, J=1.0 Hz, 3H), 1.34-1.29 (m, 4H); mp range: 190-202° C.

Example 61

(S)-6-(6-methoxy-5-(4-methyl-1H-imidazol-1-yl)pyridin-2-yl)-4-methyl-N-(3-methylbutan-2-yl)pyridazin-3-amine

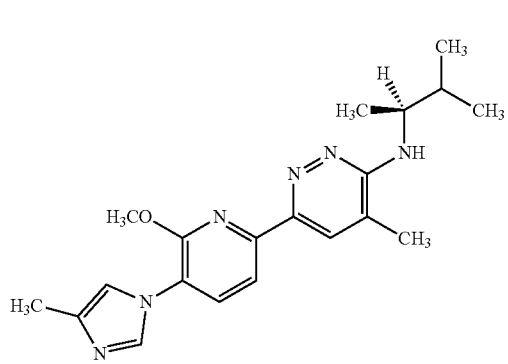 [SMILES: COc1nc(-c2cc(C)c(N[C@@H](C)C(C)C)nn2)ccc1-n1cnc(C)c1]

ESI MS (M+H) 367; $^1$H NMR (500 MHz, DMSO-d$_6$) δ 8.03 (d, J=8.0 Hz, 1H), 7.98 (s, 1H), 7.94-7.92 (m, 2H), 7.27 (s, 1H), 6.04 (d, J=8.0 Hz, 1H), 4.31-4.24 (m, 1H), 4.06 (s, 3H), 2.22 (s, 3H), 2.17 (s, 3H), 2.01-1.94 (m, 1H), 1.18 (d, J=7.0 Hz, 3H), 0.95-0.92 (m, 6H); mp range: 79-86° C.; [α]$^{20}$$_D$ +29.7° (c, 0.11, MeOH).

Example 62

(S)-6-(6-methoxy-5-(4-methyl-1H-imidazol-1-yl)pyridin-2-yl)-N-(1-methoxypropan-2-yl)-4-methyl-pyridazin-3-amine

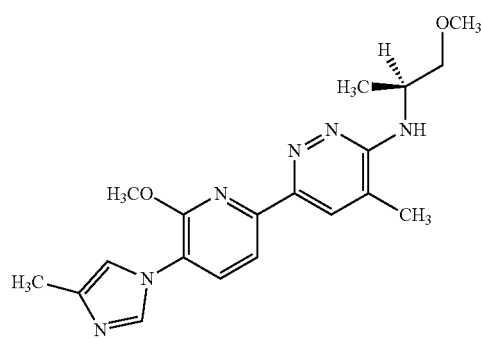 [SMILES: COC[C@H](C)Nc1nnc(-c2ccc(-n3cnc(C)c3)c(OC)n2)cc1C]

ESI MS (M+H) 369; $^1$H NMR (500 MHz, DMSO-d$_6$) δ 8.04 (d, J=8.0 Hz, 1H), 8.00 (s, 1H), 7.94-7.92 (m, 2H), 7.27 (s, 1H), 6.14 (d, J=8.0 Hz, 1H), 4.63-4.58 (m, 1H), 4.07 (s, 3H), 3.57-3.53 (m, 1H), 3.37-3.30 (m, 1H), 3.29 (s, 3H), 2.20 (s, 3H), 2.17 (s, 3H), 1.25 (d, J=6.5 Hz, 3H); mp range: 61-70° C.; [α]$^{20}$$_D$ −30.7° (c 0.08, MeOH).

Example 63

(S)—N-(sec-butyl)-6-(6-methoxy-5-(4-methyl-1H-imidazol-1-yl)pyridin-2-yl)-4-methylpyridazin-3-amine

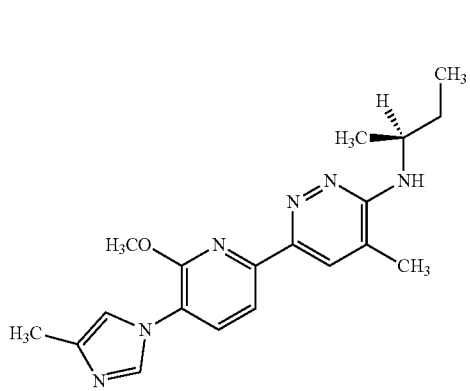 [SMILES: CC[C@H](C)Nc1nnc(-c2ccc(-n3cnc(C)c3)c(OC)n2)cc1C]

ESI MS (M+H) 353; $^1$H NMR (300 MHz, DMSO-d$_6$) δ 8.05-7.92 (m, 4H), 7.27 (t, J=1.2 Hz, 1H), 6.12 (d, J=8.1 Hz, 1H), 4.36-4.27 (m, 1H), 4.06 (s, 3H), 2.20 (d, J=0.6 Hz, 3H), 2.17 (d, J=0.9 Hz, 3H), 1.75-1.62 (m, 1H), 1.60-1.50 (m, 1H), 1.23 (d, J=6.3 Hz, 3H), 0.92 (t, J=7.5 Hz, 3H); mp range: 76-92° C.; $[α]^{20}{}_D$ +28.8° (c 0.14, MeOH).

Example 64 le;5q(S)-2-((6-(6-methoxy-5-(4-methyl-1H-imidazol-1-yl)pyridin-2-yl)-4-methylpyridazin-3-yl)amino) propan-1-ol

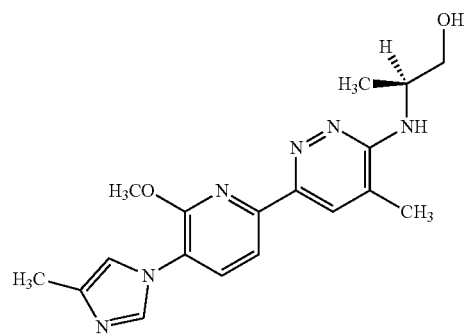 [SMILES: COc1nc(-c2cc(C)c(N[C@@H](C)CO)nn2)ccc1-n1cnc(C)c1]

ESI MS (M+H) 355; $^1$H NMR (300 MHz, DMSO-d$_6$) δ 8.05-7.92 (m, 4H), 7.28 (s, 1H), 6.03 (d, J=7.2 Hz, 1H), 4.78 (br s, 1H), 4.44-4.36 (m, 1H), 4.06 (s, 3H), 3.62-3.57 (m, 1H), 3.45-3.40 (m, 1H), 2.20 (s, 3H), 2.17 (s, 3H), 1.23 (d, J=6.3 Hz, 3H); mp range: 245-254° C.; $[α]^{20}{}_D$ −3.7° (c 0.11, MeOH).

Example 65

N-isopropyl-6-(6-methoxy-5-(4-methyl-1H-imidazol-1-yl)pyridin-2-yl)-4-methylpyridazin-3-amine

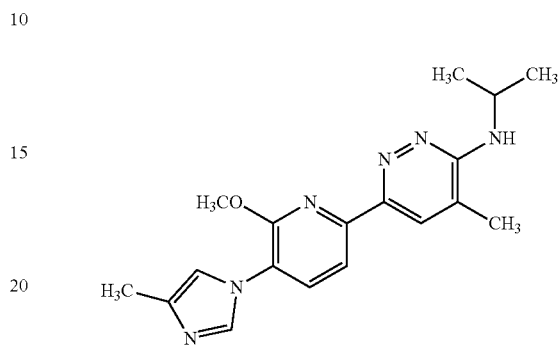

ESI MS (M+H) 339; $^1$H NMR (300 MHz, DMSO-d$_6$) δ 8.05-7.92 (m, 4H), 7.27 (t, J=1.2 Hz, 1H), 6.17 (d, J=8.1 Hz, 1H), 4.52-4.41 (m, 1H), 4.06 (s, 3H), 2.20 (d, J=0.6 Hz, 3H), 2.17 (d, J=0.9 Hz, 3H), 1.27 (d, J=6.6 Hz, 6H); mp: 228-229° C.

Example 66

(R)-6-(6-methoxy-5-(4-methyl-1H-imidazol-1-yl)pyridin-2-yl)-4-methyl-N-(3-methylbutan-2-yl)pyridazin-3-amine

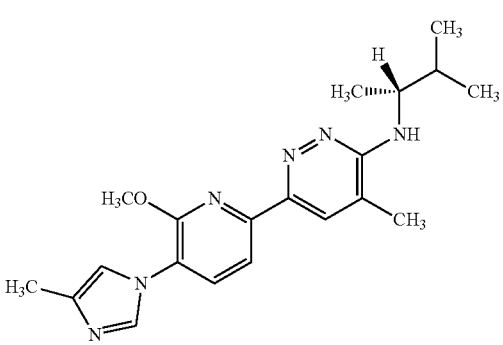 [SMILES: COc1nc(-c2cc(C)c(N[C@H](C)C(C)C)nn2)ccc1-n1cnc(C)c1]

ESI MS (M+H) 367; $^1$H NMR (500 MHz, DMSO-d$_6$) δ 8.03 (d, J=8.0 Hz, 1H), 7.98 (s, 1H), 7.93-7.92 (m, 2H), 7.27 (s, 1H), 6.04 (d, J=8.5 Hz, 1H), 4.30-4.25 (m, 1H), 4.06 (s, 3H), 2.22 (s, 3H), 2.17 (s, 3H), 2.01-1.94 (m, 1H), 1.18 (d, J=7.0 Hz, 3H), 0.95-0.92 (m, 6H); mp range: 75-80° C.; $[α]^{20}{}_D$ −38.1° (c 0.11, MeOH).

Example 67

(S)-6-(6-methoxy-5-(4-methyl-1H-imidazol-1-yl)
pyridin-2-yl)-4-methyl-N-(1-(pyridin-2-yl)ethyl)
pyridazin-3-amine

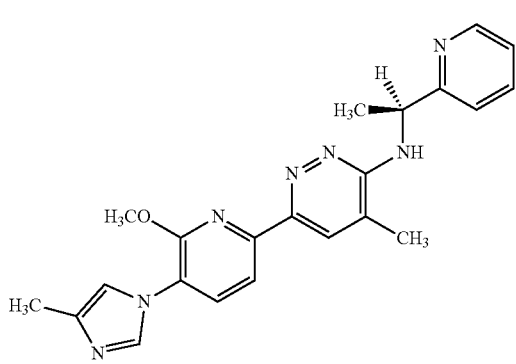 [SMILES: COc1nc(-c2cc(C)c(N[C@@H](C)c3ccccn3)nn2)ccc1-n1cnc(C)c1]

ESI MS (M+H) 402; $^1$H NMR (300 MHz, DMSO-d$_6$) δ 8.55-8.53 (m, 1H), 8.05 (d, J=1.0 Hz, 1H), 8.00-7.90 (m, 3H), 7.75-7.69 (m, 1H), 7.44-7.41 (m, 1H), 7.28-7.21 (m, 2H), 6.87 (d, J=7.2 Hz, 1H), 5.49 (sym m, 1H), 4.06 (s, 3H), 2.34 (s, 3H), 2.16 (d, J=0.60 Hz, 3H), 1.60 (d, J=7.2 Hz, 3H); mp range: 82-88° C.; [α]$^{20}_D$ −51.0° (c 0.10, MeOH).

Example 68

(R)-6-(6-methoxy-5-(4-methyl-1H-imidazol-1-yl)
pyridin-2-yl)-4-methyl-N-(1-phenylethyl)pyridazin-
3-amine

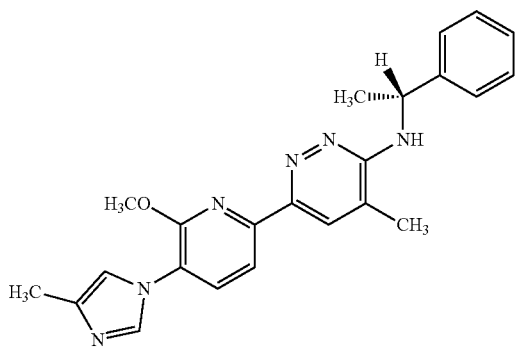 [SMILES: COc1nc(-c2cc(C)c(N[C@H](C)c3ccccc3)nn2)ccc1-n1cnc(C)c1]

ESI MS (M+H) 401; $^1$H NMR (300 MHz, DMSO-d$_6$) δ 8.01-7.89 (m, 4H), 7.46-7.32 (m, 2H), 7.30-7.26 (m, 3H), 7.21-7.16 (m, 1H), 6.83 (d, J=7.5 Hz, 1H), 5.49 (sym m, 1H), 4.05 (s, 3H), 2.31 (d, J=0.6 Hz, 3H), 2.16 (d, J=0.6 Hz, 3H), 1.57 (d, J=6.9 Hz, 3H); mp range: 91-102° C.; [α]$^{20}_D$ +102.5° (c 0.14, MeOH).

Example 69

(S)—N-(1-(4-fluoro-2-methylphenyl)ethyl)-6-(6-
methoxy-5-(4-methyl-1H-imidazol-1-yl)pyridin-2-
yl)-4-methylpyridazin-3-amine

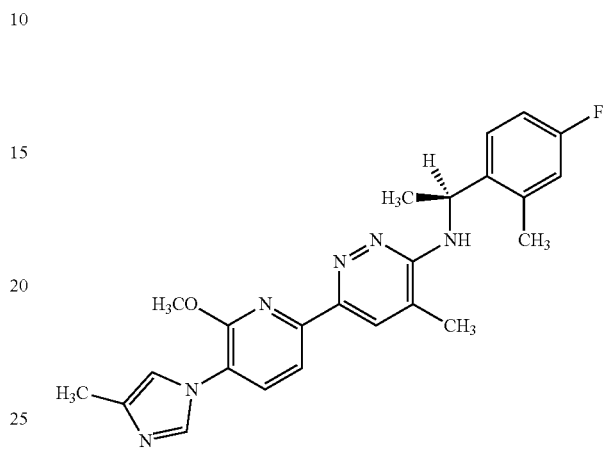

ESI MS (M+H) 433; $^1$H NMR (300 MHz, DMSO-d$_6$) δ 8.00-7.89 (m, 4H), 7.48 (dd, J=8.4, 6.6 Hz, 1H), 7.27 (s, 1H), 7.01-6.90 (m, 2H), 6.85 (d, J=7.5 Hz, 1H), 5.46 (m, 1H), 4.05 (s, 3H), 2.47 (s, 3H), 2.31 (s, 3H), 2.16 (s, 3H), 1.50 (d, J=6.6 Hz, 3H); mp range: 84-96° C.; [α]$^{20}_D$ −20.8° (c 0.17, Methanol).

Example 70

N-cyclopropyl-6-(6-methoxy-5-(4-methyl-1H-imida-
zol-1-yl)pyridin-2-yl)-4-methylpyridazin-3-amine

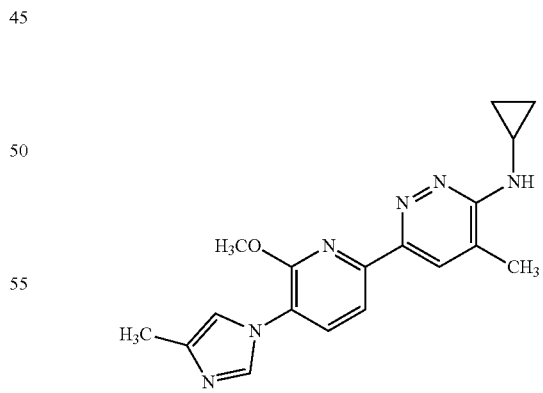

ESI MS (M+H) 337; $^1$H NMR (300 MHz, DMSO-d$_6$) δ 8.06 (d, J=8.1 Hz, 1H), 8.00-7.94 (m, 3H), 7.28 (s, 1H), 6.76 (d, J=3.0 Hz, 1H), 4.06 (s, 3H), 2.97-2.90 (m, 1H), 2.17 (d, J=0.6 Hz, 6H), 0.80-0.74 (m, 2H), 0.60-0.55 (m, 2H); mp range: 97-118° C.

Example 71

(R)-2-(4-fluorophenyl)-2-((6-(6-methoxy-5-(4-methyl-1H-imidazol-1-yl)pyridin-2-yl)-4-methyl pyridazin-3-yl)amino)ethanol

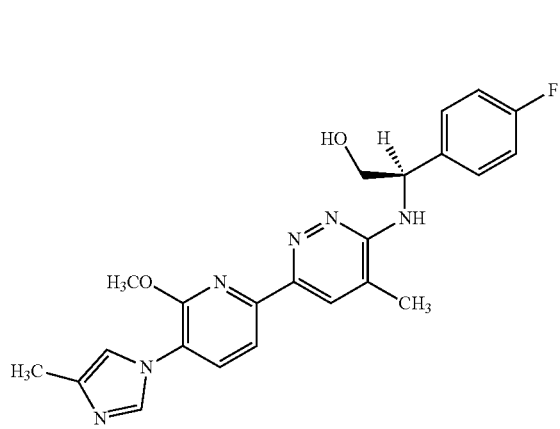 [SMILES: COc1nc(-c2cc(C)c(N[C@@H](CO)c3ccc(F)cc3)nn2)ccc1-n1cnc(C)c1]

ESI MS (M+H) 435; $^1$H NMR (300 MHz, DMSO-d$_6$) δ 8.03 (d, J=0.9 Hz, 1H), 7.99 (d, J=8.1 Hz, 1H), 7.93-7.90 (m, 2H), 7.50-7.45 (m, 2H), 7.27 (s, 1H), 7.12 (t, J=9.0 Hz, 2H), 6.69 (d, J=7.5 Hz, 1H), 5.38 (q, J=7.2 Hz, 1H), 5.03 (t, J=6.0 Hz, 1H), 4.05 (s, 3H), 3.84-3.67 (m, 2H), 2.33 (d, J=0.6 Hz, 3H), 2.16 (d, J=0.9 Hz, 3H); mp range: 130-146° C.; [α]$^{20}_D$ −62.7° (c 0.13, MeOH).

Example 72

(+/−)-trans-6-(6-methoxy-5-(4-methyl-1H-imidazol-1-yl)pyridin-2-yl)-4-methyl-N-(2-phenylcyclopropyl)pyridazin-3-amine

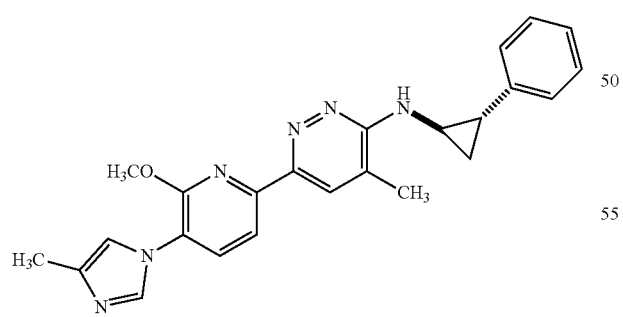

ESI MS (M+H) 413; $^1$H NMR (500 MHz, DMSO-d$_6$) δ 8.05-8.02 (m, 2H), 7.94-7.92 (m, 2H), 7.32-7.27 (m, 3H), 7.22-7.17 (m, 3H), 6.95 (d, J=3.5 Hz, 1H), 4.07 (s, 3H), 3.21-3.17 (m, 1H), 2.22 (s, 3H), 2.17 (s, 3H), 2.07-2.03 (m, 1H), 1.45-1.42 (m, 1H), 1.30-1.26 (m, 1H); mp: 99-102° C.

Example 73

N-(3-(4-fluorophenyl)propyl)-6-(6-methoxy-5-(4-methyl-1H-imidazol-1-yl)pyridin-2-yl)-4-methyl-pyridazin-3-amine

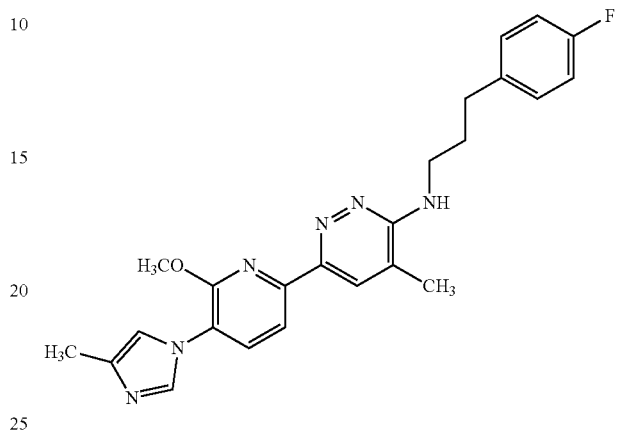

ESI MS (M+H) 433; $^1$H NMR (500 MHz, DMSO-d$_6$) δ 8.03 (d, J=8.5 Hz, 1H), 7.99 (s, 1H), 7.94-7.92 (m, 2H), 7.30-7.27 (m, 3H), 7.12-7.08 (m, 2H), 6.60-6.58 (m, 1H), 4.06 (s, 3H), 3.56-3.52 (m, 2H), 2.69 (t, J=7.5 Hz, 2H), 2.19 (s, 3H), 2.17 (s, 3H), 2.00-1.93 (m, 2H); mp: 204-206° C.

Example 74

(+/−)—N-(1-(benzo[d]oxazol-2-yl)ethyl)-6-(6-methoxy-5-(4-methyl-1H-imidazol-1-yl)pyridin-2-yl)-4-methyl-pyridazin-3-amine

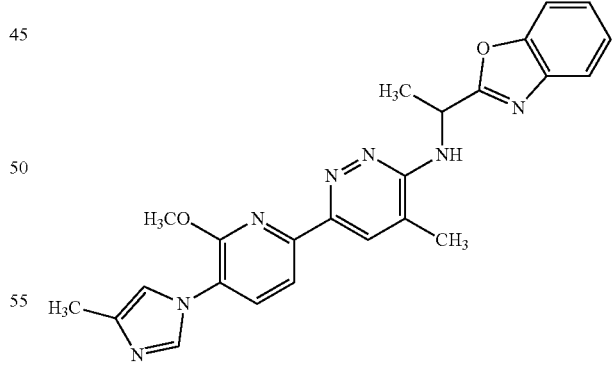

ESI MS (M+H) 442; $^1$H NMR (500 MHz, DMSO-d$_6$) δ 8.09 (d, J=1.0 Hz, 1H), 7.99 (d, J=8.0 Hz, 1H), 7.93-7.90 (m, 2H), 7.70-7.68 (m, 2H), 7.38-7.33 (m, 2H), 7.26 (s, 1H), 7.21 (d, J=7.0 Hz, 1H), 5.74 (sym m, 1H), 4.07 (s, 3H), 2.33 (s, 3H), 2.16 (s, 3H), 1.77 (d, J=7.0 Hz, 3H); mp range: 126-133° C.

Example 75

(S)-6-(6-methoxy-5-(4-methyl-1H-imidazol-1-yl)pyridin-2-yl)-4-methyl-N-(1-(2,4,6-trifluorophenyl)ethyl)pyridazin-3-amine

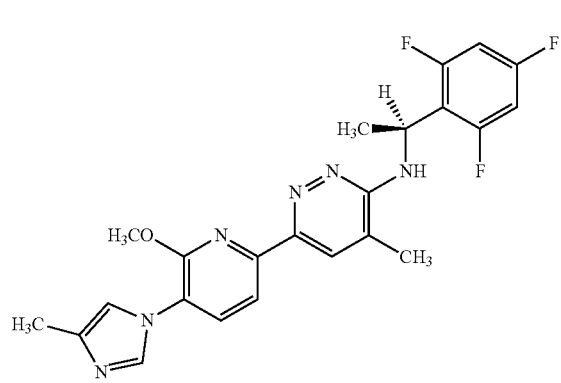 [SMILES: COc1nc(-c2cc(C)c(N[C@@H](C)c3c(F)cc(F)cc3F)nn2)ccc1-n1cnc(C)c1]

ESI MS (M+H) 455; $^1$H NMR (300 MHz, DMSO-d$_6$) δ 8.05-7.97 (m, 2H), 7.94 (d, J=1.2 Hz, 1H), 7.91 (d, J=7.8 Hz, 1H), 7.28 (t, J=1.2 Hz, 1H), 7.18-7.05 (m, 2H), 6.75 (d, J=6.9 Hz, 1H), 5.66 (sym m, 1H), 4.05 (s, 3H), 2.27 (d, J=0.6 Hz, 3H), 2.16 (d, J=0.9 Hz, 3H), 1.66 (d, J=7.2 Hz, 3H); mp range: 82-92° C.; [α]$^{20}_D$ −154.5° (c 0.18, Methanol).

Example 76

(S)—N-(3,3-dimethylbutan-2-yl)-6-(6-methoxy-5-(4-methyl-1H-imidazol-1-yl)pyridin-2-yl)-4-methyl pyridazin-3-amine

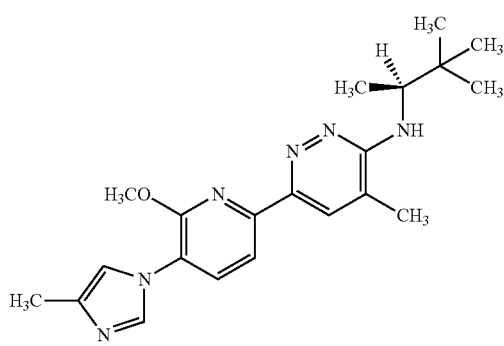 [SMILES: COc1nc(-c2cc(C)c(N[C@@H](C)C(C)(C)C)nn2)ccc1-n1cnc(C)c1]

ESI MS (M+H) 381; $^1$H NMR (300 MHz, DMSO-d$_6$) δ 8.04-7.92 (m, 4H), 7.28 (s, 1H), 5.67 (d, J=9.3 Hz, 1H), 4.65-4.55 (m, 1H), 4.06 (s, 3H), 2.24 (d, J=0.6 Hz, 3H), 2.17 (d, J=0.9 Hz, 3H), 1.17 (d, J=6.6 Hz, 3H), 0.95 (s, 9H); mp range: 268-283° C.; [α]$^{20}_D$ +55.4° (c 0.11, MeOH).

Example 77

(S)-4-(1-((6-(6-methoxy-5-(4-methyl-1H-imidazol-1-yl)pyridin-2-yl)-4-methylpyridazin-3-yl)amino)ethyl)benzonitrile

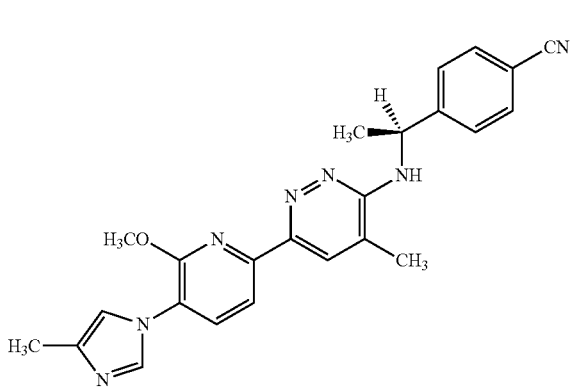 [SMILES: COc1nc(-c2cc(C)c(N[C@@H](C)c3ccc(C#N)cc3)nn2)ccc1-n1cnc(C)c1]

ESI MS (M+H) 426; $^1$H NMR (300 MHz, DMSO-d$_6$) δ 8.03 (d, J=0.9 Hz, 1H), 7.96 (d, J=8.1 Hz, 1H), 7.93 (d, J=1.2 Hz, 1H), 7.91 (d, J=8.1 Hz, 1H), 7.97-7.76 (m, 2H), 7.63 (d, J=8.1 Hz, 2H), 7.27 (t, J=1.2 Hz, 1H), 6.97 (d, J=7.2 Hz, 1H), 5.49 (sym m, 1H), 4.05 (s, 3H), 2.34 (d, J=0.9 Hz, 3H), 2.15 (d, J=0.9 Hz, 3H), 1.58 (d, J=6.9 Hz, 3H); mp range: 102-110° C.; [α]$^{20}_D$ −145.3° (c 0.26, Methanol).

Example 78

N-cyclopentyl-6-(6-methoxy-5-(4-methyl-1H-imidazol-1-yl)pyridin-2-yl)-4-methylpyridazin-3-amine

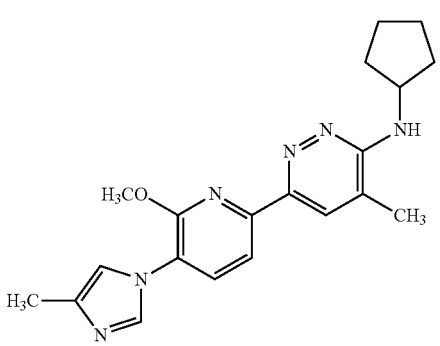 [SMILES: COc1nc(-c2cc(C)c(NC3CCCC3)nn2)ccc1-n1cnc(C)c1]

ESI MS (M+H) 365; $^1$H NMR (300 MHz, DMSO-d$_6$) δ 8.04 (d, J=7.8 Hz, 1H), 7.98 (s, 1H), 7.94-7.92 (m, 2H), 7.21 (s, 1H), 6.26 (d, J=6.6 Hz, 1H), 4.57-4.45 (m, 1H), 4.06 (s, 3H), 2.21 (s, 3H), 2.17 (d, J=0.9 Hz, 3H), 2.09-2.01 (m, 2H), 1.74-1.70 (m, 2H), 1.65-1.56 (m, 4H); mp range: 97-109° C.

Example 79

(S)—N-(1-(4-fluorophenyl)butyl)-6-(6-methoxy-5-(4-methyl-1H-imidazol-1-yl)pyridin-2-yl)-4-methyl-pyridazin-3-amine

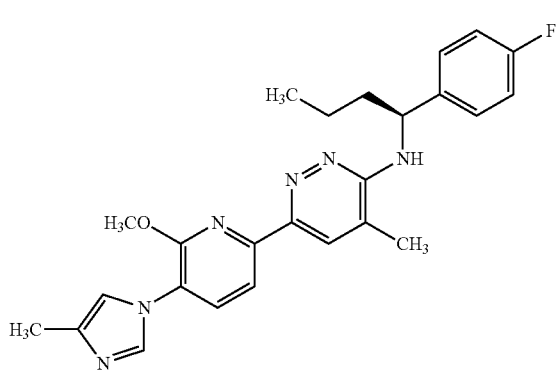 [SMILES: CCC[C@H](Nc1nnc(-c2ccc(-n3cnc(C)c3)c(OC)n2)cc1C)c1ccc(F)cc1]

ESI MS (M+H) 447; ¹H NMR (500 MHz, DMSO-d$_6$) δ 7.99-7.97 (m, 2H), 7.93-7.90 (m, 2H), 7.50-7.47 (m, 2H), 7.26 (s, 1H), 7.14-7.09 (m, 2H), 6.77 (d, J=8.0 Hz, 1H), 5.39-5.34 (m, 1H), 4.05 (s, 3H), 2.36 (s, 3H), 2.16 (s, 3H), 2.01-1.95 (m, 1H), 1.78-1.73 (m, 1H), 1.48-1.43 (m, 1H), 1.35-1.29 (m, 1H), 0.92 (t, J=7.0 Hz, 3H); mp range: 99-106° C.; [α]$^{20}_D$ −134.6° (c 0.11, MeOH).

Example 80

(S)-2-(4-fluorophenyl)-2-((6-(6-methoxy-5-(4-methyl-1H-imidazol-1-yl)pyridin-2-yl)-4-methyl pyridazin-3-yl)amino)ethanol

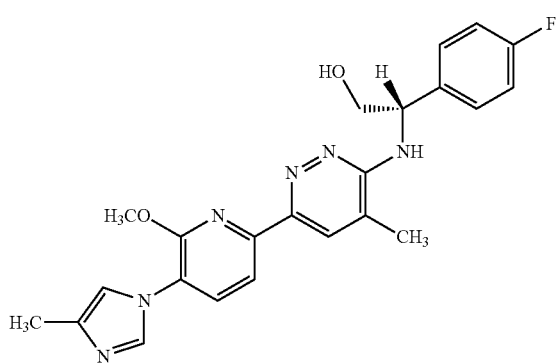 [SMILES: COc1nc(-c2cc(C)c(N[C@H](CO)c3ccc(F)cc3)nn2)ccc1-n1cnc(C)c1]

ESI MS (M+H) 435; ¹H NMR (300 MHz, DMSO-d$_6$) δ 8.03 (d, J=0.9 Hz, 1H), 7.99 (d, J=8.1 Hz, 1H), 7.93-7.90 (m, 2H), 7.50-7.45 (m, 2H), 7.27 (s, 1H), 7.12 (t, J=9.0 Hz, 2H), 6.68 (d, J=7.5 Hz, 1H), 5.38 (q, J=7.2 Hz, 1H), 5.02 (t, J=6.0 Hz, 1H), 4.05 (s, 3H), 3.84-3.67 (m, 2H), 2.33 (d, J=0.6 Hz, 3H), 2.16 (d, J=0.9 Hz, 3H); mp range: 129-142° C.; [α]$^{20}_D$ +58.2° (c 0.10, MeOH).

Example 81

N-cyclohexyl-6-(6-methoxy-5-(4-methyl-1H-imidazol-1-yl)pyridin-2-yl)-4-methylpyridazin-3-amine

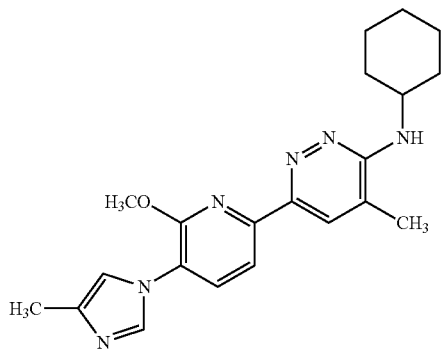 [SMILES: COc1nc(-c2cc(C)c(NC3CCCCC3)nn2)ccc1-n1cnc(C)c1]

ESI MS (M+H) 379; ¹H NMR (300 MHz, DMSO-d$_6$) δ 8.03 (d, J=7.8 Hz, 1H), 7.98 (s, 1H), 7.94-7.92 (m, 2H), 7.27 (t, J=0.9 Hz, 1H), 6.15 (d, J=6.6 Hz, 1H), 4.18-4.09 (m, 1H), 4.05 (s, 3H), 2.19 (d, J=0.6 Hz, 3H), 2.16 (d, J=0.6 Hz, 3H), 2.06-1.95 (m, 2H), 1.82-1.73 (m, 2H), 1.70-1.62 (m, 1H), 1.43-1.29 (m, 4H), 1.23-1.16 (m, 1H); mp range: 120-129° C.

Example 82

(S)—N-(1-(4-fluoro-2-(trifluoromethyl)phenyl)ethyl)-6-(6-methoxy-5-(4-methyl-1H-imidazol-1-yl)pyridin-2-yl)-4-methylpyridazin-3-amine

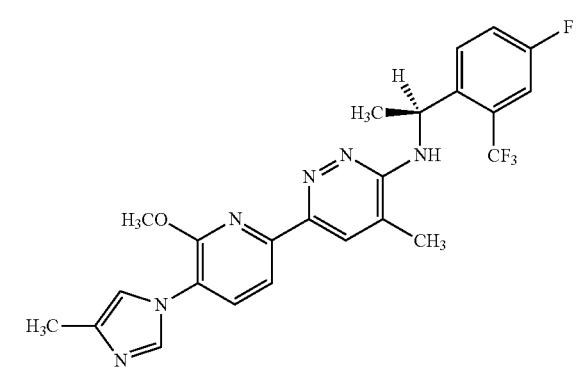 [SMILES: COc1nc(-c2cc(C)c(N[C@@H](C)c3ccc(F)cc3C(F)(F)F)nn2)ccc1-n1cnc(C)c1]

ESI MS (M+H) 487; ¹H NMR (300 MHz, DMSO-d$_6$) δ 8.02 (d, J=0.9 Hz, 1H), 8.00-7.86 (m, 1H), 7.97 (d, J=8.1 Hz, 1H), 7.93 (d, J=1.2 Hz, 1H), 7.90 (d, J=8.1 Hz, 1H), 7.58 (dd, J=9.3, 2.7 Hz, 1H), 7.52 (dt, J=8.7, 2.7 Hz, 1H), 7.27 (t, J=1.2 Hz, 1H), 6.91 (d, J=6.9 Hz, 1H), 5.72 (sym m, 1H), 4.05 (s, 3H), 2.35 (d, J=0.6 Hz, 3H), 2.15 (d, J=0.6 Hz, 3H), 1.56 (d, J=6.9 Hz, 3H); mp range: 86-98° C.; [α]$^{20}_D$ −33.1° (c 0.32, Methanol).

Example 83

N-((1R,2S)-2-(3,4-difluorophenyl)cyclopropyl)-6-(6-methoxy-5-(4-methyl-1H-imidazol-1-yl)pyridin-2-yl)-4-methylpyridazin-3-amine

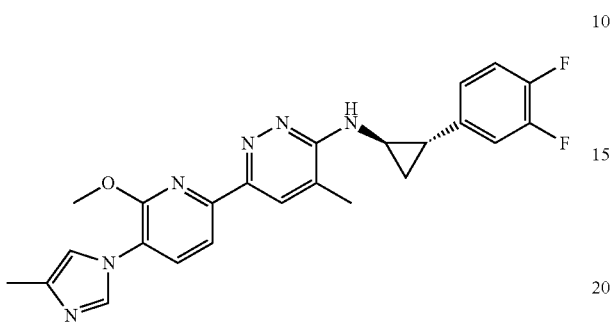

ESI MS (M+H) 449; $^1$H NMR (300 MHz, DMSO-d$_6$) δ 8.05-8.02 (m, 2H), 7.95-7.92 (m, 2H), 7.40-7.28 (m, 3H), 7.11-7.07 (m, 1H), 7.01 (d, J=3.3 Hz, 1H), 4.06 (s, 3H), 3.18-3.12 (m, 1H), 2.21 (d, J=0.6 Hz, 3H), 2.16 (d, J=0.9 Hz, 3H), 2.08-2.01 (m, 1H), 1.51-1.44 (m, 1H), 1.36-1.29 (m, 1H); mp range: 95-106° C.; [α]$^{20}$$_D$ −56.3° (c 0.14, MeOH).

Example 84

(S)-4-(1-((6-(6-methoxy-5-(4-methyl-1H-imidazol-1-yl)pyridin-2-yl)-4-methylpyridazin-3-yl)amino)propyl)benzonitrile

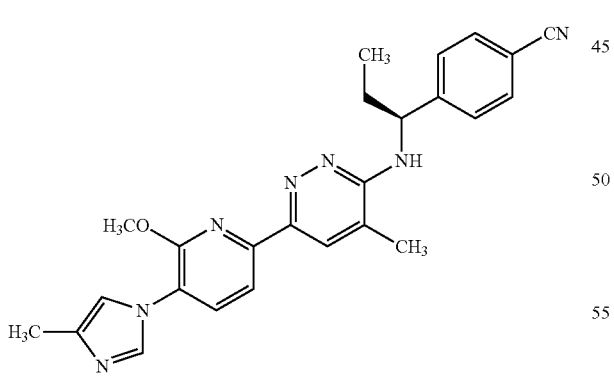

ESI MS (M+H) 440; $^1$H NMR (300 MHz, DMSO-d$_6$) δ 8.04-7.90 (m, 4H), 7.78 (d, J=8.4 Hz, 2H), 7.65 (d, J=8.4 Hz, 2H), 7.31 (s, 1H), 6.92 (d, J=7.8 Hz, 1H), 5.30-5.23 (m, 1H), 4.05 (s, 3H), 2.33 (s, 3H), 2.17 (s, 3H), 2.05-1.93 (m, 1H), 1.90-1.79 (m, 1H), 0.98 (t, J=7.2 Hz, 3H); mp range: 74-81° C.; [α]$^{20}$$_D$ −123.5° (c 0.09, MeOH).

Example 85

N-(4,4-difluorocyclohexyl)-6-(6-methoxy-5-(4-methyl-1H-imidazol-1-yl)pyridin-2-yl)-4-methylpyridazin-3-amine

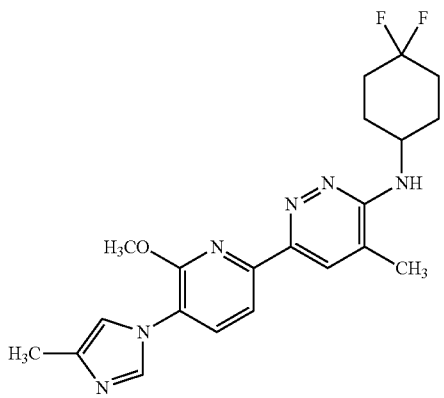 [SMILES: COc1nc(-c2cc(C)c(NC3CCC(F)(F)CC3)nn2)ccc1-n1cnc(C)c1]

ESI MS (M+H) 415; $^1$H NMR (300 MHz, DMSO-d$_6$) δ 8.06-8.01 (m, 2H), 7.95-7.92 (m, 2H), 7.27 (s, 1H), 6.28 (d, J=6.6 Hz, 1H), 4.39-4.30 (m, 1H), 4.06 (s, 3H), 2.21 (d, J=0.9 Hz, 3H), 2.17 (d, J=0.6 Hz, 3H), 2.08-1.90 (m, 6H), 1.76-1.65 (m, 2H); mp range: 118-133° C.

Example 86

(S)—N-(1-(2-fluorophenyl)butyl)-6-(6-methoxy-5-(4-methyl-1H-imidazol-1-yl)pyridin-2-yl)-4-methyl-pyridazin-3-amine

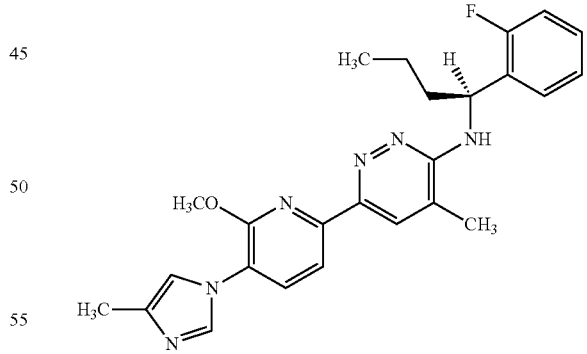

ESI MS (M+H) 447; $^1$H NMR (500 MHz, DMSO-d$_6$) δ 8.00-7.97 (m, 2H), 7.92-7.89 (m, 2H), 7.53-7.49 (m, 1H), 7.26-7.21 (m, 2H), 7.17-7.10 (m, 2H), 6.79 (d, J=8.0 Hz, 1H), 5.67 (sym m, 1H), 4.05 (s, 3H), 2.34 (s, 3H), 2.15 (s, 3H), 2.03-1.96 (m, 1H), 1.78-1.73 (m, 1H), 1.55-1.48 (m, 1H), 1.40-1.34 (m, 1H), 0.94 (t, J=7.0 Hz, 3H); mp range: 87-97° C.; [α]$^{20}$$_D$ −78.0° (c 0.12, MeOH).

Example 87

(R)—N-(1-(4-fluorophenyl)-2-methoxyethyl)-6-(6-methoxy-5-(4-methyl-1H-imidazol-1-yl)pyridin-2-yl)-4-methylpyridazin-3-amine

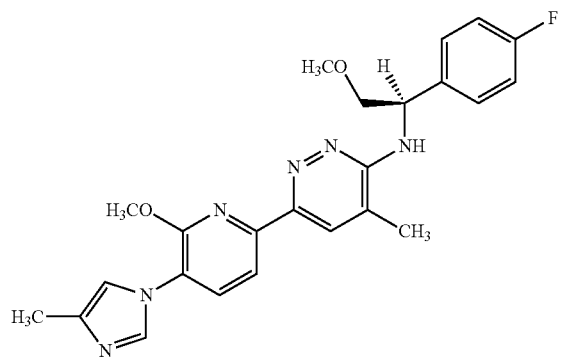

ESI MS (M+H) 449; $^1$H NMR (500 MHz, DMSO-d$_6$) δ 8.02 (d, J=1.0 Hz, 1H), 7.99 (d, J=8.0 Hz, 1H), 7.93-7.90 (m, 2H), 7.53-7.50 (m, 2H), 7.26 (s, 1H), 7.16-7.12 (m, 2H), 6.80 (d, J=7.5 Hz, 1H), 5.62 (sym m, 1H), 4.05 (s, 3H), 3.83-3.79 (m, 1H), 3.64-3.61 (m, 1H), 3.30 (s, 3H), 2.31 (d, J=0.5 Hz, 3H), 2.16 (d, J=0.5 Hz, 3H); mp range: 87-95° C.; [α]$^{20}_D$ −54.2° (c 0.14, MeOH).

Example 88

(S)—N-(1-(2-fluorophenyl)propyl)-6-(6-methoxy-5-(4-methyl-1H-imidazol-1-yl)pyridin-2-yl)-4-methylpyridazin-3-amine

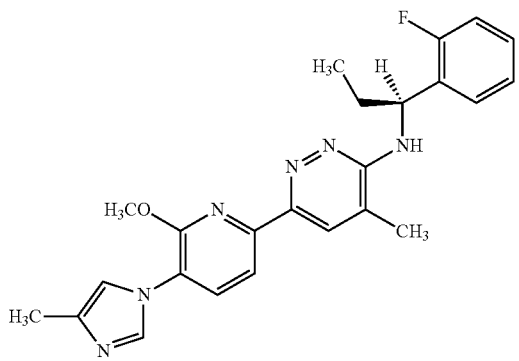 [SMILES: CC[C@H](Nc1nnc(-c2ccc(-n3cnc(C)c3)c(OC)n2)cc1C)c1ccccc1F]

ESI MS (M+H) 433; $^1$H NMR (500 MHz, DMSO-d$_6$) δ 8.01 (d, J=1.0 Hz, 1H), 7.98 (d, J=8.0 Hz, 1H), 7.92-7.90 (m, 2H), 7.59-7.49 (m, 1H), 7.26-7.22 (m, 2H), 7.18-7.10 (m, 2H), 6.78 (d, J=8.0 Hz, 1H), 5.55 (sym m, 1H), 4.05 (s, 3H), 2.34 (d, J=1.0 Hz, 3H), 2.16 (s, 3H), 2.03-1.97 (m, 1H), 1.86-1.81 (m, 1H), 0.99 (t, J=7.0 Hz, 3H); mp range: 97-103° C.; [α]$^{20}_D$+106.8° (c 0.11, MeOH).

Example 89

(S)—N-(1-(2-chloro-4-fluorophenyl)ethyl)-6-(6-methoxy-5-(4-methyl-1H-imidazol-1-yl)pyridin-2-yl)-4-methylpyridazin-3-amine

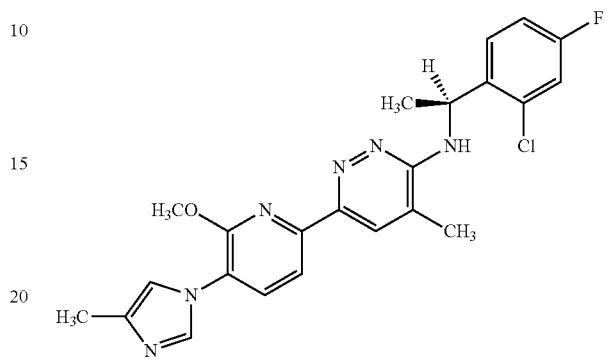

ESI MS (M+H) 453; $^1$H NMR (300 MHz, DMSO-d$_6$) δ 8.03 (d, J=0.9 Hz, 1H), 7.98 (d, J=8.1 Hz, 1H), 7.93 (d, J=1.2 Hz, 1H), 7.91 (d, J=8.1 Hz, 1H), 7.55 (dd, J=9.0, 6.6 Hz, 1H), 7.42 (dd, J=8.7, 2.7 Hz, 1H), 7.27 (t, J=1.2 Hz, 1H), 7.15 (dt, J=8.4, 2.7 Hz, 1H), 6.98 (d, J=7.2 Hz, 1H), 5.67 (sym m, 1H), 4.05 (s, 3H), 2.36 (d, J=0.9 Hz, 3H), 2.15 (d, J=0.9 Hz, 3H), 1.54 (d, J=6.9 Hz, 3H); mp range: 92-104° C.; [α]$^{20}_D$ +63.0° (c 0.18, Methanol).

Example 90

(S)—N-(1-(4-fluoro-2-methoxyphenyl)ethyl)-6-(6-methoxy-5-(4-methyl-1H-imidazol-1-yl)pyridin-2-yl)-4-methylpyridazin-3-amine

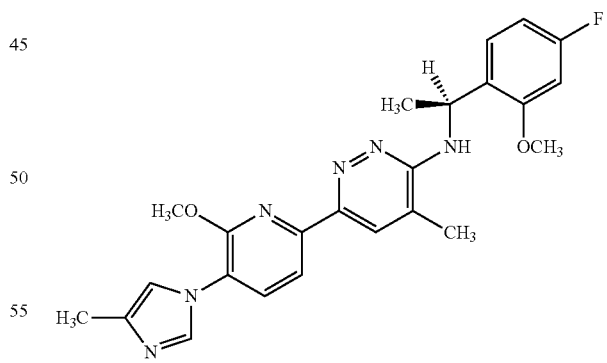

ESI MS (M+H) 449; $^1$H NMR (300 MHz, DMSO-d$_6$) δ 8.01 (d, J=0.9 Hz, 1H), 7.97 (d, J=8.1 Hz, 1H), 7.93 (s, 1H), 7.91 (d, J=8.1 Hz, 1H), 7.30 (dd, J=8.7, 7.2 Hz, 1H), 7.27 (t, J=1.2 Hz, 1H), 6.90 (dd, J=11.4, 2.4 Hz, 1H), 6.72 (d, J=7.8 Hz, 1H), 6.67 (dt, J=8.7, 2.7 Hz, 1H), 5.70 (sym m, 1H), 4.05 (s, 3H), 3.89 (s, 3H), 2.34 (d, J=0.6 Hz, 3H), 2.16 (d, J=0.9 Hz, 3H), 1.48 (d, J=6.9 Hz, 3H); mp range: 86-98° C.; [α]$^{20}_D$ −0.48° (c 0.21, Methanol).

Example 91

(S)—N-(1-(2,3-difluorophenyl)ethyl)-6-(6-methoxy-5-(4-methyl-1H-imidazol-1-yl)pyridin-2-yl)-4-methylpyridazin-3-amine

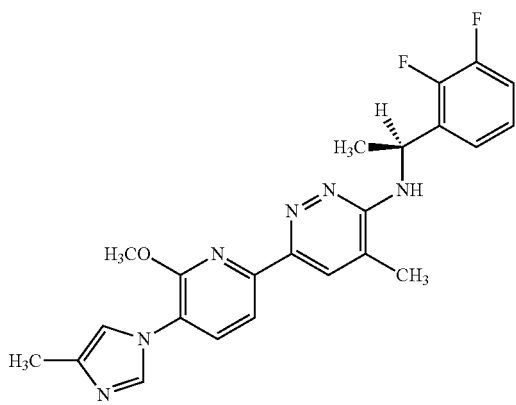 [SMILES: COc1nc(-c2cc(C)c(N[C@@H](C)c3cccc(F)c3F)nn2)ccc1-n1cnc(C)c1]

ESI MS (M+H) 437; $^1$H NMR (500 MHz, DMSO-d$_6$) δ 8.03 (d, J=1.0 Hz, 1H), 7.98 (d, J=8.0 Hz, 1H), 7.93-7.90 (m, 2H), 7.29-7.23 (m, 3H), 7.14-7.10 (m, 1H), 6.93 (d, J=7.5 Hz, 1H), 5.70 (sym m, 1H), 4.05 (s, 3H), 2.34 (d, J=1.0 Hz, 3H), 2.16 (d, J=1.0 Hz, 3H), 1.59 (d, J=7.5 Hz, 3H); mp range: 118-125° C.; $[α]^{20}_D$ −75.4° (c 0.12, MeOH).

Example 92

(S)—N-(1-(5-fluoropyridin-2-yl)ethyl)-6-(6-methoxy-5-(4-methyl-1H-imidazol-1-yl)pyridin-2-yl)-4-methylpyridazin-3-amine

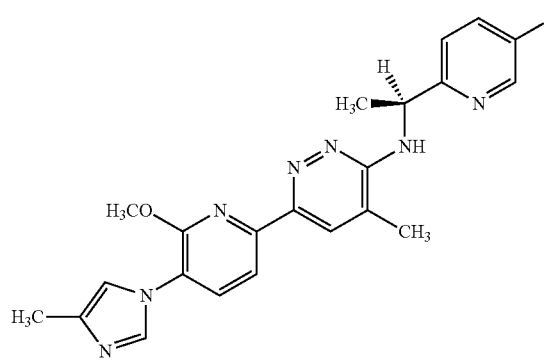

ESI MS (M+H) 420; $^1$H NMR (500 MHz, DMSO-d$_6$) δ 8.51 (d, J=3.0 Hz, 1H), 8.04 (d, J=1.0 Hz, 1H), 7.98 (d, J=8.0 Hz, 1H), 7.93-7.90 (m, 2H), 7.67-7.62 (m, 1H), 7.51-7.48 (m, 1H), 7.27-7.26 (m, 1H), 6.84 (d, J=7.0 Hz, 1H), 5.51 (sym m, 1H), 4.06 (s, 3H), 2.33 (d, J=0.5 Hz, 3H), 2.16 (d, J=1.0 Hz, 3H), 1.59 (d, J=7.0 Hz, 3H); mp range: 170-185° C.; $[α]^{20}_D$ −50.6° (c 0.14, MeOH).

Example 93

(S)-2-(1-((6-(6-methoxy-5-(4-methyl-1H-imidazol-1-yl)pyridin-2-yl)-4-methylpyridazin-3-yl)amino)ethyl)benzonitrile

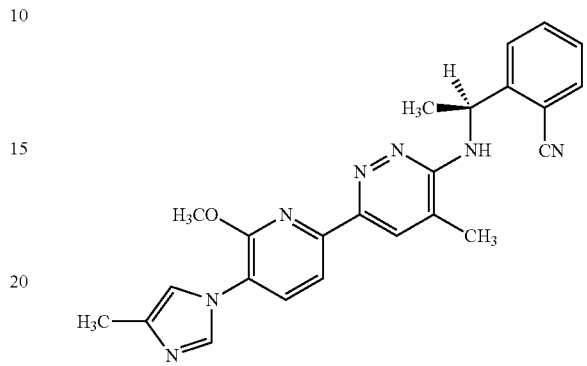

ESI MS (M+H) 426; $^1$H NMR (500 MHz, DMSO-d$_6$) δ 8.49 (s, 1H), 8.26 (d, J=8.0 Hz, 1H), 8.08 (d, J=8.0 Hz, 1H), 8.03 (m, 3H), 7.70-7.63 (m, 2H), 7.58-7.54 (m, 1H), 7.36 (s, 1H), 5.83-5.80 (m, 1H), 4.14 (s, 3H), 2.47 (s, 3H), 2.19 (s, 3H), 1.40 (d, J=6.5 Hz, 3H); mp range: 145-150° C.; $[α]^{20}_D$ +9.0° (c 0.10, MeOH).

Example 94

(S)-2-(6-(6-methoxy-5-(4-methyl-1H-imidazol-1-yl)pyridin-2-yl)-4-methylpyridazin-3-yl)-3-methyl-isoindolin-1-imine

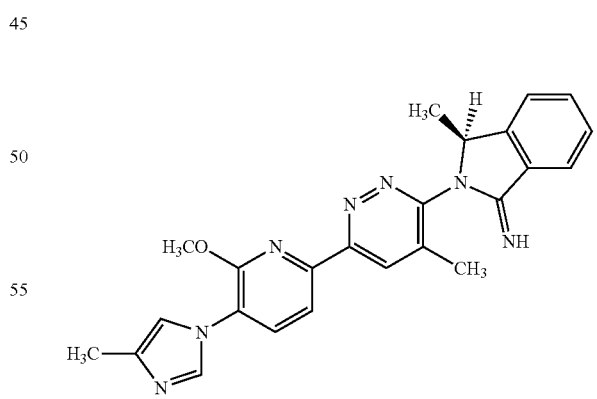

ESI MS (M+H) 426; $^1$H NMR (500 MHz, DMSO-d$_6$) δ 10.49 (s, 1H), 8.31 (s, 1H), 8.18 (d, J=7.5 Hz, 1H), 8.02-7.95 (m, 3H), 7.68-7.53 (m, 3H), 7.32 (s, 1H), 5.06-5.04 (m, 1H), 4.12 (s, 3H), 2.18 (s, 3H), 2.07 (s, 3H), 1.55 (d, J=6.0 Hz, 3H); mp range: >250° C.

Example 95

(S)-2-(1-((6-(6-methoxy-5-(4-methyl-1H-imidazol-1-yl)pyridin-2-yl)-4-methylpyridazin-3-yl)amino)propyl)benzonitrile

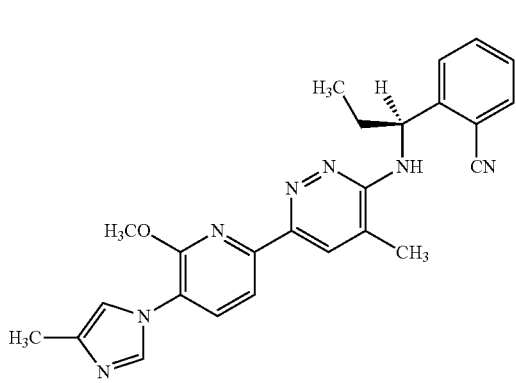 [SMILES: CC[C@H](Nc1nnc(-c2ccc(-n3cnc(C)c3)c(OC)n2)cc1C)c1ccccc1C#N]

ESI MS (M+H) 440; $^1$H NMR (500 MHz, DMSO-$d_6$) δ 8.48 (s, 1H), 8.25 (d, J=8.0 Hz, 1H), 8.09-8.02 (m, 4H), 7.66-7.62 (m, 2H), 7.56-7.53 (m, 1H), 7.35 (s, 1H), 5.93 (m, 1H), 4.14 (s, 3H), 2.19 (s, 3H), 2.50 (s, 3H), 2.06-1.95 (m, 1H), 1.89-1.81 (m, 1H), 0.58 (t, J=7.5 Hz, 3H); mp range: 144-149° C.; $[α]^{20}_D$ +7.6° (c 0.13, MeOH).

Example 96

(S)-3-ethyl-2-(6-(6-methoxy-5-(4-methyl-1H-imidazol-1-yl)pyridin-2-yl)-4-methylpyridazin-3-yl)isoindolin-1-imine

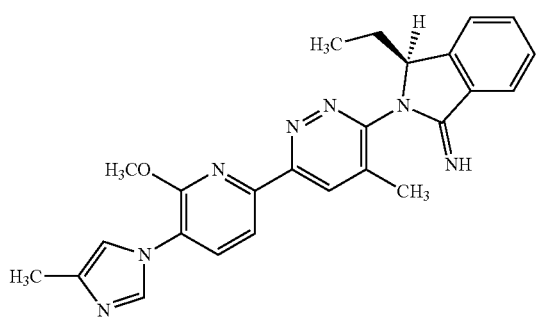 [SMILES: CC[C@H]1c2ccccc2C(=N)N1c1nnc(-c2ccc(-n3cnc(C)c3)c(OC)n2)cc1C]

ESI MS (M+H) 440; $^1$H NMR (500 MHz, DMSO-$d_6$) δ 10.44 (s, 1H), 8.31 (d, J=1.0 Hz, 1H), 8.19 (d, J=8.0 Hz, 1H), 8.02-7.95 (m, 3H), 7.66-7.63 (m, 2H), 7.57-7.55 (m, 1H), 7.32 (d, J=1.0 Hz, 1H), 5.06 (m, 1H), 4.12 (s, 3H), 2.52 (s, 3H), 2.18 (s, 3H), 2.16-2.09 (m, 1H), 1.94-1.87 (m, 1H), 0.78 (t, J=7.0 Hz, 3H); mp range: >250° C.

Example 97

N-(2,4-dimethylpentan-3-yl)-6-(6-methoxy-5-(4-methyl-1H-imidazol-1-yl)pyridin-2-yl)-4-methylpyridazin-3-amine

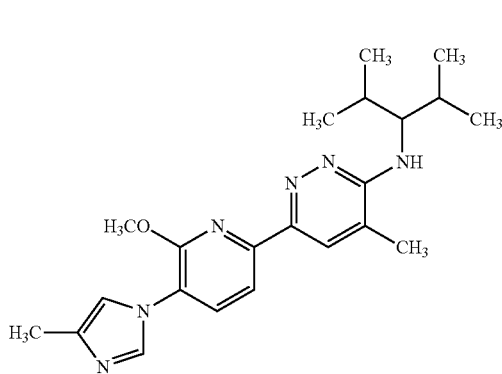 [SMILES: COc1nc(-c2cc(C)c(NC(C(C)C)C(C)C)nn2)ccc1-n1cnc(C)c1]

ESI MS (M+H) 395; $^1$H NMR (500 MHz, CD$_3$OD) δ 8.08 (d, J=1.0 Hz, 1H), 8.02 (d, J=8.0 Hz, 1H), 7.95 (d, J=1.0 Hz, 1H), 7.85 (d, J=8.0 Hz, 1H), 7.20 (s, 1H), 4.34 (d, J=7.0 Hz, 1H), 4.13 (s, 3H), 2.30 (d, J=1.0 Hz, 3H), 2.25 (d, J=1.0 Hz, 3H), 2.08-2.01 (m, 2H), 0.98-0.85 (m, 12H), N—H not observed.

Example 98

6-(6-methoxy-5-(4-methyl-1H-imidazol-1-yl)pyridin-2-yl)-4-methyl-N-(pentan-3-yl)pyridazin-3-amine

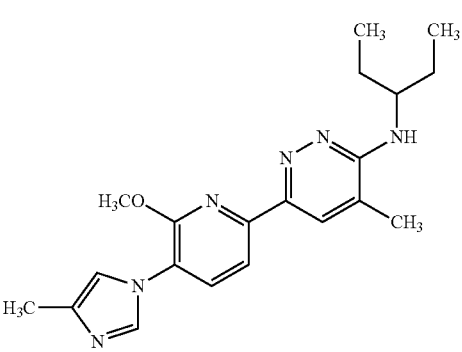 [SMILES: CCC(CC)Nc1nnc(-c2ccc(-n3cnc(C)c3)c(OC)n2)cc1C]

ESI MS (M+H) 367; $^1$H NMR (300 MHz, DMSO-$d_6$) δ 8.04-7.91 (m, 4H), 7.27 (s, 1H), 6.05 (d, J=8.4 Hz, 1H), 4.31-4.19 (m, 1H), 4.05 (s, 3H), 2.21 (s, 3H), 2.16 (d, J=0.6 Hz, 3H), 1.67-1.57 (m, 4H), 0.90 (t, J=7.2 Hz, 6H); mp range: 74-92° C.

Example 99

(cis/trans)-6-(6-methoxy-5-(4-methyl-1H-imidazol-1-yl)pyridin-2-yl)-4-methyl-N-(4-(trifluoromethyl)cyclohexyl)pyridazin-3-amine

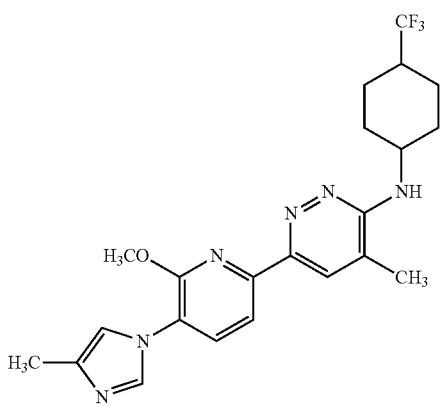 [SMILES: COc1nc(-c2cc(C)c(NC3CCC(C(F)(F)F)CC3)nn2)ccc1-n1cnc(C)c1]

ESI MS (M+H) 447; $^1$H NMR (300 MHz, DMSO-d$_6$) δ 8.06-8.02 (m, 2H), 7.95-7.92 (m, 2H), 7.28 (t, J=1.2 Hz, 1H), 5.96 (d, J=5.4 Hz, 1H), 4.37-4.29 (m, 1H), 4.06 (s, 3H), 2.43-2.38 (m, 1H), 2.27 (d, J=0.9 Hz, 3H), 2.17 (d, J=0.9 Hz, 3H), 2.10-1.95 (m, 2H), 1.79-1.68 (m, 6H); mp range: 118-130° C.

Example 100

(S)—N-(1-(2,3-dimethylphenyl)ethyl)-6-(6-methoxy-5-(4-methyl-1H-imidazol-1-yl)pyridin-2-yl)-4-methylpyridazin-3-amine

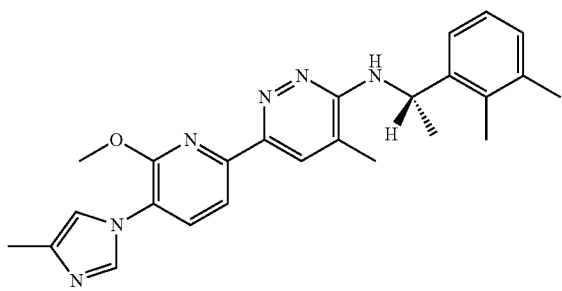

ESI MS (M+H) 429; $^1$H NMR (300 MHz, DMSO-d$_6$) δ 8.01-7.89 (m, 4H), 7.30-7.26 (m, 2H), 7.00 (t, J=1.2 Hz, 2H), 6.81 (d, J=7.2 Hz, 1H), 5.73-5.64 (m, 1H), 4.04 (s, 3H), 2.32 (s, 6H), 2.26 (s, 3H), 2.15 (s, 3H), 1.49 (d, J=6.9 Hz, 3H); mp range: 128-144° C.; [α]$^{20}$$_D$ +32.5° (c 0.12, MeOH).

Example 101

(S)—N-(1-(2-fluoro-3-(trifluoromethyl)phenyl)ethyl)-6-(6-methoxy-5-(4-methyl-1H-imidazol-1-yl)pyridin-2-yl)-4-methylpyridazin-3-amine

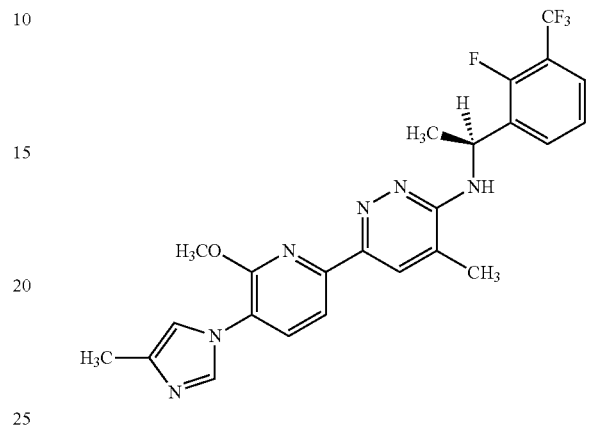

ESI MS (M+H) 487; $^1$H NMR (300 MHz, DMSO-d$_6$) δ 8.05 (d, J=0.9 Hz, 1H), 7.99-7.90 (m, 3H), 7.78 (t, J=7.5 Hz, 1H), 7.63 (t, J=7.2 Hz, 1H), 7.33 (t, J=8.1 Hz, 1H), 7.27 (s, 1H), 7.02 (d, J=4.2 Hz, 1H), 5.76-5.67 (m, 1H), 4.05 (s, 3H), 2.37 (s, 3H), 2.15 (d, J=0.6 Hz, 3H), 1.60 (d, J=6.9 Hz, 3H); mp range: 117-129° C.; [α]$^{20}$$_D$ −6.5° (c 0.11, MeOH).

Example 102

(R)-1-(4-fluorophenyl)-1-((6-(6-methoxy-5-(4-methyl-1H-imidazol-1-yl)pyridin-2-yl)-4-methylpyridazin-3-yl)amino)-2-methylpropan-2-ol

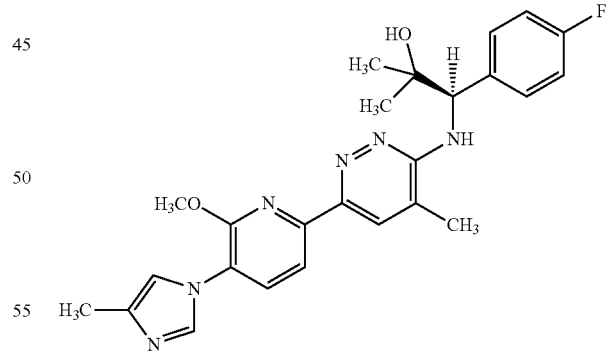

ESI MS (M+H) 463; $^1$H NMR (500 MHz, DMSO-d$_6$) δ 8.02 (d, J=1.0 Hz, 1H), 7.98 (d, J=8.0 Hz, 1H), 7.92 (d, J=1.5 Hz, 1H), 7.90 (d, J=8.0 Hz, 1H), 7.54-7.48 (m, 2H), 7.26 (t, J=1.0 Hz, 1H), 7.12-7.06 (m, 2H), 6.19 (d, J=8.0 Hz, 1H), 5.25 (d, J=8.5 Hz, 1H), 4.98 (s, 1H), 4.05 (s, 3H), 2.34 (d, J=0.5 Hz, 3H), 2.16 (d, J=1.0 Hz, 3H), 1.32 (s, 3H), 1.02 (s, 3H); mp range: 135-146° C.; [α]$^{20}$$_D$ −111.4° (c 0.11, MeOH).

Example 103

(R)—N-(1-(2-chloro-4-fluorophenyl)ethyl)-6-(6-methoxy-5-(4-methyl-1H-imidazol-1-yl)pyridin-2-yl)-4-methylpyridazin-3-amine

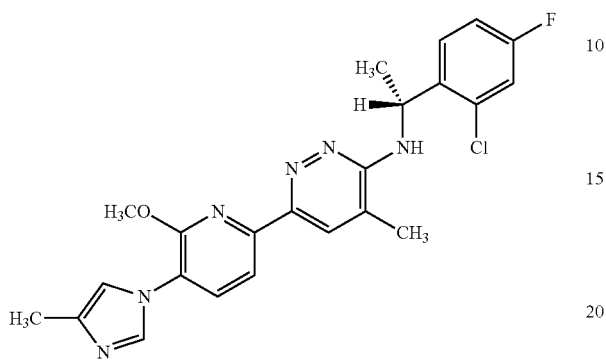

ESI MS (M+H) 453; $^1$H NMR (300 MHz, DMSO-$d_6$) δ 8.03 (d, J=0.9 Hz, 1H), 7.98 (d, J=8.1 Hz, 1H), 7.93 (d, J=1.2 Hz, 1H), 7.91 (d, J=8.1 Hz, 1H), 7.55 (dd, J=8.7, 6.3 Hz, 1H), 7.42 (dd, J=9.0, 2.7 Hz, 1H), 7.27 (t, J=0.9 Hz, 1H), 7.15 (dt, J=8.7, 2.7 Hz, 1H), 6.98 (d, J=6.9 Hz, 1H), 5.67 (sym m, 1H), 4.05 (s, 3H), 2.36 (d, J=0.9 Hz, 3H), 2.15 (d, J=0.9 Hz, 3H), 1.54 (d, J=6.9 Hz, 3H); mp range: 98-106° C.; $[\alpha]^{20}_D$ −59.3° (c 0.25, Methanol).

Example A

Tabular Results of A1142 Assays Conducted on Compounds of Examples 5-102. Assays are $A\beta_{42}$ IC$_{50}$ (nM).

TABLE A

| Example No. | $A\beta_{42}$ IC$_{50}$ (nM) |
|---|---|
| 5 | 7.8 |
| 7 | 5.5 |
| 8 | 33 |
| 9 | 46 |
| 10 | 47.5 |
| 11 | 7.5 |
| 13 | 21 |
| 14 | 7.2 |
| 15 | 67 |
| 17 | 37 |
| 18 | 82 |
| 19 | 240 |
| 20 | 132 |
| 21 | 61 |
| 22 | 16 |
| 23 | 22 |
| 24B | >10000 |
| 26 | 36 |
| 27 | 21 |
| 28 | 18 |
| 29 | 12.8 |
| 31 | 5.8 |
| 33 | 6.8 |
| 34 | 4.3 |
| 35 | 12 |
| 36 | 6.5 |
| 37 | 6.3 |
| 38 | 7 |
| 39 | 6.5 |
| 40 | 6.5 |
| 41 | 17.5 |
| 42 | 7.5 |

TABLE A-continued

| Example No. | $A\beta_{42}$ IC$_{50}$ (nM) |
|---|---|
| 43 | 7.5 |
| 44 | 10.5 |
| 45 | 2.5 |
| 46 | 4.1 |
| 47 | 15 |
| 48 | 6.3 |
| 49 | 7 |
| 50 | 38 |
| 51 | 8.3 |
| 52 | 5 |
| 53 | 9.8 |
| 54 | 29 |
| 55 | 3.3 |
| 56 | 3 |
| 57 | 4 |
| 58 | 12 |
| 59 | 778 |
| 60 | 12 |
| 61 | 27 |
| 62 | 2,158 |
| 63 | 79 |
| 64 | >10,000 |
| 65 | 188 |
| 66 | 53 |
| 67 | 95 |
| 68 | 80 |
| 69 | 4.5 |
| 70 | 425 |
| 71 | 22 |
| 72 | 7.1 |
| 73 | 26 |
| 74 | 42 |
| 75 | 3.5 |
| 76 | 29 |
| 77 | 27 |
| 78 | 61 |
| 79 | 7.5 |
| 80 | 1,099 |
| 81 | 27 |
| 82 | 3.5 |
| 83 | 27 |
| 84 | 23 |
| 85 | 70 |
| 86 | 4.5 |
| 87 | 11.5 |
| 88 | 12 |
| 100 | 4.0 |
| 101 | 5.0 |
| 102 | 6.0 |
| 103 | 13 |

Example B

Figure 2:
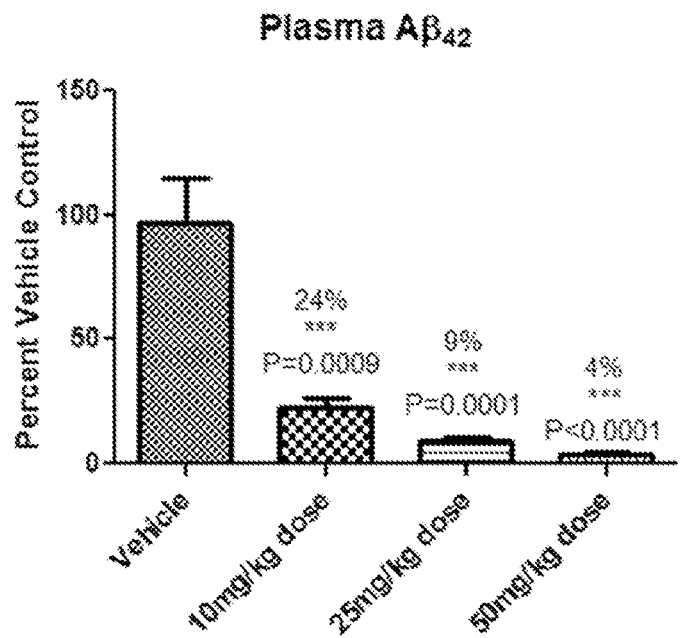
FIG. 2: The effects of Compound 1 after 7-days treatment on $A\beta_{42}$ levels in male C57BL/6J mouse plasma A) (plasma) where the percent reduction was 76%, 91% and 96% for dosages of 10, 25, and 50 mg/kg, respectively and in male C57BL/6J mouse brain B) where the percent reduction was 36%, 69% and 85% for dosages of 10, 25, and 50 mg/kg, respectively.
Figure 2:
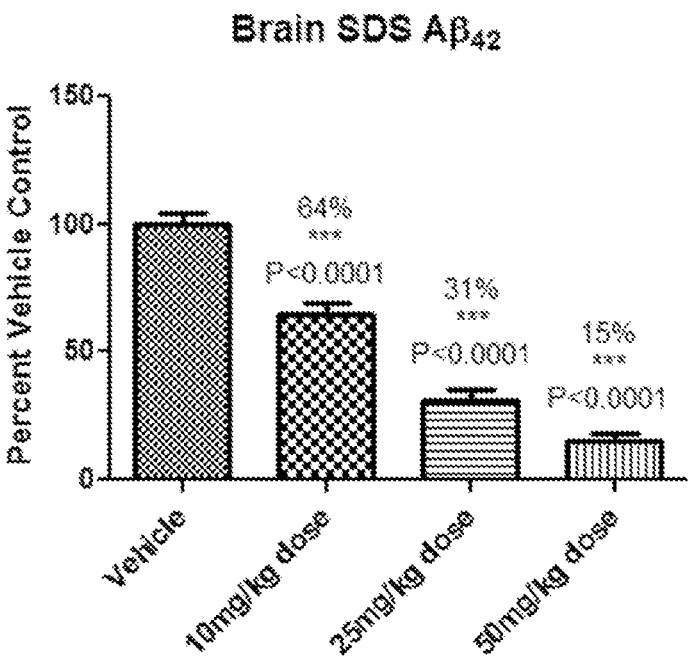

Effects of Compound 1 (7 Days Treatment) on Mouse Plasma and Brain $A\beta_{42}$ Levels. The effects of Compound 1 after 7-days treatment on $A\beta_{42}$ levels in mouse plasma and brain are depicted in FIG. 2A (plasma) and FIG. 2B (brain). For FIG. 2A, the percent reduction was 76%, 91% and 96% for dosages of 10, 25, and 50 mg/kg, respectively. For FIG. 2B, the percent reduction was 36%, 69% and 85% for dosages of 10, 25, and 50 mg/kg, respectively.

Figure 3:
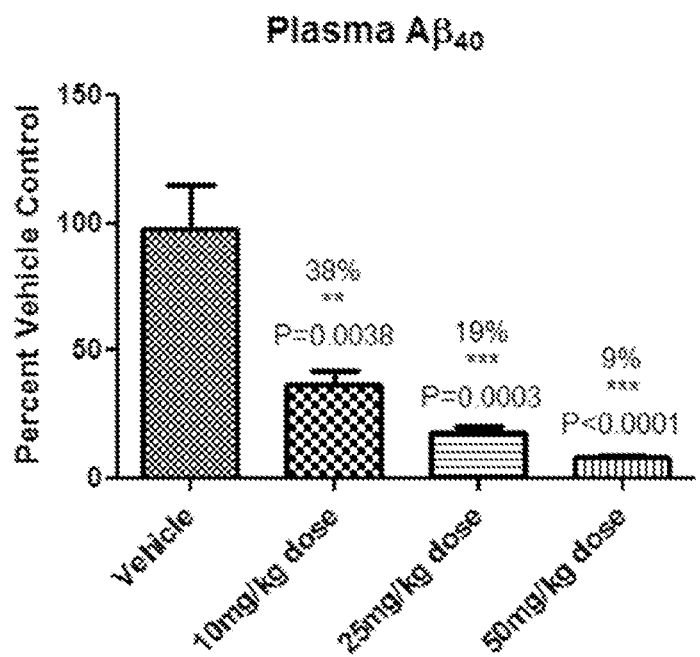
FIG. 3: The effects of Compound 1 after 7-days treatment on $A\beta_{40}$ levels in male C57BL/6J mouse plasma A) (plasma) where the percent reduction was 62%, 81% and 91% for dosages of 10, 25, and 50 mg/kg, respectively and male C57BL/6J mouse brain B) where the percent reduction was 46%, 69% and 82% for dosages of 10, 25, and 50 mg/kg, respectively.
Figure 3:
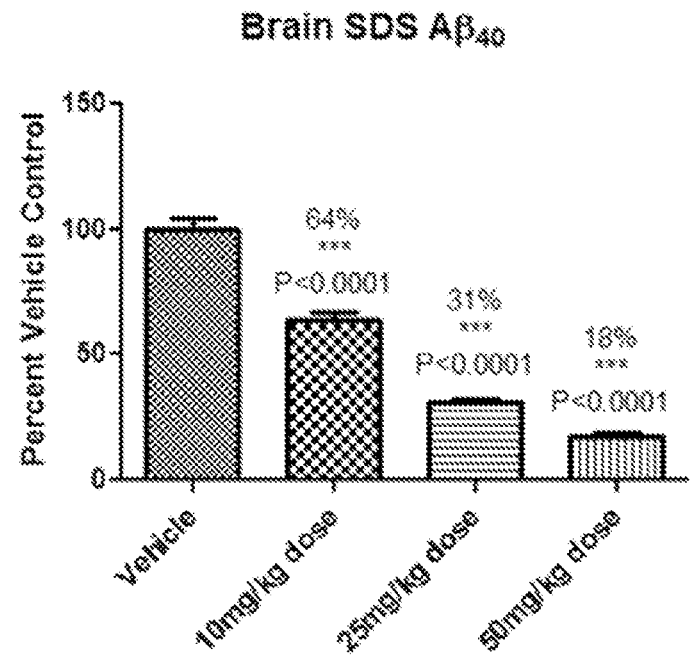

Effects of Compound 1 (7 Days Treatment) on Mouse Plasma and Brain $A\beta_{40}$ Levels. The effects of Compound 1 after 7-days treatment on $A\beta_{40}$ levels in mouse plasma and brain are depicted in FIG. 3A (plasma) and FIG. 3B (brain). For FIG. 3A, the percent reduction was 62%, 81% and 91% for dosages of 10, 25, and 50 mg/kg, respectively. For FIG. 3B, the percent reduction was 46%, 69% and 82% for dosages of 10, 25, and 50 mg/kg, respectively.

Example C

Figure 4:
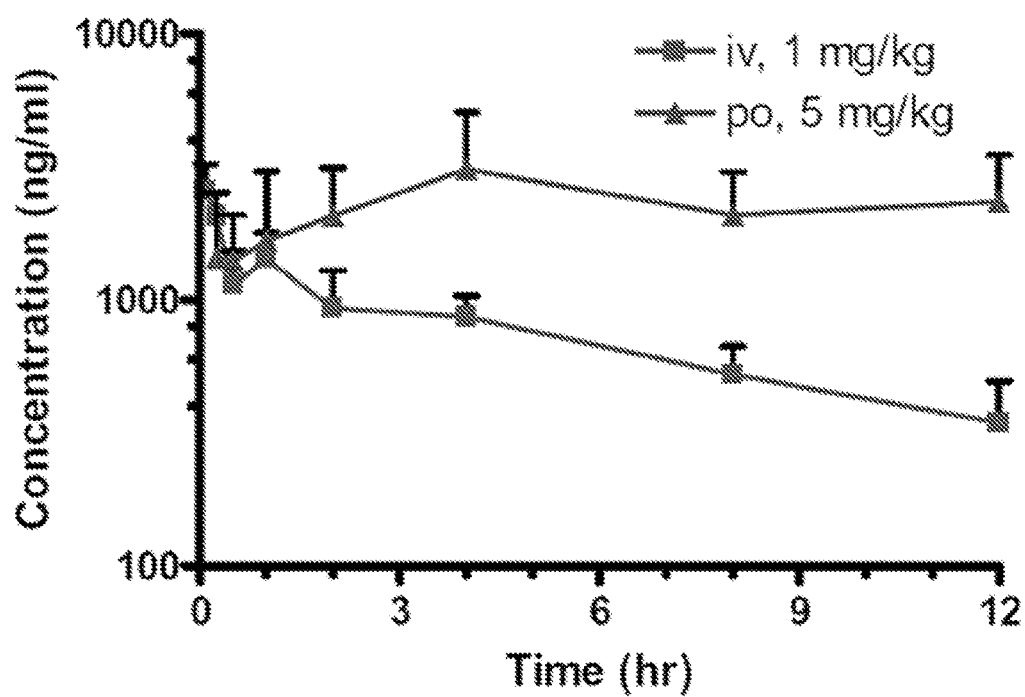
FIG. 4. Time course of administration of Compound 1 to male Sprague Dawley rats: iv (1 mg/kg) or po (5 mg/kg). Oral bioavailability was 60.3%. Clearance was 89 mL/hr/kg. $T_{1/2}$ (iv) was 5.9 hrs.

Efficacy Studies in Rat. Plasma Concentrations of Compound 1 in Male Sprague Dawley Rats. FIG. 4 depicts the time course of administration of Compound 1 to male Sprague Dawley rats: iv (1 mg/kg) or [p (5 mg/kg). Oral bioavailability was 60.3%. Clearance was 89 mL/hr/kg. $T_{1/2}$ (iv) was 5.9 hrs.

Figure 5:
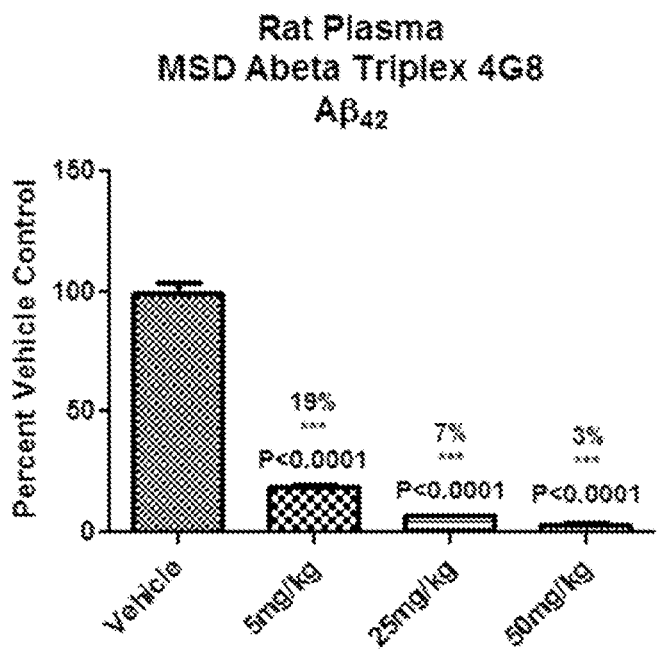
FIG. 5: The effects of Compound 1 after 9-days treatment on $A\beta_{42}$ levels in male Sprague-Dawley rat plasma A) where the reduction in plasma levels was 81%, 93% and 97%, for dosages of 5, 25, and 50 mg/kg, respectively and male Sprague-Dawley rat CSF B) where the reduction in CSF levels was 43%, 73% and 86%, for dosages of 5, 25, and 50 mg/kg, respectively.
Figure 5:
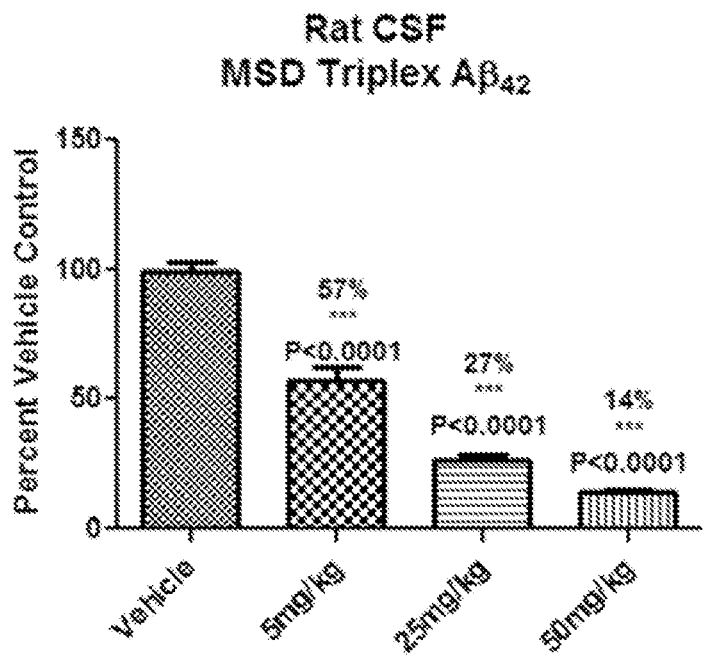

Effects of Compound 1 (9 Days Treatment) on Rat Plasma and CSF $A\beta_{42}$ Levels. The effects of Compound 1 after 9-days treatment on $A\beta_{42}$ levels in rat plasma and CSF are depicted in FIG. 5A (plasma) and FIG. 5B (CSF). For FIG. 5A, the reduction in plasma levels was 81%, 93% and 97%, for dosages of 5, 25, and 50 mg/kg, respectively. For FIG. 5B, the reduction in CSF levels was 43%, 73% and 86%, for dosages of 5, 25, and 50 mg/kg, respectively.

Figure 6:
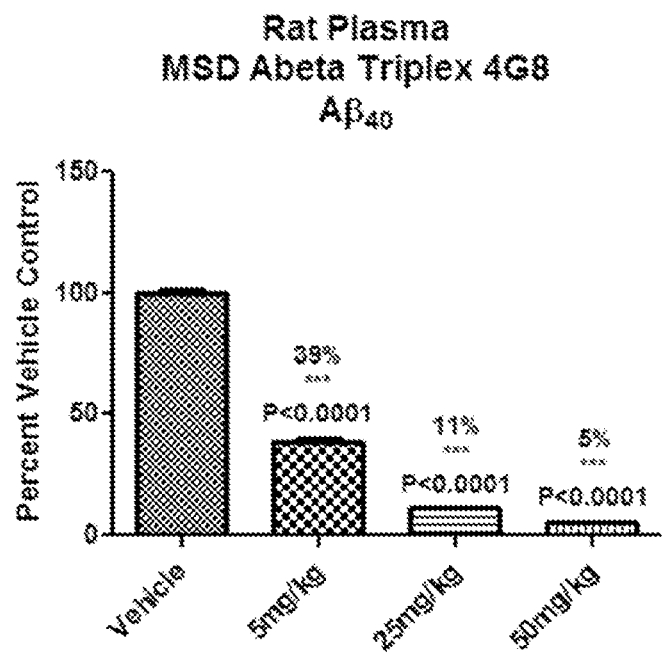
FIG. 6: The effects of Compound 1 after 9-days treatment on $A\beta_{40}$ levels in male Sprague-Dawley rat plasma A) where the reduction in plasma levels was 61%, 89% and 95%, for dosages of 5, 25, and 50 mg/kg, respectively and in male Sprague-Dawley rat CSF B) where the reduction in CSF levels was 47%, 75% and 85%, for dosages of 5, 25, and 50 mg/kg, respectively.
Figure 6:
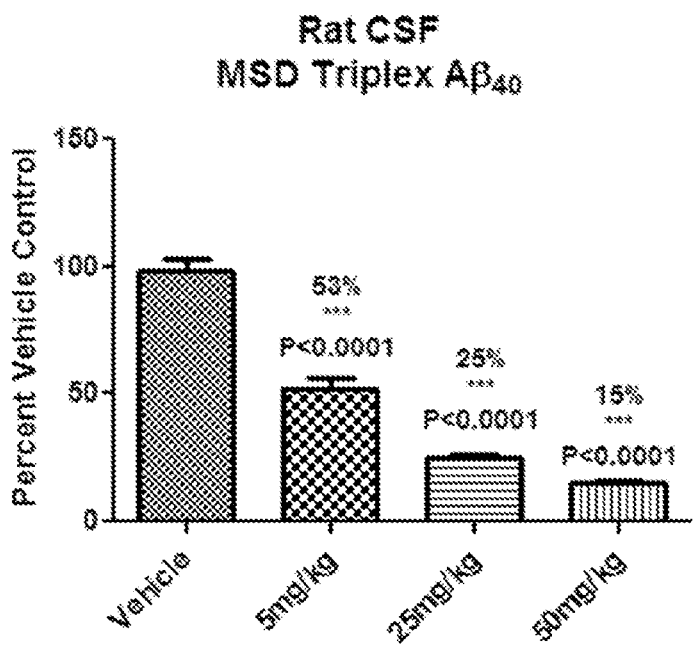

Effects of Compound 1 (9 Days Treatment) on Rat Plasma and CSF $A\beta_{40}$ Levels. The effects of Compound 1 after 9-days treatment on $A\beta_{40}$ levels in rat plasma and CSF are depicted in FIG. 6A (plasma) and FIG. 6B (CSF). For FIG. 6A, the reduction in plasma levels was 61%, 89% and 95%, for dosages of 5, 25, and 50 mg/kg, respectively. For FIG. 6B, the reduction in CSF levels was 47%, 75% and 85%, for dosages of 5, 25, and 50 mg/kg, respectively.

Example D

Figure 7:
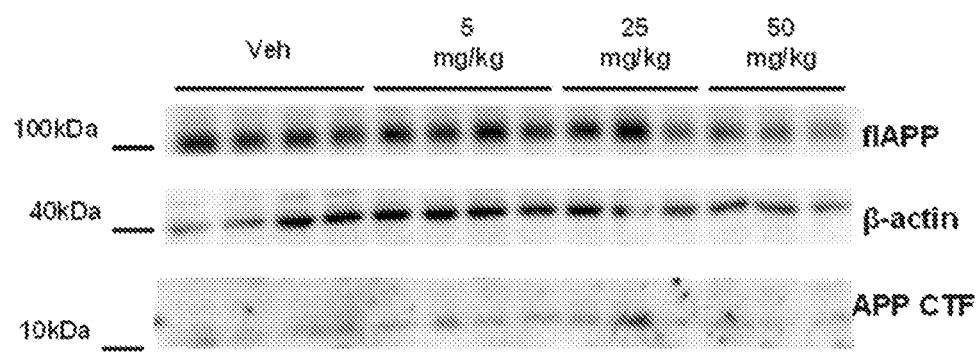
FIG. 7: Protein blots of indicated proteins from subjects administered vehicle and Compound 1 at doses of 5, 25 and 50 mg/kg.
Figure 7:
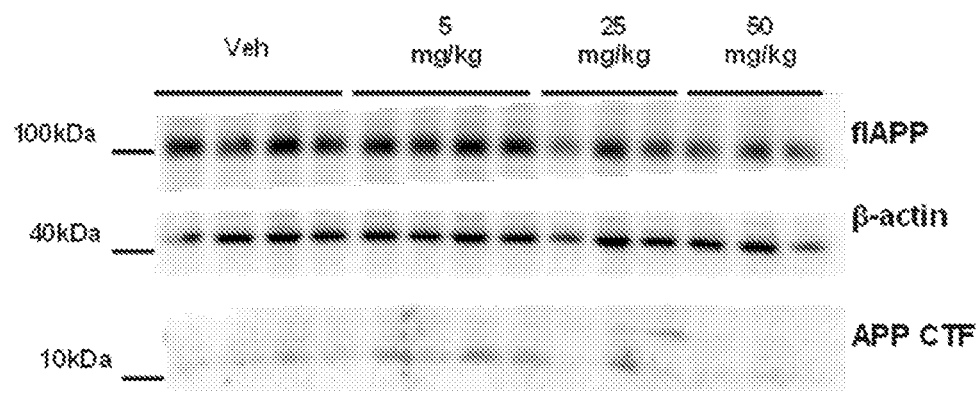

Compound 1 Does Not Cause Accumulation of APP-CTFs. As depicted in FIG. 7, administration of Compound 1 does not cause accumulation of APP-CTF (C-terminal fragment) at administered doses of 5, 25 or 50 mg/kg. flAPP and b-actin are control species in the figure. Brain extracts which were prepared using 1.0% SDS run on SDS-PAGE, transferred to PVDF membranes and immunoblots were performed using an anti-APP carboxyl-terminal antibody.

Example E

Figure 8:
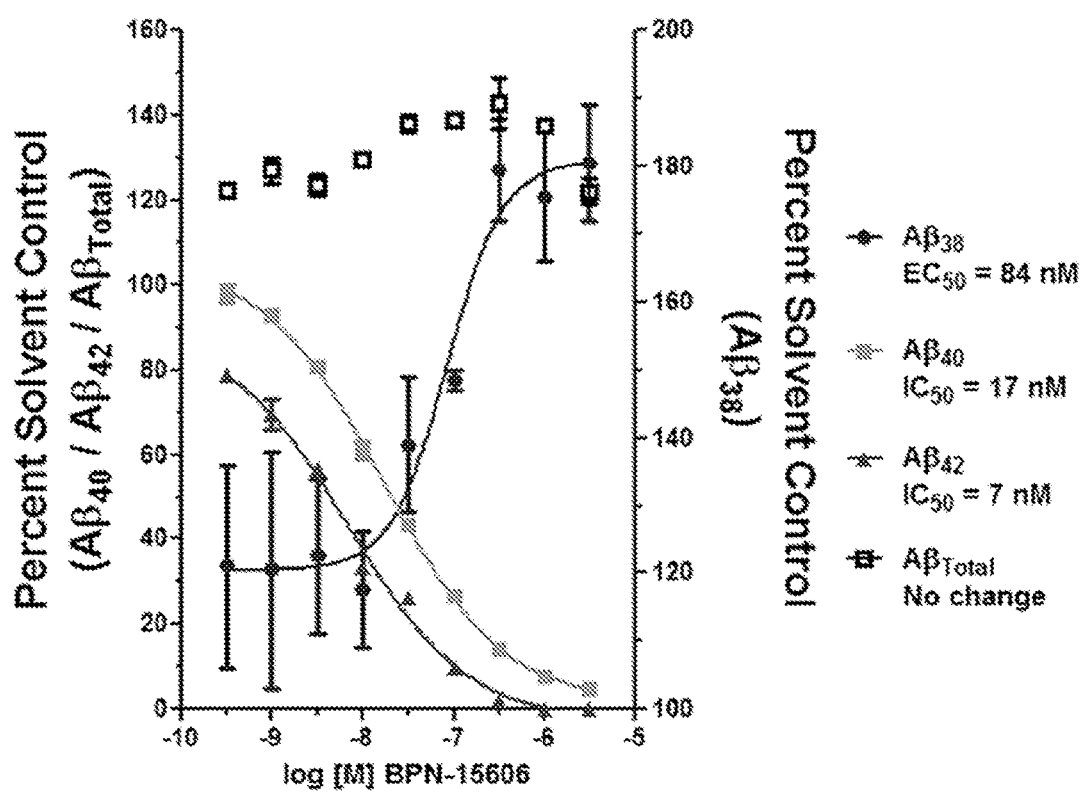
FIG. 8: Representative concentration response curves of Compound 1 using our primary and orthogonal medium throughput SHSYSY-APP cell-based screening assays (10). Compounds are first screened two times in triplicate in our UCSD sandwich Aβ42 ELISA on sequential days and the average of the two assays must be within 3-fold of each other before being entered into the CDD relational database. The UCSD sandwich ELISA assay can easily handle 20 compounds per week. Compounds with $A\beta_{42}$ IC50 values <100 nM continue through the testing funnel. The Z' score and the % CV for the UCSD Aβ42 sandwich ELISA assay are 0.8 and 4, respectively. For the Meso Scale triplex assay the Z' scores are 0.7, 0.9 and 0.6 Aβ42, Aβ40 and Aβ38, respectively and the % CV's are 7, 2 and 1 for Aβ42, Aβ40 and Aβ38, respectively. Aβ total peptides are measured using a sandwich ELISA.

Compound 1 Does Not Decrease Levels of Total Aβ Peptides. As depicted in FIG. 8, Compound 1 does not decrease levels of total Aβ peptides. The figure depicts percent solvent control ($A\beta_{40}/A\beta_{42}/A\beta_{Total}$) (left axis) and percent solvent control ($A\beta_{38}$) again log of, concentration of Compound 1.

Example F

Figure 9:
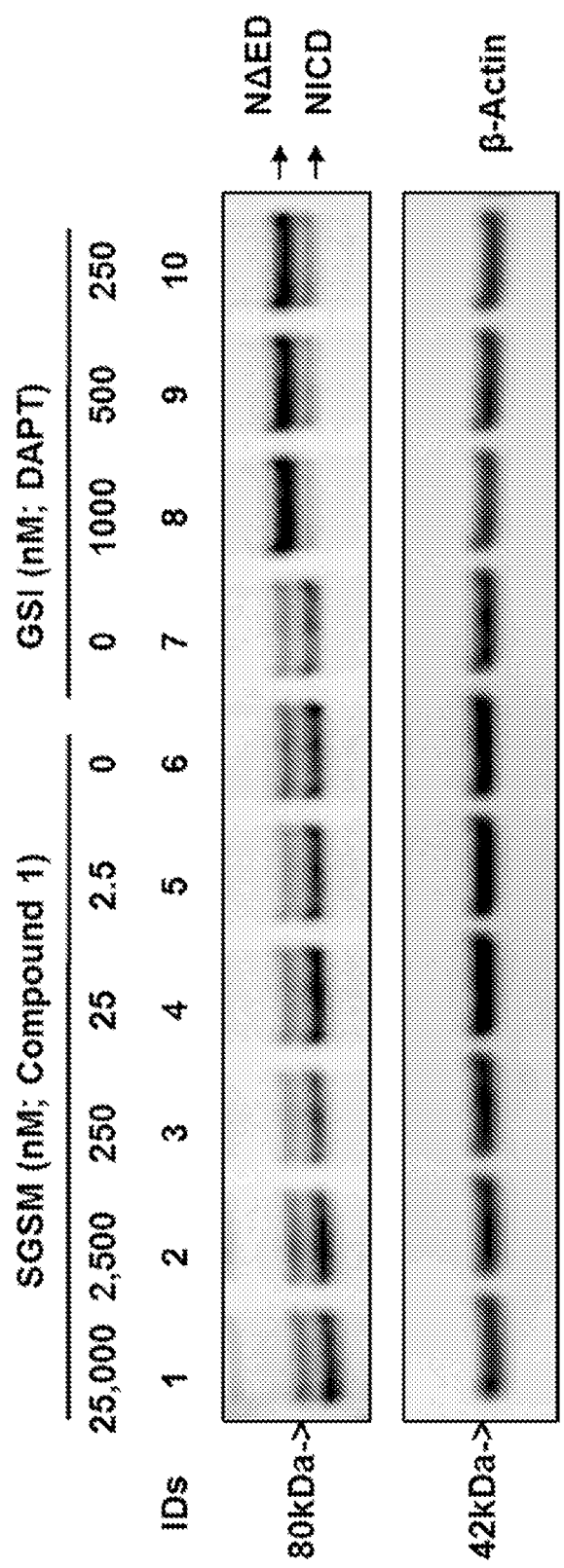
FIG. 9: Compound 1 did not affect Notch processing in H4-APP751 cells; Stable H4 human neuroglioma cells over-expressing human APP751, or H4-APP751 cells, were transfected with the NAE construct, and then treated with different concentrations SGSM Compound 1 (Lanes 1-6) or DAPT (Lanes 7-10) for another 24 hrs. Cells were harvested 48 hrs post transfection and applied to Western blotting analysis. Myc antibody was utilized to assess the NAED and NICD tagged with Myc on their N-termini. β-Actin was utilized as the loading control. Compound 1 did not inhibit Notch processing; however, DAPT a gamma-secretase inhibitor or GSI significantly inhibits Notch processing.

Stable H4 human neuroglioma cells over-expressing human APP751, or H4-APP751 cells, were transfected with the NAE construct, and then treated with different concentrations SGSM Compound 1 (Lanes 1-6) or DAPT (Lanes 7-10) for another 24 hrs and are shown in FIG. 9. Cells were harvested 48 hrs post transfection and applied to Western blotting analysis. Myc antibody was utilized to assess the NAED and NICD tagged with Myc on their N-termini β-Actin was utilized as the loading control. Compound 1 did not inhibit Notch processing; however, DAPT a gamma-secretase inhibitor or GSI significantly inhibits Notch processing.

Example G

Stably-transfected H4 human neuroglioma cells over-expressing human APP751 (H4-APP751) cells, were transfected with the Notch NδED construct, and then treated with vehicle, or different doses of GSMs (40 nM, 200 nM, 1000 nM, and 5000 nM) for 24 hrs. Cells were harvested 48 hrs post transfection and subjected to Western blotting analysis. Myc antibody was utilized to assess the NδED and NICD tagged with Myc on their N-termini GSMs in our studies did not decrease the NICD levels at all concentrations studied, while the control compound, gamma-secretase inhibitor, DAPT, significantly inhibited NOTCH processing in the same experiments.

Figure 10:
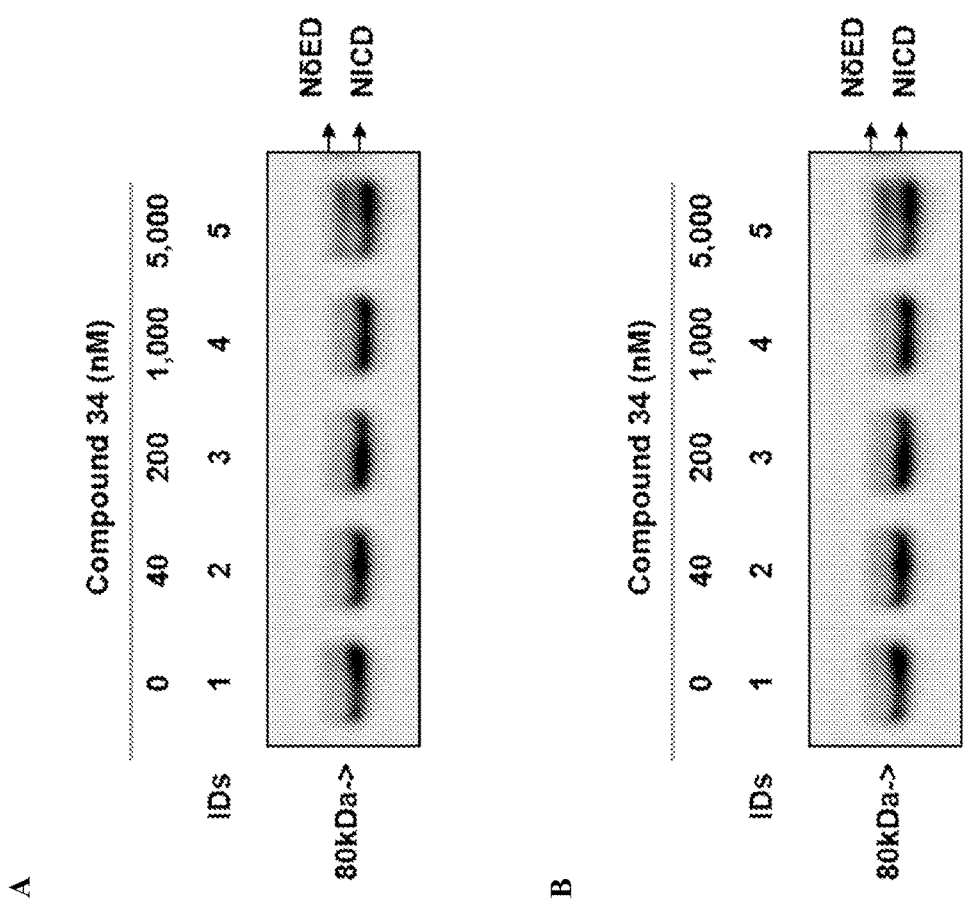
FIG. 10: Compounds 34, 45, and 46 did not affect Notch processing in stably-transfected H4 human neuroglioma cells over-expressing human APP751 (H4-APP751) cells, were transfected with the Notch NδED construct, and then treated with vehicle, or different doses of Compounds 34, 45, and 46 (40 nM, 200 nM, 1000 nM, and 5000 nM) for 24 hrs. Cells were harvested 48 hrs post transfection and subjected to Western blotting analysis. Myc antibody was utilized to assess the NδED and NICD tagged with Myc on their N-termini. Compounds 34 (FIG. 10A), 45 (FIG. 10B), and 46 (FIG. 10C) in our studies did not decrease the NICD levels at all concentrations studied, while the control compound, gamma-secretase inhibitor, DAPT (FIG. 10D), significantly inhibited NOTCH processing in the same experiments.

Results of these experiments for Compounds 34, 45, 46 and control DAPT are shown in FIG. 10. Compounds 34, 45, and 46 not inhibit Notch processing; however, DAPT a gamma-secretase inhibitor or GSI significantly inhibits Notch processing.

What is claimed is:
1. A compound of Formula (A):

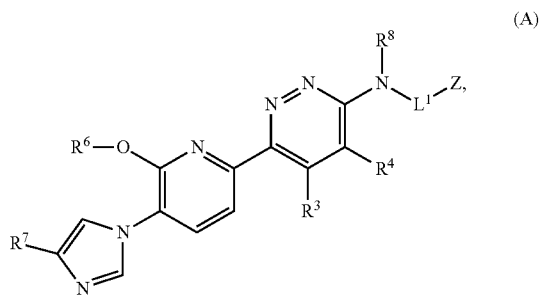

or a pharmaceutically acceptable salt thereof, wherein,
$L^1$ is selected from the group consisting of C(O), C(R$^1$) (R$^2$), substituted or unsubstituted —C$_{2-6}$ alkylene-, and substituted or unsubstituted —C$_{3-6}$ cycloalkylene-;
Z is selected from the group consisting of halo, CN, OH, C$_{1-6}$ alkyl, C$_{1-6}$ alkoxy, C$_{1-3}$ haloalkyl, C$_{1-3}$ haloalkoxy, amino, C$_{1-3}$ alkylamino, di(C$_{1-3}$ alkyl)amino, substituted or unsubstituted C$_{3-6}$ cycloalkyl, substituted or unsubstituted C$_{4-6}$ heterocycloalkyl, substituted or unsubstituted heteroaryl, and a group of Formula (Z-1):

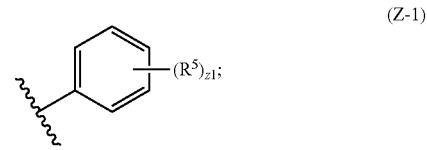

or L$^1$ is absent and Z is selected from the group consisting of substituted or unsubstituted cycloalkyl, substituted or unsubstituted heterocycloalkyl, and substituted or unsubstituted heteroaryl;
R$^1$ and R$^2$ are independently selected from the group consisting of hydrogen, substituted or unsubstituted alkyl, substituted or unsubstituted heteroalkyl, COOR$^{1A}$, and —CONR$^{1A}$R$^{1B}$, or
R$^1$ and R$^2$ are optionally joined together to form a substituted or unsubstituted cycloalkyl;
R$^3$ is selected from the group consisting of hydrogen, halogen, —CF$_3$, —CN, —OR$^{3A}$, —NR$^{3A}$R$^{3B}$, —COOR$^{3A}$, —CONR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;
R$^4$ is selected from the group consisting of hydrogen, halogen, —CF$_3$, —CN, —OR$^{4A}$, —NR$^{4A}$R$^{4B}$, —COOR$^{4A}$, —CONR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; or R³ and R⁴ are optionally joined together to form a substituted or unsubstituted cycloalkyl;

each $R^5$ is independently selected from the group consisting of hydrogen, halogen, —CF₃, —CN, —OR$^{5A}$, —NR$^{5A}$R$^{5B}$, —COOR$^{5A}$, —CONR$^{5A}$R$^{5B}$, —SR$^{5A}$, —OCF₃, —OCHF₂, substituted or unsubstituted alkyl, and substituted or unsubstituted heteroalkyl;

$R^6$ and $R^7$ are independently substituted or unsubstituted C₁-C₅ alkyl;

$R^{1A}$, $R^{1B}$, $R^{3A}$, $R^{3B}$, $R^{4A}$, $R^{4B}$, $R^{5A}$, and $R^{5B}$ are independently selected from the group consisting of hydrogen, —OH, —NH₂, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; or $R^{1A}$ and $R^{1B}$, $R^{3A}$ and $R^{3B}$, $R^{4A}$ and $R^{4B}$, or $R^{5A}$ and $R^{5B}$ are independently optionally joined together to independently form a substituted or unsubstituted heterocycloalkyl, or substituted or unsubstituted heteroaryl;

$R^8$ is selected from the group consisting of hydrogen, substituted or unsubstituted alkyl, and substituted or unsubstituted heteroalkyl; and z1 is an integer of 0, 1, 2, 3, 4, or 5.

2. The compound of claim 1 having formula:

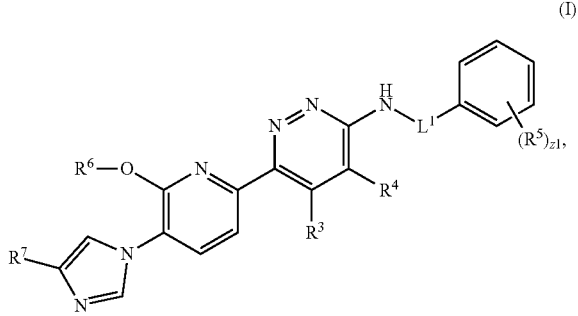

(I)

or a pharmaceutically acceptable salt thereof, wherein,

L¹ is selected from the group consisting of C(O) and C(R¹)(R²); and

R¹ and R² are independently selected from the group consisting of hydrogen, substituted or unsubstituted alkyl, and substituted or unsubstituted heteroalkyl, or R¹ and R² are optionally joined together to form a substituted or unsubstituted cycloalkyl.

3. The compound of claim 1, wherein:

L¹ is selected from the group consisting of C(O), C(R¹)(R²), —C₂₋₆ alkylene-, and —C₃₋₆ cycloalkylene-, wherein the C₁₋₆ alkylene group is optionally substituted with 1, 2, or 3 substituents independently selected from halo, CN, OH, C₁₋₃ alkyl, C₁₋₃ alkoxy, C₁₋₃ haloalkoxy, amino, C₁₋₃ alkylamino, and di(C₁₋₃ alkyl)amino;

Z is selected from the group consisting of halo, CN, OH, C₁₋₆ alkyl, substituted or unsubstituted C₃₋₆ cycloalkyl, substituted or unsubstituted C₄₋₆ heterocycloalkyl, substituted or unsubstituted heteroaryl, and a group of Formula (Z-1):

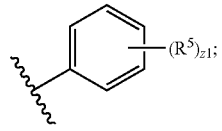

(Z-1)

or L¹ is absent and Z is selected from the group consisting of substituted or unsubstituted cycloalkyl, and substituted or unsubstituted heteroaryl;

R¹ is selected from the group consisting of hydrogen and substituted or unsubstituted alkyl;

R² is selected from the group consisting of hydrogen, substituted or unsubstituted alkyl, substituted or unsubstituted heteroalkyl, and CONR$^{1A}$R$^{1B}$; or R¹ and R² are optionally joined together to form a substituted or unsubstituted cycloalkyl;

R³ is selected from the group consisting of hydrogen, halogen, —CN, —CF₃, —OR$^{3A}$, —NR$^{3A}$R$^{3B}$, substituted or unsubstituted alkyl, and substituted or unsubstituted heteroalkyl;

R$^{3A}$ and R$^{3B}$ are independently selected from the group consisting of hydrogen, substituted or unsubstituted alkyl, and substituted or unsubstituted aryl;

R⁴ is selected from the group consisting of hydrogen, halogen, —CF₃, —CN, —OR$^{4A}$, substituted or unsubstituted alkyl, and substituted or unsubstituted heteroalkyl; or R³ and R⁴ are optionally joined together to form a substituted or unsubstituted cycloalkyl;

R⁵ is selected from the group consisting of halogen, —CF₃, —CN, —OR$^{5A}$, —NR$^{5A}$R$^{5B}$, and substituted or unsubstituted alkyl;

R$^{5A}$ and R$^{5B}$ are each independently selected from the group consisting of hydrogen, substituted or unsubstituted C₁-C₅ alkyl, and substituted or unsubstituted aryl; and z1 is 0, 1, 2, or 3.

4. The compound of claim 1, wherein:

L¹ is selected from the group consisting of C(O), C(R¹)(R²), —C₂₋₆ alkylene-, and —C₃₋₆ cycloalkylene-, wherein the C₁₋₆ alkylene group is optionally substituted with 1 or 2 substituents independently selected from halo, CN, OH, C₁₋₃ alkyl and C₁₋₃ alkoxy;

Z is selected from the group consisting of halo, OH, C₁₋₆ alkyl, and a cyclic group of the following Formulae (Z-1) to (Z-18):

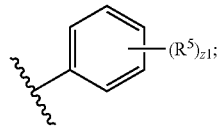

(Z-1)

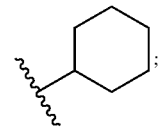

(Z-2)

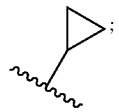

(Z-3)

-continued (Z-4)

(Z-5)

(Z-6)

(Z-7)

(Z-8)

(Z-9)

(Z-10)

(Z-11)

(Z-12)

(Z-13)

(Z-14)

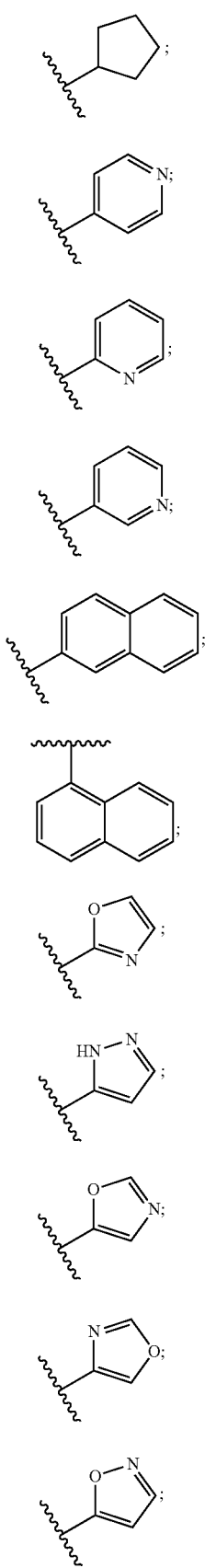

-continued (Z-15) 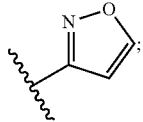

(Z-16) 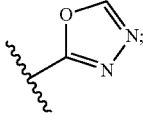

(Z-17) 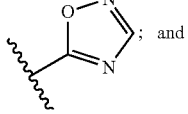 ; and (Z-18) 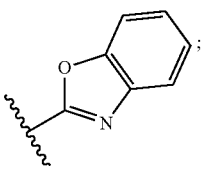

or L$^1$ is absent and Z is selected from the group consisting of a cyclic group of Formulae (Z-2), (Z-3), (Z-4), and the following Formulae (Z-19) and (Z-20):

(Z-19)

(Z-20)

wherein any one of the Formulae (Z-2) to (Z-20) is unsubstituted or substituted;

R$^1$ is selected from the group consisting of hydrogen and substituted or unsubstituted alkyl;

R$^2$ is selected from the group consisting of substituted or unsubstituted alkyl, —CH$_2$OR$^{2A}$ and —C(CH$_3$)$_2$OR$^{2A}$;

R$^{2A}$ is selected from the group consisting of hydrogen and substituted or unsubstituted alkyl; or R$^1$ and R$^2$ are joined together to form a substituted or unsubstituted C$_3$ cycloalkyl;

R$^3$ is selected from the group consisting of hydrogen, substituted or unsubstituted alkyl, and substituted or unsubstituted heteroalkyl;

R$^4$ is selected from the group consisting of hydrogen, halogen, —CF$_3$, —CN, —OR$^{4A}$, substituted or unsubstituted alkyl, and substituted or unsubstituted heteroalkyl; or R$^3$ and R$^4$ are optionally joined together to form a substituted or unsubstituted cycloalkyl;

R⁵ is selected from the group consisting of halogen, —CF₃, —CN, —OR⁵⁴, and substituted or unsubstituted alkyl;

R⁵⁴ is selected from the group consisting of hydrogen, substituted or unsubstituted C₁-C₅ alkyl, and substituted or unsubstituted aryl; and z1 is 0, 1, or 2.

5. The compound of claim 1, wherein:

L¹ is selected from the group consisting of C(O), C(R¹)(R²), -ethylene-, -2-methylethylene-, -propylene-, and -cyclopropylene-;

wherein Z is selected from the group consisting of halo, OH, C₁₋₆ alkyl, and a cyclic group of the following Formulae (Z-1), (Z-2), (Z-5) and (Z-6):

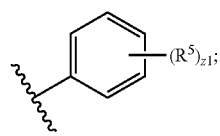
(Z-1)

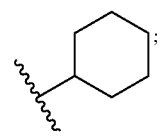
(Z-2)

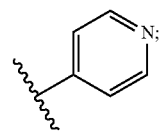
(Z-5)

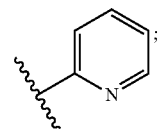
(Z-6)

or L¹ is absent and Z is selected from the group consisting of a cyclic group of Formulae (Z-2), and the following Formulae (Z-3), (Z-4) and (Z-19):

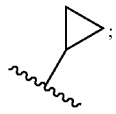
(Z-3)

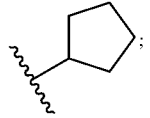
(Z-4)

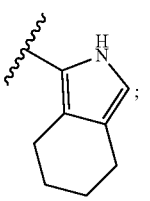
(Z-19)

wherein any one of the Formulae (Z-2), (Z-3), (Z-4), (Z-5), (Z-6), and (Z-19) is unsubstituted or substituted;

R¹ is selected from the group consisting of hydrogen and methyl;

R² is selected from the group consisting of hydrogen, methyl, ethyl, propyl, isopropyl, hydroxymethyl, methoxymethyl, fluoromethyl, 3,3,3-trifluoroethyl, trifluoromethyl, 2-methyl-2-hydroxyethyl, N,N-dimethylaminocarbonyl, and N-pyrrolidinocarbonyl; or R¹ and R² are joined together to form a cyclopropyl ring;

R³ is selected from the group consisting of hydrogen, methyl, ethyl, and methoxy;

R⁴ is selected from the group consisting of hydrogen, methyl, ethyl, isopropyl, methoxy, —CN, Cl, F, and —CF₃; or R³ and R⁴ are optionally joined together to form a cyclic ring selected from the group consisting of cyclopentyl and cyclohexyl;

R⁵ is selected from the group consisting of fluoro, chloro, CN, methoxy, methyl, thrifluoromethyl, OH, and NH₂;

R⁶ is methyl;

R⁷ is methyl;

R⁸ is selected from the group consisting of methyl, ethyl, fluoroethyl, and methoxymethyl; and z1 is 0, 1, or 2.

6. The compound of claim 1, wherein the compound is selected from:

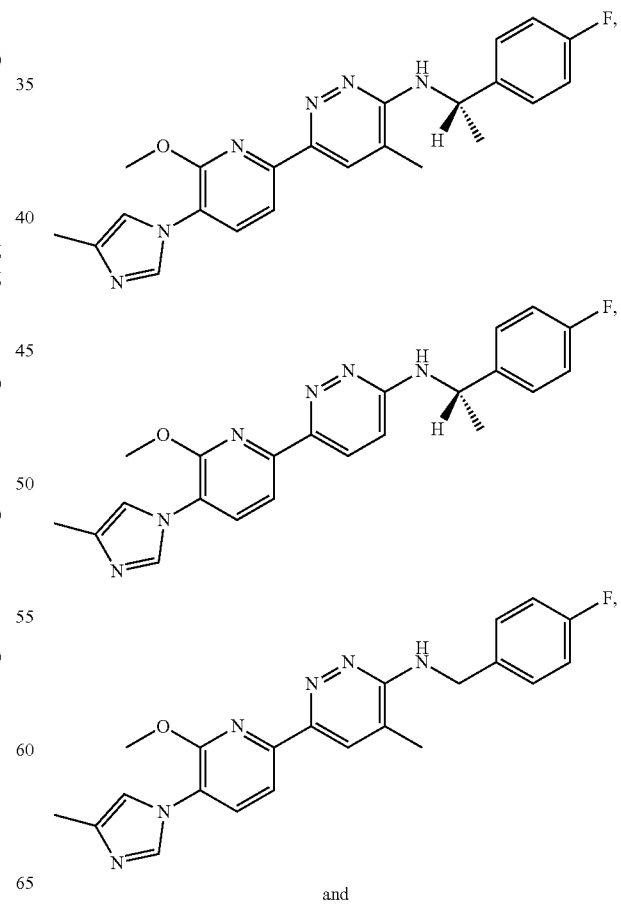

and

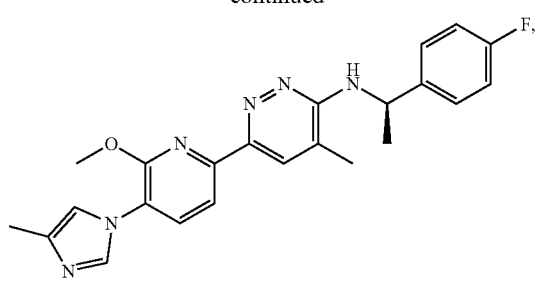
or a pharmaceutically acceptable salt thereof.
7. The compound of claim 1, wherein the compound is selected from:
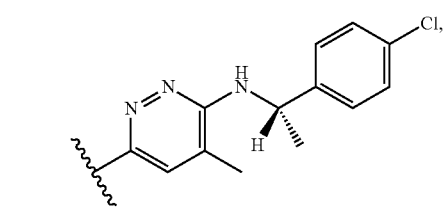
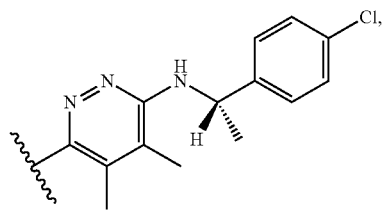
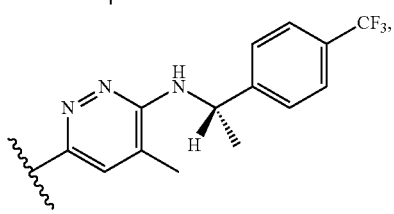
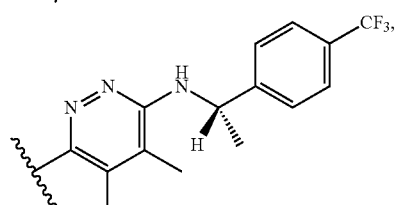
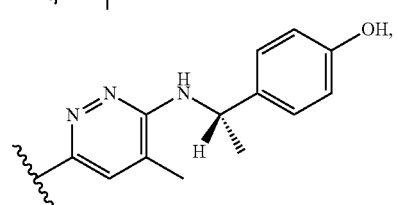
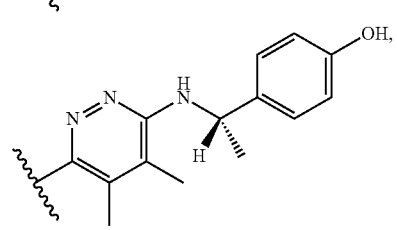
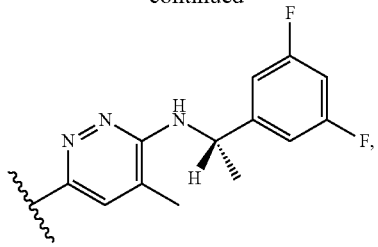
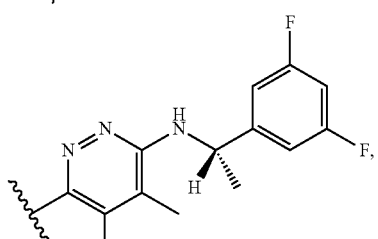
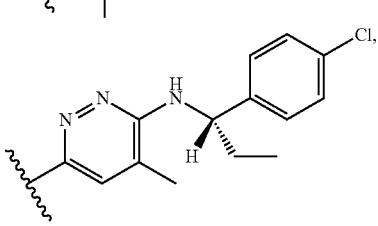
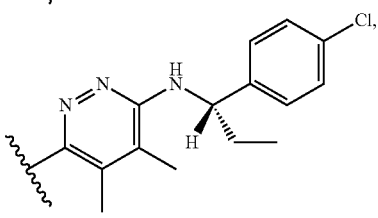
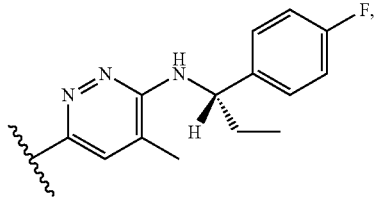
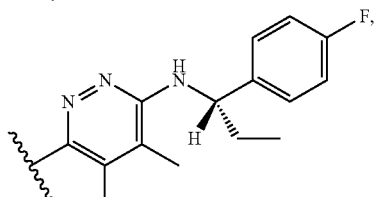
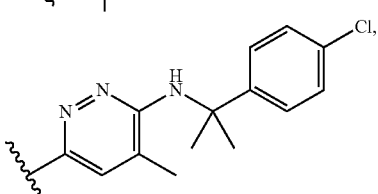
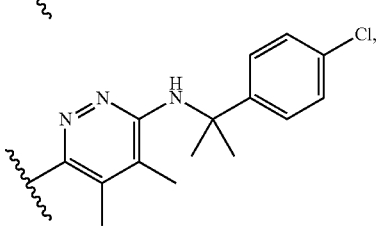

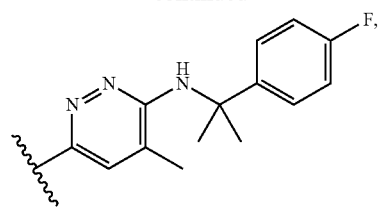
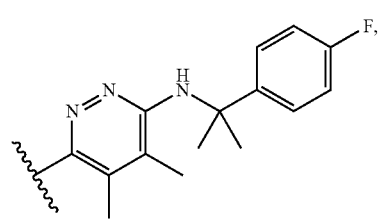
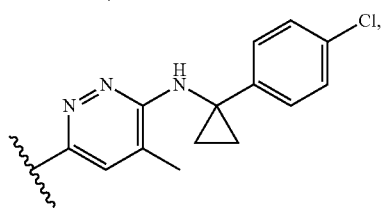
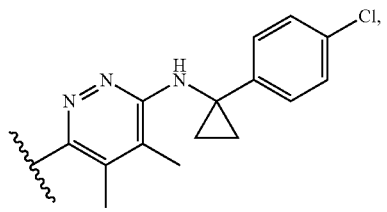
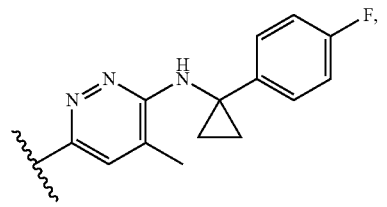
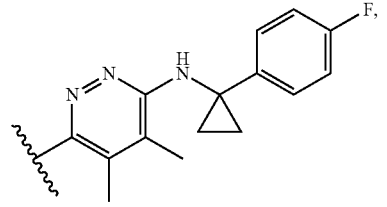
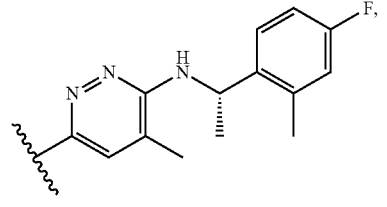
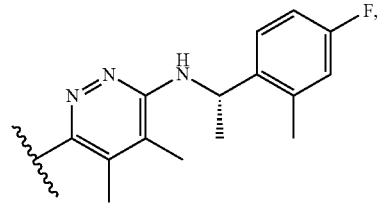
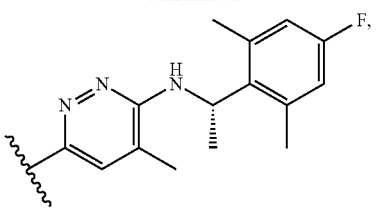
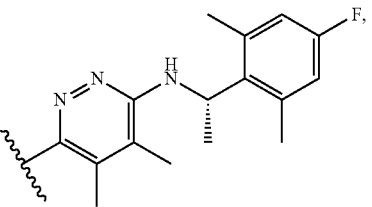
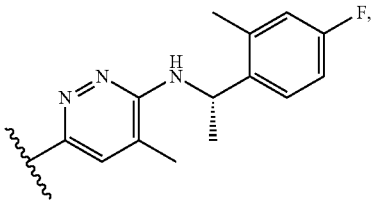
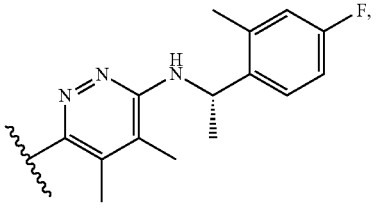
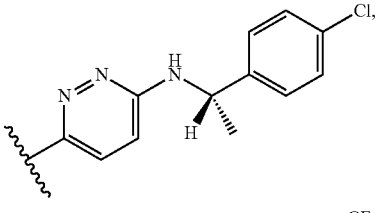
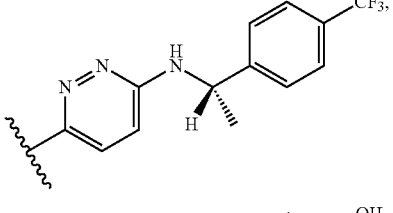
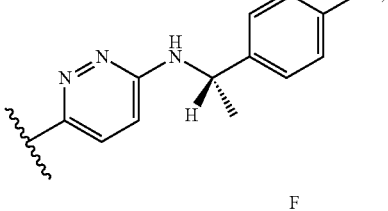
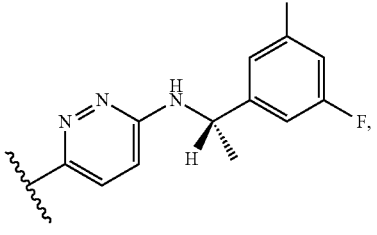

-continued
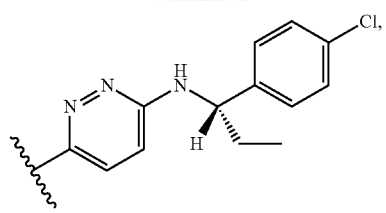
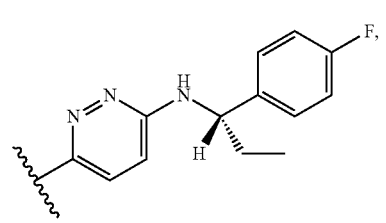
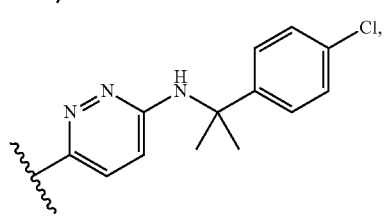
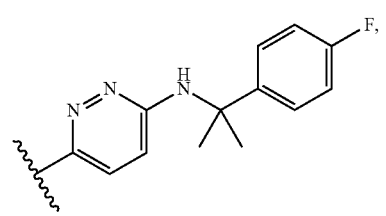
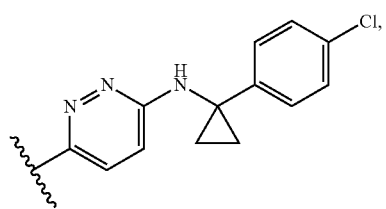
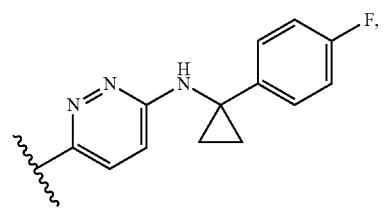
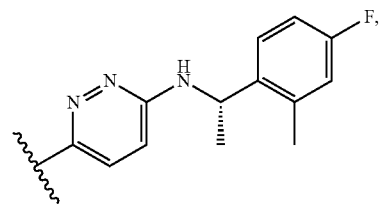
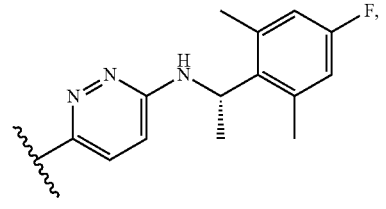
-continued
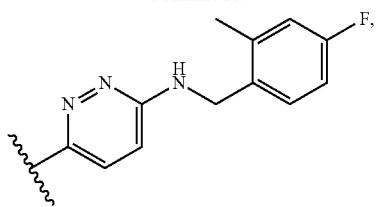
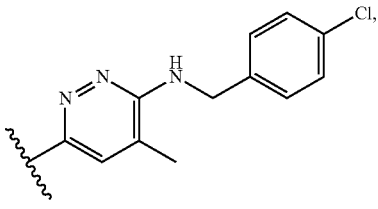
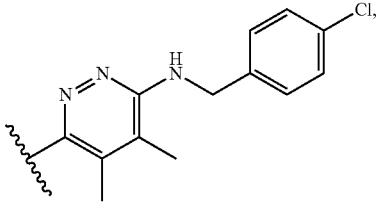
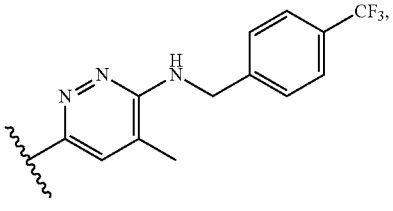
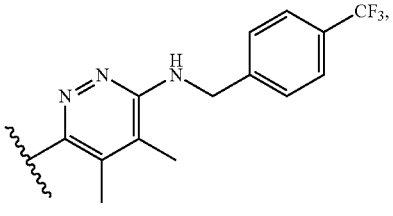
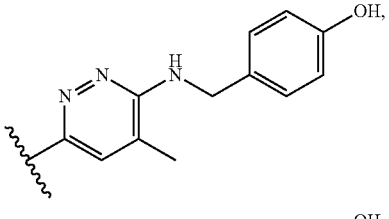
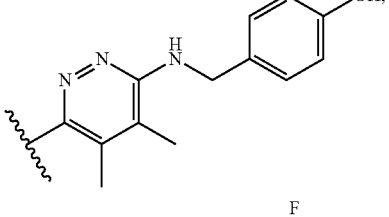
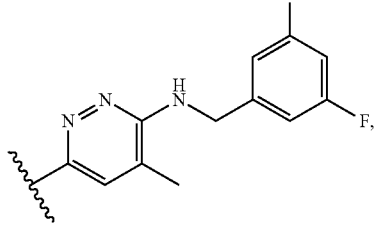

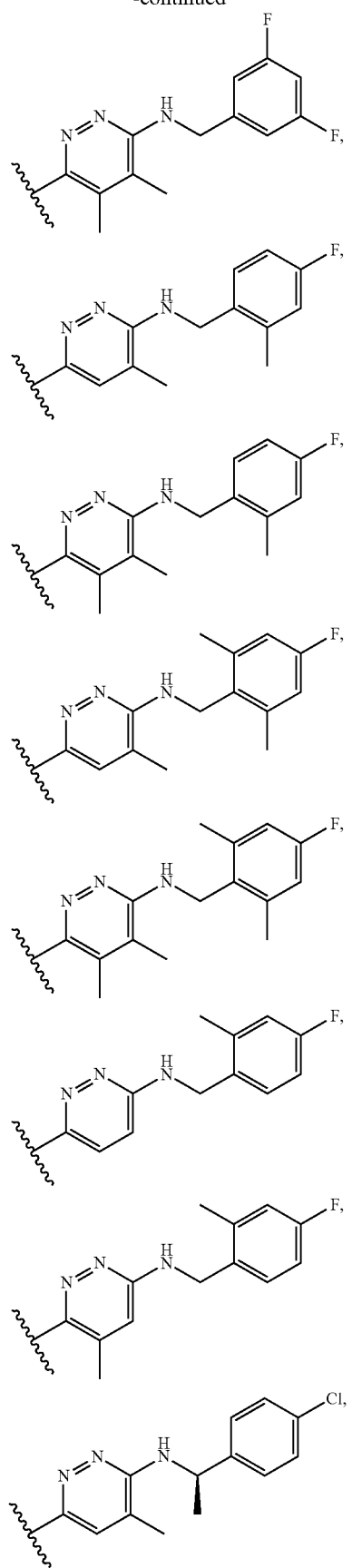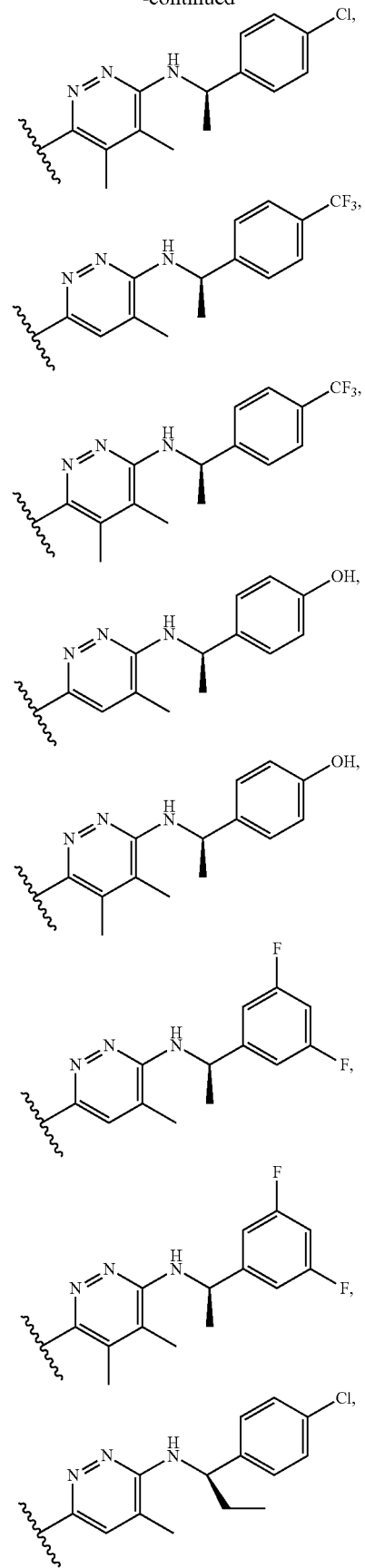

-continued
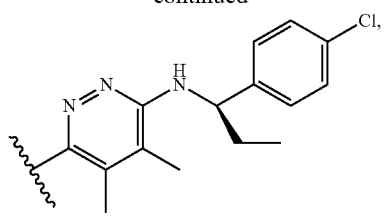
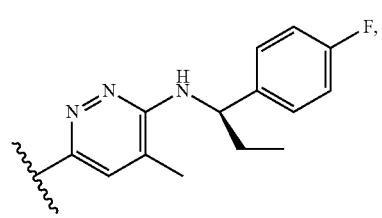
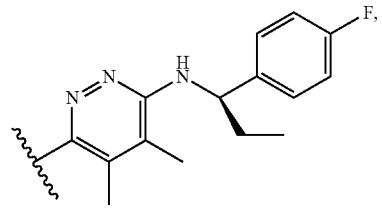
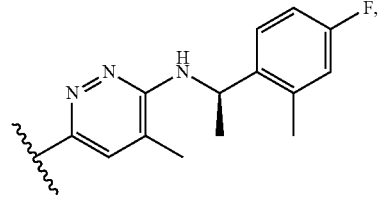
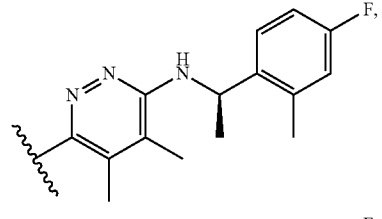
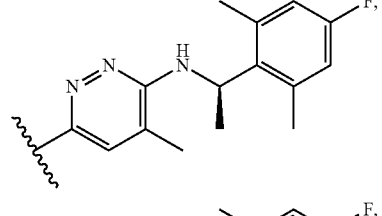
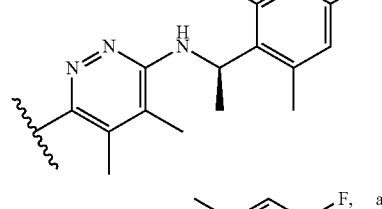
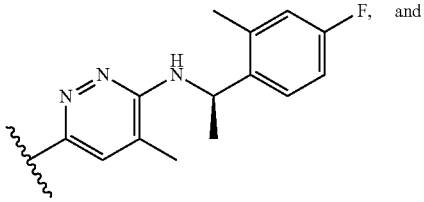
-continued
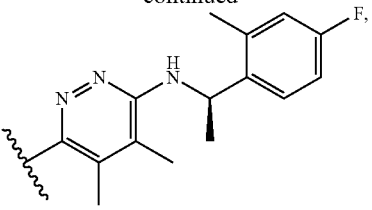
wherein
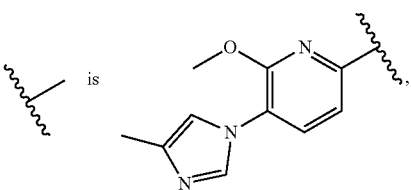 is
or a pharmaceutically acceptable salt thereof.
8. The compound of claim 1, wherein the compound is selected from:
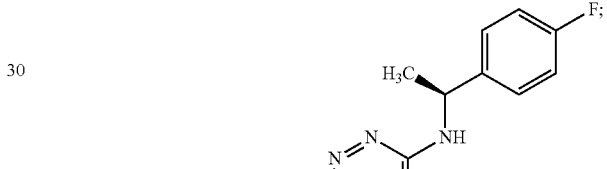
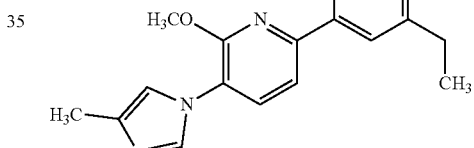
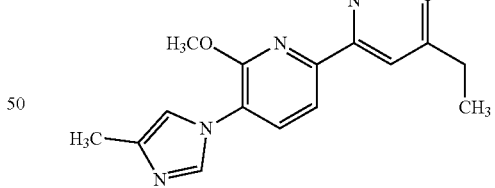
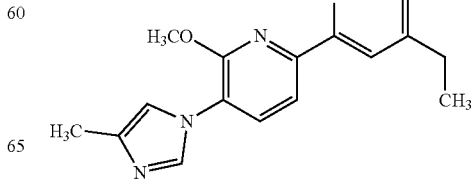

-continued
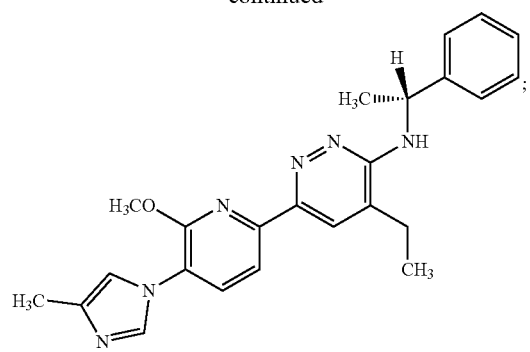
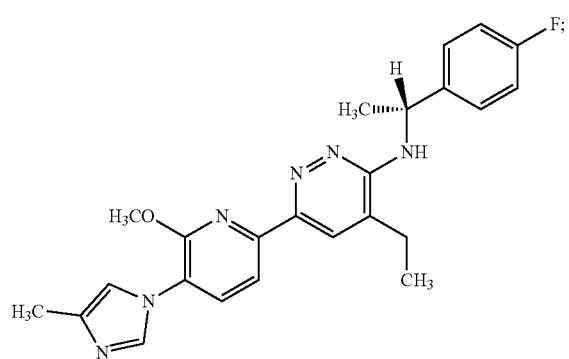
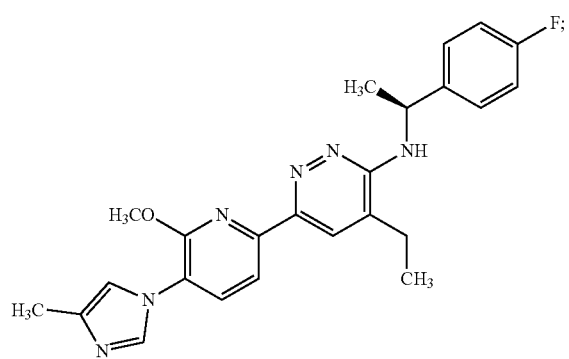
-continued
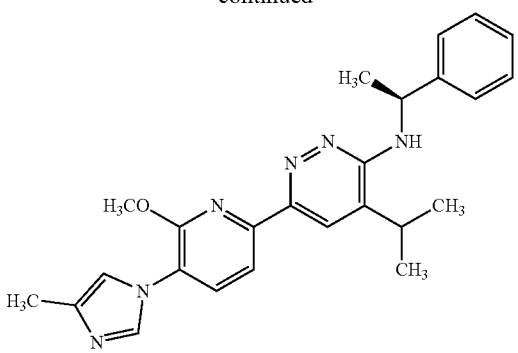
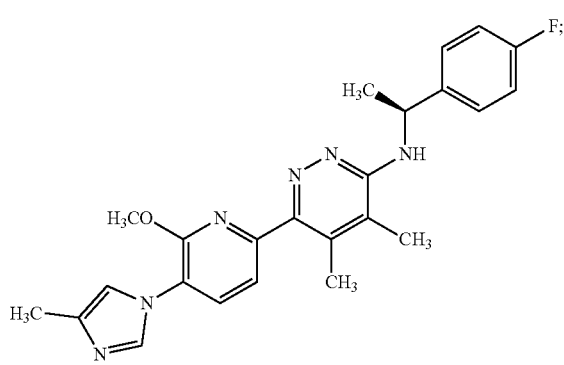
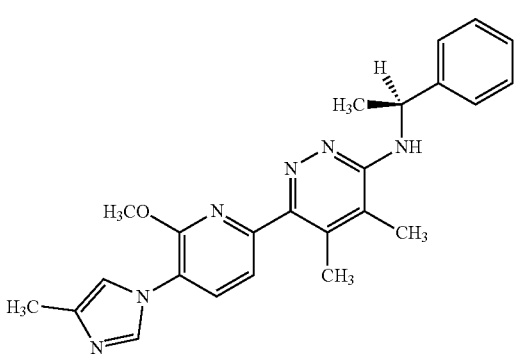
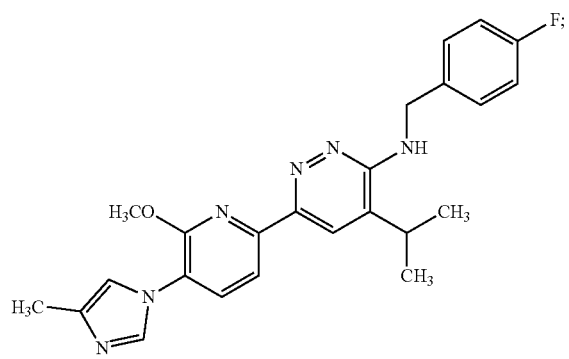

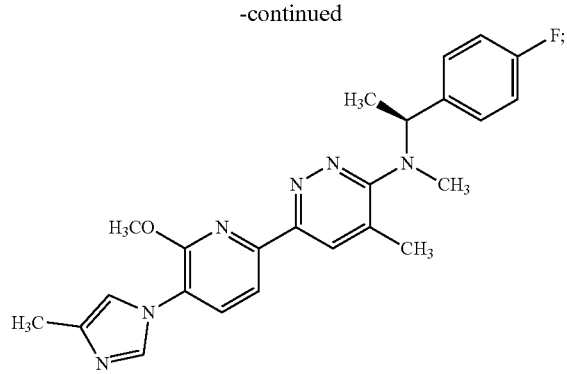
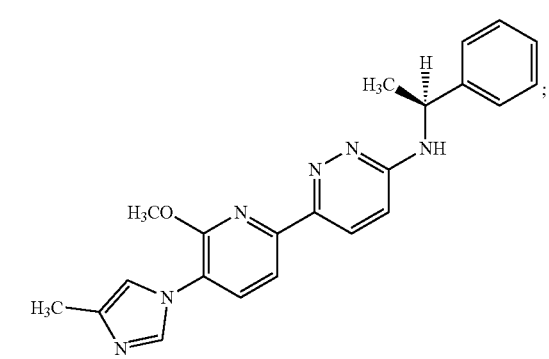
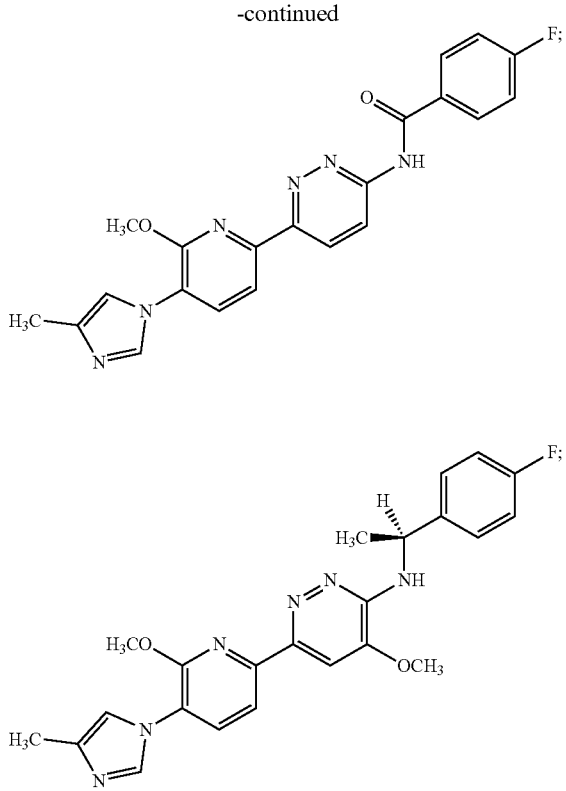

-continued

187
-continued
188
-continued
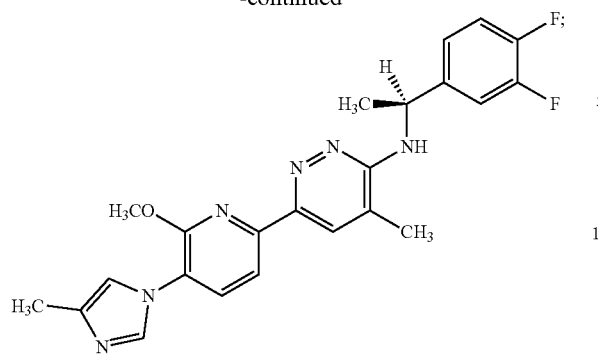
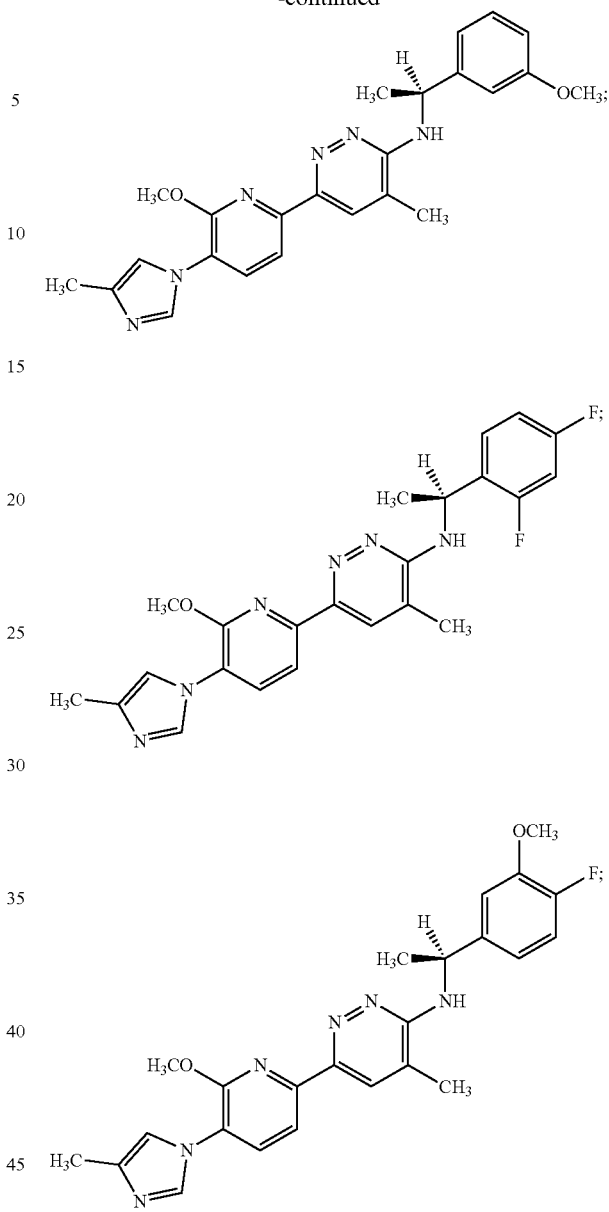
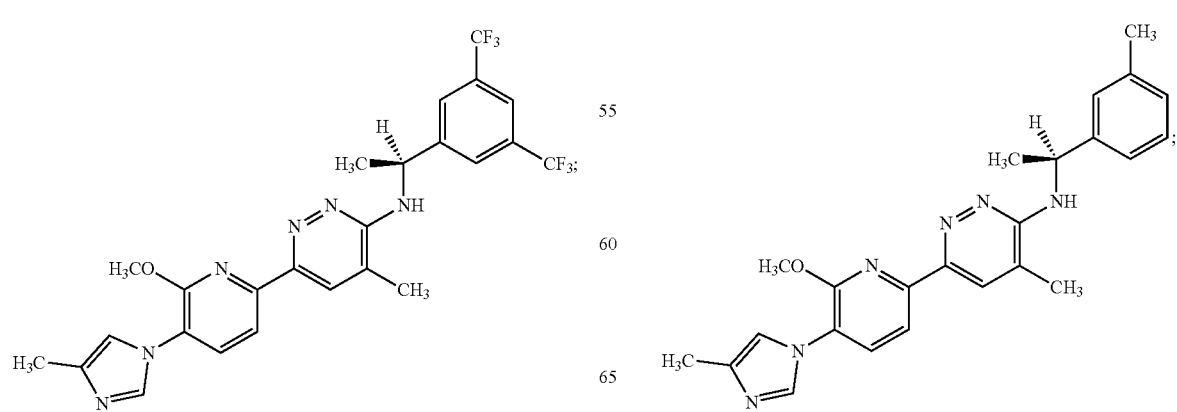

-continued
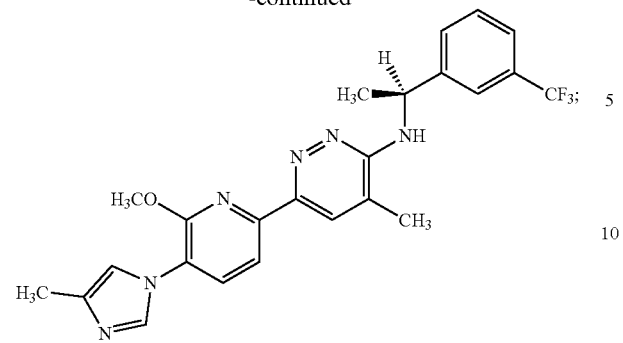
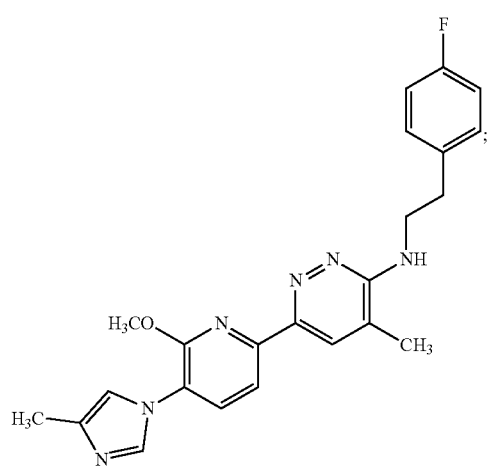
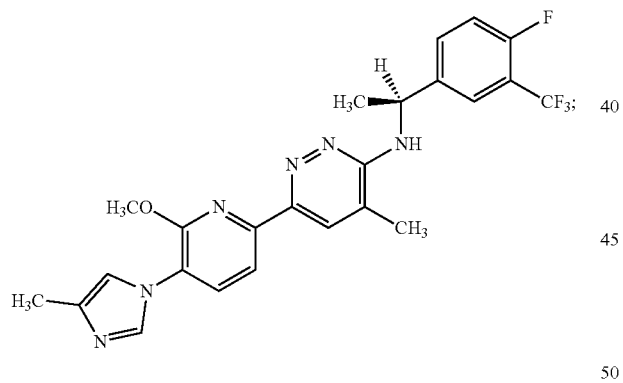
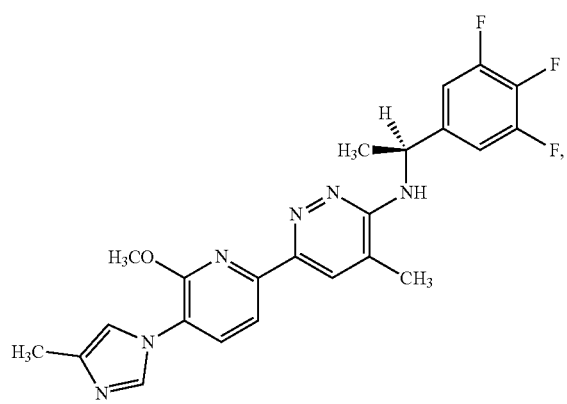
-continued
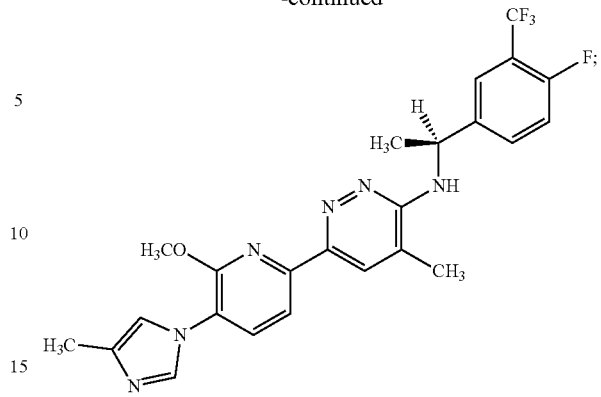
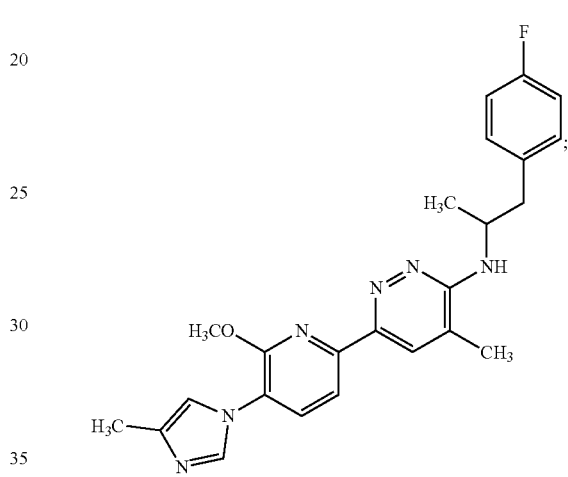
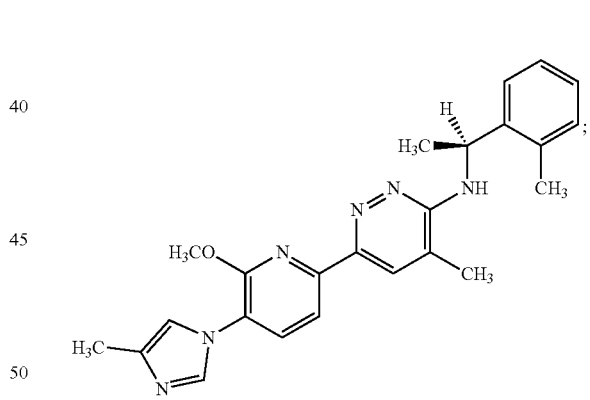
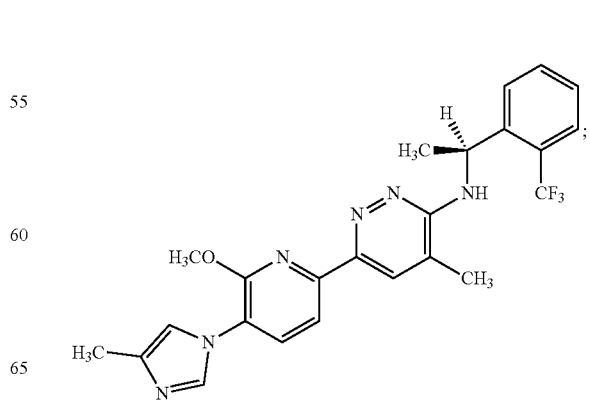

191
-continued
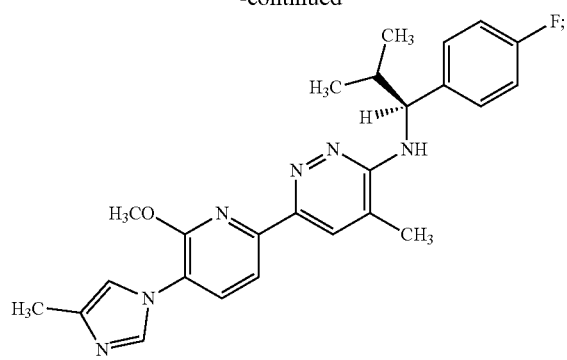
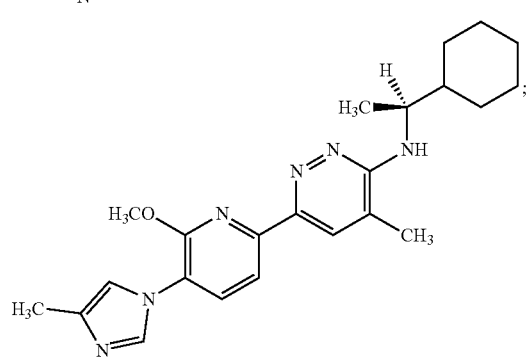
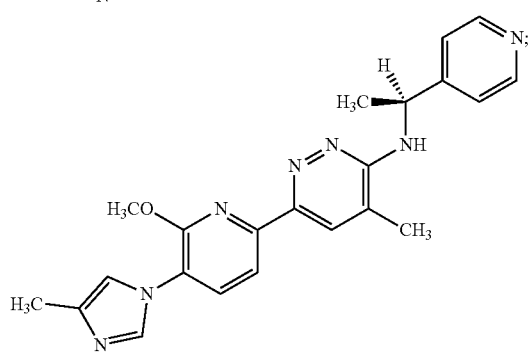
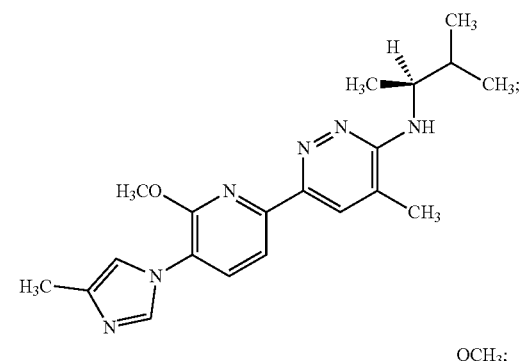
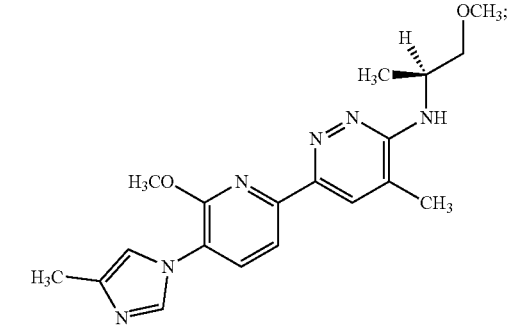
192
-continued
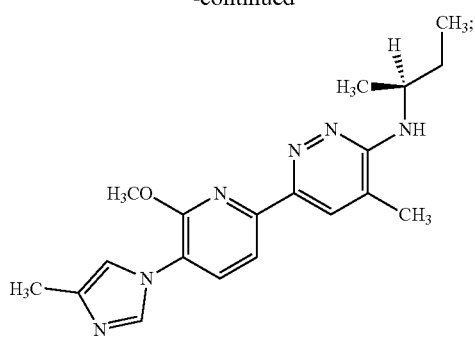
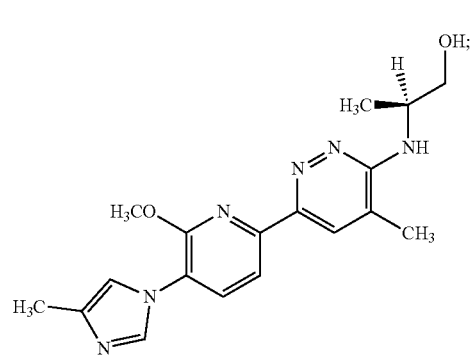
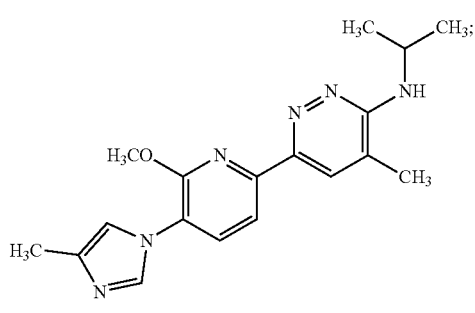
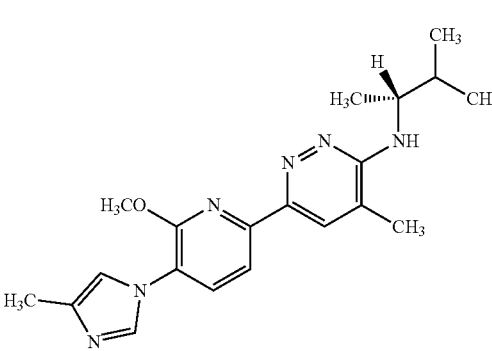
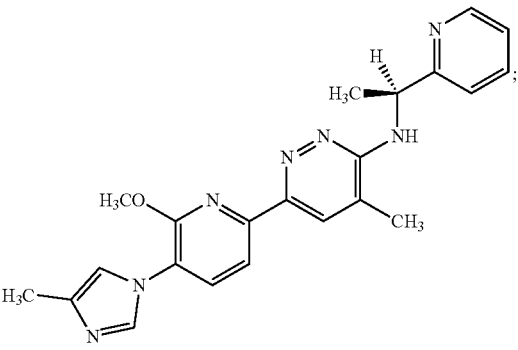

193
-continued
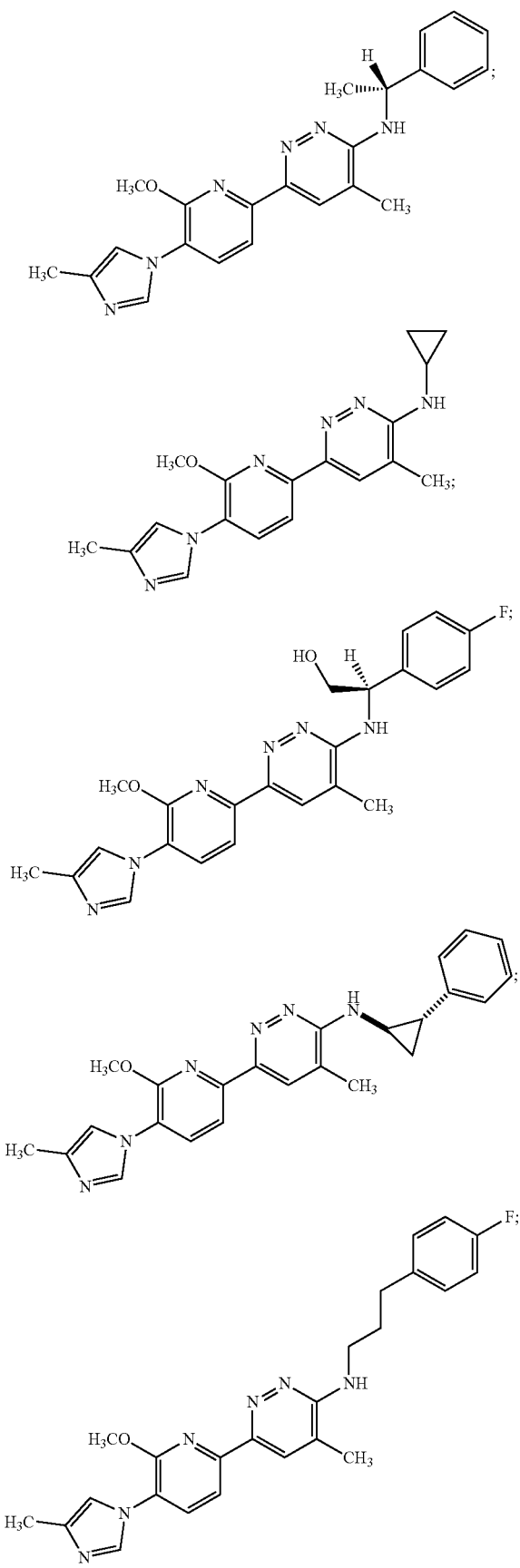
194
-continued
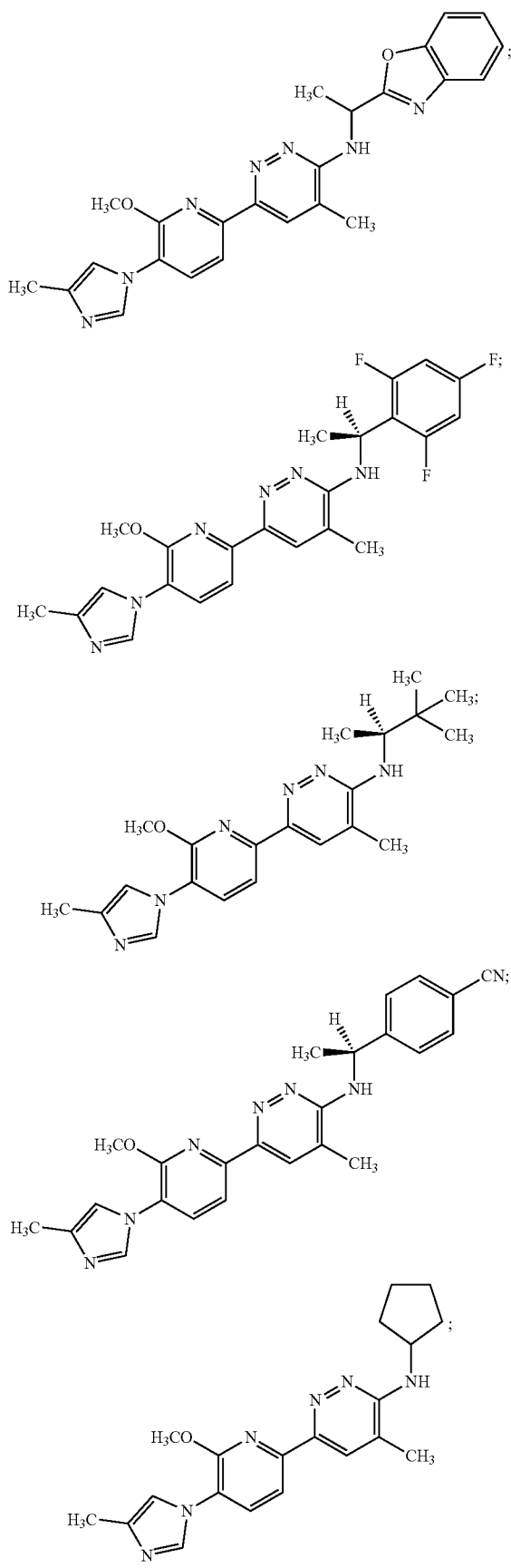

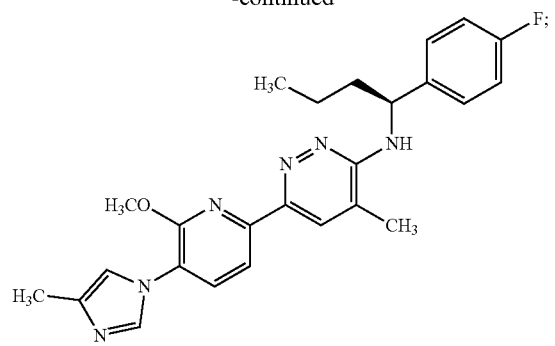
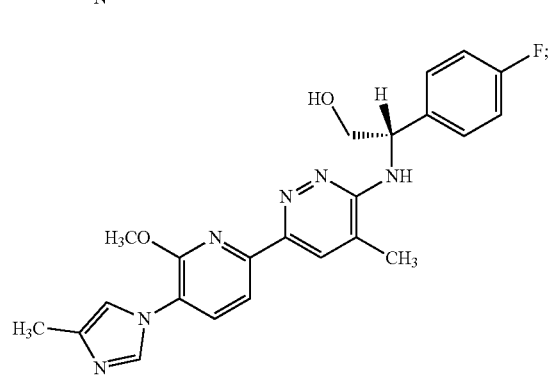
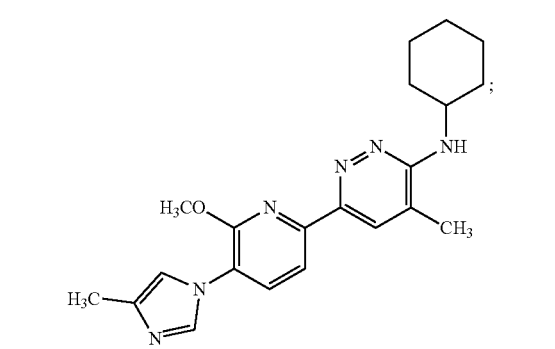
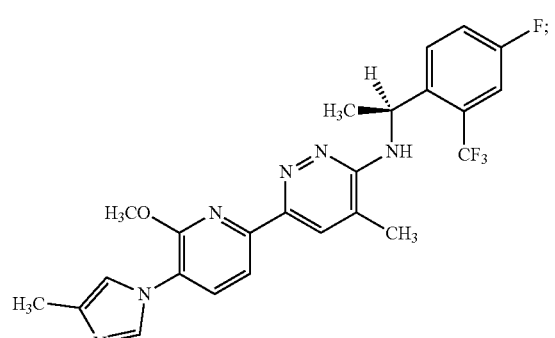
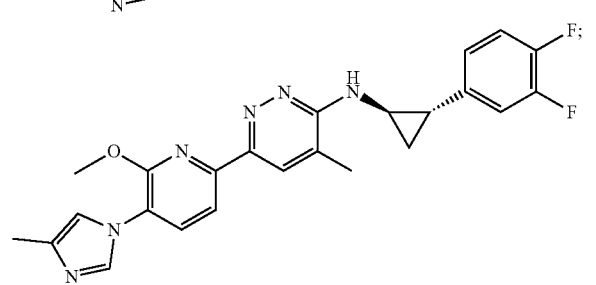
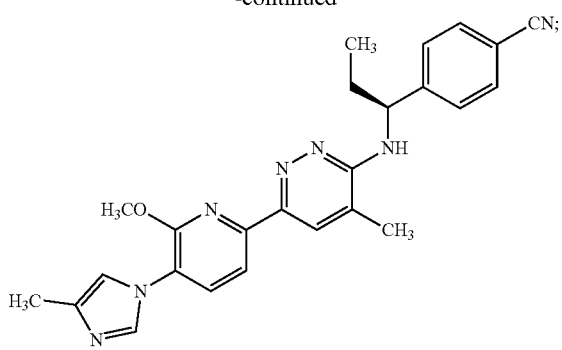
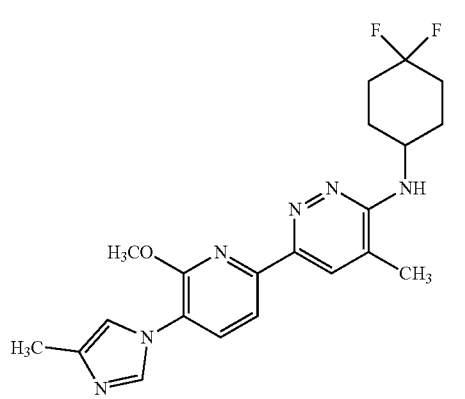
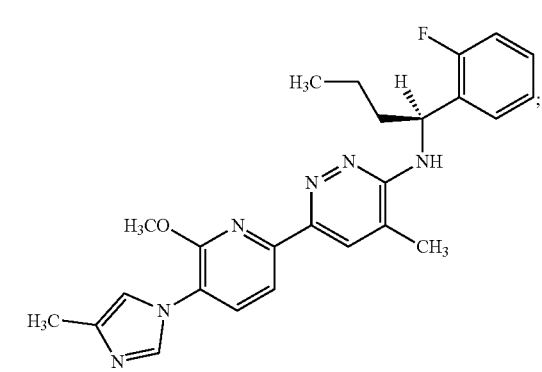
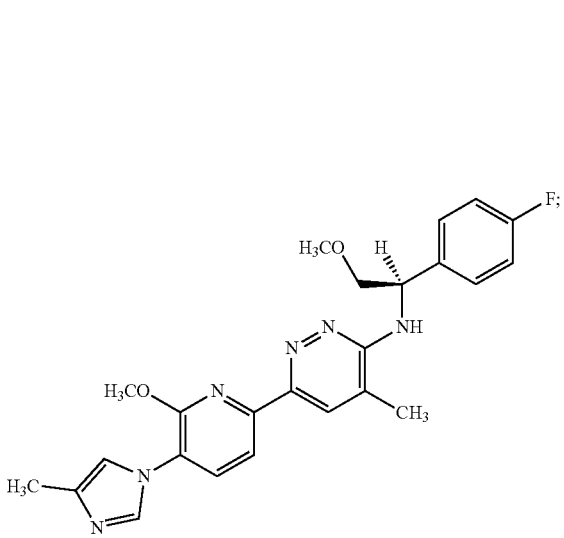

197
-continued
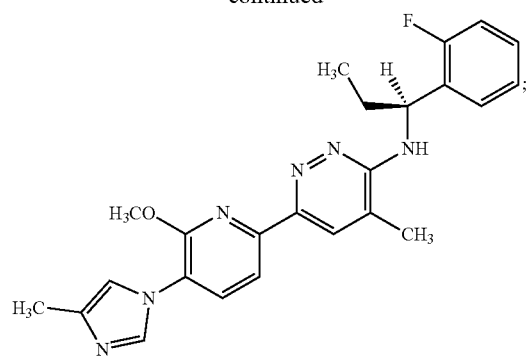
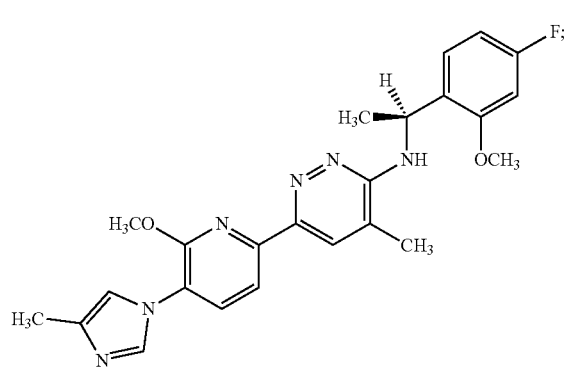
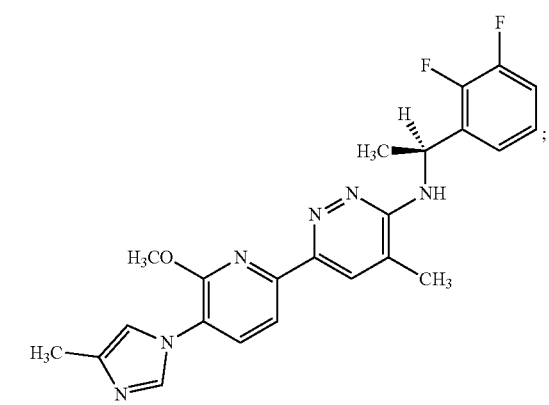
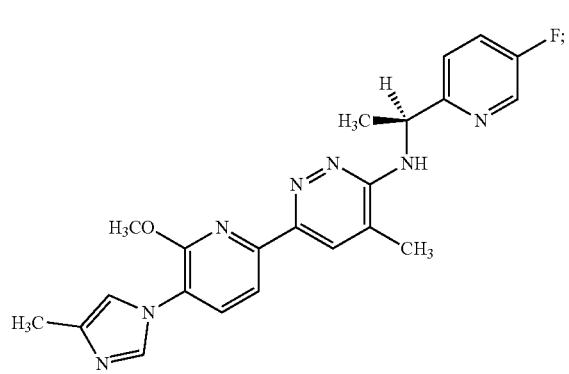
198
-continued
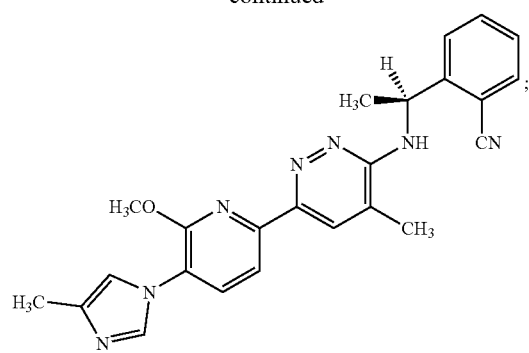
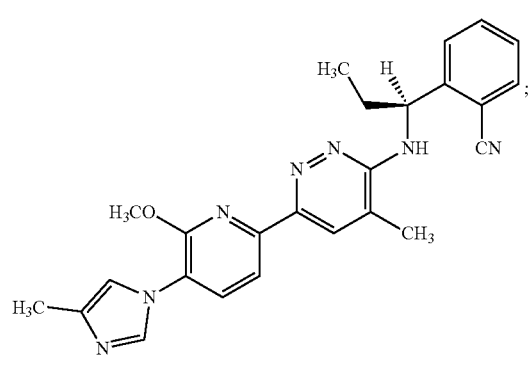
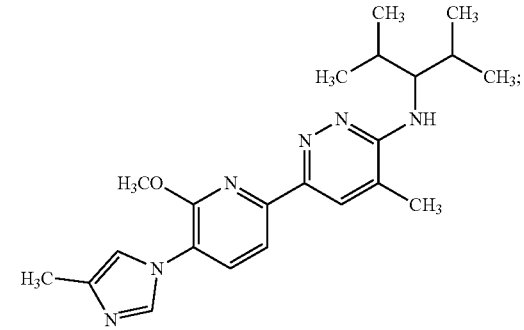
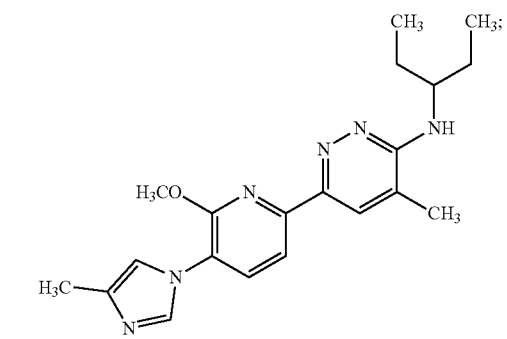

199
-continued
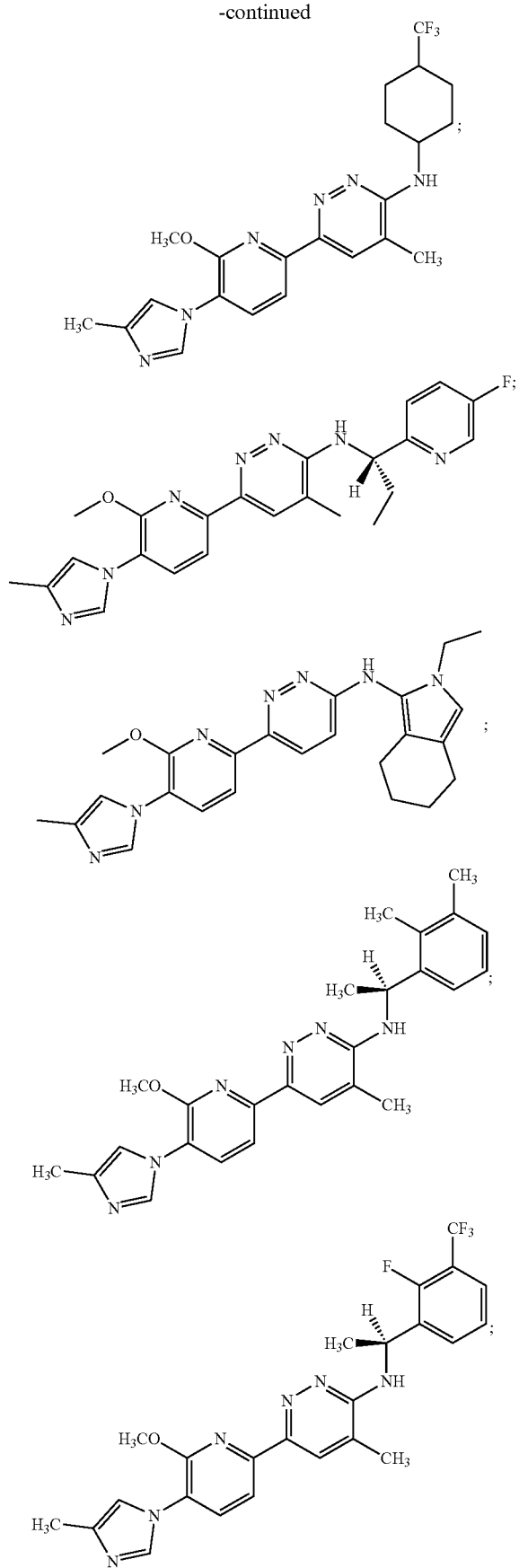
200
-continued
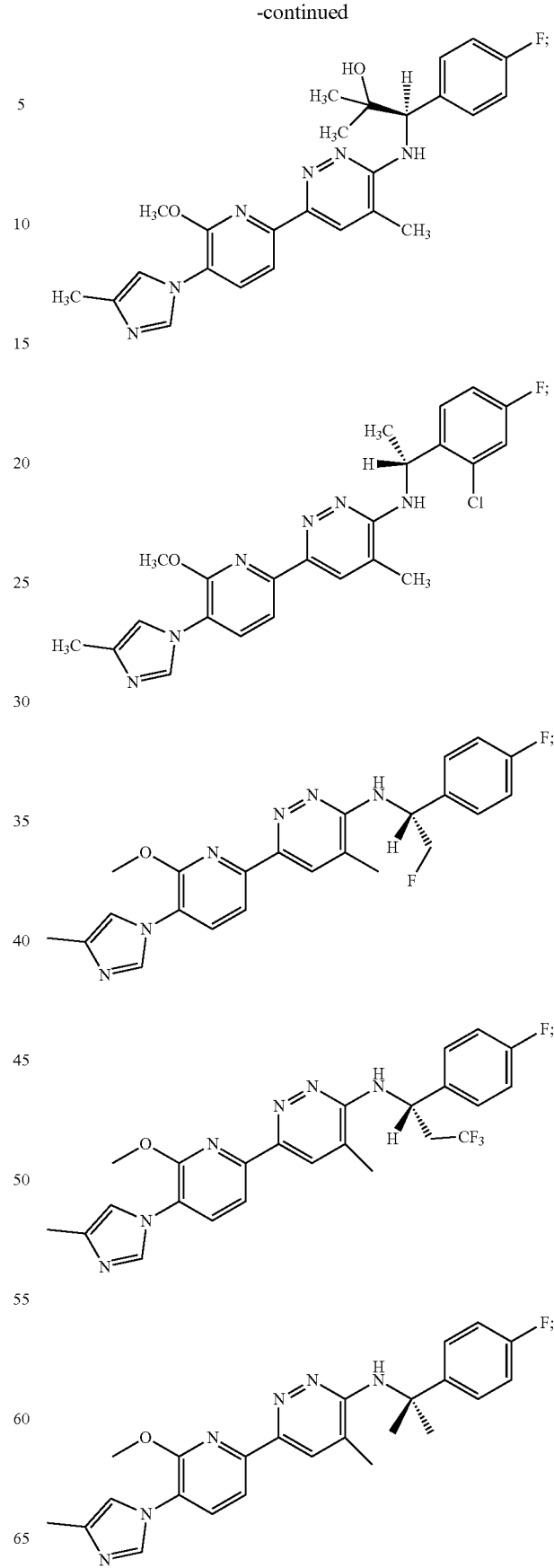

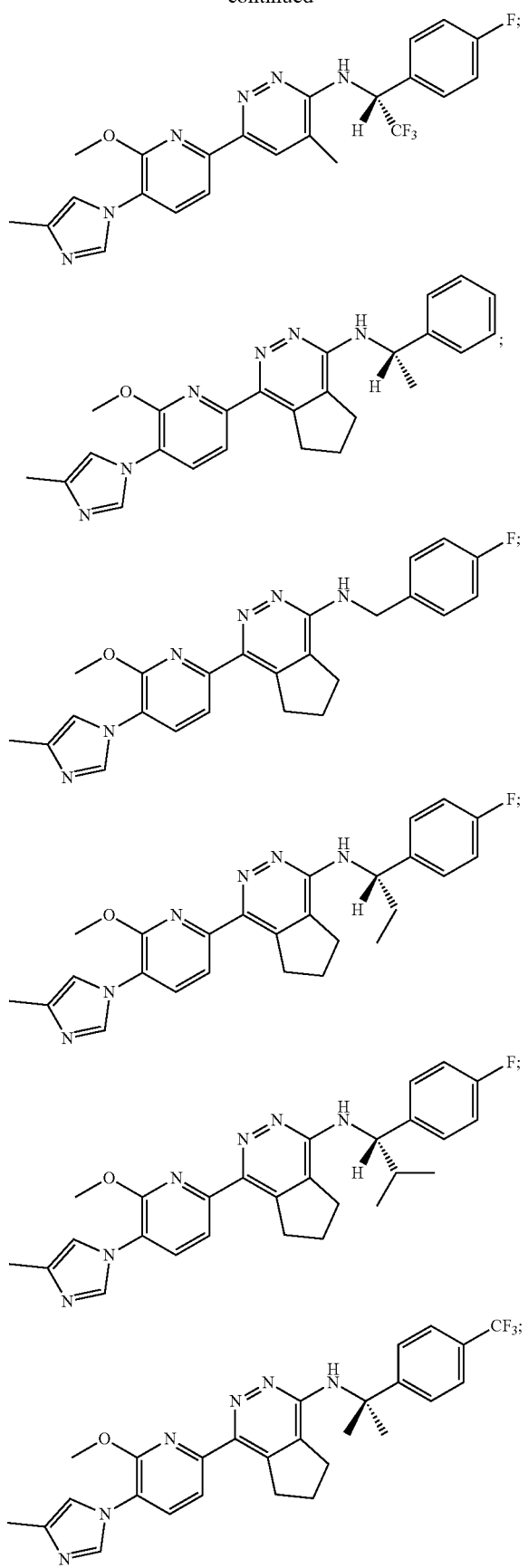
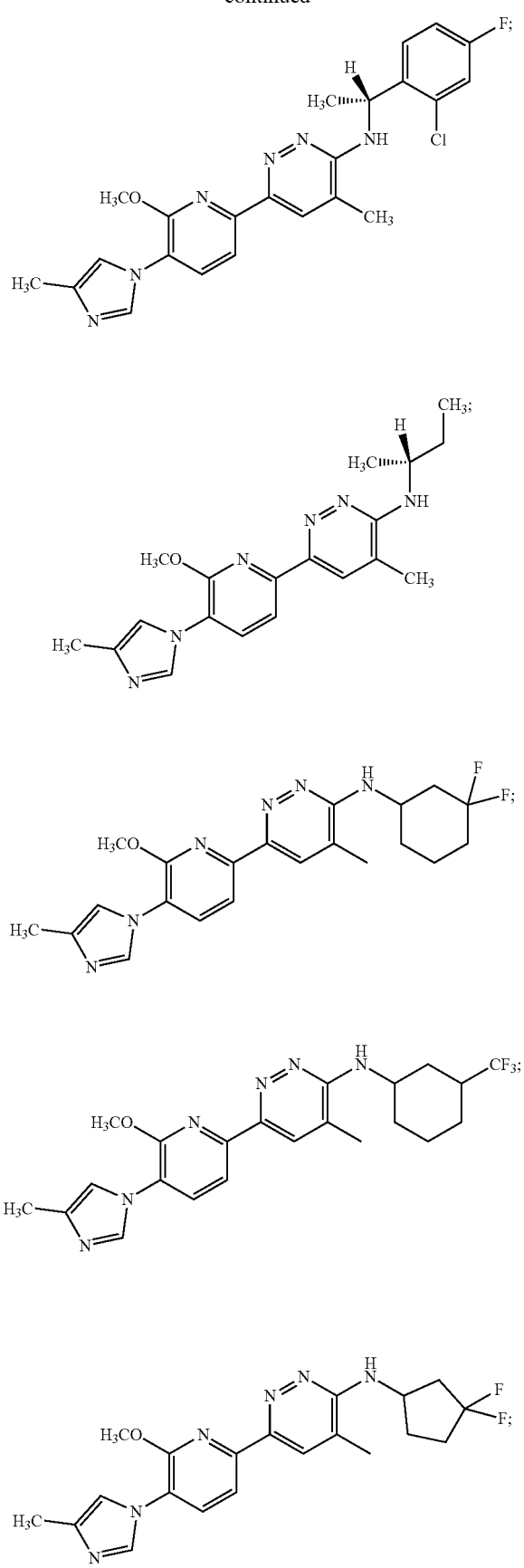

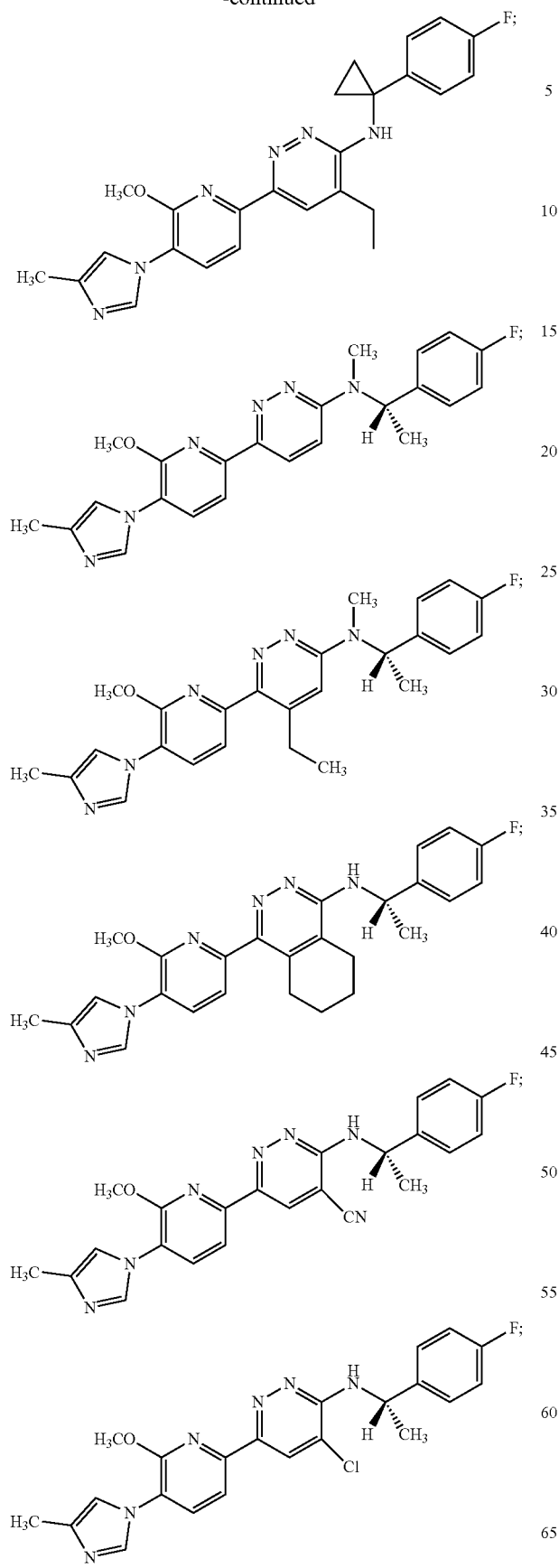
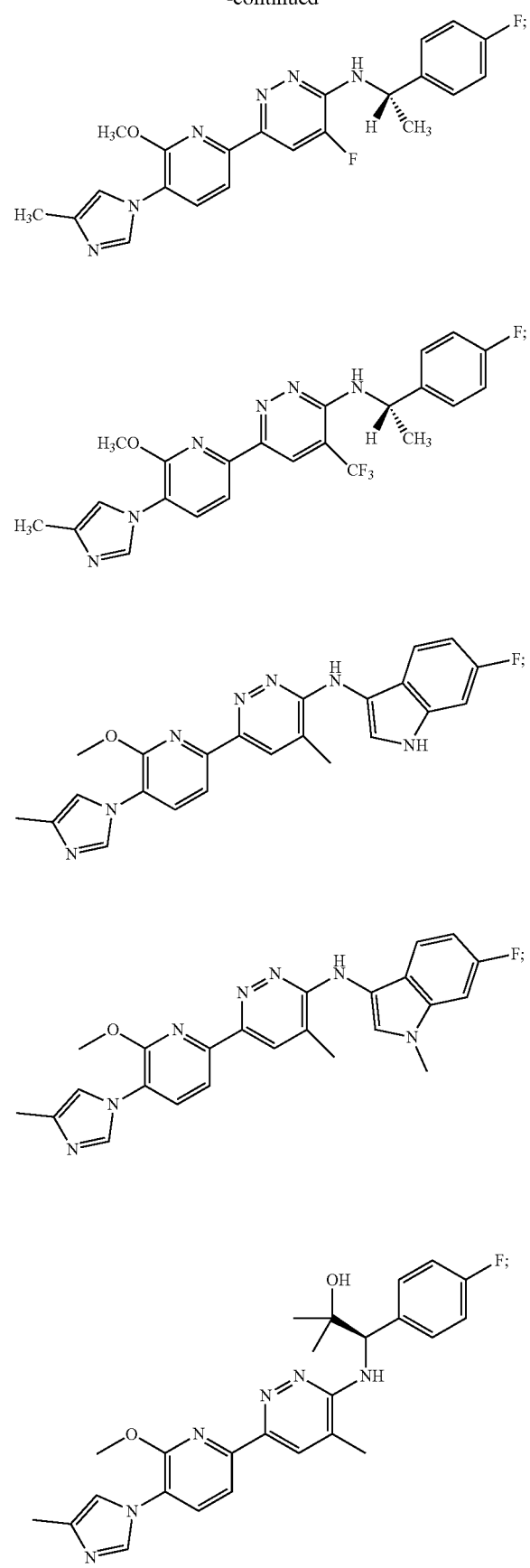

205
-continued
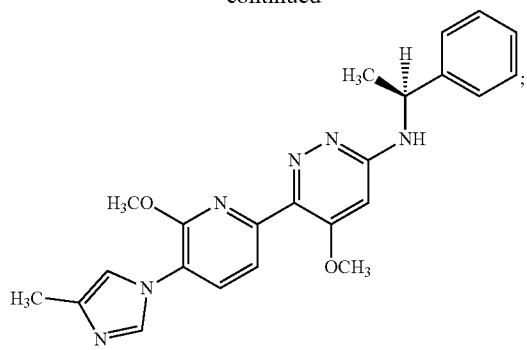
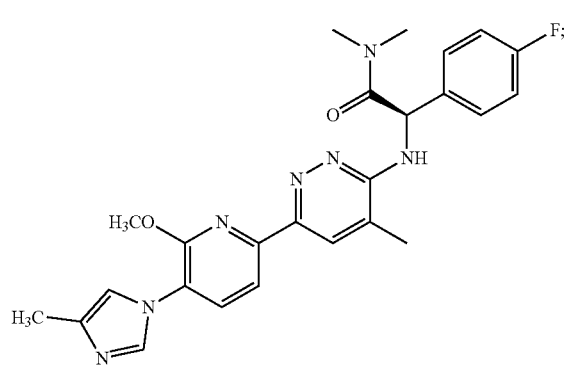
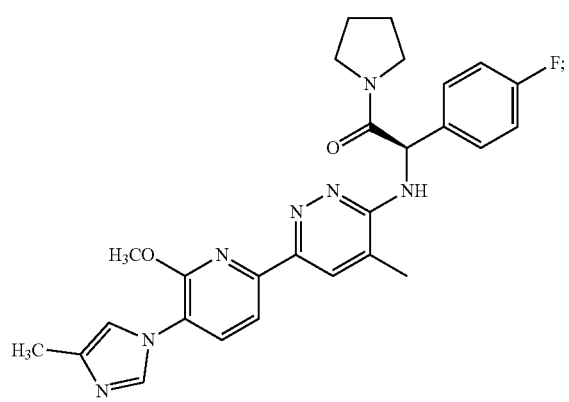
206
-continued
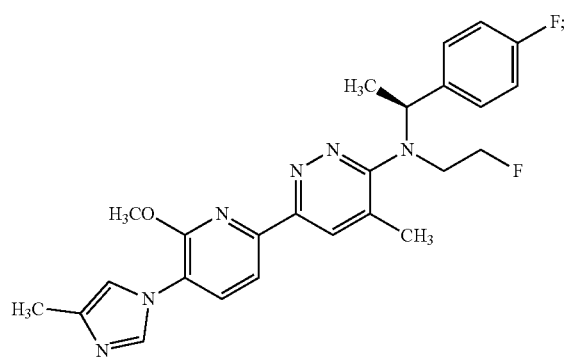
and
or a pharmaceutically acceptable salt thereof.
9. The compound of claim 1, wherein the compound is selected from:
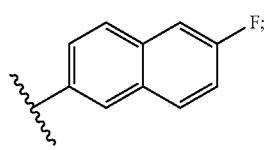
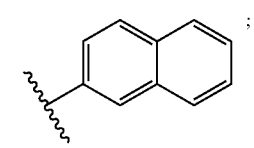
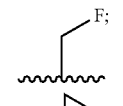
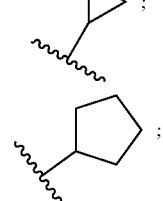
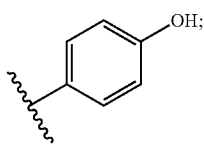

-continued
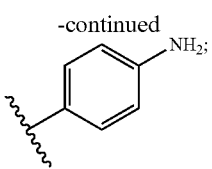
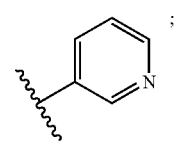
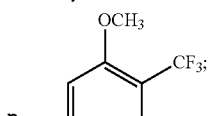
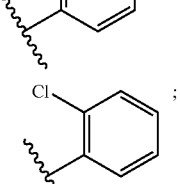
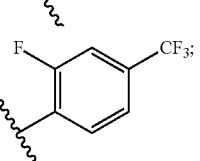
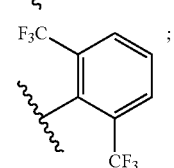
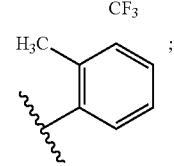
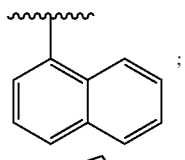
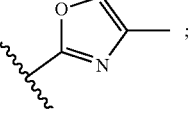
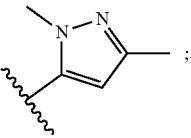
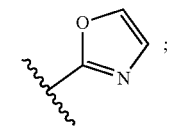
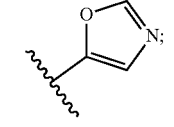
-continued
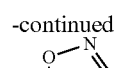
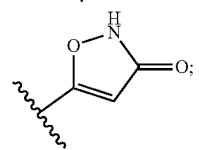
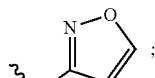
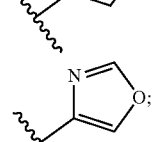
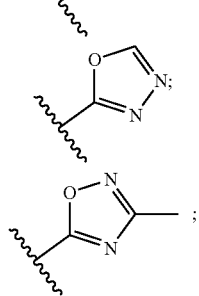
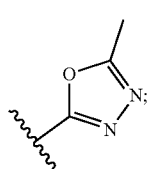
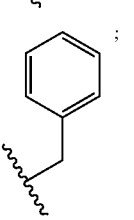
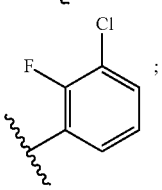
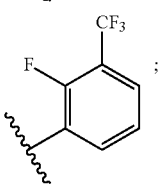
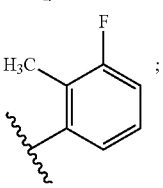

-continued

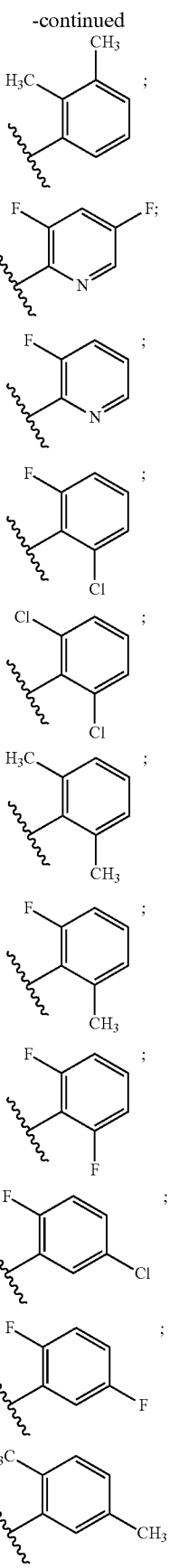

wherein

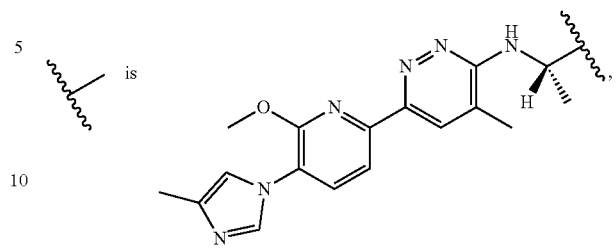is or a pharmaceutically acceptable salt thereof.

10. A pharmaceutical composition comprising a compound of claim 1, or a pharmaceutically acceptable salt thereof, and a pharmaceutically acceptable excipient.

11. A method of decreasing a level of an Aβ-peptide alloform in a cell, the method comprising;
   (i) contacting the cell with a compound of claim 1, or a pharmaceutically acceptable salt thereof; and
   (ii) allowing the compound to modulate the activity or processivity of a γ-secretase protein, wherein the modulation decreases the level of the Aβ-peptide alloform.

12. The method of claim 11, wherein the Aβ-peptide alloform is Aβ42 or Aβ40.

13. A compound having Formula (II):

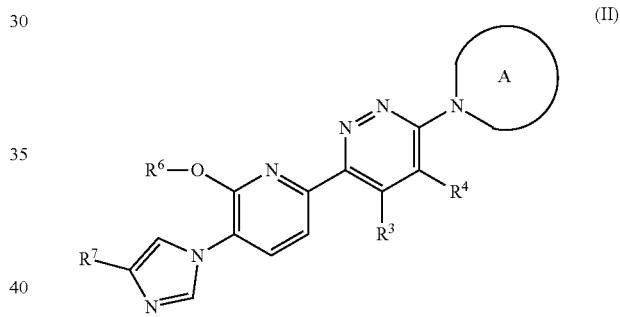

(II)

or a pharmaceutically acceptable salt thereof, wherein:

A is selected from the group consisting of substituted or unsubstituted fused ring aryl-heterocycloalkyl; and substituted or unsubstituted fused ring heteroaryl-heterocycloalkyl;

$R^3$ is selected from the group consisting of hydrogen, halogen, —$CF_3$, —CN, —$OR^{3A}$, —$NR^{3A}R^{3B}$, —$COOR^{3A}$, —$CONR^{3A}R^{3B}$, —$OR^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^4$ is selected from the group consisting of hydrogen, halogen, —$CF_3$, —CN, —$OR^{4A}$, —$NR^{4A}R^{4B}$, —$COOR^{4A}$, —$CONR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

or $R^3$ and $R^4$ are optionally joined together to form a substituted or unsubstituted cycloalkyl;

$R^6$ and $R^7$ are independently substituted or unsubstituted $C_1$-$C_5$ alkyl; and $R^{3A}$, $R^{3B}$, $R^{4A}$, and $R^{4B}$ are independently selected from the group consisting of hydrogen, —OH, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, or $R^{1A}$ and $R^{1B}$, $R^{3A}$ and $R^{3B}$, $R^{4A}$ and $R^{4B}$, or $R^{5A}$ and $R^{5B}$ are independently optionally joined together to independently form a substituted or unsubstituted heterocycloalkyl, or substituted or unsubstituted heteroaryl.

14. The compound of claim 13, wherein:

A is selected from the group consisting of substituted or unsubstituted fused ring 6,5-aryl-heterocycloalkyl; and substituted or unsubstituted fused ring 6,5,6-cycloalkyl-heteroaryl-heterocycloalkyl;

$R^3$ is hydrogen; and $R^4$ is selected from the group consisting of hydrogen and substituted or unsubstituted alkyl.

15. The compound of claim 13, wherein the compound is selected from the group consisting of:

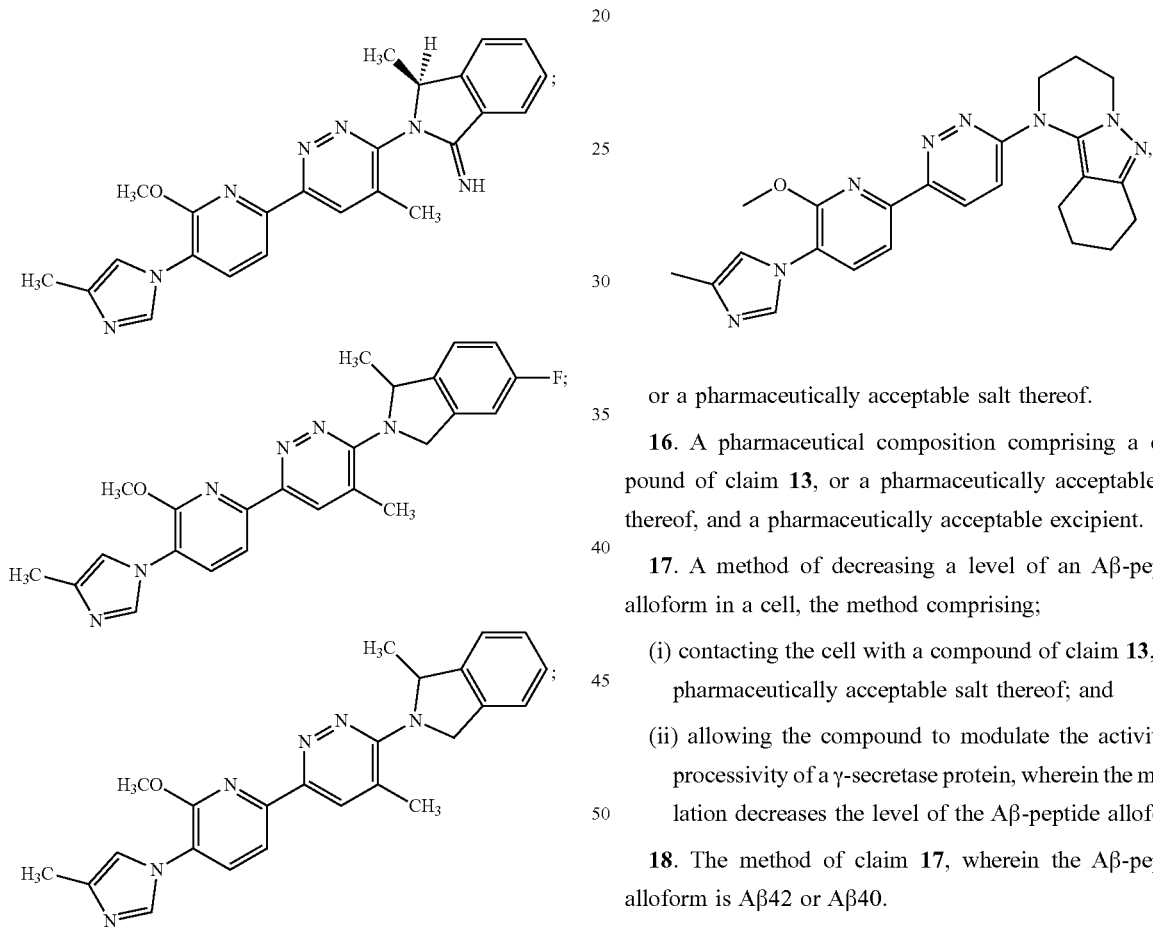

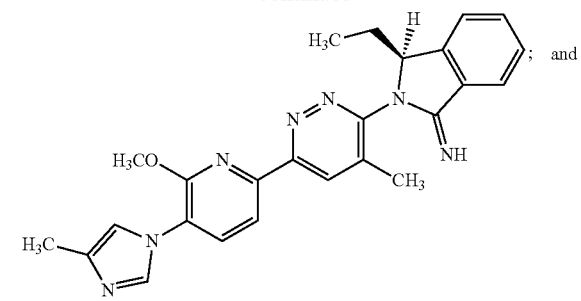

or a pharmaceutically acceptable salt thereof.

16. A pharmaceutical composition comprising a compound of claim 13, or a pharmaceutically acceptable salt thereof, and a pharmaceutically acceptable excipient.

17. A method of decreasing a level of an Aβ-peptide alloform in a cell, the method comprising;

(i) contacting the cell with a compound of claim 13, or a pharmaceutically acceptable salt thereof; and (ii) allowing the compound to modulate the activity or processivity of a γ-secretase protein, wherein the modulation decreases the level of the Aβ-peptide alloform.

18. The method of claim 17, wherein the Aβ-peptide alloform is Aβ42 or Aβ40.

* * * * *

UNITED STATES PATENT AND TRADEMARK OFFICE
CERTIFICATE OF CORRECTION

PATENT NO. : 10,472,346 B2
APPLICATION NO. : 15/522969
DATED : November 12, 2019
INVENTOR(S) : Steven L. Wagner et al.

It is certified that error appears in the above-identified patent and that said Letters Patent is hereby corrected as shown below:

On the Title Page

Column 1 (Applicants), Lines 1-11, delete "The General Hospital Coporation, Boston, MA (US); The Regents of the University of California, Oakland, CA (US); Steven L. Wagner, San Diego, CA (US); William C. Mobley, La Jolla, CA (US); Rudolph E. Tanzi, Hull, MA (US); Graham Johnson, Sanbornton, NH (US); Ronald Buckle, Delmar, NY (US); Nicholas Mayhew, Niskayuna, NY (US); Robert Jason Herr, Voorheesville, NY (US)" and insert -- The General Hospital Corporation, Boston, MA (US); The Regents of the University of California, Oakland, CA (US) --, In the Claims In Column 209, Line 55, in Claim 9, after " 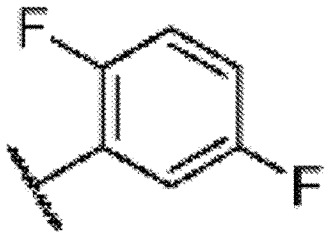 ;" insert -- and --, In Column 209, Line 63, in Claim 9, after " 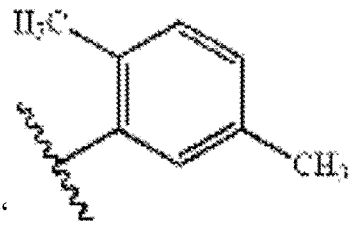 " insert -- , --, In Column 210, Line 30, in Claim 13, delete "(II)" and insert -- (II), --, Signed and Sealed this
Seventh Day of July, 2020

Andrei Iancu
*Director of the United States Patent and Trademark Office*

CERTIFICATE OF CORRECTION (continued)
U.S. Pat. No. 10,472,346 B2

In Column 210, Line 50, in Claim 13, delete "-OR$^{3A}$ ," and insert -- -OR$^{3A}$, --, In Column 211, Line 12, in Claim 14, delete "6,5-aryl -heterocycloalkyl;" and insert -- 6,5-aryl-heterocycloalkyl --, In Column 211, Lines 13-14, in Claim 14, delete "-cyclolakyl-" and insert -- -cycloalkyl- --.